US010700725B2

(12) United States Patent
Ruttler et al.

(10) Patent No.: US 10,700,725 B2
(45) Date of Patent: Jun. 30, 2020

(54) SMART AVIATION COMMUNICATION HEADSET AND PERIPHERAL COMPONENTS

(71) Applicant: Seabeck Holdings, LLC, Seabeck, WA (US)

(72) Inventors: James J. Ruttler, Seabeck, WA (US); Zuzana E. Melherova, Seabeck, WA (US)

(73) Assignee: Seabeck Holdings, LLC, Seabeck, WA (US)

( * ) Notice: Subject to any disclaimer, the term of this patent is extended or adjusted under 35 U.S.C. 154(b) by 0 days.

(21) Appl. No.: 16/533,459

(22) Filed: Aug. 6, 2019

(65) Prior Publication Data
US 2020/0099411 A1 Mar. 26, 2020

Related U.S. Application Data

(63) Continuation of application No. 15/495,672, filed on Apr. 24, 2017, now Pat. No. 10,419,053.
(Continued)

(51) Int. Cl.
G08B 21/02 (2006.01)
H04B 1/3827 (2015.01)
(Continued)

(52) U.S. Cl.
CPC ............ H04B 1/385 (2013.01); A61B 5/0205 (2013.01); A61B 5/02438 (2013.01); A61B 5/1112 (2013.01); A61B 5/145 (2013.01); A61B 5/14551 (2013.01); A61B 5/14552 (2013.01); A61B 5/18 (2013.01); A61B 5/6803 (2013.01);
(Continued)

(58) Field of Classification Search
CPC ......... A61B 5/18; A61B 5/16; A61B 5/14551; A61B 5/746; A61B 5/7405; A61B 5/742; A62B 7/14; G08B 21/02; G08B 21/0211; G08B 21/0415; G08B 21/0453
See application file for complete search history.

(56) References Cited

U.S. PATENT DOCUMENTS 7,881,832 B2 2/2011 Komer et al.
9,102,417 B1 8/2015 Young
(Continued)

OTHER PUBLICATIONS

Boeing Phantom Works. Jarvis (Trey) J. Arthur, III, Lawrence J. Prinzel, III, Steven P. Williams, Randall E. Bailey, Kevin J. Shelton, and R. Mike Norman. Enhanced/synthetic vision and head-worn display technologies for terminal maneuvering area NextGen operrations pp. 1-15. NASA Langley Research Center, Hampton, VA.
(Continued)

Primary Examiner — Benyam Haile
(74) Attorney, Agent, or Firm — Ruttler Mills, PLLC; James J. Ruttler

(57) ABSTRACT

In one embodiment, an aviation communication headset includes, but is not limited to, at least one microphone; one or more speakers; one or more physiological sensors operable to monitor one or more health parameters of a wearer; and at least one control unit operable to perform operations including at least: obtaining one or more values from the one or more physiological sensors; and outputting information regarding the one or more values via the one or more speakers.

19 Claims, 131 Drawing Sheets

Related U.S. Application Data

(60) Provisional application No. 62/326,657, filed on Apr. 22, 2016, provisional application No. 62/326,938, filed on Apr. 25, 2016, provisional application No. 62/327,369, filed on Apr. 25, 2016, provisional application No. 62/328,482, filed on Apr. 27, 2016, provisional application No. 62/329,550, filed on Apr. 29, 2016, provisional application No. 62/343,491, filed on May 31, 2016, provisional application No. 62/357,893, filed on Jul. 1, 2016, provisional application No. 62/376,143, filed on Aug. 17, 2016, provisional application No. 62/395,052, filed on Sep. 15, 2016, provisional application No. 62/414,175, filed on Oct. 28, 2016.

(51) Int. Cl.
| | |
|---|---|
| *A61B 5/024* | (2006.01) |
| *A61B 5/1455* | (2006.01) |
| *A61B 5/00* | (2006.01) |
| *A61B 5/11* | (2006.01) |
| *A61B 5/145* | (2006.01) |
| *A61B 5/0205* | (2006.01) |
| *A61B 5/18* | (2006.01) |
| *H04W 76/14* | (2018.01) |
| *H04N 21/422* | (2011.01) |
| *A61B 5/16* | (2006.01) |
| *G06F 3/16* | (2006.01) |
| *H04W 4/80* | (2018.01) |
| *G08B 21/04* | (2006.01) |

(52) U.S. Cl.
CPC .......... *G08B 21/02* (2013.01); *G08B 21/0211* (2013.01); *H04W 76/14* (2018.02); *A61B 5/163* (2017.08); *A61B 5/165* (2013.01); *A61B 5/6814* (2013.01); *A61B 2503/22* (2013.01); *G06F 3/167* (2013.01); *G08B 21/0415* (2013.01); *G08B 21/0453* (2013.01); *H04B 2001/3866* (2013.01); *H04N 21/42201* (2013.01); *H04W 4/80* (2018.02)

(56) References Cited

U.S. PATENT DOCUMENTS

| | | | |
|---|---|---|---|
| 2003/0062046 A1 | 4/2003 | Wiesmann | |
| 2004/0206353 A1 | 10/2004 | Conroy, Jr. | |
| 2008/0146890 A1* | 6/2008 | LeBoeuf | A61B 5/11 600/300 |
| 2012/0075122 A1 | 3/2012 | Whitlow | |
| 2014/0072136 A1* | 3/2014 | Tenenbaum | G08B 21/06 381/74 |
| 2014/0243631 A1 | 8/2014 | Melker | |
| 2017/0039045 A1 | 2/2017 | Abrahami | |
| 2017/0061951 A1 | 3/2017 | Starobin | |
| 2017/0236405 A1* | 8/2017 | Khazanov | G08B 29/185 340/601 |
| 2018/0028114 A1* | 2/2018 | Cronin | A61B 5/16 |
| 2019/0007540 A1 | 1/2019 | Shaik | |

OTHER PUBLICATIONS

NBAA Convention News. Matt Thurber. TopMax Places Headworn HUD on Headsets pp. 1-2. Nov. 12, 2015.

Department of Defense. Presentation to the House Armed Services Committee Subcommittee on Tactical Air and Land Forces U.S. House of Representatives. Sep. 13, 2012.

Naval Medical Research Unit—Dayton. A Comparison of Pulse-Oximetry, Near-Infrared Spectroscopy (NIRS), and Gas Sensors for In-Cockpit Hypoxia Detection. J.B. Phillips, D.S. Horning, & R.E. Dory. Technical Memorandum Report No. 12-60. Sep. 12, 2012.

* cited by examiner

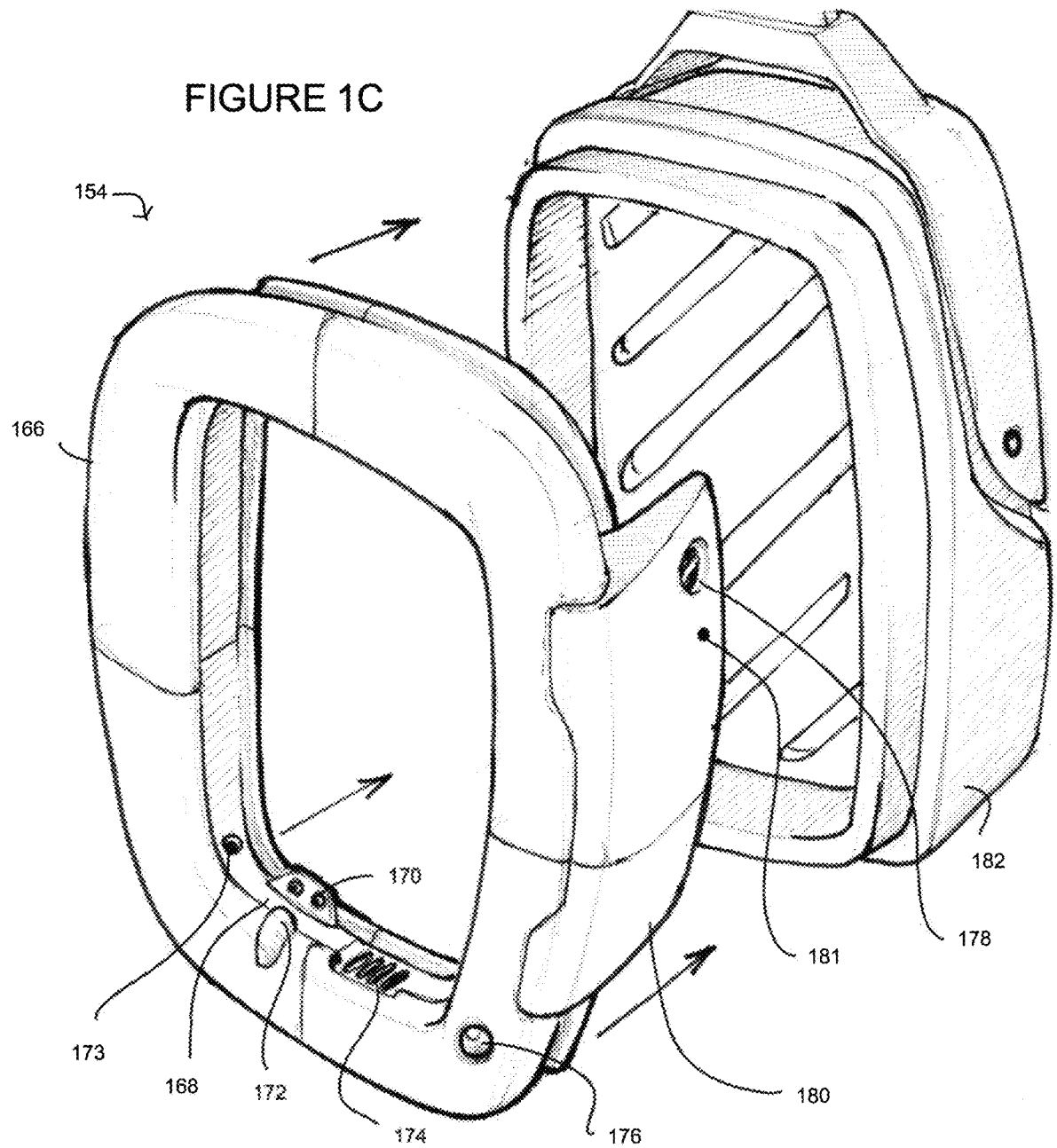

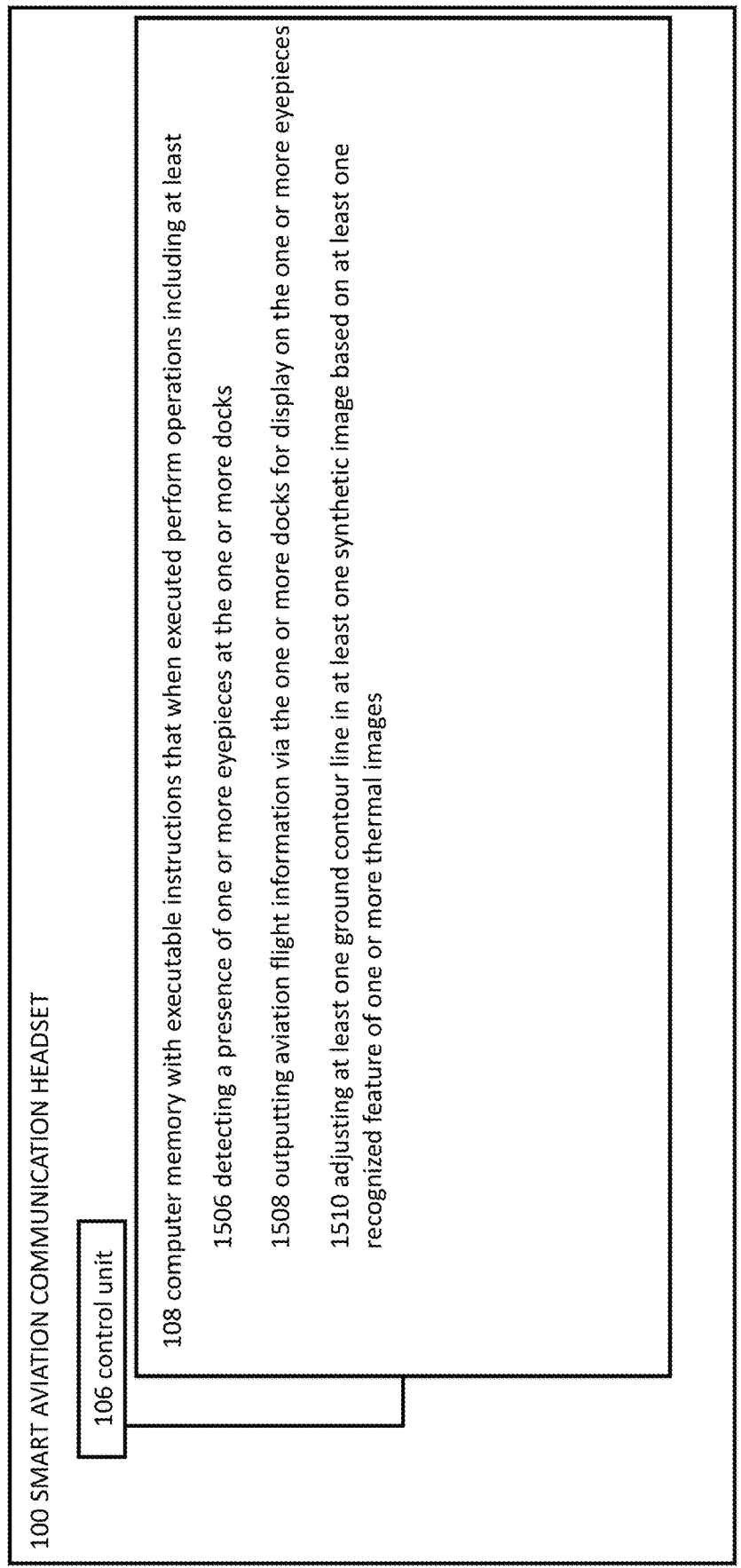

FIGURE 15

100 SMART AVIATION COMMUNICATION HEADSET
106 control unit
108 computer memory with executable instructions that when executed perform operations including at least
1506 detecting a presence of one or more eyepieces at the one or more docks
1508 outputting aviation flight information via the one or more docks for display on the one or more eyepieces
1510 adjusting at least one ground contour line in at least one synthetic image based on at least one recognized feature of one or more thermal images

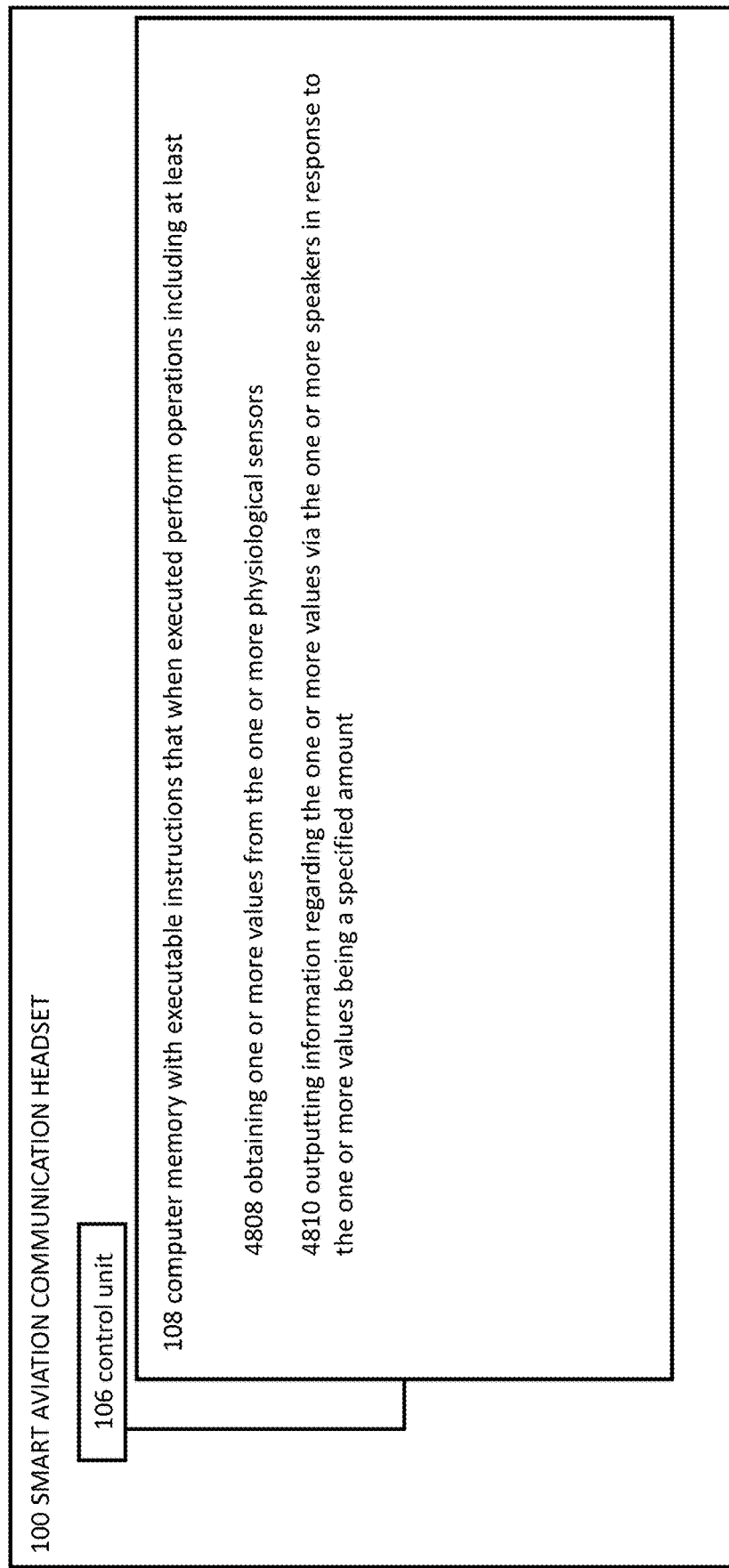

FIGURE 48

100 SMART AVIATION COMMUNICATION HEADSET
106 control unit
108 computer memory with executable instructions that when executed perform operations including at least
4808 obtaining one or more values from the one or more physiological sensors
4810 outputting information regarding the one or more values via the one or more speakers in response to the one or more values being a specified amount

FIGURE 52

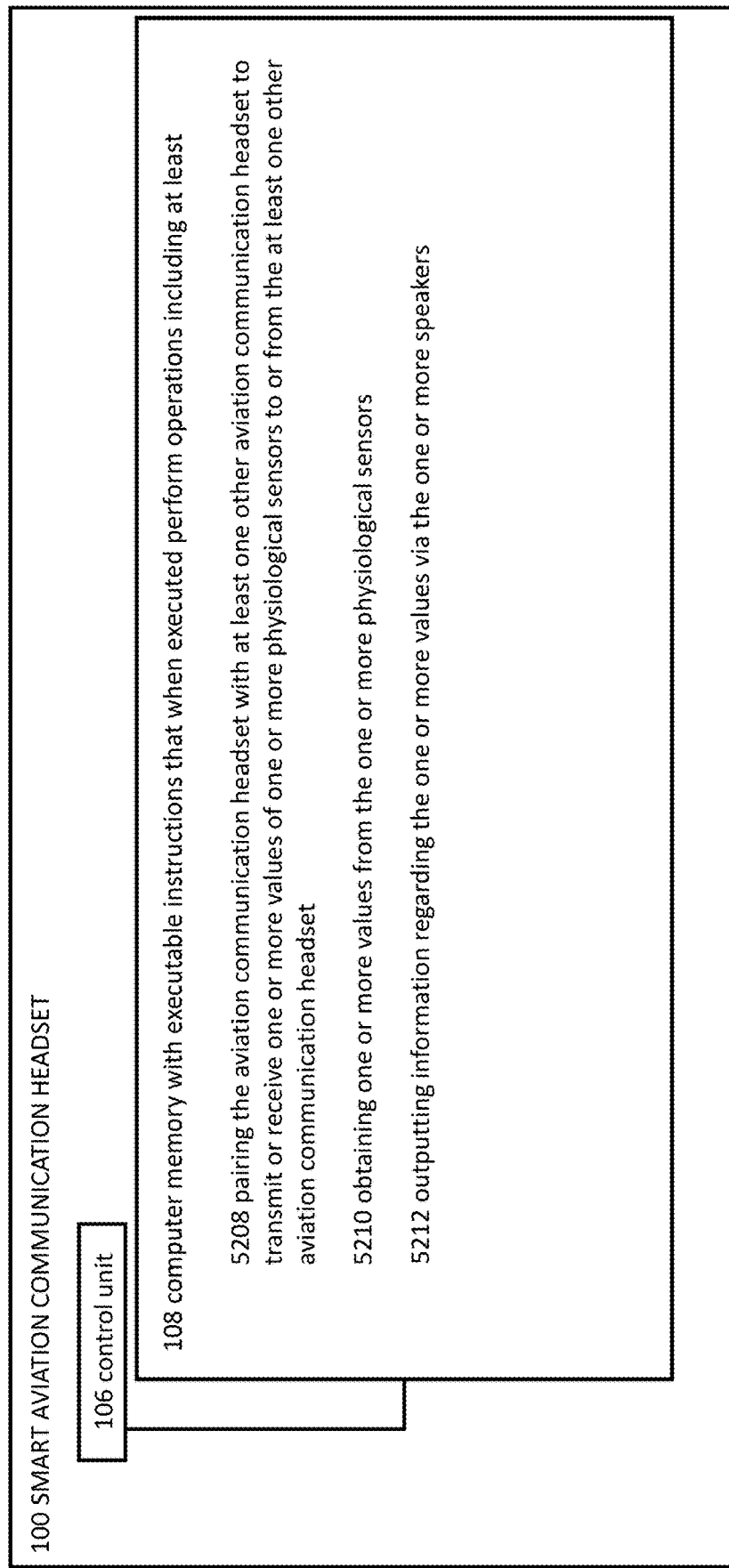

100 SMART AVIATION COMMUNICATION HEADSET 106 control unit 108 computer memory with executable instructions that when executed perform operations including at least 5208 pairing the aviation communication headset with at least one other aviation communication headset to transmit or receive one or more values of one or more physiological sensors to or from the at least one other aviation communication headset 5210 obtaining one or more values from the one or more physiological sensors 5212 outputting information regarding the one or more values via the one or more speakers

FIGURE 56

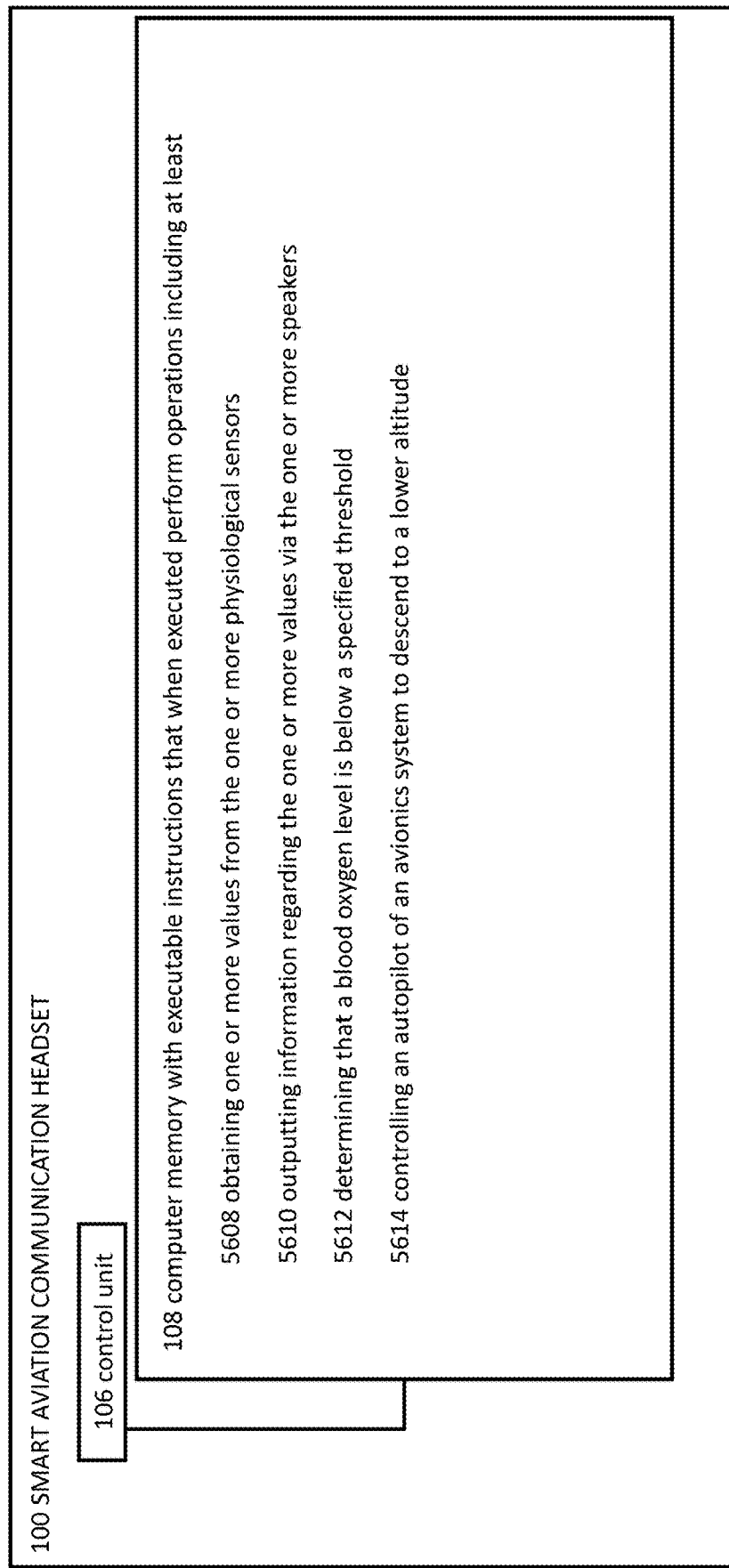

100 SMART AVIATION COMMUNICATION HEADSET 106 control unit 108 computer memory with executable instructions that when executed perform operations including at least 5608 obtaining one or more values from the one or more physiological sensors 5610 outputting information regarding the one or more values via the one or more speakers 5612 determining that a blood oxygen level is below a specified threshold 5614 controlling an autopilot of an avionics system to descend to a lower altitude

FIGURE 101

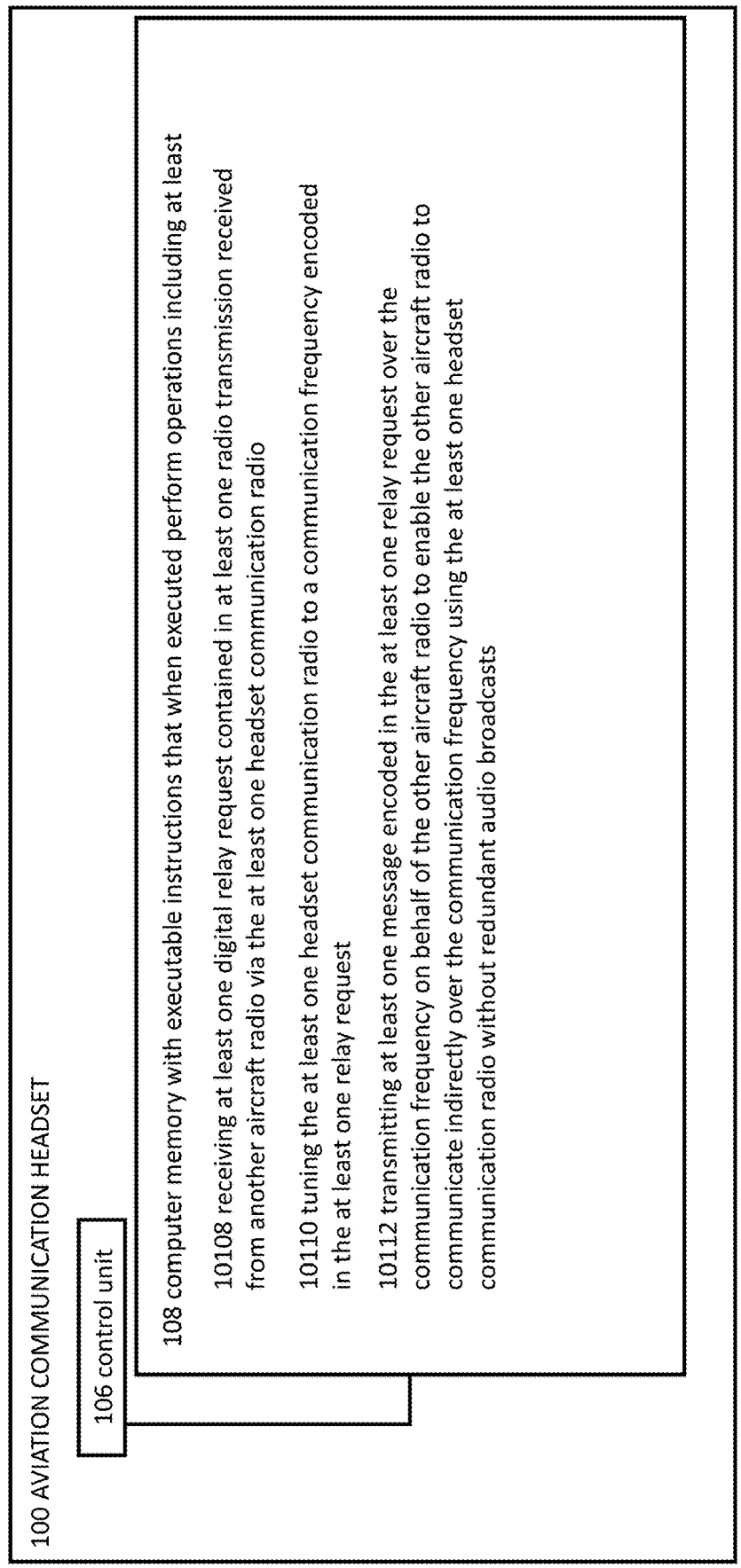

100 AVIATION COMMUNICATION HEADSET 106 control unit 108 computer memory with executable instructions that when executed perform operations including at least 10108 receiving at least one digital relay request contained in at least one radio transmission received from another aircraft radio via the at least one headset communication radio 10110 tuning the at least one headset communication radio to a communication frequency encoded in the at least one relay request 10112 transmitting at least one message encoded in the at least one relay request over the communication frequency on behalf of the other aircraft radio to enable the other aircraft radio to communicate indirectly over the communication frequency using the at least one headset communication radio without redundant audio broadcasts

FIGURE 103

100 AVIATION COMMUNICATION HEADSET 106 control unit 108 computer memory with executable instructions that when executed perform operations including at least 10308 receiving voice data following activation of the at least one headset push-to-talk button 10310 recognizing at least one relay request, communication frequency, and message based at least partly on speech recognition performed on the voice data 10312 digitally encoding the at least one relay request and message for transmission 10314 transmitting a digital relay request and message over a communication frequency to enable the at least one headset communication radio to extend or modify communication range through another aircraft radio without redundant audio broadcasts

FIGURE 111

100 AVIATION COMMUNICATION HEADSET 106 control unit 108 computer memory with executable instructions that when executed perform operations including at least 11108 obtaining visual field of view information using the at least one camera 11110 performing speech recognition to identify at least one ATC command received as audio to enter at least one specified altimeter setting 11112 detecting at least one discrepancy involving an altimeter when at least one altimeter setting detected using the at least one camera is not consistent with the at least one ATC command to enter the at least one specified altimeter setting 11114 outputting feedback information via the at least one speaker

FIGURE 112

100 AVIATION COMMUNICATION HEADSET 106 control unit 108 computer memory with executable instructions that when executed perform operations including at least 11208 obtaining visual field of view information using the at least one camera 11210 performing speech recognition to identify at least one ATC command received as audio to climb or descend to a specified altitude, turn or maintain a specified heading, or maintain a specified airspeed 11212 detecting at least one discrepancy involving altitude, heading, or airspeed when at least one avionics indication detected using the at least one camera is not consistent with the at least one ATC command 11214 outputting feedback information via the at least one speaker

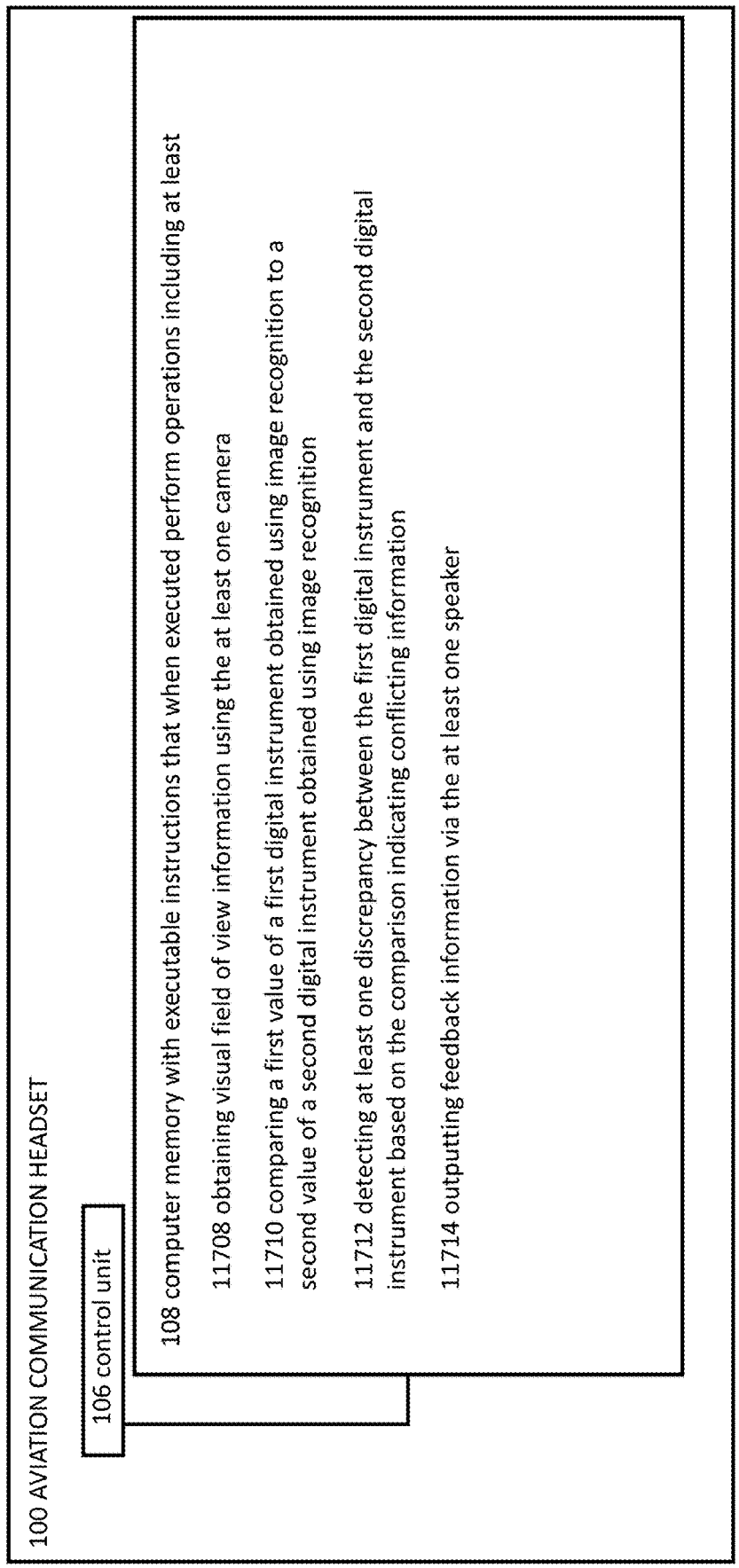

FIGURE 117

100 AVIATION COMMUNICATION HEADSET 106 control unit 108 computer memory with executable instructions that when executed perform operations including at least 11708 obtaining visual field of view information using the at least one camera 11710 comparing a first value of a first digital instrument obtained using image recognition to a second value of a second digital instrument obtained using image recognition 11712 detecting at least one discrepancy between the first digital instrument and the second digital instrument based on the comparison indicating conflicting information 11714 outputting feedback information via the at least one speaker

FIGURE 119

100 AVIATION COMMUNICATION HEADSET 106 control unit 108 computer memory with executable instructions that when executed perform operations including at least 11908 obtaining visual field of view information using the at least one camera 11910 comparing a value of an avionics instrument obtained using image recognition to at least one specified range of acceptable values for the avionics instrument 11912 detecting at least one discrepancy involving the avionics instrument based on the value being outside the at least one specified range of acceptable values for the avionics instrument 11914 outputting feedback information via the at least one speaker

FIGURE 121

100 AVIATION COMMUNICATION HEADSET 106 control unit 108 computer memory with executable instructions that when executed perform operations including at least 12108 obtaining visual field of view information using the at least one camera 12110 outputting feedback information via the at least one speaker 12112 detecting at least one urgent or emergency situation based at least partly on at least one detected discrepancy 12114 capturing at least one image or video stream of at least one field of view using at least one camera 12116 transmitting the at least one image or video stream to at least one specified recipient 12118 establishing at least one communication link with the at least one specified recipient to assist with the at least one urgent or emergency situation

SMART AVIATION COMMUNICATION HEADSET AND PERIPHERAL COMPONENTS

PRIORITY CLAIM

This application is a continuation of U.S. non-provisional patent application Ser. No. 15/495,672 filed Apr. 24, 2017, which application claims the benefit of U.S. provisional patent application Ser. No. 62/326,657 filed Apr. 22, 2016; U.S. provisional patent application Ser. No. 62/326,938 filed Apr. 25, 2016; U.S. provisional patent application Ser. No. 62/327,369 filed Apr. 25, 2016; U.S. provisional patent application 62/328,482 filed Apr. 27, 2016; U.S. provisional patent application 62/329,550 filed Apr. 29, 2016; U.S. provisional patent application 62/343,491 filed May 31, 2016; U.S. provisional patent application 62/357,893 filed Jul. 1, 2016; U.S. provisional patent application 62/376,143 filed Aug. 17, 2016; U.S. provisional patent application 62/395,052 filed Sep. 15, 2016; and U.S. provisional patent application 62/414,175 filed Oct. 28, 2016. The foregoing applications are incorporated by reference in their entirety as if fully set forth herein.

FIELD OF THE INVENTION

This invention relates generally to aviation technology, and more specifically, to a smart aviation communication headset and its peripheral components.

BACKGROUND

One of the inventors, in addition to being a patent attorney, is a private pilot with an instrument rating and also is a builder/owner of an Vans RV-10 experimental aircraft. In the course of flight training and building the RV-10 aircraft, this inventor was exposed to the most advanced experimental and/or certified aviation technology on the market and their respective limitations. These efforts led to the inventions disclosed herein which significantly improve upon current aviation technologies to enhance aviation safety and decrease pilot workload.

SUMMARY

This invention relates generally to aviation technology, and more specifically, to a smart aviation communication headset and its peripheral components.

In one embodiment, an aviation communication headset includes, but is not limited to, at least one microphone; one or more speakers; one or more docks configured to interface with one or more eyepieces; and at least one control unit operable to perform operations including at least: detecting a presence of one or more eyepieces at the one or more docks; and outputting aviation flight information via the one or more docks for display on the one or more eyepieces.

In another embodiment, an aviation communication headset includes, but is not limited to, at least one microphone; one or more speakers; one or more physiological sensors operable to monitor one or more health parameters of a wearer; and at least one control unit operable to perform operations including at least: obtaining one or more values from the one or more physiological sensors; and outputting information regarding the one or more values via the one or more speakers.

In a further embodiment, an aviation communication headset includes, but is not limited to, one or more speakers; at least one microphone; at least one receptacle for mounting an oxygen container; and at least one cannula for dispensing oxygen.

In yet another embodiment, an aviation communication headset insert device includes, but is not limited to, an earlobe receptacle; tension members extending from opposing ends of the earlobe receptacle to tensionally brace the insert device within an ear cup of an aviation headset; a physiological sensor incorporated into the earlobe receptacle; a speaker; computer readable memory; and a control unit configured to perform operations including at least: obtaining one or more physiological measurements using the physiological sensor; and outputting one or more audible indications associated with the one or more physiological measurements via the speaker.

In another embodiment, an aviation communication headset includes, but is not limited to, at least one speaker; at least one microphone; at least one control unit; at least one global positioning system (GPS) unit; at least one panel communication link operable to interface with a panel-mounted communication system of an aircraft; at least one headset communication radio; and at least one headset push-to-talk button that when activated causes the at least one control unit to bypass the at least one panel communication link and transmit one or more radio broadcasts using the at least one headset communication radio.

In one other embodiment, an aviation communication headset includes, but is not limited to, at least one speaker; at least one microphone; at least one camera for capturing one or more images in a field of view; and at least one control unit operable to perform operations including at least: obtaining visual field of view information using the at least one camera; and outputting feedback information via the at least one speaker.

In another embodiment, an aviation communication headset cushion replacement includes, but is not limited to, an earlobe receptacle; a physiological sensor incorporated into the earlobe receptacle; a speaker; computer readable memory; and a control unit configured to perform operations including at least: obtaining one or more physiological measurements using the physiological sensor; and outputting one or more audible indications associated with the one or more physiological measurements via the speaker.

Additional details may be included in any of these embodiments as illustrated, discussed, or claimed herein.

BRIEF DESCRIPTION OF THE DRAWINGS

Embodiments of the present invention are described in detail below with references to the following drawings

FIG. 1C is a perspective view of an aviation communication headset replacement cushion device, in accordance with embodiments of the invention;

DETAILED DESCRIPTION

This invention relates generally to aviation technology, and more specifically, to a smart aviation communication headset and its peripheral components. Specific details of certain embodiments of the invention are set forth in the following description and in FIGS. 1-126 to provide a thorough understanding of such embodiments. The present invention may have additional embodiments, may be practiced without one or more of the details described for any particular described embodiment, or may have any detail described for one particular embodiment practiced with any other detail described for another embodiment.

Figure 1A:
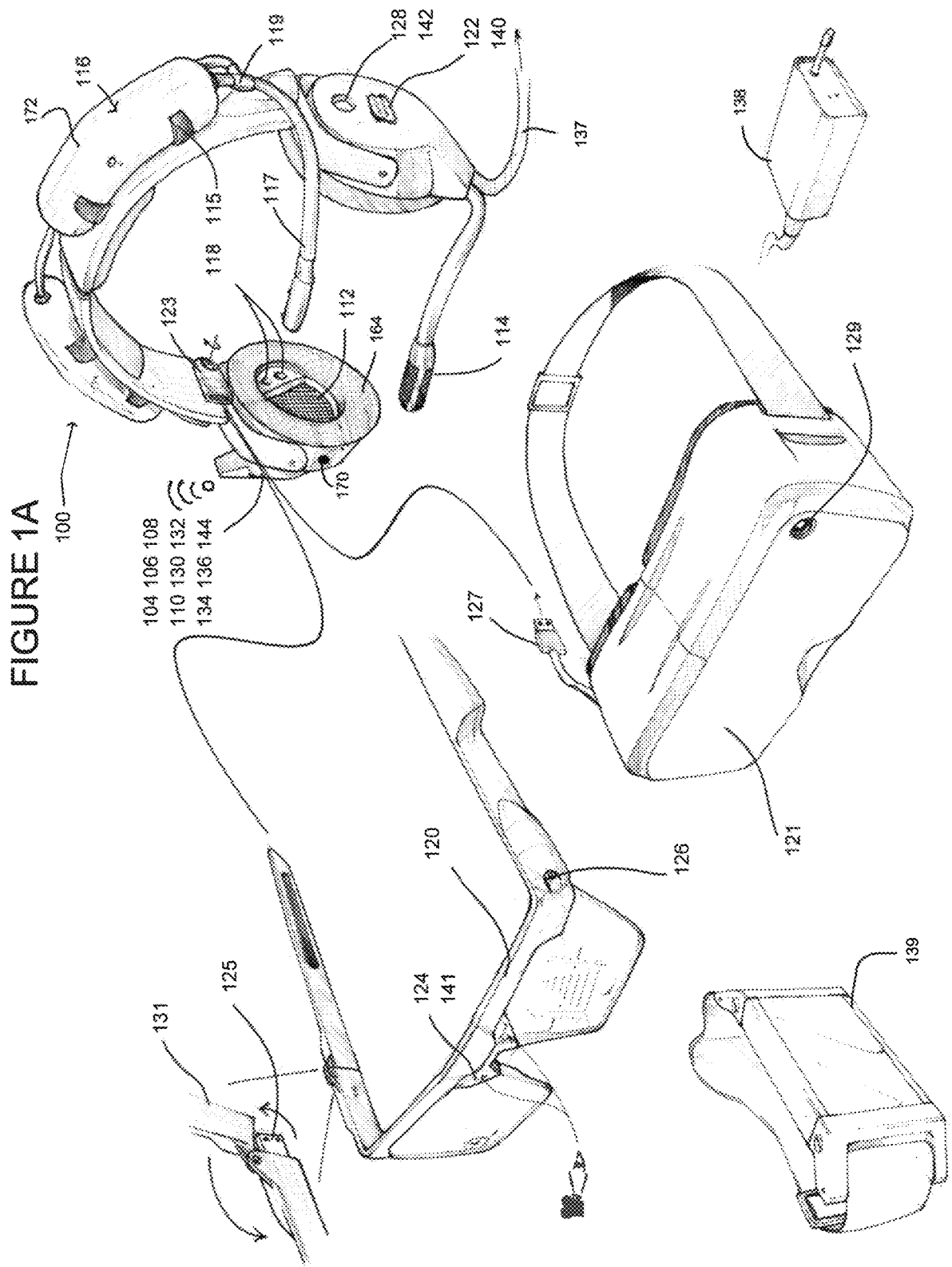
FIG. 1A is a perspective view of a smart aviation communication headset system, in accordance with embodiments of the invention.
Figure 1B:
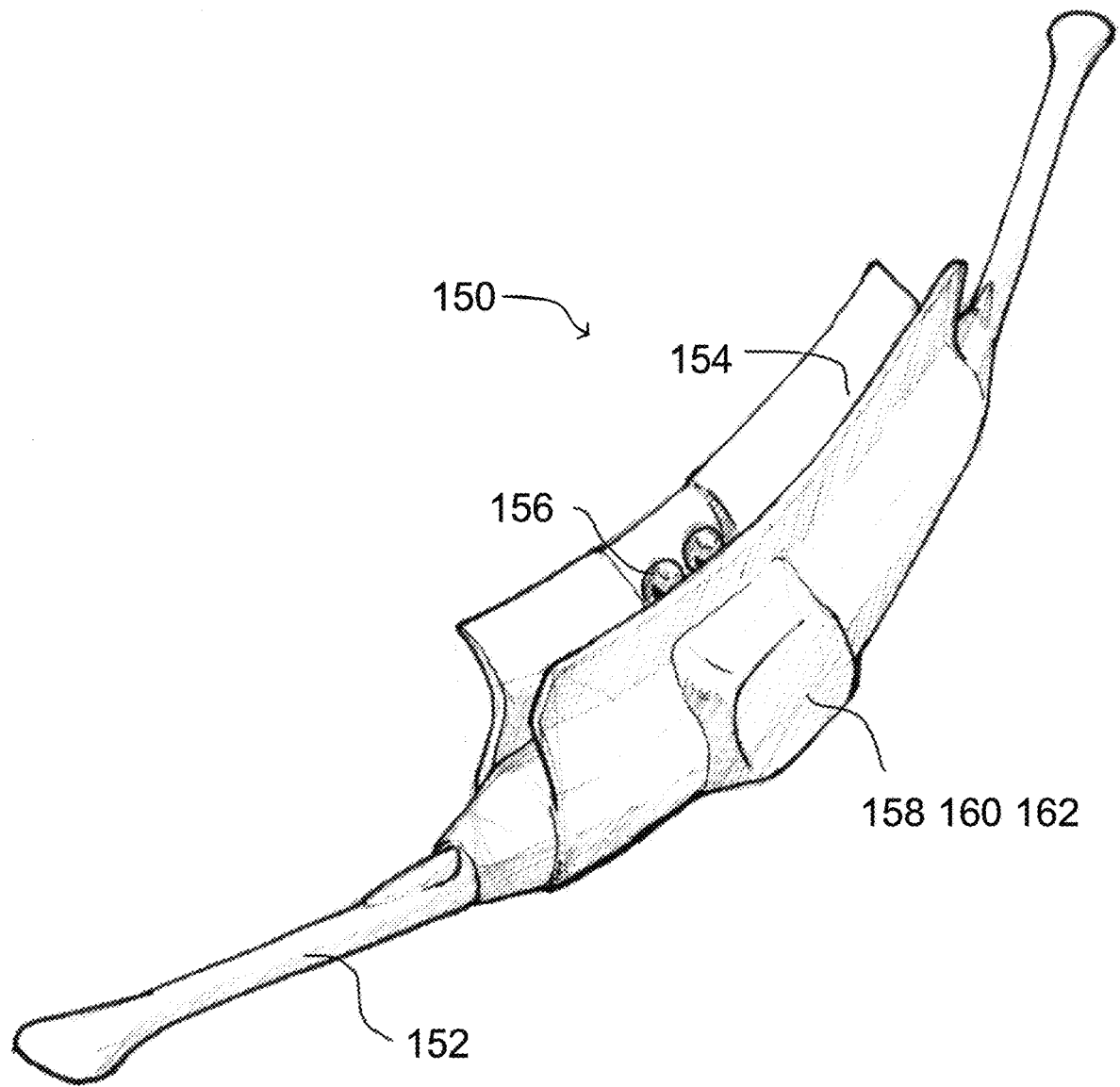
FIG. 1B is a perspective view of an aviation communication headset insert device, in accordance with embodiments of the invention.
Figure 1D:
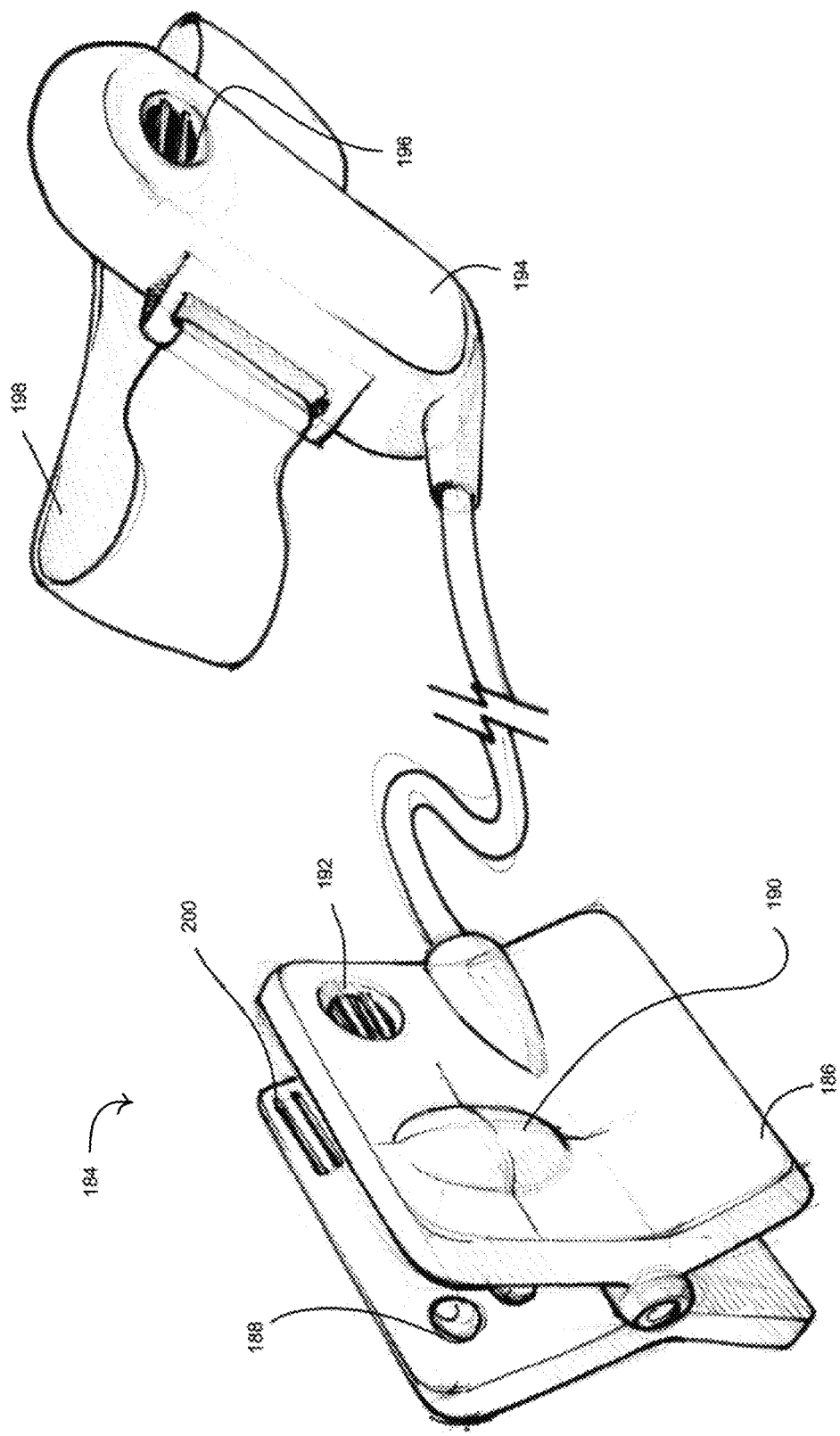
FIG. 1D is a perspective view of a clip device wearable with an aviation communication headset, in accordance with embodiments of the invention.
Figure 1E:
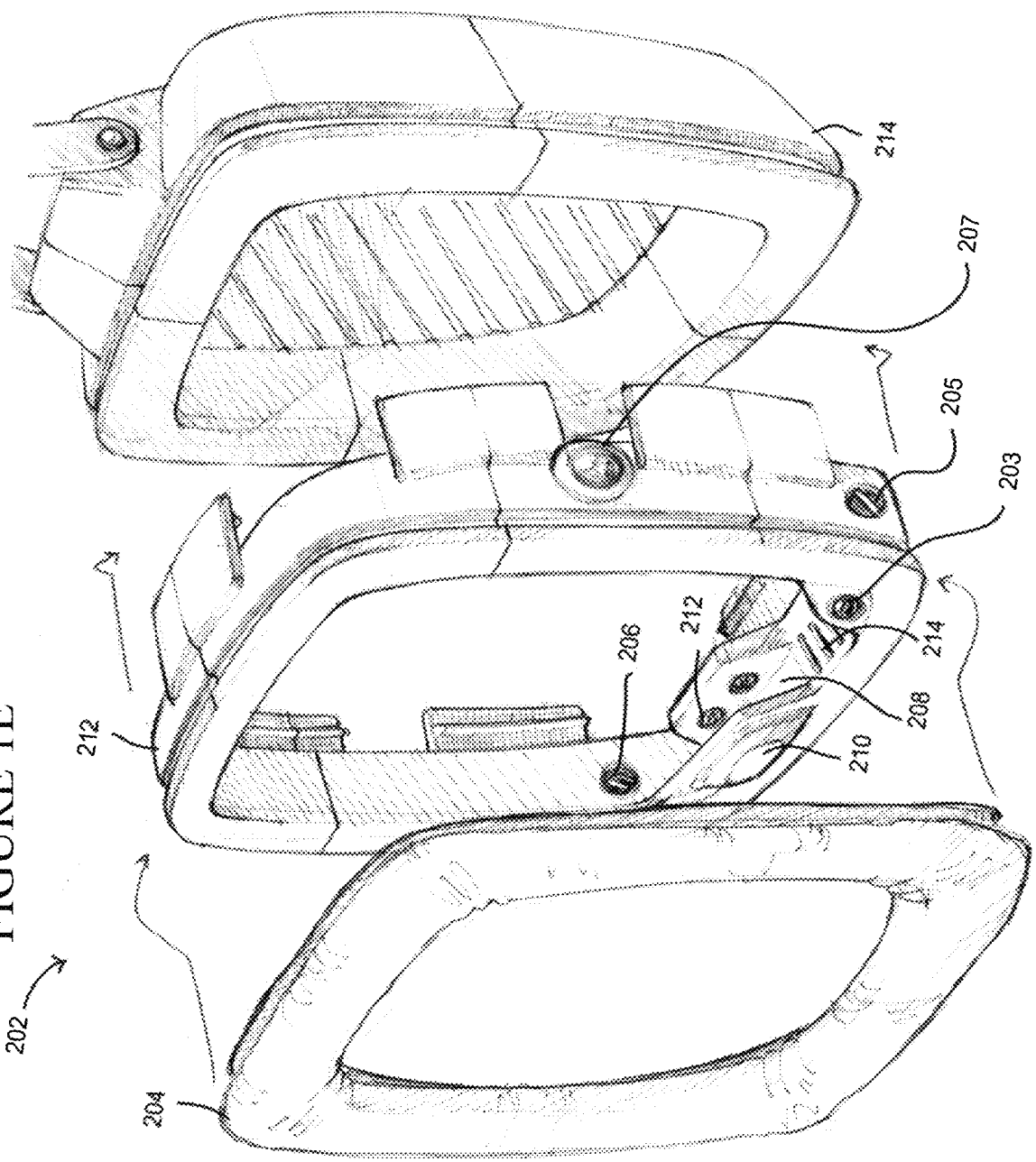
FIG. 1E is a perspective view of an aviation communication headset cushion interface device, in accordance with embodiments of the invention.
Figure 1F:
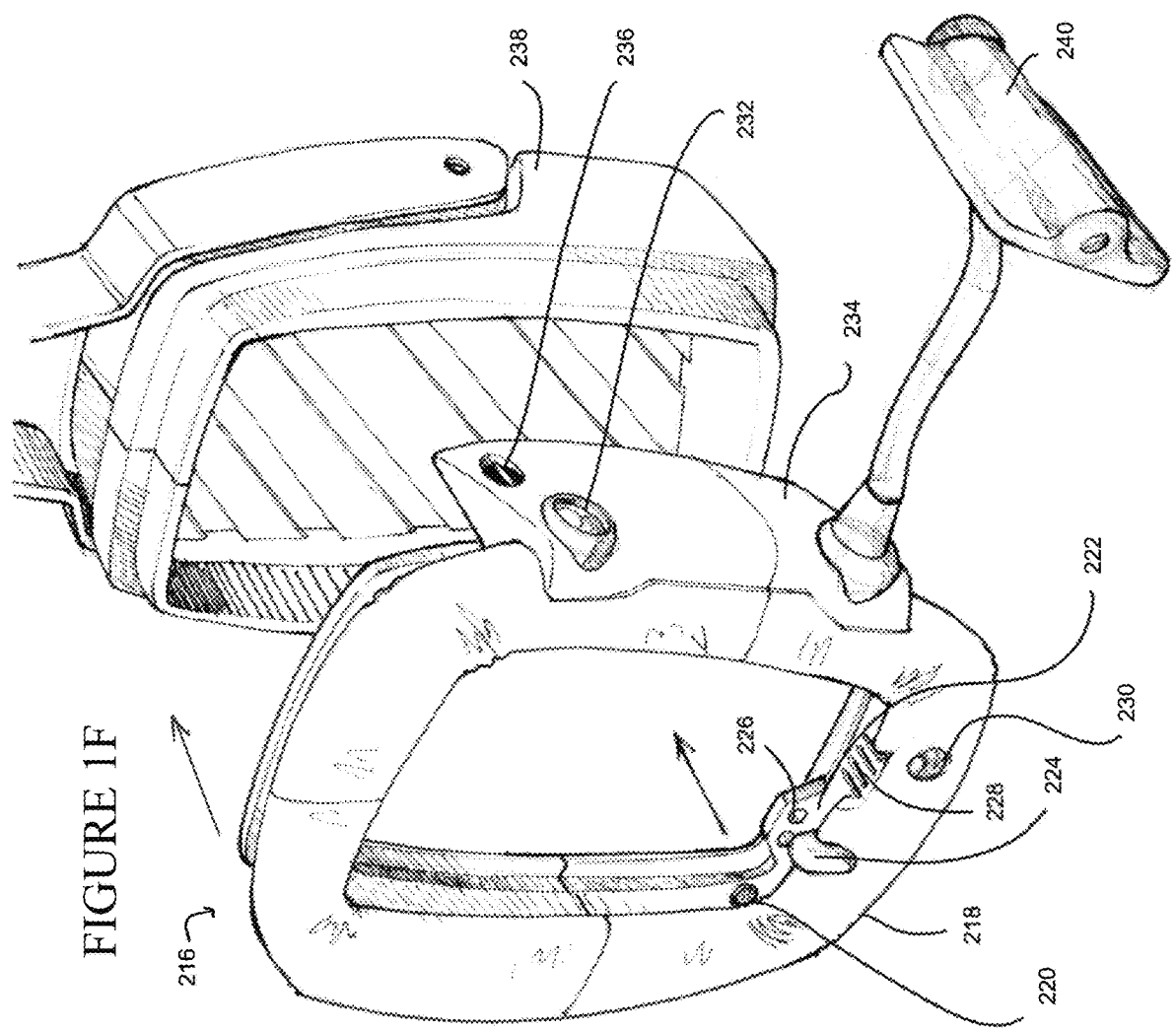
FIG. 1F is a perspective view of an aviation communication headset replacement cushion device with a heads up display, in accordance with embodiments of the invention.

FIG. 1A is a perspective view of a smart aviation communication headset system, in accordance with embodiments of the invention. FIG. 1B is a perspective view of an aviation communication headset insert device, in accordance with embodiments of the invention. FIG. 1C is a perspective view of an aviation communication headset replacement cushion device, in accordance with embodiments of the invention. FIG. 1D is a perspective view of a clip device wearable with an aviation communication headset, in accordance with embodiments of the invention. FIG. 1E is a perspective view of an aviation communication headset cushion interface device, in accordance with embodiments of the invention. FIG. 1F is a perspective view of an aviation communication headset replacement cushion device with a heads up display, in accordance with embodiments of the invention.

In one embodiment, the aviation communication headset 100 includes, but is not limited to, a headset 100, augmented reality eyewear 120, virtual reality or synthetic vision eyewear 121, an oxygen system 116, and an auxiliary communication radio 138. Certain embodiments further include an earpiece insert device 150, a replacement cushion device 164, an earclip device 184, an earcup attachment device 202, or a replacement cushion device 216.

In some embodiments, the aviation communication headset 100 can include any combination of a control unit 106, computer memory with executable instructions 108, a wireless communication unit 110, speakers 112, a microphone 114, cushion 164, a physiological sensor 118, an auxiliary push to talk button 122, a field of view camera 170, an oxygen sensor 128, an ADS-B receiver 130, a magnetometer 132, a GPS receiver 134, an ADAHRS 136, a biometric sensor 140 or 141, a carbon monoxide sensor 142, an orientation movement sensor 144, DC power 104, an eyewear dock 123, and an avionics panel communication link 137. The aviation communication headset 100 can interface with and/or incorporate augmented reality eyewear 120, virtual reality or synthetic vision eyewear 121, earpiece insert device 150, a replacement cushion device 164, an earclip device 184, an earcup attachment device 202, a replacement cushion device 216, armband display 139, oxygen system 116, or auxiliary com radio 138. Thus, the headset 100 is modular and can include any one or more of the herein referenced features or embodiments.

The control unit 106, memory 108, and DC power 104 are configured to perform various special purpose operations involving the headset 100, the oxygen system 116, the auxiliary communication radio 138, the augmented reality eyewear 120, the virtual or synthetic vision eyewear 121, the armband display 139, the earpiece insert device 150, a replacement cushion device 164, an earclip device 184, an earcup attachment device 202, or a replacement cushion device 216. These operations will be discussed further herein.

In certain embodiments, the wireless communication unit 110 is configured to wirelessly communicate data to or from any of the following aircraft systems: avionics, navigation unit, radio, transponder, autopilot, intercom, ADS-B transmitter/receiver, GPS unit, ADAHRS, or ELT. The wireless communication unit 110 can wireless communicate data to or from any of the following electronic flight accessories: smartphone or tablet, smartwatch, armband electronic display, electronic display visor, or electronic display kneeboard (see FIG. 2).

In certain embodiments, the ADS-B receiver 130 includes a receiver to capture traffic and weather information broadcast from other ADS-B transmitters (e.g., aircraft, ground, or satellite based). The ADS-B receiver 130 can be physically incorporated into the smart aviation communication headset 100 or can be wirelessly linked as a portable unit or aircraft panel mounted device. The ADS-B receiver 130 can include an incorporated antenna or can be linked to an externally-mounted antenna. The ADS-B receiver 130 enables enhanced functionalities of the smart aviation communication headset 100. For example, information obtained from the ADS-B receiver 130 (e.g., traffic and weather), can be used to output audible indications via the speakers 112 or visual indications via the augmented/virtual reality eyewear 120 or eyewear 121 or the armband display 139. Additionally, information obtained from the ADS-B receiver 130 can be used to enhance traffic recognition of the augmented/virtual reality eyewear 120, or tune the auxiliary com radio 138. Many other functions involving the ADS-B receiver 130 are discussed herein.

In certain embodiments, the magnetometer 132, GPS receiver 134, ADAHRS 236, and the orientation/movement sensor 144 provide magnetic heading, position, altitude, pitch, bank, yaw, heading, turn coordination, position data, speed, person's head orientation, person's head bank, person's head movement information for use by the aviation communication headset 100. Any of the foregoing components can be physically incorporated into the smart aviation communication headset 100 or can be wirelessly linked, such as a portable unit or a panel mounted device. Any of the foregoing components can use gyroscopes and/or solid state sensors. Any of the foregoing components can include integrated antennas or can be linked to externally mounted antennas. The magnetometer 132, GPS receiver 134, ADAHRS 136, and the orientation/movement sensor 144 provide enhanced functionalities for the smart aviation communication headset 100. For example, the magnetometer 132, GPS receiver 134, ADAHRS 136, and the orientation/movement sensor 144 can be used to obtain information for output via the speakers 112, the augmented/virtual reality eyewear 120 or eyewear 121, and/or the auxiliary com radio 138. As one specific example, the eyewear 121 can display synthetic vision information for a particular orientation and position determined using any of the magnetometer 132, GPS receiver 134, ADAHRS 136, and the orientation/ movement sensor 144, permitting complete 360 field of view in both horizontal and vertical planes. Additionally, the synthetic vision can be decoupled from a present position to enable a wearer to explore areas different from the actual present location, using head movements or voice commands to 'navigate' through space. This can be useful in exploring navigational paths, terrain, weather, and traffic ahead before arrival or as a potential alternate. Many other functions using the magnetometer 132, GPS receiver 134, ADAHRS 136, and the orientation/movement sensor 144 are discussed herein.

In certain embodiments, the aviation communication headset 100 includes various sensors to generate and/or provide feedback information. The physiological sensors 118 can be disposed on or within a headband or earcup, the eyepiece 120 or 121, the earpiece insert device 150, a replacement cushion device 164, an earclip device 184, an earcup attachment device 202, or a replacement cushion device 216 to obtain measurements using an ear, earlobe, temple area, eye, head, or skin of an individual. The physiological sensor 218 can include a sensor for oxygen level, heart rate, pupil dilation, movement, blood pressure, respiration, skin coloration, chemical composition, perspiration, temperature, neurological electrical impulse, or other similar bodily attribute. The control unit 106 uses this obtained physiological information and communicates the information and any warnings to various outputs such as speakers 112, augmented/virtual reality eyewear 120 or eyewear 121, armband display 139, and/or oxygen system 116. The integration of the physiological sensors 218 into the smart aviation communication headset 100 enables enhanced functionalities. For instance, if blood oxygen levels are below a specified threshold amount (which may account for time) an audible warning can be output via the speakers 112, a visual warning can be output via the augmented/virtual reality eyewear 120 or eyewear 121 or the armband display 139, an autopilot can initiate a descent, and the oxygen system 116 can be controlled to dispense supplemental oxygen. Many additional functions involving the physiological sensor 218 are described herein.

The oxygen sensor 128 is physically associated with or incorporated into the smart aviation communication headset 100, such as an earcup or headband portion, the eyepiece 120/121, a replacement cushion device 164, an earclip device 184, an earcup attachment device 202, a replacement cushion device 216, or the armband display 139. The oxygen sensor 128 is configured to monitor and detect a level of ambient oxygen present. As an aircraft climbs, the level of oxygen decreases. However, a level of decrease is not precise as it can be influenced by temperature, pressure, and humidity levels. Accordingly, the oxygen sensor 128 captures actual oxygen level measurements. The control unit 106 uses this obtained oxygen concentration/level information and communicates the information and any warnings to various outputs such as speakers 112, augmented/virtual reality eyewear 120 or eyewear 121, armband display 139, and/or oxygen system 116. The integration of the oxygen sensor 128 into the smart aviation communication headset 100 enables enhanced functionalities. For instance, if oxygen levels are below a specified threshold amount an audible warning can be output via the speakers 112, a visual warning can be output via the augmented/virtual reality eyewear 120 or eyewear 121 or armband display 139, the autopilot can initiate a descent, and the oxygen system 116 can be controlled to dispense supplemental oxygen, which control can include regulation based on the level of atmospheric oxygen detected and/or information obtained from the physiological sensor 118. Many additional functions involving the oxygen sensor 128 are described herein.

In some embodiments, the aviation communication headset 100 includes the carbon monoxide sensor 142 that is configured to detect carbon monoxide above a specified threshold level. The carbon monoxide sensor 142 is incorporated in an earcup or headband portion of the smart aviation communication headset 100, the earpiece insert device 150, a replacement cushion device 164, an earclip device 184, an earcup attachment device 202, a replacement cushion device 216, or the armband display 139. The information obtained from the carbon monoxide sensor 142 is usable to perform enhanced functions using the smart aviation communication headset 100. For instance, in an event of an engine exhaust leak, carbon monoxide can build up within a cabin. Because carbon monoxide is odorless and colorless and toxic, such carbon monoxide buildup can result in harm to occupants. The information obtained from the carbon monoxide sensor 142 can be output to the speakers 112, the augmented virtual reality eyewear 120 or eyewear 121, or the armband 139. This information can be an audible or visual warning of dangerous levels of detected carbon monoxide. The information obtained from the carbon monoxide sensor 142 can also be used to control, regulate, and dispense oxygen from the oxygen system 116, such as an emergency release of high levels of oxygen via a cannula or mask 117 despite being at an altitude where supplemental oxygen is unneeded. The information obtained from the carbon monoxide sensor 142 can also be used to tune the auxiliary com radio 138 to an emergency or local ATC frequency based on GPS position information, tune the transponder to an emergency code, broadcast an automated 'mayday' or 'pan pan' message over the auxiliary com radio 138 or aircraft radio, control a navigation unit and autopilot to divert to a local airport, activate the ELT, and output emergency instructions via the augmented/virtual reality eyewear 120 or eyewear 121 or armband display 139 to address the carbon monoxide levels. Many other functions involving the carbon monoxide sensor 142 are disclosed herein.

The biometric touch sensor 140 can detect fingerprint information of an individual. This data can be stored, processed, and/or output to the various components such as via the speakers 112, the augmented reality eyewear 120, the virtual reality or synthetic vision eyewear 121, or the armband display 139. The biometric sensor 140 is provided to identify a wearer of the smart aviation communication headset 100. The biometric sensor 140 can be incorporated in an earcup or headband of the aviation communication headset 100 or can be incorporated in the auxiliary push-to-talk button 122 or can be incorporated into the augmented/virtual reality eyewear 120 or eyewear 121 or the armband display 139. The incorporation of the biometric sensor 140 into the smart aviation communication headset 100 enables enhanced functionality. For example, identification of a user as a pilot can result in calibration of the aviation communication headset 100 for pilot functionality. For instance, the oxygen system 116 can be adjusted to adhere to FAA pilot required oxygen requirements as opposed to FAA passenger or crew member oxygen requirements. The augmented/virtual reality eyewear 120 or eyewear 121 or the armband display 139 can be calibrated to provide more technical situational, navigation, system, and communication information appropriate for a pilot as opposed to a sight-seeing passenger or navigating-only copilot. Additionally, the auxiliary push-to-talk button 122 and the auxiliary com radio 138 can be enabled vs. disabled for non-pilot wearers. Further, the smart aviation communication headset 100 can be enabled as the hub to collect information communicated wirelessly from other headsets, such as physiological information or oxygen system information. In certain embodiments, similar calibrations can be made for unrecognized wearers, recognized passengers, recognized co-pilots. The calibrations can be user-determined or set to predetermined default values. Many other functions involving the biometric sensors 140 are disclosed herein.

In one embodiment, camera 170 is configured to capture field of view imagery associated with the headset 100, including cockpit and external-to-aircraft imagery. The camera 170 can be disposed or incorporated on the headband or earcup portion of the headset 100 or the eyepiece 120/121. The imagery data can be still or moving image data and can be used for various special purpose operations as discussed further herein. The incorporation of the camera 170 into the smart aviation communication headset 100 enables enhanced functionality. For example, the camera 170 can be used to capture images of the avionics panel of an aircraft. This information can be used to detect abnormal instrument readings, lack of cross-check consistency between instruments, incorrect radio or navigation frequencies, incorrect control inputs (e.g., mixture, prop, flap position, or trim position), low fuel situations, or the like. Similarly, the camera 170 can be used to capture images of the environment outside the aircraft. This information can be used to detect traffic, determine weather conditions such as cloud coverage or height or visibility, determine geographic location, determine distances to geographic locations, identify buildings, cities, towns, airports, ground features, or the like. Many other functions involving the camera 170 are disclosed herein.

In certain embodiments, the one or more eyewear docks 123 can include at least one power pin and at least one data pin. The one or more docks can be configured to interface with one or more virtual reality goggles 121 or one or more augmented reality glasses 120 interchangeably. The one or more docks 123 can be configured to pivot, rotate, shift, slide, or retractably extend to permit position adjustment of one or more removably coupled eyepieces 120 or 121. Therefore, the docks 123 thereby extend the functionality of the eyepieces 120 and 121 as well as the headset 100 by permitting exchange of information as discussed further herein. For example, the docks 123 enable communication information obtained by the headset 100 to be output as visual information via the eyepieces 120 or 121. This information can include ATC instructions, weather broadcasts, traffic alerts, common traffic broadcasts, plane-to-plane broadcasts, oxygen/physiological/carbon monoxide data, oxygen dispenser level and rate, or other similar information. Similarly, the docks 123 enable communication information obtained by the eyepieces 120 or 121 to be output as visual information such as via the armband display 139 or as audio information via the speakers 112. Such information can include traffic alerts, airspace alerts, weather information, avionics or instrument or control information, or the like. Many other functions involving the camera dock 123 are disclosed herein.

In certain embodiments, the speakers 112 are audio outputs that produce sound for reception by a wearer of the headset 100. The audio outputs can be associated with aircraft intercom, communication radio, and avionics, such as via the communication link 137, or can be associated with outputs from the eyewear 120 or 121, the oxygen system 116, the auxiliary communication radio 138, the control unit 106, the earpiece insert device 150, the earpiece insert device 150, a replacement cushion device 164, an earclip device 184, an earcup attachment device 202, or a replacement cushion device 216.

In certain embodiments, the microphone 114 accepts speech audio inputs that produce audio analog or audio digital signals for use by and/or transmission from the headset 100. The audio signals can be output to the speakers 112, aircraft intercom, communication radio, and avionics, such as via the communication link 137. Furthermore, the audio signals can be output as control signals and/or as speech-to-text or speech-to-graphic data to the eyewear 120 or 121, the oxygen system 116, the auxiliary communication radio 138, the control unit 106, the earpiece insert device 150, a replacement cushion device 164, an earclip device 184, an earcup attachment device 202, or a replacement cushion device 216.

The communication link 137 is an input/output link with the aircraft avionics system, intercom, or communication radio. The link 137 can be wired or wireless. Additionally, the link 137 can communicate information to and/or from the auxiliary communication radio 138.

In certain embodiments, the one or more augmented reality glasses 120 can include at least one sideframe 131 that folds for docking and unfolds for wearing independent of the aviation communication headset 100. The at least one sideframe 131 can include at least one power and data port 125 that is contained therein and that is exposed upon folding of the at least one sideframe 131. The augmented reality glasses 120 provide additional information on a display to augment the actual reality view.

The augmented reality eyewear 120/121 can include a field of view camera 126 that captures still and/or video imagery, such as from within the cockpit or of outside the aircraft. The field of view camera 126 can be incorporated into an earcup or frame of the smart aviation communication headset 100 (e.g., depicted as camera 170) or can be incorporated into the augmented/virtual reality eyewear 120. The field of view camera 126 can be one, two, or more cameras and may also capture images outside a field of view of an individual (e.g., peripheral, side, top, rear field capture). The field of view camera 126 ocan also include peripheral cameras such as GO PRO or GARMIN cameras, which can be mounted within a cabin or externally on an airframe. The field of view camera 126 provides many enhanced functionalities for the smart aviation communication headset 100. For example, information obtained from the field of view camera 126 can be used to stitch together a non-synthetic view of the world from a particular GPS coordinate and vantage point for enhancing or supplementing synthetic views, which information can be shared with multiple other smart aviation communication headsets 100 to create a comprehensive set of views. Additionally, information obtained from the field of view camera 126 or 170 can be used for traffic identification, airport/runway/taxiway/business identification, navigation, location/position identification, instrument calibration, instrument and avionics monitoring and cross-referencing, visibility detection, weather monitoring and data collection, augmented reality enhancement, or virtual reality inlay. Many other functions involving the field of view camera 126 are discussed herein.

The augmented reality eyewear 120/121 can include a user gaze tracking camera 124 that is directed at the eyes of a wearer and is configured to capture visual data associated with gaze direction, location, and persistence or duration of gaze using pupil or iris movements. The user gaze tracking camera 124 can therefore determine a real, virtual, or augmented reality object of focus or interest. The user gaze tracking camera 124 can include one camera for one eye or two cameras with one camera for each eye. Information obtained from the user gaze tracking camera 124 can be used to perform enhanced functionalities using the smart aviation communication headset 100. For example, focus on an augmentation of an airport identifier can result in display of airport frequency and approach information for the airport associated with the identifier, tuning of the auxiliary com radio 138 to a frequency associated with the airport and a current GPS location, outputting audio information associated with the airport via speakers 112, adjusting or outputting information to the armband display 139. Many other functions involving the user gaze tracking camera 124 are discussed herein.

The augmented reality eyewear 120/121 can include a biometric sensor 141 to capture image data associated with a retina or iris of a wearer for authentication purposes. The biometric sensor 141 is provided to identify a wearer of the smart aviation communication headset 100 and/or the eyewear 120/121. The incorporation of the biometric sensor 140 into the eyewear 120/121 enables enhanced functionality. For example, identification of a user as a pilot can result in calibration of the aviation communication headset 100, eyewear 120/121, or oxygen system 116 for pilot functionality. For instance, the oxygen system 116 can be adjusted to adhere to FAA pilot required oxygen requirements as opposed to FAA passenger or crew member oxygen requirements. The augmented/virtual reality eyewear 120/121 can be calibrated to provide more technical situational, navigation, system, and communication information appropriate for a pilot as opposed to a sight-seeing passenger or navigating-only copilot. Additionally, the auxiliary push-to-talk button 122 and the auxiliary com radio 138 can be enabled vs. disabled for non-pilot wearers. Further, the smart aviation communication headset 100 can be enabled as the hub to collect information communicated wirelessly from other headsets, such as physiological information or oxygen system information. In certain embodiments, similar calibrations can be made for unrecognized wearers, recognized passengers, or recognized co-pilots. The calibrations can be user-determined or set to predetermined default values. Many other functions involving the biometric sensor 141 are disclosed herein.

In certain embodiments, the augmented reality glasses 120 are usable independent of the aviation communication headset 100, such as for non-aviation related purposes like driving, walking, socializing, etc. However, when desired to be used in conjunction with the aviation communication headset, such as for visual condition (VFR) conditions, navigation, situational awareness, speech to text display, etc., the frame 131 is folded about a hinge to expose the data/power plug 125. The data/power plug 125 is then inserted into the dock 123 to permit data from the augmented reality glasses 120 to be communicated to the control unit 106 and for data from the control unit 106 to be communicated to the augmented reality glasses 120. The augmented reality glasses 120 can dock on both sides of the frame or on one or either side as depicted. The dock 123 pivots to permit the augmented reality glasses 120 to be positioned out of a field of view, such as on a forehead of an individual. When desired, the augmented reality glasses 120 can be decoupled from the aviation communication headset 100 and stored or used independently. The physical coupling of the augmented reality glasses 120 and the aviation communication 100 headset permits fast data transfer therebetween and permits each device to benefit from the other's information (e.g., speech data form the headset 100 to be displayed in the augmented reality eyewear 120 and visual field information detected using the augmented reality eyewear 120 or displayed in the augmented reality eyewear 120 to be transformed into audio output from the headset 100). It is possible, however, to use wireless communication, such as BLUETOOTH or WIFI between the augmented reality glasses 120 and the aviation communication headset 100 instead of direct physical coupling. Many functions are disclosed herein that utilize the augmented reality glasses 120 and associated components.

The one or more virtual reality or synthetic vision goggles 121 can include at least one power and data port 127 dongle for docking. The one or more virtual reality goggles 121 can include at least one camera 129 that provides a real-world image view of the cockpit or external of an aircraft, within the one or more virtual reality goggles 121. Differently from the augmented reality glasses 120, the virtual reality/synthetic vision goggles 121 provide a virtual/synthetic view of the outside world to simulate actual vision. In certain embodiments, the virtual reality/synthetic vision goggles 121 are usable independent of the aviation communication headset 100, such as for non-aviation related purposes like gaming, socializing, learning, working, etc. However, when desired to be used in conjunction with the aviation communication headset, such as for instrument flight (IFR), the data/power plug 127 is then inserted into the dock 123 to permit data from the virtual reality/synthetic vision goggles 121 to be communicated to the control unit 106 and for data from the control unit 106 to be communicated to the virtual reality/synthetic vision goggles 121. As is discussed further herein, the virtual reality/synthetic vision goggles 121 include a field of view camera 129 that enhances operation of the virtual reality/synthetic vision goggles 121. For instance, when visual conditions (VFR) are detected using the field of view camera 129, the virtual reality/synthetic vision goggles 121 can alert a user to remove the same or, as another option, can present a thumbnail or full display view of the actual field of view within the virtual reality/synthetic vision goggles 121. Various sensors and/or imagers can be incorporated into the virtual reality/synthetic vision goggles 121. For instance, a biometric eye scanner 141 or a user gaze tracking camera 124 can be included in the virtual reality/synthetic vision goggles 121. When desired, the virtual reality/synthetic vision goggles 121 can be decoupled from the aviation communication headset 100 and stored or used independently. The physical coupling of the virtual reality/synthetic vision goggles 121 and the aviation communication headset 100 permits fast data transfer therebetween and permits each device to benefit from the other's information (e.g., speech data from the headset 100 to be displayed within the goggles 121 and visual field information from the goggles 121 to be transformed into audio output of the headset 100). It is possible, however, to use wireless communication between the virtual reality/synthetic vision goggles 121 instead of direct physical coupling. Many functions are disclosed herein that utilize the virtual reality/synthetic vision goggles 121 and associated components.

The aviation communication headset 100 can include an oxygen system 116 including at least one receptacle 115 for mounting at least one oxygen container 172, at least one oxygen regulator 119 operable to adjust a flow or concentration of dispensed oxygen via the cannula 117, and/or a control unit 106 operable to control operation of the oxygen system. The oxygen system 116 is usable during flight above certain altitudes in unpressurized planes or during emergency decompression of pressurized planes. Receptacles 115 are provided that can receive oxygen containers 172. No oxygen containers 172 are required or needed during many altitudes (e.g., less than 10000 feet during the day or less than 5000 feet at night or depending on personal health attributes or acclimatization). Thus, the receptacles 115 and headset 100 can be devoid of any oxygen containers 172 when not needed to minimize weight. The oxygen container 172 is intended for limited duration use (e.g. 5 min to 1 hr) and can be replaced by another oxygen container 172 upon depletion. The cannula or the mask 117 can be movable in and out of position for use, disconnected when not in use, or substituted for one another depending upon needs or desires. Thus, when needed, the oxygen containers 172 can be snapped or removably secured into place within to the receptacles 115. The regulator 119 adjusts the flow of oxygen and the cannula 117 is usable to deliver oxygen to a nasal passage of an individual, which regulator 119 can be controlled by the control unit 106 or can be set to a single one-size-fits-all setting. When depleted, replacement oxygen container 172 can be interchanged with depleted oxygen container 172, which can be carried in bulk or singularly with an aircraft. The oxygen container 172 can be refilled or exchanged at FBOs or via mail. Many functions are disclosed herein that utilize the oxygen system 116.

The aviation communication headset 100 can include at least one auxiliary communication radio 138 wired or wirelessly linked; and at least one auxiliary push-to-talk button 122 that when activated broadcasts using the at least one auxiliary communication radio 138, bypassing the aircraft communication radio to transmit one or more radio signals. The auxiliary com radio 138 is physically or wirelessly coupled to the smart aviation communication headset 100. Accordingly, the auxiliary com radio 138 can be physically integrated into the smart aviation communication headset 100 or can be integrated into a speaker/microphone wire or link 137 associated with the smart aviation communication headset 100 or can be positioned in a flight bag, dashboard, seat, luggage compartment, or other location within a cabin of an aircraft. Alternatively, the auxiliary com radio 138 can be physically installed within a panel or aircraft structure of an aircraft. The auxiliary com radio 138 can include a com antenna integrated therewith or can be coupled to an exterior mounted com antenna for improved reception. The button 122 can be a soft button, switch, mechanical button, or a voice activated button. The auxiliary push-to-talk button 122 is incorporated into an earcup, the armband display 139, or speaker/microphone cable or link 137 of the smart aviation communication headset 100. In certain embodiments, the auxiliary PTT button 122 can incorporate an fingerprint biometric reader 140 for authentication purposes or the biometric reader 140 can be separate and independent of the PTT button 122. Many operations and details of the auxiliary communication radio 138 are discussed herein.

In one embodiment, the earpiece insert device 150 includes a physiological sensor 156, an earlobe receptacle 154, tension members 152, a speaker 158, memory 160, a control unit 162, and/or a wireless communication unit such as BLUETOOTH. The insert device 150 is separate from the headset 100 and is easily insertable and removable within the ear cup cavities of a variety of aviation headsets 100 to monitor blood oxygen, pulse, skin coloration, blood pressure, perspiration, and even bodily temperature or other physiological measurements of a wearer and to output feedback information via the self-contained speaker 158 of the ear lobe receptacle 154 or via the wireless communication unit to other headsets 100, the eyewear 120 or 121, or the armband display 139. In one particular embodiment, the physiological sensor 118 includes a pulse oximeter having a red LED and an infrared LED and at least one light sensor tuned to red and infrared wavelengths (e.g., approximately 660 nm and 940 nm), collectively labeled 156, housed in a ear lobe receptacle 154. The ear lobe receptacle 154 is formed from rubber, plastic, silicone, foam, or other soft malleable substrate or even rigid substrate, and is designed to accommodate an ear lobe. The ear lobe receptacle 154 can contain the ear lobe loosely, with a slight pressure, or with high pressure, such as using a clip, a channel, a slit, a gap, or a recess. The ear piece insert device 150 is insertable and removable within and on a bottom of the earcup of the headset 100 where the speakers 112 are located. The tension members 152 are bent to permit insertion of the device 150 within the earcup and then released to press against internal walls of the earcup, thereby bracing the device 150 within the earcup of the headset using tension. Although, it is possible to wear the device 150 on an ear as a clip, to secure the device 150 within the earpiece of the headset 100 using glue, adhesive, or a fastener, or to incorporate the earpiece 150 as an integral part of the headset 100 (e.g., the tension members 152 are optional in some embodiments). Thus, when the insert device 150 is installed/placed and the headset 100 is donned, the ear lobe receptacle 154 is positioned to receive and contain the ear lobe for blood oxygen concentration and pulse monitoring. Within the ear lobe receptacle 154 the red and infrared LEDs are positioned on one side for interfacing with one surface of an ear lobe and the at least one light sensor, collectively labeled 156, is positioned on the other side for interfacing with an opposite surface of the ear lobe. Light from the LEDs is transmitted through the ear lobe and detected by the at least one light sensor and this information is communicated to the control unit 162 to determine a level of absorbance, pulse, and/or the blood oxygen concentration. Feedback information regarding the pulse or the blood oxygen level is then provided audible by the speakers 158 or visually via any of the augmented reality eyewear 120, the virtual reality or synthetic vision eyewear 121, or the armband display 139. The feedback information regarding the pulse and/or the blood oxygen level can also be used to control the oxygen regulator 119 to dispense oxygen from the oxygen system 116 via the cannula 117. In one particular embodiment, the ear lobe receptacle 154 can include a plurality of LEDs (red/infrared) along a length and a plurality of opposing light transducer/sensors along the length to accommodate different sizes of ear lobes and to enhance the sampling of information using multiple measurement points from around the ear lobe tip upward toward the back and even top of an ear. This feature also accommodates non-perfect positioning of an ear lobe within the ear lobe receptacle 154. In certain embodiments, the insert device 150 includes a microphone and the control unit 162 is operable to perform speech recognition on audio received and control operation of the device 150 based thereon. Thus, when the insert device 150 is positioned within the earcup of the headset 100, the microphone 114 of the headset can be used to control operation of the insert device 150 given that the speakers 112 output the audio spoken into the microphone 114. Thus, despite the insert device 150 being acoustically isolated, the proximity to the speaker 112 can be used to pass audio commands to the insert device 150 through the acoustic barrier formed by the cushions 164. Similarly, the microphone of the insert device 150 can be used to capture audio emitted via the speaker 112 of the headset 100, such audio can include ATC instructions, common traffic advisory information, pilot-to-pilot communication, weather advisory, and intercom information. Upon receipt of the audio by the microphone, the control unit 162 can perform speech recognition to the data and output the data wirelessly via the armband display 139 or the eyepieces 120/121. For instance, ATC commands can be converted to text and displayed as instructions on the armband display 139, which can include heading, altitude, speed, navigation, squawk code, radio frequency, navigation frequency, traffic advisory, or weather information. In another embodiment, the insert device 150 can be part of a collection of insert devices that can be paired, such as in a master-slave configuration as supported by BLUETOOTH. This pairing enables the insert device 150 and the control unit 162 thereof to collect information from one or more other insert devices 150 and to output that information via the speaker 158, the eyepieces 120/121, or the armband display 139. This information can include other passenger's pulse, blood oxygen level, or other physiological data for review by a pilot or co-pilot. Many other functions pertaining to the insert device 150 are disclosed herein.

In one embodiment, the replacement cushion device 164 includes cushion 116, a microphone 173, an earlobe receptacle 168, a photosensor 172, an LED 170, a speaker 174, a physiological sensor 176, a camera 181, a housing 180 containing control circuitry, memory, and/or a power supply, and a carbon monoxide detector 178. The replacement cushion device 164 may include BLUETOOTH and/or can be linked wirelessly or wiredly to an armband display 139, which armband display 139 can include any or all of the circuitry, memory, and/or power supply. The replacement cushion device 164 is adapted to snap/attach to an earcup 182 of an aviation communication headset 100 to replace the 'dumb' cushion 164 commonly present, to monitor blood oxygen, pulse, skin coloration, blood pressure, perspiration, and even bodily temperature or other physiological measurements of a wearer and to output feedback information via the self-contained speaker 174 of the replacement cushion device 164 or via wireless or wired communication to other headsets 100, other replacement cushion devices 164, the eyewear 120 or 121, or the armband display 139. In one particular embodiment, the physiological sensor includes a pulse oximeter having a red LED and an infrared LED (together LED 170) and at least one light sensor 172 tuned to red and infrared wavelengths (e.g., approximately 660 nm and 940 nm) positioned in the ear lobe receptacle 168. The ear lobe receptacle 168 is formed from rubber, plastic, silicone, foam, or other soft malleable substrate or even rigid substrate, and is designed to accommodate an ear lobe. The receptacle 168 can be part of the cushion 166 or can include a separate part or can be formed from the cushion 166 on one side and an opposing rigid, flexible, or soft backing. The ear lobe receptacle 168 can contain the ear lobe loosely, with a slight pressure, or with high pressure, such as using a clip, a channel, a slit, a gap, or a recess. The cushion 166 can be soft and compressible material such as rubber, silicone rubber, foam, or the like. The physiological sensor 176 can include a temperature, skin coloration, chemical composition, perspiration, heart rate, or other type of sensor that can interface directly with a temple or other skin surface of an individual. The housing 180 can be metal, plastic, composite or other similar material and adapted to contain the circuitry, memory, battery, and/or wireless communication device. The replacement cushion device 164 can include a flange, flap, lip, or the like to fit over and secure to a lip, impression, detent, protrusion or the like of the earcup 182. Thus, when the replacement cushion device 164 is installed and the headset 100 is donned, the ear lobe receptacle 168 is positioned to receive and contain the ear lobe for blood oxygen concentration and pulse monitoring. The red and infrared LEDs are positioned on one side for interfacing with one surface of an ear lobe and the at least one light sensor 172, is positioned on the other side for interfacing with an opposite surface of the ear lobe. Light from the LEDs 170 is transmitted through the ear lobe and detected by the at least one light sensor 172 and this information is communicated to the control unit to determine a level of absorbance, pulse, and/or the blood oxygen concentration. The physiological sensor 176 and the carbon monoxide detector 178 can similarly be used to obtain data and pass the data to the control unit. Feedback information regarding the pulse or the blood oxygen level or carbon monoxide levels or other physiological parameters is then provided audibly by the speaker 174 or visually via any of the augmented reality eyewear 120, the virtual reality or synthetic vision eyewear 121, or the armband display 139. The feedback information regarding the pulse and/or the blood oxygen level can also be used to control the oxygen regulator 119 to dispense oxygen from the oxygen system 116 via the cannula 117. In one particular embodiment, the ear lobe receptacle 168 can include a plurality of LEDs 170 (red/infrared) along a length and a plurality of opposing light transducer/sensors 172 along the length to accommodate different sizes of ear lobes and to enhance the sampling of information using multiple measurement points from around the ear lobe tip upward toward the back and even top of an ear. This feature also accommodates non-perfect positioning of an ear lobe within the ear lobe receptacle 168. In certain embodiments, the replacement cushion device 164 includes a microphone 173 and the control unit is operable to perform speech recognition on audio received and control operation of the device 164 based thereon. Thus, when the replacement cushion device 164 is positioned on the earcup 182 of the headset 100, the microphone 114 of the headset can be used to control operation of the replacement cushion device 164 given that the speakers 112 output the audio spoken into the microphone 114. Thus, despite the earlobe receptacle 168 of the replacement cushion device 164 being acoustically isolated by the cushion 166, the speaker 112 can be used to pass audio commands through the acoustic barrier formed by the cushions 166 to the control unit of the replacement cushion device 164. Similarly, the microphone 178 can be used to capture audio emitted via the speaker 112 of the headset 100, such audio can include ATC instructions, common traffic advisory information, pilot-to-pilot communication, weather advisory, and intercom information. Upon receipt of the audio, by the microphone 178, the control unit of the replacement cushion 164 can perform speech recognition to the data and output the data via the armband display 139 or the eyepieces 120/121. For instance, ATC commands can be converted to text and displayed as instructions on the armband display 139, which can include heading, altitude, speed, navigation, squawk code, radio frequency, navigation frequency, traffic advisory, or weather information. In another embodiment, the replacement cushion device 164 can be part of a collection of replacement cushion devices that can be paired, such as in a master-slave configuration as supported by BLUETOOTH. This pairing enables the replacement cushion device 164 and the control unit thereof to collect information from one or more other replacement cushion devices 164 and to output that information via the speaker 174, the eyepieces 120/121, or the armband display 139. This information can include other passenger's pulse, blood oxygen level, or other physiological data for review by a pilot or co-pilot. Many other functions pertaining to the replacement cushion device 164 are disclosed herein. In certain embodiments, the replacement cushion device 164 can be integrated with the headset 100.

In one embodiment, the earclip device 184 includes clip 186 having an LED 188, photosensor 190, microphone 100, and speaker 192. The clip 186 is coupled via a wire to housing 194 having an attachment band 198 and a carbon monoxide detector 196. The housing 194 includes control circuitry, memory, and/or a power supply. In certain embodiments, the housing 194 further includes a display screen. The housing 194 may include BLUETOOTH. The clip 186 is adapted to clip to an earlobe to monitor blood oxygen, pulse, skin coloration, blood pressure, perspiration, and even bodily temperature or other physiological measurements of a wearer and to output feedback information via the self-contained speaker 192 of the clip 186 or via wireless or wired communication to other headsets 100, other clips 186, the eyewear 120 or 121, the armband display 139, or a display incorporated in the housing 194. In one particular embodiment, the physiological sensor includes a pulse oximeter having a red LED and an infrared LED (together LED 188) and at least one light sensor 190 tuned to red and infrared wavelengths (e.g., approximately 660 nm and 940 nm). The clip 186 can contain the ear lobe loosely, with a slight pressure, or with high pressure. The clip 186 can be soft and compressible material such as rubber, silicone rubber, foam, or the like. The clip 186 can include a physiological sensor of temperature, skin coloration, chemical composition, perspiration, heart rate, or other type of sensor that can interface directly with a skin surface of an individual. The housing 194 can be metal, plastic, composite or other similar material and adapted to contain the circuitry, memory, battery, and/or wireless communication device. Thus, when the clip 186 attached to an earlobe and the headset 100 is donned, the clip 186 is positioned to receive and contain the ear lobe for blood oxygen concentration and pulse monitoring. The red and infrared LEDs 188 are positioned on one side for interfacing with one surface of an ear lobe and the at least one light sensor 190 is positioned on the other side for interfacing with an opposite surface of the ear lobe. Light from the LEDs 188 is transmitted through the ear lobe and detected by the at least one light sensor 190 and this information is communicated to the control unit to determine a level of absorbance, pulse, and/or the blood oxygen concentration. The physiological sensor and the carbon monoxide detector 196 can similarly be used to obtain data and pass the data to the control unit. Feedback information regarding the pulse or the blood oxygen level or carbon monoxide levels or other physiological parameters is then provided audibly by the speaker 192 or visually via any of the augmented reality eyewear 120, the virtual reality or synthetic vision eyewear 121, the armband display 139, or an integrated display in the housing 194. The feedback information regarding the pulse and/or the blood oxygen level can also be used to control the oxygen regulator 119 to dispense oxygen from the oxygen system 116 via the cannula 117. In certain embodiments, the clip 186 includes a microphone 114 and the control unit is operable to perform speech recognition on audio received and control operation of the clip 184 based thereon. Thus, when the clip 186 is positioned within the earcup of the headset 100, the microphone 114 of the headset can be used to control operation of the clip 186 given that the speakers 112 output the audio spoken into the microphone 114. Thus, despite the clip 186 being acoustically isolated by the cushion 164, the speaker 112 can be used to pass audio commands through the acoustic barrier formed by the cushions 164 to the control unit of the clip 186. Similarly, the microphone 114 can be used to capture audio emitted via the speaker 112 of the headset 100, such audio can include ATC instructions, common traffic advisory information, pilot-to-pilot communication, weather advisory, and intercom information. Upon receipt of the audio, by the microphone 114, the control unit of the clip 186 can perform speech recognition to the data and output the data via the armband display 139 or the eyepieces 120/121 or an integrated display of the housing 194. For instance, ATC commands can be converted to text and displayed as instructions on the armband display 139, which can include heading, altitude, speed, navigation, squawk code, radio frequency, navigation frequency, traffic advisory, or weather information. In another embodiment, the clip 186 can be part of a collection of replacement cushion devices that can be paired, such as in a master-slave configuration as supported by BLUETOOTH. This pairing enables the clip 186 and the control unit thereof to collect information from one or more other clips 186 and to output that information via the speaker 192, the eyepieces 120/121, the armband display 139, or integrated display of the housing 194. This information can include other passenger's pulse, blood oxygen level, or other physiological data for review by a pilot or co-pilot. Many other functions pertaining to the clip 186 are disclosed herein. In certain embodiments, the clip 186 can be integrated with the headset 100.

In one embodiment, the earcup attachment device 202 includes a microphone 206, an earlobe receptacle 208, a photosensor 210, an LED 212, a speaker 214, a physiological sensor 203, a housing 212 containing control circuitry, memory, and/or a power supply, a carbon monoxide detector 205, and a field of view camera 207. The earcup attachment device 202 may include BLUETOOTH and/or can be linked wirelessly or wiredly to an armband display 139, which armband display 139 can include any or all of the circuitry, memory, and/or power supply. The earcup attachment device 202 is adapted to snap/attach to an earcup 214 of an aviation communication headset 100 and the 'dumb' cushion 204 is then slipped over the earcup attachment device 202. Thus the earcup attachment device 202 interfaces between the aviation communication headset earcup 214 and the existing cushion 204 to monitor blood oxygen, pulse, skin coloration, blood pressure, perspiration, and even bodily temperature or other physiological measurements of a wearer and to output feedback information via the self-contained speaker 214 of the earcup attachment device 202 or via wireless or wired communication to other headsets 100, other earcup attachment devices 202, the eyewear 120 or 121, or the armband display 139. In one particular embodiment, the physiological sensor includes a pulse oximeter having a red LED and an infrared LED (together LED 212) and at least one light sensor 210 tuned to red and infrared wavelengths (e.g., approximately 660 nm and 940 nm) positioned in the ear lobe receptacle 208. The ear lobe receptacle 208 is formed from rubber, plastic, silicone, foam, or other soft malleable substrate or even rigid substrate, and is designed to accommodate an ear lobe. The receptacle 208 can include a separate part or can be formed from the cushion 204 on one side and an opposing rigid, flexible, or soft backing. The ear lobe receptacle 208 can contain the ear lobe loosely, with a slight pressure, or with high pressure, such as using a clip, a channel, a slit, a gap, or a recess. The physiological sensor 203 can include a temperature, skin coloration, chemical composition, perspiration, heart rate, or other type of sensor that can interface directly with a temple or other skin surface of an individual. The housing 234 can be metal, plastic, composite or other similar material and adapted to contain the circuitry, memory, battery, and/or wireless communication device. The earcup attachment device 202 can include a flange, flap, lip, or the like to fit over and secure to a lip, impression, detent, protrusion or the like of the earcup 214. Thus, when the earcup attachment device 202 is installed and the headset 100 is donned, the ear lobe receptacle 208 is positioned to receive and contain the ear lobe for blood oxygen concentration and pulse monitoring. The red and infrared LEDs 212 are positioned on one side for interfacing with one surface of an ear lobe and the at least one light sensor 210, is positioned on the other side for interfacing with an opposite surface of the ear lobe. Light from the LEDs 212 is transmitted through the ear lobe and detected by the at least one light sensor 210 and this information is communicated to the control unit to determine a level of absorbance, pulse, and/or the blood oxygen concentration. The physiological sensor 203 and the carbon monoxide detector 205 can similarly be used to obtain data and pass the data to the control unit. Feedback information regarding the pulse or the blood oxygen level or carbon monoxide levels or other physiological parameters is then provided audibly by the speaker 214 or visually via any of the augmented reality eyewear 120, the virtual reality or synthetic vision eyewear 121, or the armband display 139. The feedback information regarding the pulse and/or the blood oxygen level can also be used to control the oxygen regulator 119 to dispense oxygen from the oxygen system 116 via the cannula 117. In one particular embodiment, the ear lobe receptacle 208 can include a plurality of LEDs 212 (red/infrared) along a length and a plurality of opposing light transducer/sensors 210 along the length to accommodate different sizes of ear lobes and to enhance the sampling of information using multiple measurement points from around the ear lobe tip upward toward the back and even top of an ear. This feature also accommodates non-perfect positioning of an ear lobe within the ear lobe receptacle 208. In certain embodiments, the earcup attachment device 202 includes a microphone 206 and the control unit is operable to perform speech recognition on audio received and control operation of the device 202 based thereon. Thus, when the r earcup attachment device 202 is positioned on the earcup 214 of the headset 100, the microphone 206 of the headset can be used to control operation of the earcup attachment device 202 given that the speakers 112 output the audio spoken into the microphone 114. Thus, despite the earlobe receptacle 208 of the earcup attachment device 202 being acoustically isolated by the cushion 204, the speaker 112 can be used to pass audio commands through the acoustic barrier formed by the cushions 204 to the control unit of the earcup attachment device 202. Similarly, the microphone 206 can be used to capture audio emitted via the speaker 112 of the headset 100, such audio can include ATC instructions, common traffic advisory information, pilot-to-pilot communication, weather advisory, and intercom information. Upon receipt of the audio, by the microphone 206, the control unit of the earcup attachment device 202 can perform speech recognition to the data and output the data via the armband display 139 or the eyepieces 120/121. For instance, ATC commands can be converted to text and displayed as instructions on the armband display 139, which can include heading, altitude, speed, navigation, squawk code, radio frequency, navigation frequency, traffic advisory, or weather information. In another embodiment, the earcup attachment device 202 can be part of a collection of earcup attachment devices 202 that can be paired, such as in a master-slave configuration as supported by BLUETOOTH. This pairing enables the earcup attachment device 202 and the control unit thereof to collect information from one or more other earcup attachment devices 202 and to output that information via the speaker 214, the eyepieces 120/121, or the armband display 139. This information can include other passenger's pulse, blood oxygen level, or other physiological data for review by a pilot or co-pilot. Many other functions pertaining to the earcup attachment device 202 are disclosed herein. In certain embodiments, the earcup attachment device 202 can be integrated with the headset 100.

In one embodiment, the replacement cushion device 216 includes cushion 218, a microphone 220, an earlobe receptacle 222, a photosensor 224, an LED 226, a speaker 228, a physiological sensor 230, a housing 234 containing control circuitry, memory, and/or a power supply, a carbon monoxide detector 236, a field of view camera 232, and a heads-up display 240. The replacement cushion device 216 may include BLUETOOTH and/or can be linked wirelessly or wiredly to an armband display 139, which armband display 139 can include any or all of the circuitry, memory, and/or power supply. The replacement cushion device 216 is adapted to snap/attach to an earcup 238 of an aviation communication headset 100 to replace the 'dumb' cushion 164 commonly present, to monitor blood oxygen, pulse, skin coloration, blood pressure, perspiration, and even bodily temperature or other physiological measurements of a wearer and to output feedback information via the self-contained speaker 228 or the heads-up display 240 of the replacement cushion device 216 or via wireless or wired communication to other headsets 100, other replacement cushion devices 216, the eyewear 120 or 121, or the armband display 139. In one particular embodiment, the physiological sensor includes a pulse oximeter having a red LED and an infrared LED (together LED 226) and at least one light sensor 224 tuned to red and infrared wavelengths (e.g., approximately 660 nm and 940 nm) positioned in the ear lobe receptacle 222. The ear lobe receptacle 222 is formed from rubber, plastic, silicone, foam, or other soft malleable substrate or even rigid substrate, and is designed to accommodate an ear lobe. The receptacle 222 can be part of the cushion 218 or can include a separate part or can be formed from the cushion 218 on one side and an opposing rigid, flexible, or soft backing. The ear lobe receptacle 222 can contain the ear lobe loosely, with a slight pressure, or with high pressure, such as using a clip, a channel, a slit, a gap, or a recess. The cushion 218 can be soft and compressible material such as rubber, silicone rubber, foam, or the like. The physiological sensor 230 can include a temperature, skin coloration, chemical composition, perspiration, heart rate, or other type of sensor that can interface directly with a temple or other skin surface of an individual. The housing 234 can be metal, plastic, composite or other similar material and adapted to contain the circuitry, memory, battery, and/or wireless communication device. The replacement cushion device 216 can include a flange, flap, lip, or the like to fit over and secure to a lip, impression, detent, protrusion or the like of the earcup 238. Thus, when the replacement cushion device 216 is installed and the headset 100 is donned, the ear lobe receptacle 222 is positioned to receive and contain the ear lobe for blood oxygen concentration and pulse monitoring. The red and infrared LEDs 226 are positioned on one side for interfacing with one surface of an ear lobe and the at least one light sensor 224, is positioned on the other side for interfacing with an opposite surface of the ear lobe. Light from the LEDs 226 is transmitted through the ear lobe and detected by the at least one light sensor 224 and this information is communicated to the control unit to determine a level of absorbance, pulse, and/or the blood oxygen concentration. The physiological sensor 230 and the carbon monoxide detector 236 can similarly be used to obtain data and pass the data to the control unit. Feedback information regarding the pulse or the blood oxygen level or carbon monoxide levels or other physiological parameters is then provided audibly by the speaker 238 or visually via the heads-up display 240 or any of the augmented reality eyewear 120, the virtual reality or synthetic vision eyewear 121, or the armband display 139. The feedback information regarding the pulse and/or the blood oxygen level can also be used to control the oxygen regulator 119 to dispense oxygen from the oxygen system 116 via the cannula 117. In one particular embodiment, the ear lobe receptacle 222 can include a plurality of LEDs 226 (red/infrared) along a length and a plurality of opposing light transducer/sensors 224 along the length to accommodate different sizes of ear lobes and to enhance the sampling of information using multiple measurement points from around the ear lobe tip upward toward the back and even top of an ear. This feature also accommodates non-perfect positioning of an ear lobe within the ear lobe receptacle 222. In certain embodiments, the replacement cushion device 216 includes a microphone 220 and the control unit is operable to perform speech recognition on audio received and control operation of the device 216 based thereon. Thus, when the replacement cushion device 216 is positioned on the earcup 238 of the headset 100, the microphone 220 of the headset can be used to control operation of the replacement cushion device 216 given that the speakers 112 output the audio spoken into the microphone 114. Thus, despite the earlobe receptacle 222 of the replacement cushion device 216 being acoustically isolated by the cushion 218, the speaker 112 can be used to pass audio commands through the acoustic barrier formed by the cushions 218 to the control unit of the replacement cushion device 216. Similarly, the microphone 220 can be used to capture audio emitted via the speaker 112 of the headset 100, such audio can include ATC instructions, common traffic advisory information, pilot-to-pilot communication, weather advisory, and intercom information. Upon receipt of the audio, by the microphone 220, the control unit of the replacement cushion 216 can perform speech recognition to the data and output the data via the heads-up display 240, the armband display 139, or the eyepieces 120/121. For instance, ATC commands can be converted to text and displayed as instructions on the heads-up display 240, the armband display 139, which can include heading, altitude, speed, navigation, squawk code, radio frequency, navigation frequency, traffic advisory, or weather information. In another embodiment, the replacement cushion device 216 can be part of a collection of replacement cushion devices 216 that can be paired, such as in a master-slave configuration as supported by BLUETOOTH. This pairing enables the replacement cushion device 216 and the control unit thereof to collect information from one or more other replacement cushion devices 216 and to output that information via the heads-up display 240, the speaker 228, the eyepieces 120/121, or the armband display 139. This information can include other passenger's pulse, blood oxygen level, or other physiological data for review by a pilot or co-pilot. Many other functions pertaining to the replacement cushion device 216 are disclosed herein. In certain embodiments, the replacement cushion device 216 can be integrated with the headset 100.

Figure 2:
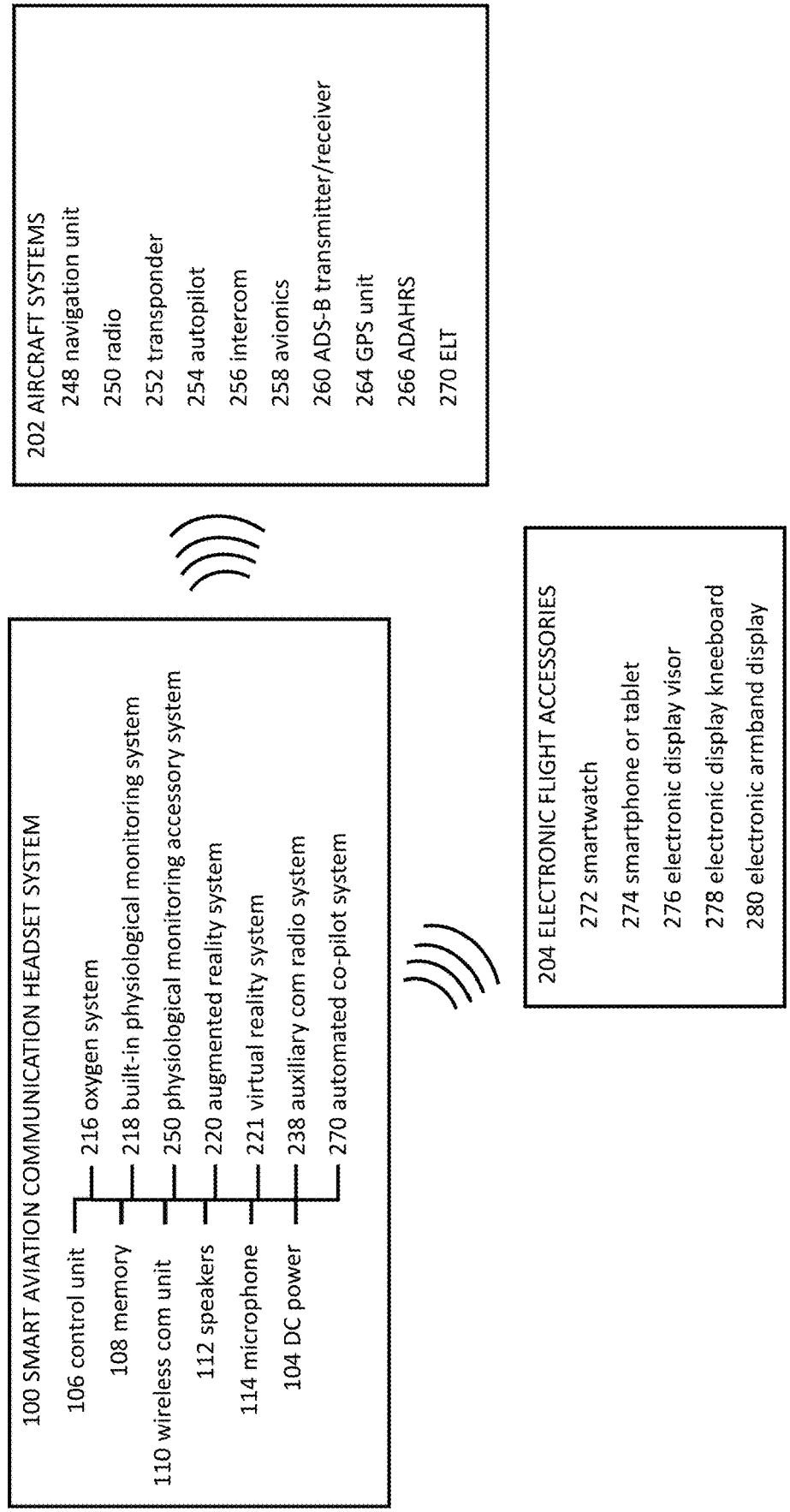
FIG. 2 is a systems diagram of a smart aviation communication headset in communication with aircraft systems and electronic flight accessories, in accordance with various embodiments of the invention.

FIG. 2 is a systems diagram of a smart aviation communication headset system 100 in communication with aircraft systems and electronic flight accessories, in accordance with various embodiments of the invention. A smart aviation communication headset system 100, can include any of the components of FIG. 1, such as the following components: control unit 106, computer memory with executable instructions 108, wireless communication unit 110, speakers 112, microphone 114, DC power 104, oxygen system 216, built-in physiological monitoring system 218, physiological monitoring earcup insert system 250, augmented reality system 220, virtual reality system 221, auxiliary com radio system 238, and automated co-pilot system 270. Not all of the foregoing components are required to be included within the smart aviation communication headset system 100. Likewise, additional components may be present within the smart aviation communication headset system 100. Moreover, any of the foregoing components can be physically separate from the smart aviation communication headset system 100, physically integrated within the smart aviation communication headset 100, or electronically or communicably coupled to the smart aviation communication headset 100 via one or more wires or a wireless connection.

The control unit 106 operates in conjunction with the computer memory 108 to execute the executable instructions to perform operations disclosed herein. The control unit 106 can include hardware or software or be a combination of the two. For instance, the control unit 106 can be ARDUINO or ATMEGA or RASBERRY PI or INTEL or equivalent.

The DC power 104 can include a portable battery (e.g., 3.5V-12 volt) or a linkage to the aircraft power supply (e.g., 12 volt or 24 volt).

The wireless communication unit 110 is a wireless transmitter and/or wireless receiver that communicates using various protocols. For example, the wireless communication unit can enable BLUETOOTH connectivity or other similar communication link with any of the aircraft systems 202, any of the electronic flight accessories 204, the oxygen system 216, the physiological earcup insert system 250, the augmented reality system 220, the virtual reality system 221, or the auxiliary com radio system 238.

The speakers 112 include earbud, earplug, earcup, or earmuff type speakers such as those found with typical headsets like those offered through BOSE, LIGHTSPEED, or DAVID CLARK. Similarly, the microphone 114 includes a boom-mounted type microphone also found with typical headsets offered through BOSE, LIGHTSPEED, or DAVID CLARK. The speakers 112 can be used for intercom and radio communication as well as to output sound for voice control of the earcup insert system 250. The microphone 114 can be used for intercom and radio communication as well as to control and interact via speech the functionality of the earcup insert system 250, the oxygen system 216, the built-in physiological monitoring system 218, the augmented reality system 220, the virtual reality system 221, the auxiliary com radio system 238, and/or the automated co-pilot system 270.

The oxygen system 216 dispenses oxygen from the container 172 via the dispenser mask or cannula 117 for consumption in accordance with the regulator 119 and any control unit 106 software instructions. The control unit 106 can adjust the regulator based on instructions received via a physical user interface or a voice controlled interface to enable adjustment of the flow of oxygen (e.g., adjust the flow or concentration of oxygen based on commands received via the microphone 114, the avionics 258, or any of the electronic flight accessories 204). The control unit 106 can also adjust the regulator automatically based on GPS attitude, density altitude, ambient oxygen levels, or based on measurements obtained from the physiological sensor 118 (e.g., blood oxygen level, pulse, heart rate, coloration) or sensor(s) that measure the flow or concentration of oxygen. The quantity and flow characteristics of oxygen can be measured by the sensor(s) and communicated to the control unit 106 or for user output via the speakers 112 or the augmented/virtual reality eyewear 120 or via the avionics 258 or any of the electronic flight accessories 204.

The built-in physiological monitoring system 218 monitors one or more physical parameters of an individual via the sensors 118 using the control unit 106 and analyzes and outputs the information associated with the physical parameters. Information obtained from the physiological sensors 118 can be communicated to the avionics 258 or any of the electronic flight accessories 204 or output via the speakers 112 or the augmented/virtual reality eyewear 120, 121 for monitoring. Information from the physiological sensor 118 can also be used by the control unit 106 to adjust one or more components of the smart aviation communication headset system 100, the aircraft systems 202, or the electronic flight accessories 204. For instance, the oxygen regulator 119 can be controlled based on information from the physiological sensors 118 (e.g., low blood oxygen level can result in increased oxygen output). Likewise, the avionics 258, the navigation unit 248, the transponder 252, the autopilot 254, the ELT 270, or the smartphone or tablet 274 can be controlled based on information from the physiological sensors 118. For instance, a low oxygen level detected can trigger a warning via the speakers 112, initiation of oxygen flow via the regulator 119, a descent to a lower altitude via the navigation unit 248 and the autopilot 254, a mayday or pan pan call via the radio 250, setting of 7700 on the transponder 252, emergency transmission via 121.5 via the ELT 270, or a phone call to a family member or ATC via the smartphone 274. Thus, information from the physiological sensors 118 can be used to monitor attribute(s) of a user, provide alerts of values that deviate from normal or expected ranges, and, in the event of an emergency condition, result in automated actions being taken through various components to address any detected condition.

The physiological monitoring earcup insert system 250 monitors one or more physical parameters of an individual via the sensors 156 using the control unit 160 and analyzes and outputs the information associated with the physical parameters. Information obtained from the physiological sensors 118 can be communicated to wearer using the speaker 158. In certain embodiments, the insert system 250 is wired or wirelessly linked with the headset 100, the avionics 258, any of the electronic flight accessories 204. Health data may therefore also be output via the avionics 258, the accessories 204, the speakers 112, or the augmented/virtual reality eyewear 120, 121. Information from the physiological sensor 156 can also be used by the control unit 106 to adjust one or more components of the smart aviation communication headset system 100, the aircraft systems 202, or the electronic flight accessories 204. For instance, the oxygen regulator 119 can be controlled based on information from the physiological sensors 156 (e.g., low blood oxygen level can result in increased oxygen output). Likewise, the avionics 258, the navigation unit 248, the transponder 252, the autopilot 254, the ELT 270, or the smartphone or tablet 274 can be controlled based on information from the physiological sensors 156. For instance, a low oxygen level detected can trigger a warning via the speakers 112, initiation of oxygen flow via the regulator 119, a descent to a lower altitude via the navigation unit 248 and the autopilot 254, a mayday or pan pan call via the radio 250, setting of 7700 on the transponder 252, emergency transmission via 121.5 via the ELT 270, or a phone call to a family member or ATC via the smartphone 274. Thus, information from the physiological sensors 118 can be used to monitor attribute(s) of a user, provide alerts of values that deviate from normal or expected ranges, and, in the event of an emergency condition, result in automated actions being taken through various components to address any detected condition.

The augmented reality system 220 of the communication headset system 100 enables enhanced functionality to occur. For instance, the eyewear 120 can communicate with the control unit 106 to obtain information such as microphone 114 and speaker 112 speech-to-text converted information for display, oxygen system 116 status information, physiological sensor 118 information, oxygen sensor 128 and carbon monoxide sensor 142 information, as well as information from any of the aircraft systems 202 or the electronic flight accessories 204. Additionally, the eyewear 120 can communicate with the control unit 106 to provide information for output via the speakers 112, the auxiliary com radio 138, any of the aircraft systems 202, or any of the electronic flight accessories 204. Furthermore, the eyewear 120 can be commanded using information from the microphone 114, the physiological sensor 118, the biometric sensor 140, any of the aircraft systems 202, or any of the electronic flight accessories 204. Likewise, the control unit 106 can be commanded with information obtained from the eyewear 120, such as gaze tracking information or field of view information. As an example, the eyewear 120 can output ATC commands received via the radio 250 or the auxiliary radio 138 as text, navigation pathways or boxes using information from an aircraft panel mounted certified GPS 264, heading/altitude/speed/minimum bug information obtained from an aircraft navigation system 248, oxygen/carbon monoxide level information obtained from a sensor 128, body temperature or oxygen level information obtained from a sensor 118 or 156, traffic and weather information obtained from a ADS-B receiver 260, mismatch/inconsistent avionics/engine/system information from a camera 170 with an aircraft-panel field of view. Likewise, as further examples the speakers 112 can output information being displayed on the eyewear 120 or detected by a camera 126 associated with the eyewear, such as an alert about traffic within a field of view, flight visibility being below or above a specified threshold, an upcoming runway, taxiway, airport, or navaid, or a mismatch between viewed or displayed information and received ATC instructions.

The virtual reality system 221 of the communication headset system 100 enables enhanced functionality to occur. For instance, the eyewear 121 can communicate with the control unit 106 to obtain information such as microphone 114 and speaker 112 speech-to-text converted information for display, oxygen system 116 status information, physiological sensor 118 information, oxygen sensor 128 and carbon monoxide sensor 142 information, as well as information from any of the aircraft systems 202 or the electronic flight accessories 204. Additionally, the eyewear 121 can communicate with the control unit 106 to provide information for output via the speakers 112, the auxiliary com radio 138, any of the aircraft systems 202, or any of the electronic flight accessories 204. Furthermore, the eyewear 120 can be commanded using information from the microphone 114, the physiological sensor 118, the biometric sensor 140, any of the aircraft systems 202, or any of the electronic flight accessories 204. Likewise, the control unit 106 can be commanded with information obtained from the eyewear 121, such as gaze tracking information or eye focus information. As an example, the eyewear 121 can output ATC commands received via the radio 250 or the auxiliary radio 138 as text, navigation pathways or boxes using information from an aircraft panel mounted certified GPS 264, heading/altitude/speed/minimum bug information obtained from an aircraft navigation system 248, oxygen/carbon monoxide level information obtained from a sensor 128, body temperature or oxygen level information obtained from a sensor 118 or 156, traffic and weather information obtained from a ADS-B receiver 260, mismatch/inconsistent avionics/engine/system information from a camera 170 with an aircraft-panel field of view. Likewise, as further examples the speakers 112 can output information being displayed on the eyewear 121 or detected by a camera 129 associated with the eyewear, such as an alert about traffic within a field of view, flight visibility being below or above a specified threshold, an upcoming runway, taxiway, airport, or navaid, or a mismatch between viewed or displayed information and received ATC instructions.

The auxiliary com radio system 238 enables smart radio control and functionality using an independent communication radio 138 that is separate from an aircraft integrated communication radio 250. The auxiliary push-to-talk button 122 controls transmission using the auxiliary radio 138. When depressed or activated, the PTT button 122 causes voice information received from the microphone 114 to be transmitted using the auxiliary com radio 138, thereby bypassing any aircraft radio 250 for transmission of a radio broadcast. The auxiliary com radio system 238 therefore enables enhanced functionality of the smart aviation communication headset 100. For example, the auxiliary com radio 138 can accept and process voice commands to appropriate frequencies, accept and perform relay broadcast operations, auto-tune to desired frequencies, record and perform iterative broadcasts over different local frequencies, or perform speech-to-text conversions. Communications received via the auxiliary com radio system 238 can be output via the speakers 112. Moreover, the control unit 106 can perform speech recognition with respect to signals received via the auxiliary com radio 138 for graphical and/or textual output via the augmented eyewear 120, the virtual reality goggles 121, the avionics 258, and/or any of the electronic flight accessories 204.

The automated co-pilot system 270 enables visual monitoring of aircraft systems 202, detection of discrepancies or problems, alerts, and resolution functionality. For instance, the field of view camera 170 can obtain images of the aircraft avionics 258 including engine, propeller, fuel, electrical, and/or flight instruments and the control unit 106 can process the images to detect discrepancies or issues. Such issues can include inconsistent readings between cross-check instruments, below or above threshold readings, and/or unexpected changes in readings over time. Additionally, the field of view camera 170 can obtain images of the external aircraft environment and the control unit 106 can process those images to detect environmental issues. Such issues can include visibility below or above a specified threshold, cloud proximity, cloud ceiling values, or icing conditions. The control unit 106 can use information obtained from a field of view camera 126 or 129, as needed or if such information is available. Any detected issues, discrepancies, or notification information generated by the control unit 106 can be output for evaluation such as via the speakers 112, the eyewear 120/121, the avionics 258, or any of the electronic flight accessories.

The aircraft systems 202 can include navigation unit 248, radio 250, transponder 252, autopilot 254, intercom 256, avionics 258, ADS-B transmitter/receiver 260, GPS unit 264, ADAHRS or AHRS 266, or ELT 270. Examples of such devices are provided through GARMIN, DYNON, STRATUS, BENDIX KING, and MID-CONTINENTAL—for example. The aircraft systems 202 can be wired or wirelessly linked with the smart aviation communication headset 100. The electronic flight accessories 204 can include a smartwatch 272, a tablet/smartphone 274, an electronic display visor 276, and an electronic display kneeboard 278. The smartwatch 272 and the smartphone/tablet 274 can include those devices available from GARMIN, SAMSUNG, APPLE, MICROSOFT, GOOGLE, AMAZON, LG, or FACEBOOK, for example. The electronic display visor 276 is a visor similar in appearance to a ROSEN type visor with the added functionality of a display screen, such as an electrophoretic, OLED, LED, or twist ball display or a see-through display. The electronic display kneeboard 278 is a kneeboard commonly worn by pilots with the added functionality of a display screen, such as an electrophoretic, twistball, OLED, or LED display. Any of the aircraft systems 202 or the electronic flight accessories 204 can be wirelessly linked (or wiredly linked) with the smart aviation communication headset 100 such as using BLUETOOTH. Such linkage enables enhanced functionalities involving the smart aviation communication headset 100. For example, text converted from speech ATC instructions can be displayed on the electronic display visor 276, commands or acknowledgements entered (e.g., via touch or buttons) on the electronic display kneeboard 278 or the electronic avionics 258 or the navigation unit 248 can be transmitted via the auxiliary com radio 138, traffic identified via the ADS-B receiver 260 can be used to highlight traffic in the field of view of the augmented/virtual reality eyewear 120, relay requests from the auxiliary com radio 138 can be provided via the smartwatch 272, or speech data received via the radio 250 can be output as text on the augmented/virtual reality eyewear 120. Many additional features involving the linkage between the aircraft systems 202 and the electronic flight accessories 204 and the smart aviation communication headset system 100 and headset 100 are discussed herein.

Figure 3:
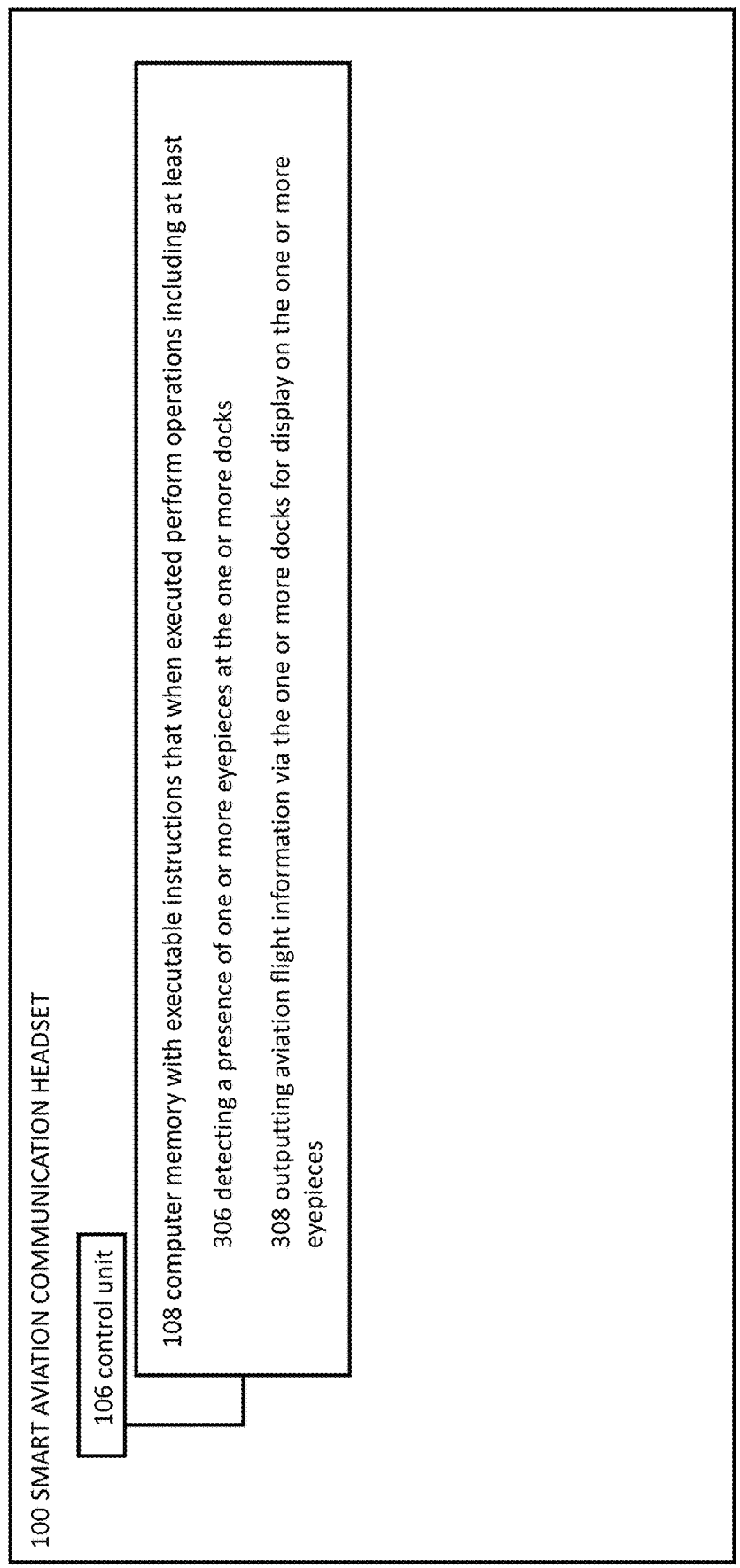
FIGS. 3-126 are system diagrams of various devices including a control unit that is configured to perform specified functional operations, in accordance with various embodiments of the invention.

FIG. 3 is a system diagram of a smart aviation communication headset 100, in accordance with an embodiment of the invention. In one embodiment, an aviation communication headset 100 includes, but is not limited to, at least one microphone 114; one or more speakers 112; one or more docks 123 configured to interface with one or more eyepieces 120/121; and at least one control unit 106 configured by one or more executable instructions stored on computer memory 108 to perform operations including at least: detecting a presence of one or more eyepieces at the one or more docks at 306; and outputting aviation flight information via the one or more docks for display on the one or more eyepieces at 308. For example, the eyepiece can be removed when not needed or desired and then docked when needed or desired. Also, various eyepieces can be used interchangeably. This enables use of synthetic vision or augmented reality or enhanced vision goggles interchangeably. Once docked, the presence of the eyepiece is detected and flight information can automatically be output for display. The flight information can include speech-to-text air traffic control (ATC) instructions, speech-to-text communication information, oxygen level or flow, physiological sensor information, blood oxygen or pulse information, ambient oxygen or carbon monoxide information, ADS-B traffic or weather information, heading information, GPS information, attitude, heading, pitch information, orientation or movement information, any information received from communication with the aircraft systems, or any information received from electronic flight accessories. Furthermore, when one of the eyepieces is docked flight information can be communicated from the eyepiece for output, which output can be audible via the one or more speakers or a to any of the aircraft systems or any of the electronic flight accessories. For example, the following information can be communicated: user gaze tracking information regarding an object of focus or camera detected radio frequency or camera detected instrument status or information or determined information about an object such as airport. Additionally, a biometric sensor can be used to identify a wearer and/or calibrate functions, such as tailor the flight information communicated and displayed (e.g. VFR only information for non-IFR pilots, IFR information for IFR pilots, non-technical scenic information for non-pilots, etc).

Figure 4:
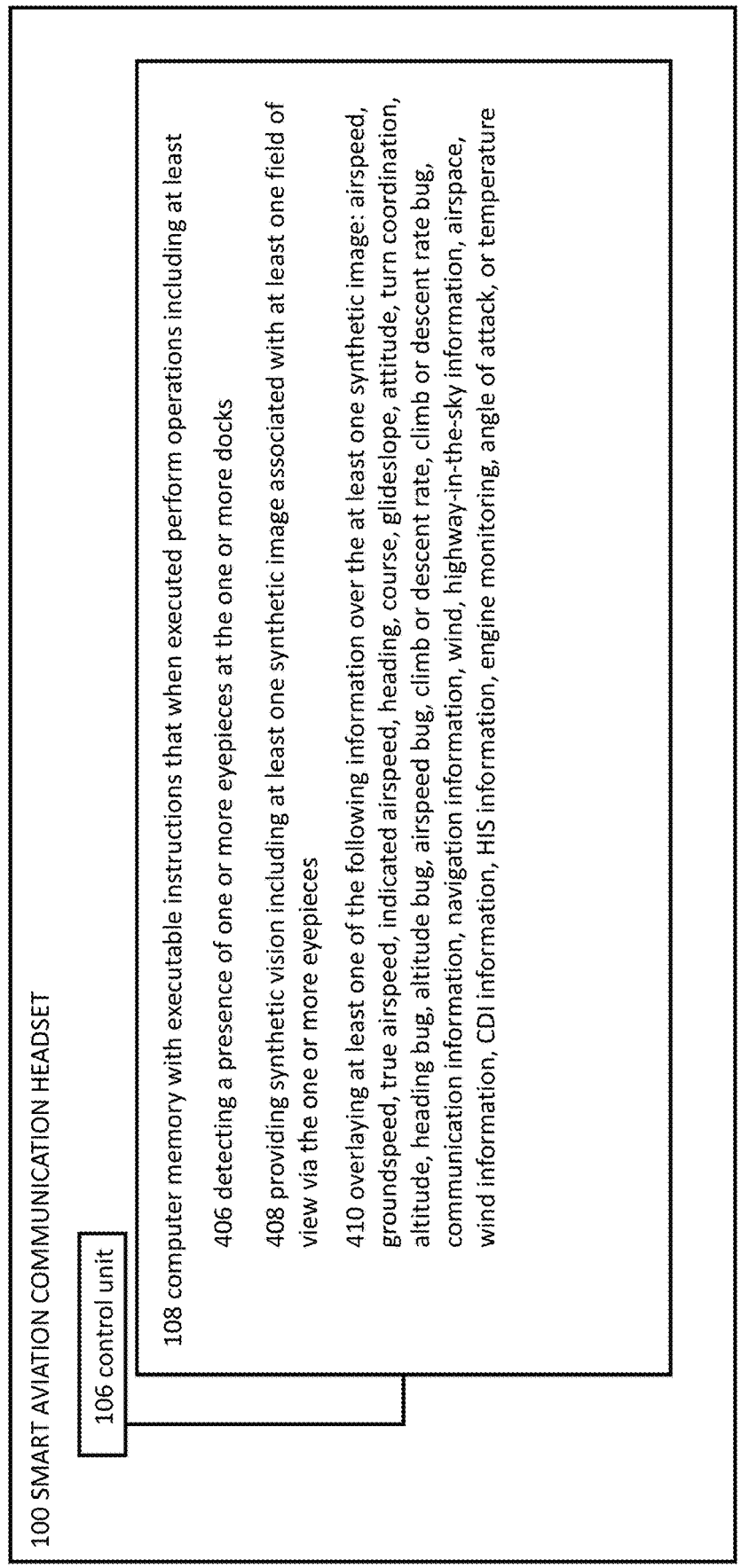

FIG. 4 is a system diagram of a smart aviation communication headset 100, in accordance with an embodiment of the invention. In one embodiment, an aviation communication headset 100 includes, but is not limited to, at least one microphone 114; one or more speakers 112; one or more docks 123 configured to interface with one or more eyepieces 120/121; and at least one control unit 106 configured by one or more executable instructions stored on computer memory 108 to perform operations including at least: detecting a presence of one or more eyepieces at the one or more docks at 406; providing synthetic vision including at least one synthetic image associated with at least one field of view via the one or more eyepieces at 308; and overlaying at least one of the following information over the at least one synthetic image: airspeed, groundspeed, true airspeed, indicated airspeed, heading, course, glideslope, attitude, turn coordination, altitude, heading bug, altitude bug, airspeed bug, climb or descent rate, climb or descent rate bug, communication information, navigation information, wind, highway-in-the-sky information, airspace, wind information, CDI information, HIS information, engine monitoring, angle of attack, or temperature at 410. For example, a pilot can be flying visually under VFR (visual flight rules) without use of any eyepieces. However, upon transitioning to IFR (instrument flight rules) or entering IMC (instrument meteorological conditions), the pilot can couple the synthetic vision goggles to the aviation communication headset. Upon doing so, the synthetic vision goggles are detected and the synthetic vision imagery is transmitted and displayed via the synthetic vision goggles. The use of the synthetic vision goggles can thereby supplement or replace panel mounted synthetic vision systems. Note that the synthetic vision goggles may also be docked during VFR or VMC (visual meteorological conditions) as desired.

Figure 5:
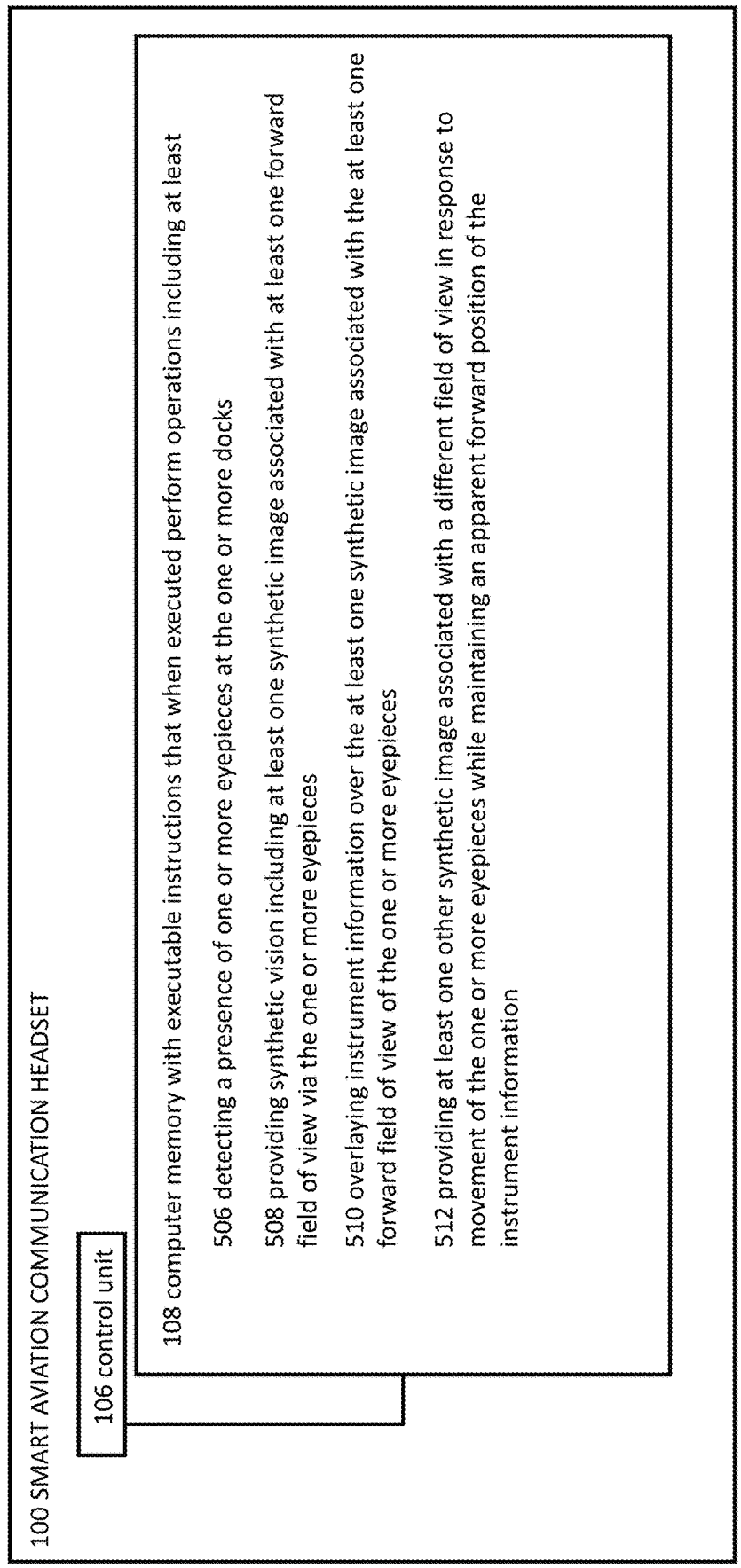

FIG. 5 is a system diagram of a smart aviation communication headset 100, in accordance with an embodiment of the invention. In one embodiment, an aviation communication headset 100 includes, but is not limited to, at least one microphone 114; one or more speakers 112; one or more docks 123 configured to interface with one or more eyepieces 120/121; and at least one control unit 106 configured by one or more executable instructions stored on computer memory 108 to perform operations including at least: detecting a presence of one or more eyepieces at the one or more docks at 506; providing synthetic vision including at least one synthetic image associated with at least one forward field of view via the one or more eyepieces at 508; overlaying instrument information over the at least one synthetic image associated with the at least one forward field of view of the one or more eyepieces at 510; and providing at least one other synthetic image associated with a different field of view in response to movement of the one or more eyepieces while maintaining an apparent forward position of the instrument information at 512. For example, the synthetic vision goggles can provide a synthetic view of reality from the current position and head orientation of a pilot. However, as the pilot turns his or her head, some of the critical or otherwise desired instrument information will remain overlaid in the field of view. Thus, as the pilot looks forward, a synthetic forward view of reality is provided. However, as the pilot turns left or right or up or down or backwards, the synthetic view will change to correspond with the new orientation. This feature enables the pilot to explore not just in the forward direction that tracks the movement of the plane, but also other areas that surround the pilot. As an example, the pilot may be flying in a valley surrounded by mountainous terrain and the synthetic vision goggles will enable the pilot to view synthetic reality of the valley as well as the mountains merely by turning his or her head. This simulates actual free vision in three-dimensional space. However, despite the synthetic reality being fluid, some of the flight instrument information is desired to remain within the field of view regardless of the pilot's head orientation. This flight information can include airspeed, traffic warnings, angle of attack information, altitude, engine information, or other similar critical information. The information that remains static can be customized or based on default values.

Figure 6:
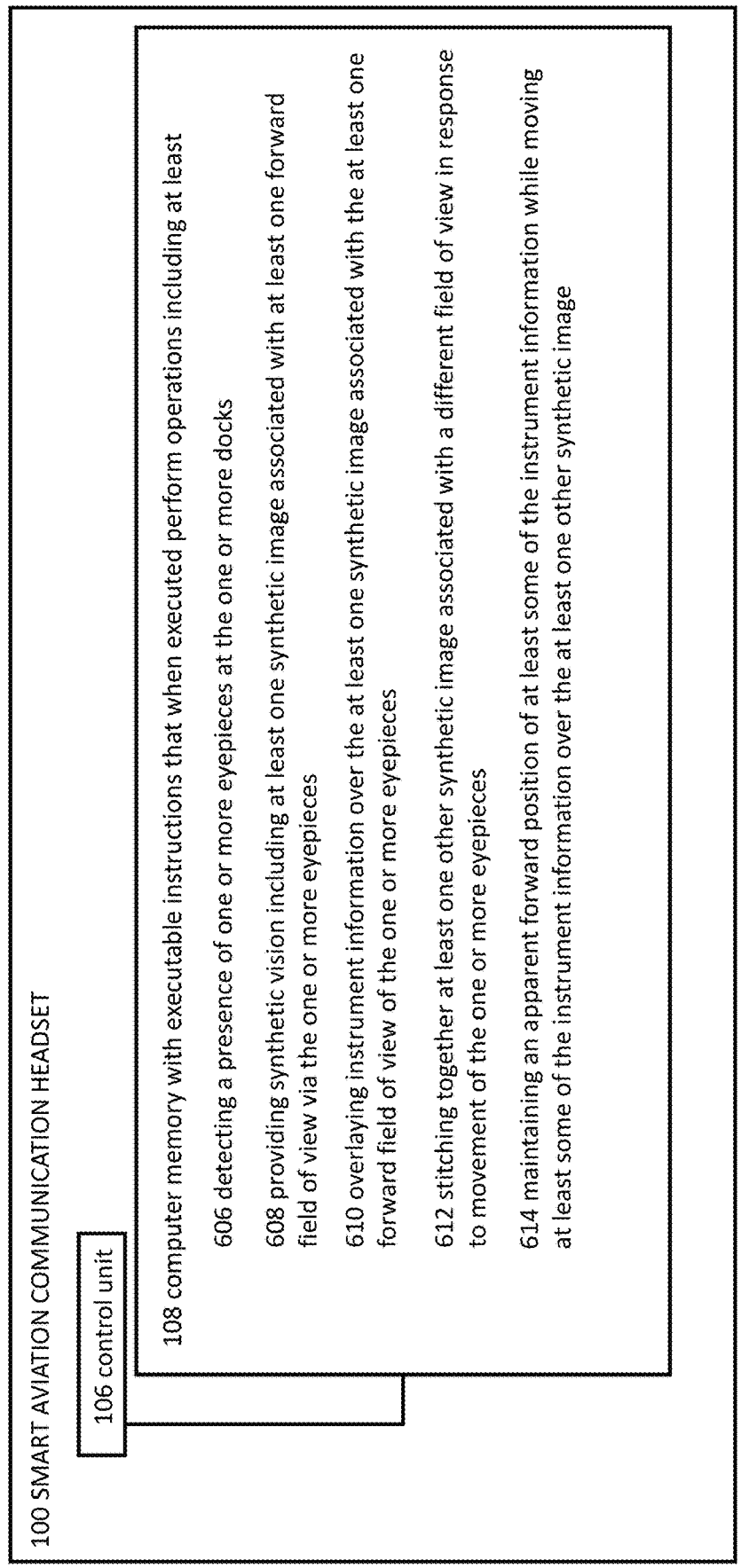

FIG. 6 is a system diagram of a smart aviation communication headset 100, in accordance with an embodiment of the invention. In one embodiment, an aviation communication headset 100 includes, but is not limited to, at least one microphone 114; one or more speakers 112; one or more docks 123 configured to interface with one or more eyepieces 120/121; and at least one control unit 106 configured by one or more executable instructions stored on computer memory 108 to perform operations including at least: detecting a presence of one or more eyepieces at the one or more docks at 606; providing synthetic vision including at least one synthetic image associated with at least one forward field of view via the one or more eyepieces at 608; overlaying instrument information over the at least one synthetic image associated with the at least one forward field of view of the one or more eyepieces at 610; stitching together at least one other synthetic image associated with a different field of view in response to movement of the one or more eyepieces at 612; and maintaining an apparent forward position of at least some of the instrument information while moving at least some of the instrument information over the at least one other synthetic image at 614. For example, upon docking the synthetic vision goggles to the headset, the synthetic view of reality can be displayed. As discussed previously, the synthetic reality can be untethered to the movement or direction of the plane enabling free exploration of three-dimensional space based on head movement and orientation of the pilot. Some flight information can be anchored in view independently of changes in synthetic vision content. However, some of the flight information can be anchored to a forward field of view that tracks the movement of the aircraft. This anchoring of flight information can declutter certain information from the field of view during synthetic reality exploration and also assist in providing a cue to the pilot as to the forward direction of flight. The anchored flight information can include avionics information such as altimeter information, turn coordination, heading and track information, highway in the sky indications, or other similar flight information. The anchored and floating flight information can be user selected, customized, or based on default values. In certain embodiments, indicators are provided in the field of view that direct or point back to a forward orientation that corresponds to the track of the aircraft to further aid in situational awareness.

Figure 7:
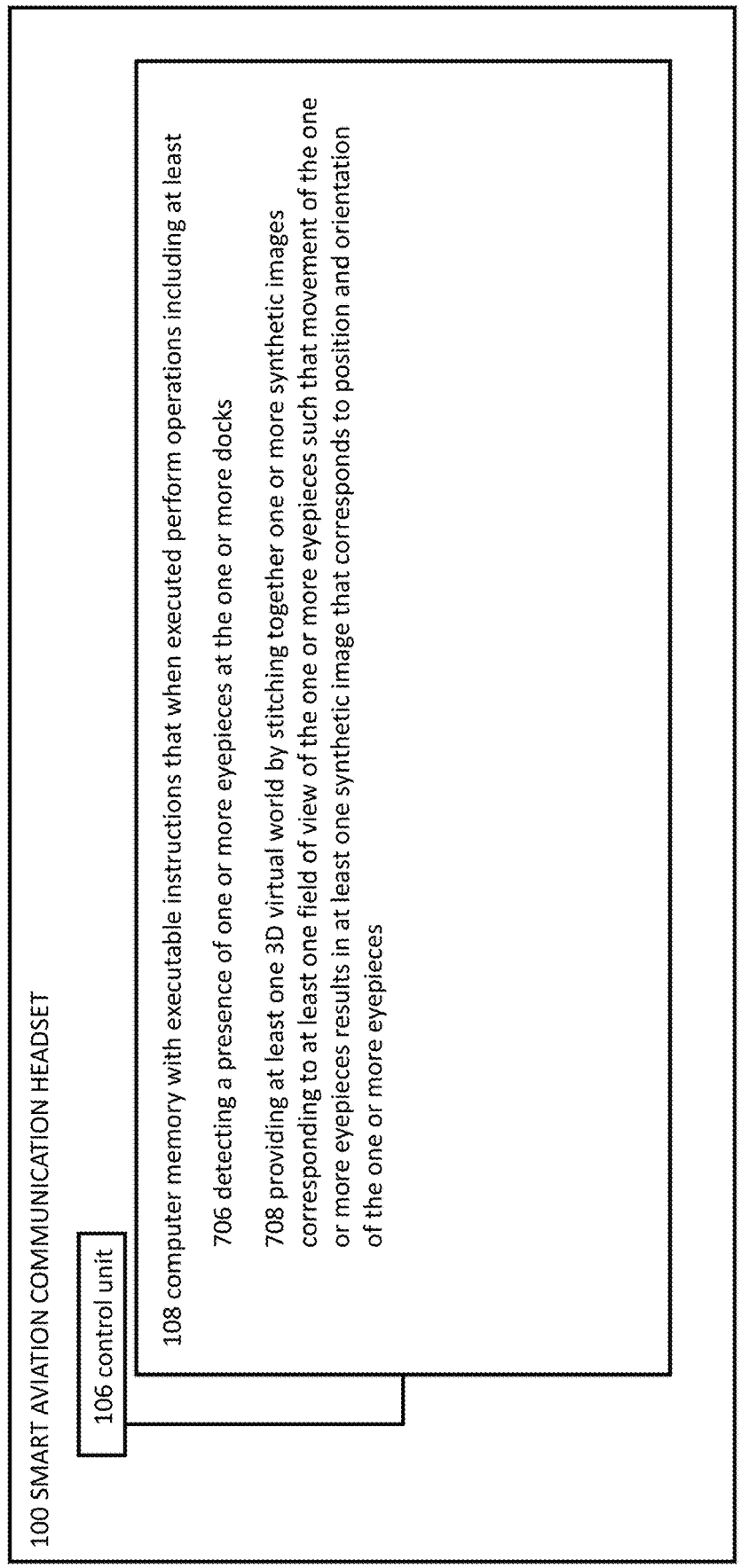

FIG. 7 is a system diagram of a smart aviation communication headset 100, in accordance with an embodiment of the invention. In one embodiment, an aviation communication headset 100 includes, but is not limited to, at least one microphone 114; one or more speakers 112; one or more docks 123 configured to interface with one or more eyepieces 120/121; and at least one control unit 106 configured by one or more executable instructions stored on computer memory 108 to perform operations including at least: detecting a presence of one or more eyepieces at the one or more docks at 706 and providing at least one 3D virtual world by stitching together one or more synthetic images corresponding to at least one field of view of the one or more eyepieces such that movement of the one or more eyepieces results in at least one synthetic image that corresponds to position and orientation of the one or more eyepieces at 708. For example, with the synthetic goggles docked, the synthetic images can be output to the display in a manner that corresponds to a position of the pilot in space and to the orientation of a head of the pilot. As the synthetic goggles are turned left, right, up, down, backwards, sideways, downwards, the images provided correspond to the view of reality from that position and orientation. As movement is detected in a certain direction or orientation, images for that orientation and/or future anticipated orientations can be loaded, cued, or buffered to enable a synchronous transition and simulation of viewing the actual world.

Figure 8:
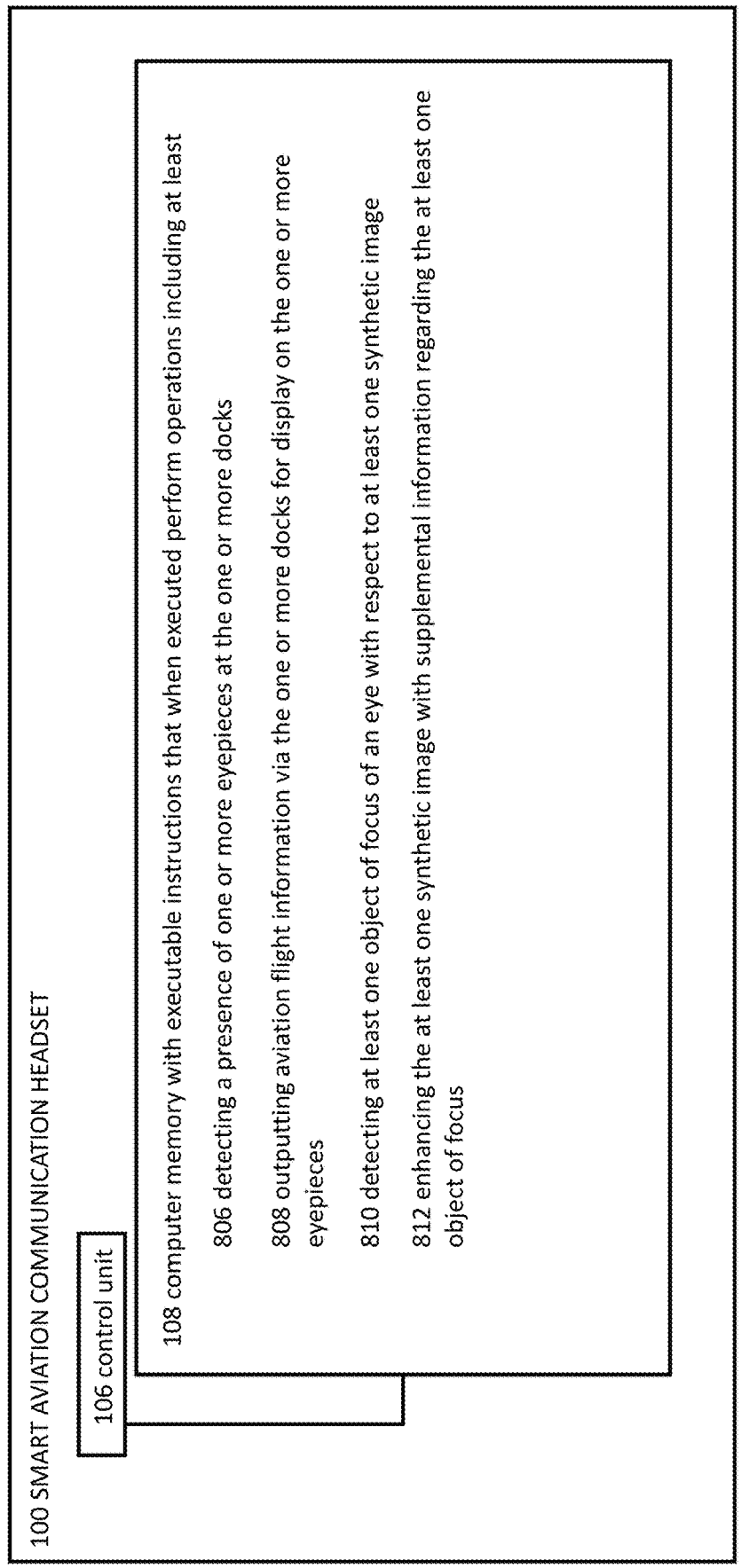

FIG. 8 is a system diagram of a smart aviation communication headset 100, in accordance with an embodiment of the invention. In one embodiment, an aviation communication headset 100 includes, but is not limited to, at least one microphone 114; one or more speakers 112; one or more docks 123 configured to interface with one or more eyepieces 120/121; and at least one control unit 106 configured by one or more executable instructions stored on computer memory 108 to perform operations including at least: detecting a presence of one or more eyepieces at the one or more docks at 806; outputting aviation flight information via the one or more docks for display on the one or more eyepieces at 808; detecting at least one object of focus of an eye with respect to at least one synthetic image at 810; and enhancing the at least one synthetic image with supplemental information regarding the at least one object of focus at 812. For example, the synthetic view of reality can include various features of interest to a pilot. These can include cities, runways, mountains, water features, airports, obstacles, waypoints, airspace indications, or the like. The eye focus of a pilot can be tracked and used to identify any particular object of focus. This combined with dwell time, a speech command, a button push, or other similar indication can signal an interest for additional information. The additional information on any object of focus can be provided to assist the pilot in learning or understanding more about the particular object of focus. For instance, upon detected focus on an airport, additional information can be displayed in association with the airport in the synthetic view. The additional information can include runway lengths, traffic pattern altitude, traffic pattern direction, preferred runways, wind direction, weather for the airport, communication frequencies, navigational aid frequencies, available instrument approaches, or the like. Similarly, detected focus on a distant town or terrain feature can result in expanded display of distance, name, altitude, weather, or the like. The supplemental information can be output via a speaker and/or transmitted to one or more avionics systems or navigational systems to enable control of such.

Figure 9:
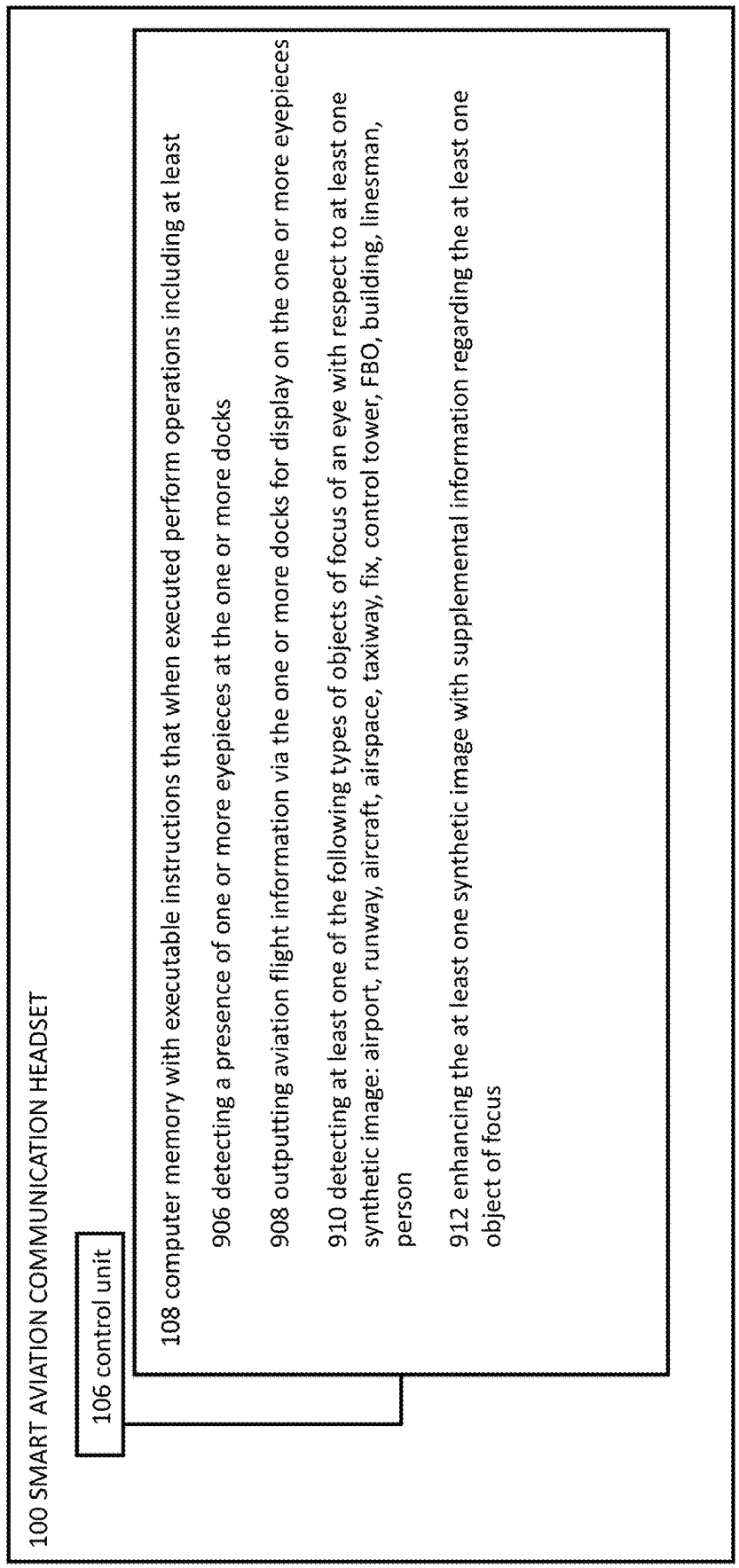

FIG. 9 is a system diagram of a smart aviation communication headset 100, in accordance with an embodiment of the invention. In one embodiment, an aviation communication headset 100 includes, but is not limited to, at least one microphone 114; one or more speakers 112; one or more docks 123 configured to interface with one or more eyepieces 120/121; and at least one control unit 106 configured by one or more executable instructions stored on computer memory 108 to perform operations including at least: detecting a presence of one or more eyepieces at the one or more docks at 906; outputting aviation flight information via the one or more docks for display on the one or more eyepieces at 908; detecting at least one of the following types of objects of focus of an eye with respect to at least one synthetic image: airport, runway, aircraft, airspace, taxiway, fix, control tower, FBO, building, linesman, person at 910; and enhancing the at least one synthetic image with supplemental information regarding the at least one object of focus at 912. For example, upon detected focus on a taxiway in the synthetic vision, supplemental information can be overlaid on the taxiway such as taxiway name and/or upcoming taxiway, ramp, or runways. Likewise, upon detected focus on a fix that is part of a highway in the sky output in the synthetic view, a name of the fix, an MEA (minimum enroute altitude) of the fix, an MCA (minimum crossing altitude of the fix), MRA (minimum reception altitude) of the fix, and/or any holding pattern directions or indications can be displayed in association with the fix in the synthetic view. Additionally, upon detected focus on a tower in the synthetic view, tower frequency information, hours of operation, ground control frequency information, clearance delivery frequency information, and/or one or more phone numbers can be displayed in association with the tower in the synthetic view. Note that the synthetic goggles can be enhanced with one or more actual reality objects or persons. This enables the synthetic goggles to remain worn in visual conditions and for the synthetic view to be more accurately aligned with reality. For instance, a linesman in reality can be added to the synthetic reality display and focus on the linesman can result in output of a communication frequency for speaking with the linesman.

Figure 10:
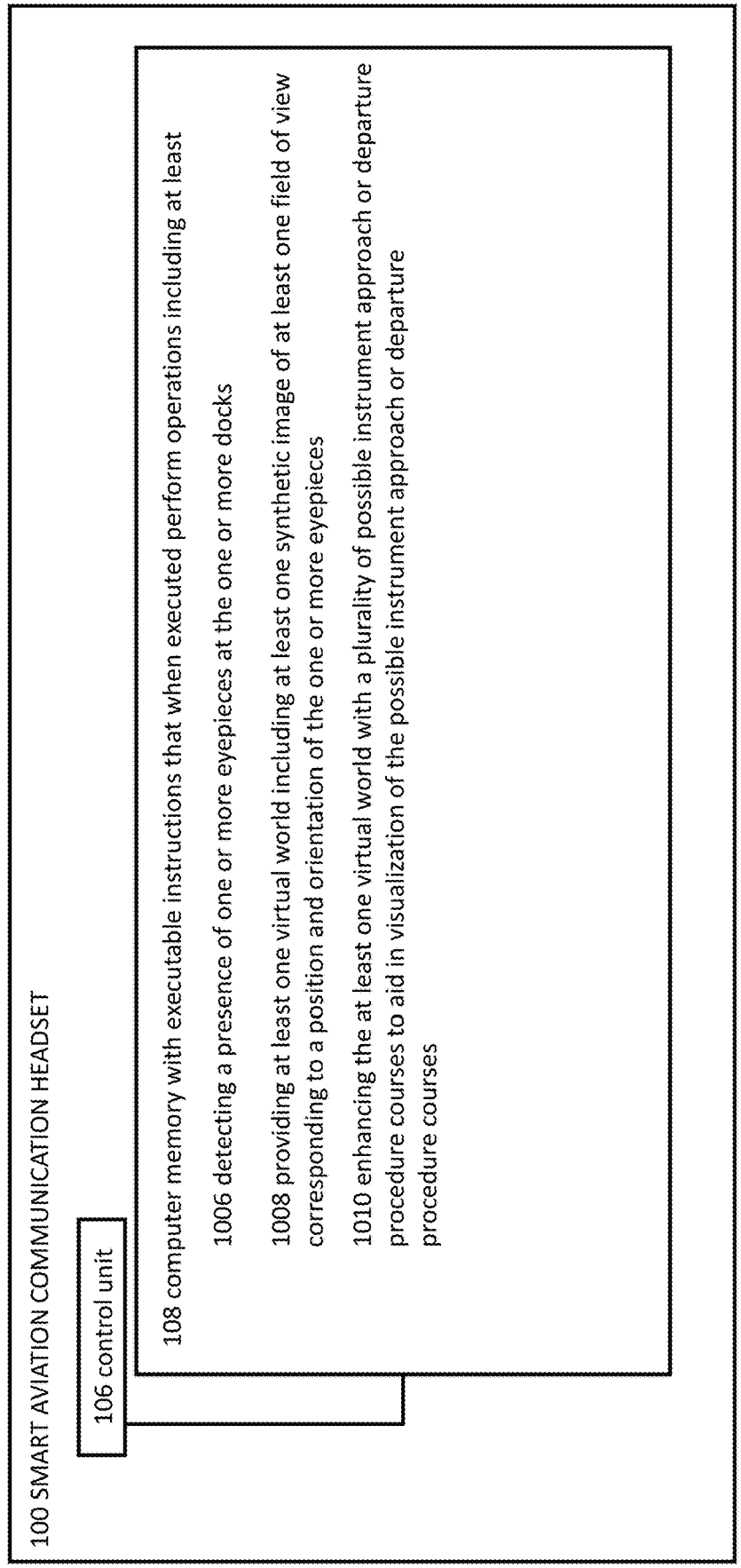

FIG. 10 is a system diagram of a smart aviation communication headset 100, in accordance with an embodiment of the invention. In one embodiment, an aviation communication headset 100 includes, but is not limited to, at least one microphone 114; one or more speakers 112; one or more docks 123 configured to interface with one or more eyepieces 120/121; and at least one control unit 106 configured by one or more executable instructions stored on computer memory 108 to perform operations including at least: detecting a presence of one or more eyepieces at the one or more docks at 1006; providing at least one virtual world including at least one synthetic image of at least one field of view corresponding to a position and orientation of the one or more eyepieces at 1008; and enhancing the at least one virtual world with a plurality of possible instrument approach or departure procedure courses to aid in visualization of the possible instrument approach or departure procedure courses at 1010. For example, the synthetic vision goggles can detect that a pilot is approaching or in proximity to an airport and display the pathways corresponding to various instrument approaches available for the airport. These instrument approaches do not necessarily need to be active, but can be simultaneously or sequentially displayed to facilitate visualization in the synthetic view of the approach for planning purposes. The approaches or departure procedures can include VOR, ILS, NDB, LOC, LPV, LNAV, LNAV+V, or other similar type approaches. The synthetic vision goggles can then be used to explore the approach or departure in three-dimensional space, such as in response to detected head movement or orientation changes.

Figure 11:
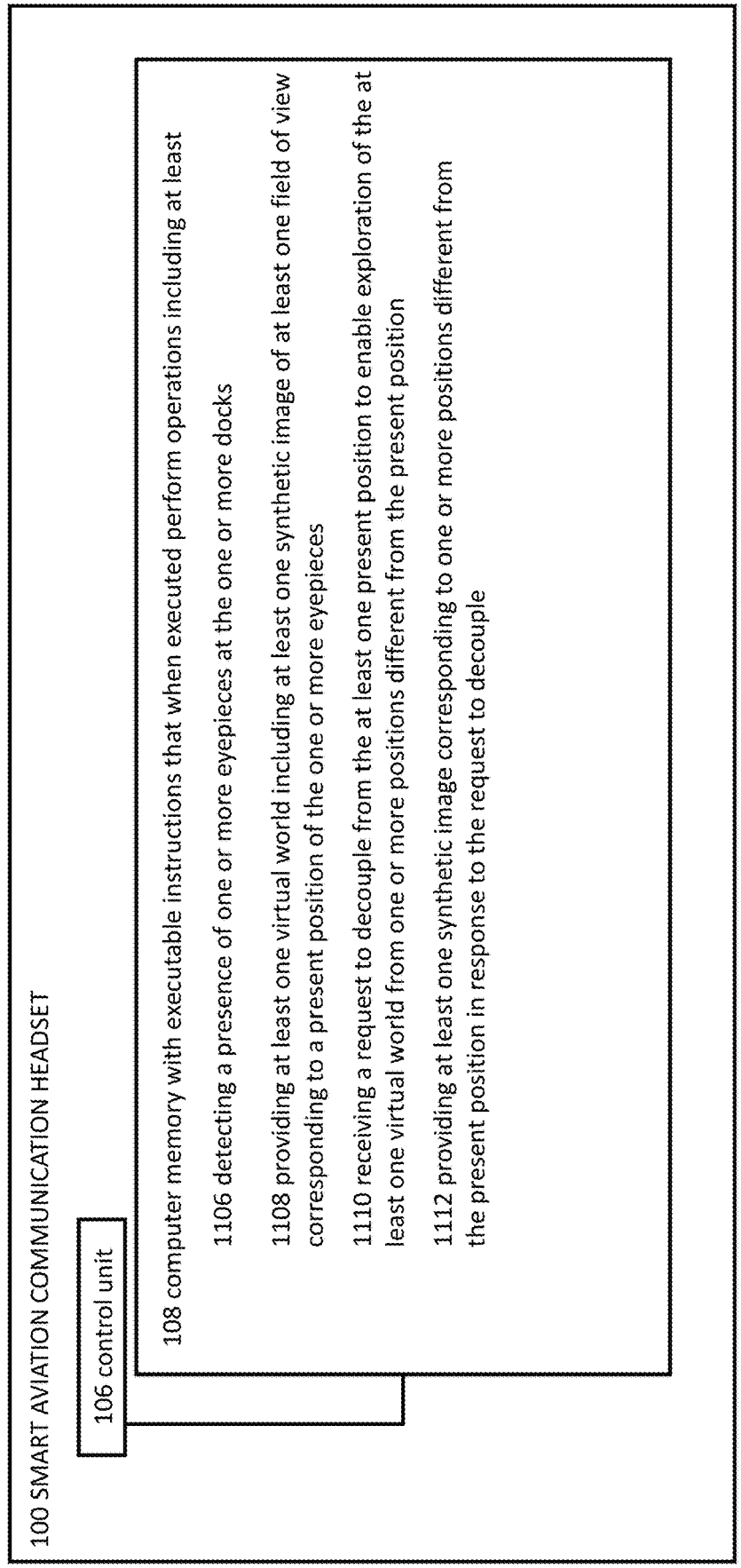

FIG. 11 is a system diagram of a smart aviation communication headset 100, in accordance with an embodiment of the invention. In one embodiment, an aviation communication headset 100 includes, but is not limited to, at least one microphone 114; one or more speakers 112; one or more docks 123 configured to interface with one or more eyepieces 120/121; and at least one control unit 106 configured by one or more executable instructions stored on computer memory 108 to perform operations including at least: detecting a presence of one or more eyepieces at the one or more docks at 1106; providing at least one virtual world including at least one synthetic image of at least one field of view corresponding to a present position of the one or more eyepieces at 1108; and receiving a request to decouple from the at least one present position to enable exploration of the at least one virtual world from one or more positions different from the present position at 1110; and providing at least one synthetic image corresponding to one or more positions different from the present position in response to the request to decouple at 1112. For example, the synthetic goggles can output one or more synthetic views of reality at a position and orientation corresponding to the pilot or plane or helicopter or balloon or drone copter (note that the subject matter herein applies and is usable in any of these contexts) in actual reality. Additionally, the synthetic vision goggles can upon receipt of request, such as spoken, gesture, eye dwell, or button push, decouple from the present position and orientation in reality to permit synthetic vision exploration of various different points in reality. That is, the synthetic vision goggles can be switched to decoupled/untethered synthetic vision goggles. This functionality enables a pilot or copilot to explore other areas different from the present position within the synthetic reality. For instance, a pilot may be approaching an airport on autopilot and upon detected request, the synthetic vision goggles can be switched to untethered mode to enable exploration of an approach path and terrain surrounding the airport prior to arrival at the airport for planning purposes. Alternatively, a pilot may be approaching a mountainous area and upon detection of request, the synthetic vision goggles can be switched to uncoupled mode to enable exploration around and through the mountainous area for planning purposes. The synthetic vision goggles can be returned to the current position and orientation coupled or tethered mode upon request.

Figure 12:
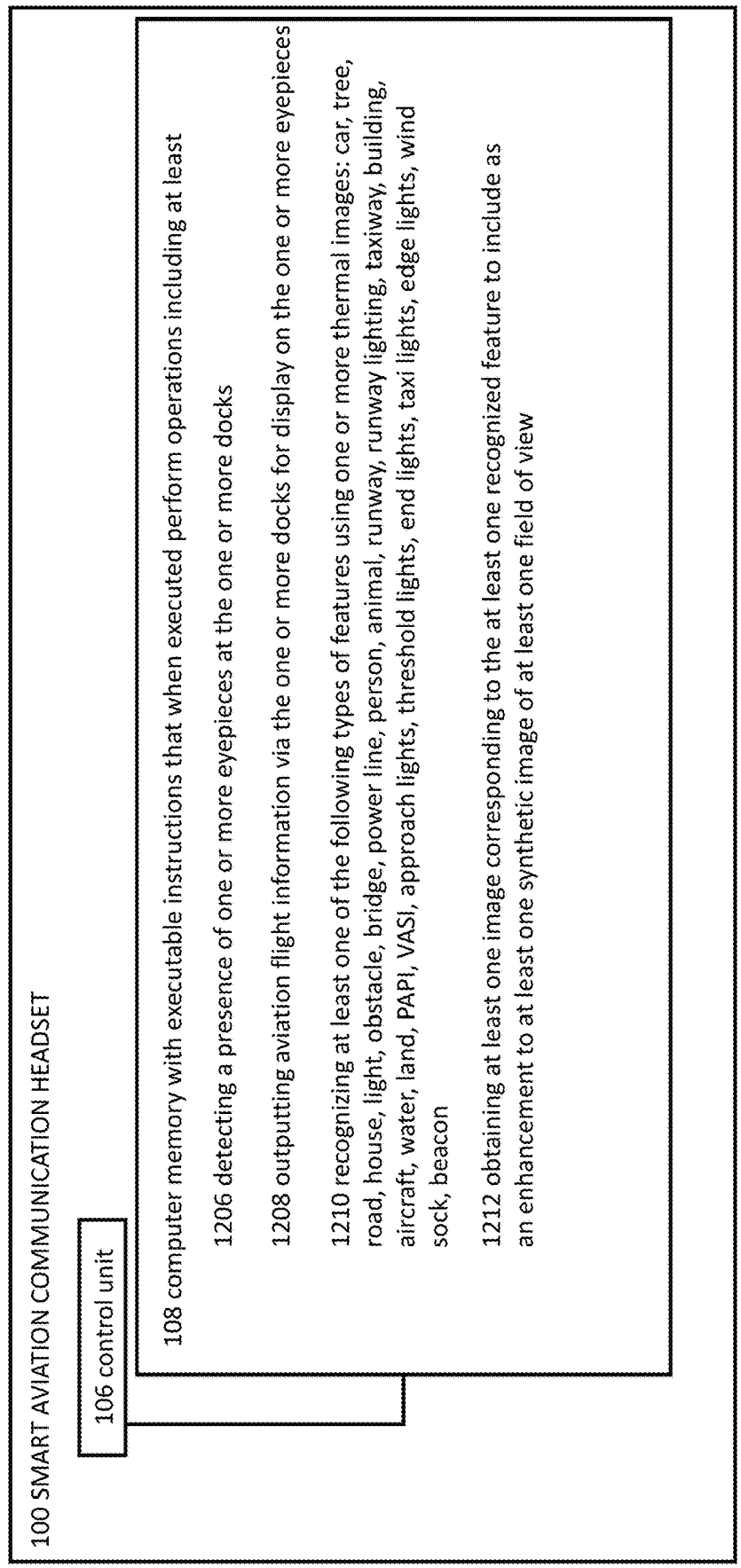

FIG. 12 is a system diagram of a smart aviation communication headset 100, in accordance with an embodiment of the invention. In one embodiment, an aviation communication headset 100 includes, but is not limited to, at least one microphone 114; one or more speakers 112; one or more docks 123 configured to interface with one or more eyepieces 120/121; and at least one control unit 106 configured by one or more executable instructions stored on computer memory 108 to perform operations including at least: detecting a presence of one or more eyepieces at the one or more docks at 1206; outputting aviation flight information via the one or more docks for display on the one or more eyepieces at 1208; recognizing at least one of the following types of features using one or more thermal images: car, tree, road, house, light, obstacle, bridge, power line, person, animal, runway, runway lighting, taxiway, building, aircraft, water, land, PAPI, VASI, approach lights, threshold lights, end lights, taxi lights, edge lights, wind sock, beacon at 1210; and obtaining at least one image corresponding to the at least one recognized feature to include as an enhancement to at least one synthetic image of at least one field of view at 1212. For example, thermal imagery can be obtained by a thermal imaging device of the aircraft or the headset. The thermal imagery can be parsed and filtered for objects of interest, such as terrain, houses, lights, people, or obstacles. Imagery associated with the objects, which may be actual imagery or stock/generic imagery is then obtained and added into the synthetic reality view at the position or location that corresponds to the actual position or location of the object. In this manner, the synthetic vision of reality can be blended or enhanced with actual reality objects that may not be visible via the visible spectrum of light by using heat recognition of the objects. For instance, on an approach in IMC the synthetic vision of reality can be supplemented with the actual approach and runway lights to facilitate a safe transition to VMC and landing. Upon entering VMC, in one particular embodiment, the synthetic vision can transition to an actual displayed view of reality as provided by one or more cameras associated with the headset.

Figure 13:
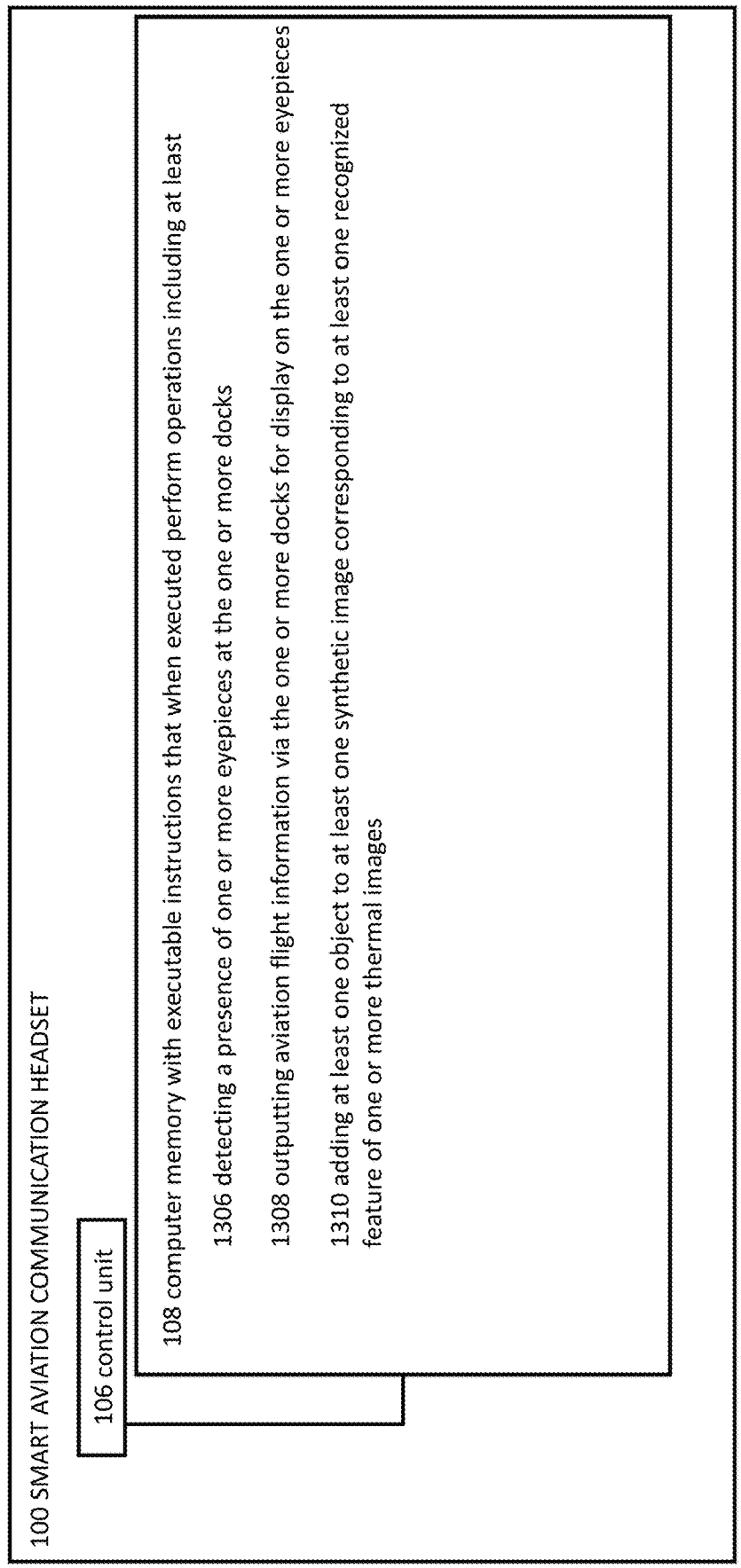

FIG. 13 is a system diagram of a smart aviation communication headset 100, in accordance with an embodiment of the invention. In one embodiment, an aviation communication headset 100 includes, but is not limited to, at least one microphone 114; one or more speakers 112; one or more docks 123 configured to interface with one or more eyepieces 120/121; and at least one control unit 106 configured by one or more executable instructions stored on computer memory 108 to perform operations including at least: detecting a presence of one or more eyepieces at the one or more docks at 1306; outputting aviation flight information via the one or more docks for display on the one or more eyepieces at 1308; and adding at least one object to at least one synthetic image corresponding to at least one recognized feature of one or more thermal images at 1310. For example, various objects in the actual world can be identified generally by an outline or thermal image pattern of the object. Humans will have a different thermal image profile than a car or lights or a group of people or an animal or a building or the like. Therefore, the different thermal imagery profiles can be used to identify a class or type of object that is detected. Imagery for these types or classes of commonly recognized objects can be stored in memory. Thus, when a particular thermal image pattern is detected, the type or class can be identified based on the profile of the thermal image patter and the appropriate representative imagery can be obtained from memory. The representative imagery is then output within the synthetic view to supplement or enhance the synthetic vision with imagery that corresponds to the detected object.

Figure 14:
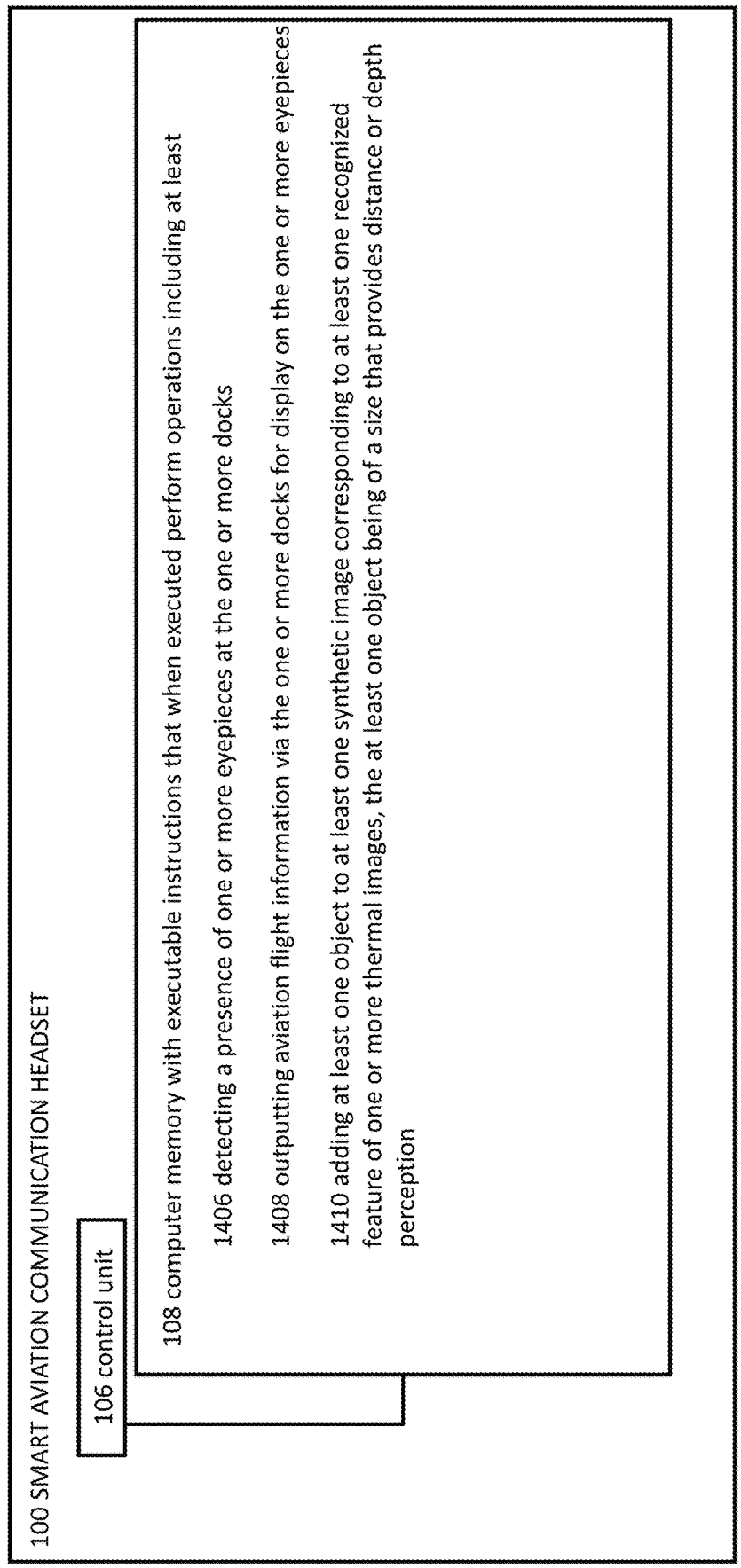

FIG. 14 is a system diagram of a smart aviation communication headset 100, in accordance with an embodiment of the invention. In one embodiment, an aviation communication headset 100 includes, but is not limited to, at least one microphone 114; one or more speakers 112; one or more docks 123 configured to interface with one or more eyepieces 120/121; and at least one control unit 106 configured by one or more executable instructions stored on computer memory 108 to perform operations including at least: detecting a presence of one or more eyepieces at the one or more docks at 1406; outputting aviation flight information via the one or more docks for display on the one or more eyepieces at 1408; and adding at least one object to at least one synthetic image corresponding to at least one recognized feature of one or more thermal images, the at least one object being of a size that provides distance or depth perception at 1410. For example, the thermal imagery may detect a person or approach lights or an animal. The representative images can be obtained from memory to depict that person or approach lighting and output within the synthetic vision at a size and shape and dimension that facilitates distance or depth perception.

FIG. 15 is a system diagram of a smart aviation communication headset 100, in accordance with an embodiment of the invention. In one embodiment, an aviation communication headset 100 includes, but is not limited to, at least one microphone 114; one or more speakers 112; one or more docks 123 configured to interface with one or more eyepieces 120/121; and at least one control unit 106 configured by one or more executable instructions stored on computer memory 108 to perform operations including at least: detecting a presence of one or more eyepieces at the one or more docks at 1506; outputting aviation flight information via the one or more docks for display on the one or more eyepieces at 1508; and adjusting at least one ground contour line in at least one synthetic image based on at least one recognized feature of one or more thermal images at 1510. Synthetic vision can be less than accurate at times as compared to actual reality. For instance, synthetic vision can deviate with actual orientation over time depending on whether the heading information is accurately representative of reality. Likewise, contours of terrain or surface features may be slightly different from actual reality. Similarly, locations of airports, runway orientations, or terrain features may also not exactly correspond to actual reality. In these situations, the thermal imagery of objects and their known position in reality can be used to adjust the alignment and contour lines in the synthetic reality view. That is, the thermal imagery of a runway can be detected through IMC and the position and orientation of the runway can be compared to what is being displayed in the synthetic vision. Upon detecting a mismatch, the synthetic vision can be corrected to more closely tie to actual reality and to enable course and altitude perceptions to be similarly more closely tied to actual reality.

Figure 16:
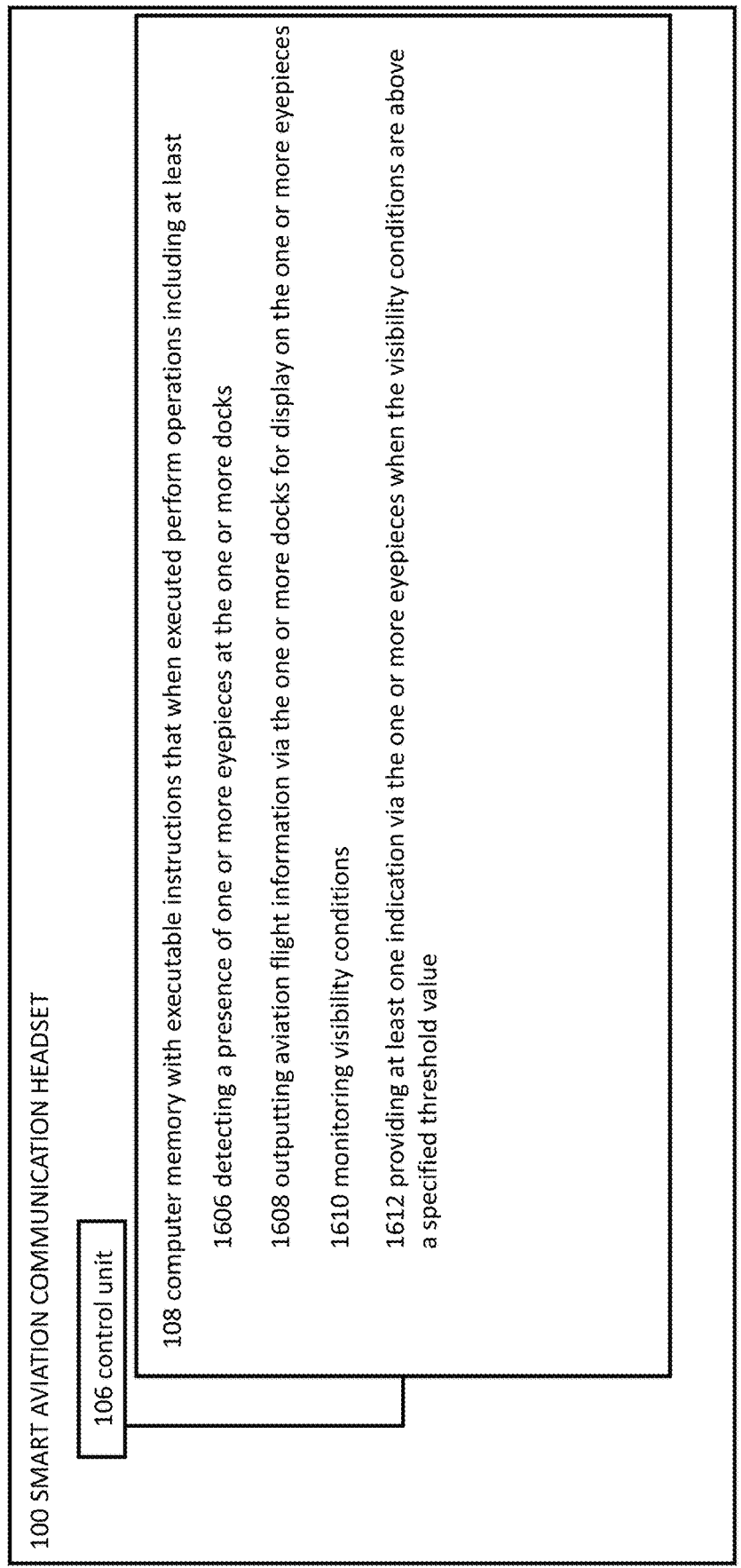

FIG. 16 is a system diagram of a smart aviation communication headset 100, in accordance with an embodiment of the invention. In one embodiment, an aviation communication headset 100 includes, but is not limited to, at least one microphone 114; one or more speakers 112; one or more docks 123 configured to interface with one or more eyepieces 120/121; and at least one control unit 106 configured by one or more executable instructions stored on computer memory 108 to perform operations including at least: detecting a presence of one or more eyepieces at the one or more docks at 1606, outputting aviation flight information via the one or more docks for display on the one or more eyepieces at 1608, monitoring visibility conditions at 1610, and providing at least one indication via the one or more eyepieces when the visibility conditions are above a specified threshold value at 1612. For example, the synthetic vision eyewear can provide a synthetic reality view of actual reality. This is useful during times of low visibility or no visibility, such as during IMC conditions or at night. However, while these conditions may prompt usage of the synthetic vision goggles, the conditions may change during usage of the synthetic goggles. For instance, IMC conditions may be broken out of, such as by exiting a cloud or descending through a cloud base or ascending above a cloud deck. The synthetic vision goggles can include a camera or other light or visibility sensor that determines when visibility increases beyond a specified limit, such as beyond ¼ mile or beyond ½ mile or beyond ¾ mile or beyond 1 mile or beyond 5 miles or the like. When such determination is made, the synethic vision goggles output an indication of such within the synthetic vision environment to enable the pilot to disconnect the synthetic vision goggles and transition to visual flight. Alternatively, upon detecting improved visibility conditions beyond a specified threshold, the synthetic vision goggles can transition from a display of synthetic reality to a display of actual reality, such as by passing through camera images of actual reality to be displayed within the synthetic vision goggles. This feature can also be useful during an approach when the synthetic vision goggles can indicate that minimum requirements are satisfied for a particular approach. In this particular embodiment, the visibility condition threshold can be automatically loaded and changed based on which instrument approach is active or flown (e.g., Category A or B plane with LPV/WAAS capability may trigger a threshold visibility of ¼ mile for a particular RNAV approach to a runway).

Figure 17:
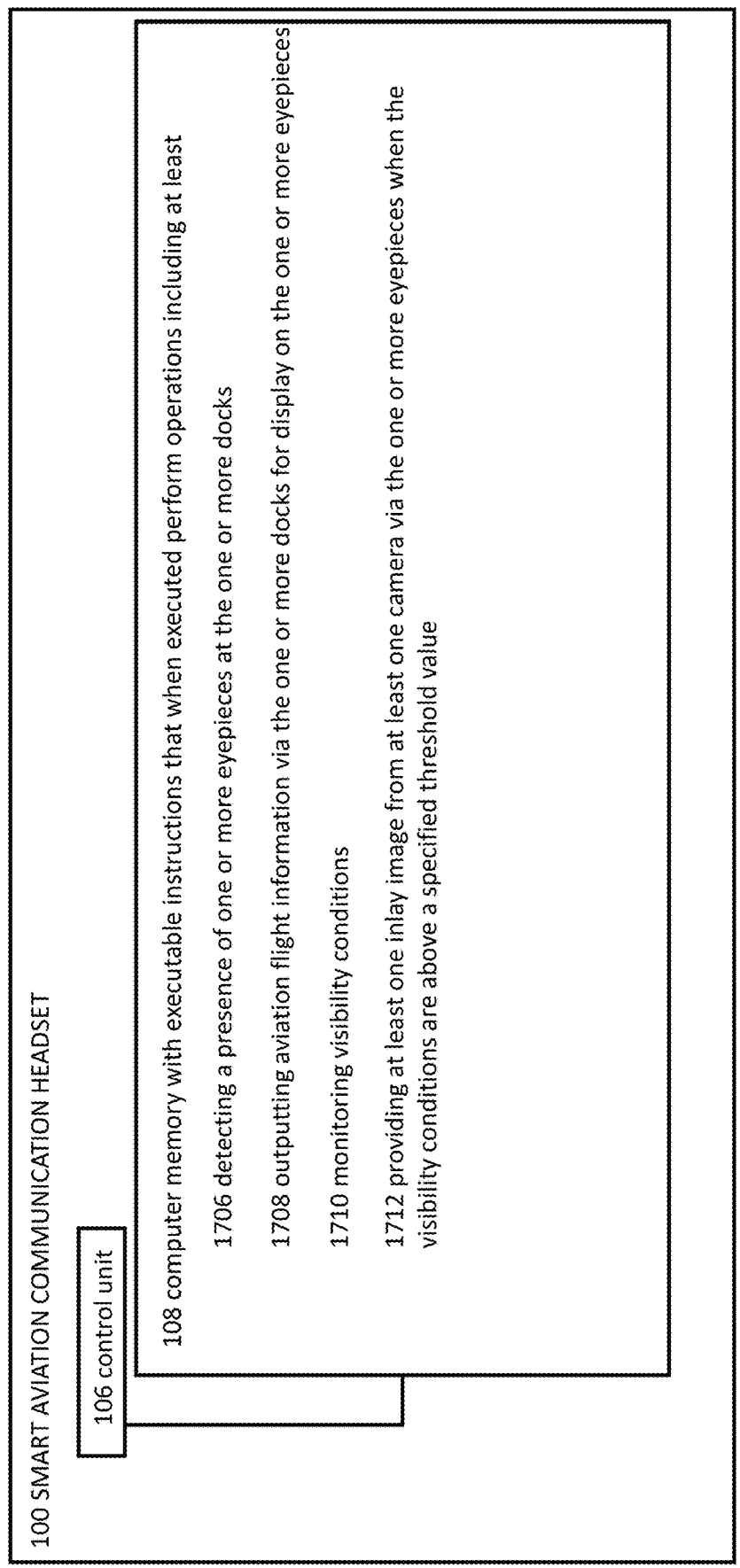

FIG. 17 is a system diagram of a smart aviation communication headset 100, in accordance with an embodiment of the invention. In one embodiment, an aviation communication headset 100 includes, but is not limited to, at least one microphone 114; one or more speakers 112; one or more docks 123 configured to interface with one or more eyepieces 120/121; and at least one control unit 106 configured by one or more executable instructions stored on computer memory 108 to perform operations including at least: detecting a presence of one or more eyepieces at the one or more docks at 1706, outputting aviation flight information via the one or more docks for display on the one or more eyepieces at 1708, monitoring visibility conditions at 1710, providing at least one inlay image from at least one camera via the one or more eyepieces when the visibility conditions are above a specified threshold value at 1712. When visibility conditions change the need or desire to dock and use the synthetic vision goggles to the aviation headset, the camera or other detector can sense the visibility condition improvement and output the indication to enable disconnection or de-docking of the synthetic vision goggles. However, in certain circumstances, such as on a high workload instrument approach at minimums, decoupling the eyepieces may be less desirable. In these cases, an optional pass through imagery mode may be automatically enabled whereby the synthetic imagery of reality is replaced or supplemented with actual reality images obtained from a camera associated with the headset or the synthetic vision goggles. Thus, during breakout from a cloud base, the synthetic imagery that facilitated situational awareness can be seamlessly transitioned to actual reality images that are usable to descend below minimums for the approach and safely land. Another situation where this feature can be enabled is when transitioning into and out of IMC conditions. The synthetic imagery and the actual reality images can be iteratively transitioned therebetween to facilitate safety while visibility conditions are constantly changing.

Figure 18:
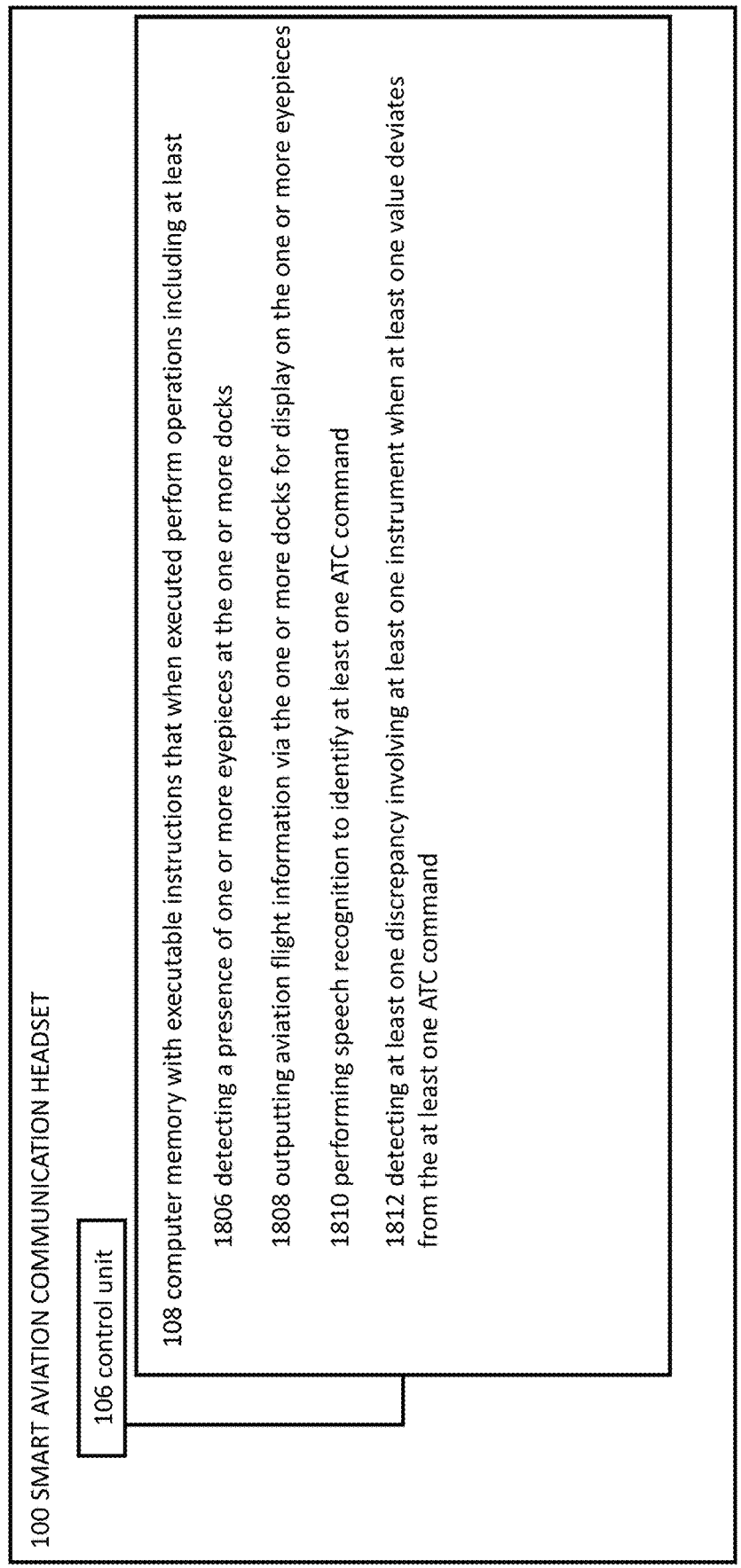

FIG. 18 is a system diagram of a smart aviation communication headset 100, in accordance with an embodiment of the invention. In one embodiment, an aviation communication headset 100 includes, but is not limited to, at least one microphone 114; one or more speakers 112; one or more docks 123 configured to interface with one or more eyepieces 120/121; and at least one control unit 106 configured by one or more executable instructions stored on computer memory 108 to perform operations including at least: detecting a presence of one or more eyepieces at the one or more docks at 1806, outputting aviation flight information via the one or more docks for display on the one or more eyepieces at 1808, performing speech recognition to identify at least one ATC command at 1810, and detecting at least one discrepancy involving at least one instrument when at least one value deviates from the at least one ATC command at 1812. The aviation communication headset receives data or voice signals that are output as speech sounds via one or more speakers. The speech sounds often include ATC (Air Traffic Control) instructions, such as turn to a heading, descend to an altitude, reduce speed to a certain airspeed, turn to a course, cleared to a fix, cleared for an approach, communicate on a certain frequency, and the like. A processor associated with the synthetic vision goggles or the aviation communication headset can perform speech recognition on these signals to identify commands and compare those commands to the flight information being output via the synthetic vision goggles. For instance, flight information such as heading, course, altitude, airspeed, navigation, radio frequency, and the like can be identified and compared to the expected values as determined through speech recognition of the speaker sounds. In an event of a discrepancy, an indicator can be displayed via the synthetic vision goggles proximate to the aviation flight information at issue to notify the pilot. The speech recognition can filter commands received based on the aircraft identification information, such as tail number, that is included in the speech sounds. Furthermore, the detection of the discrepancy can include a delay time to permit time for the speech commands to be processed by the pilot and changed as directed. For example, ATC speech commands can be detected and recognized as an indication to turn left to a heading of 140 and descend to 2500 feet. After approximately 5 to 15 seconds, the processor can determine whether the heading of 140 and altitude of 2500 feet has been satisfied or is being satisfied using the flight information associated with the synthetic goggles. In the event not, a pulsation of the heading and altitude can appear within the synthetic goggles to remind or notify the pilot of the ATC command.

Figure 19:
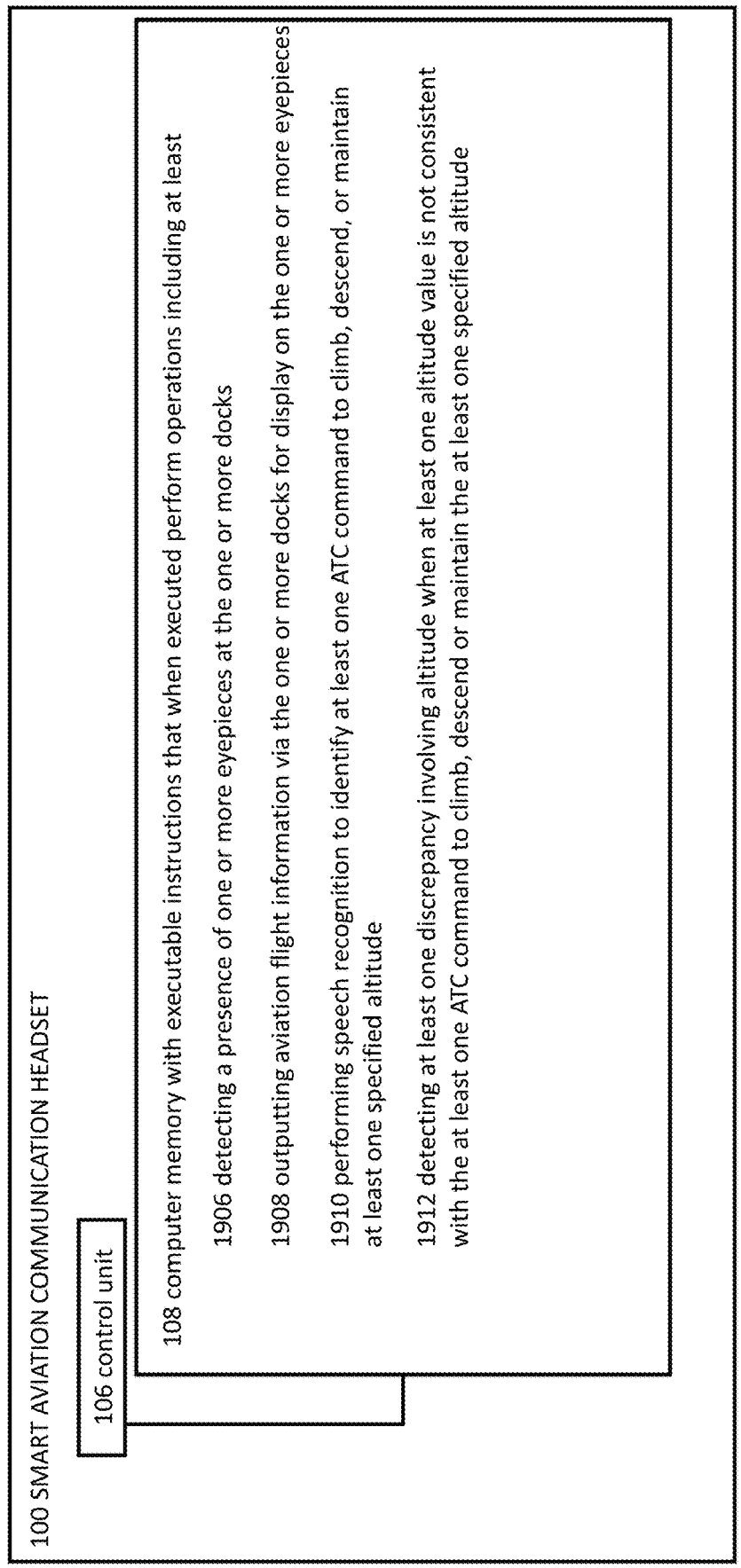

FIG. 19 is a system diagram of a smart aviation communication headset 100, in accordance with an embodiment of the invention. In one embodiment, an aviation communication headset 100 includes, but is not limited to, at least one microphone 114; one or more speakers 112; one or more docks 123 configured to interface with one or more eyepieces 120/121; and at least one control unit 106 configured by one or more executable instructions stored on computer memory 108 to perform operations including at least: detecting a presence of one or more eyepieces at the one or more docks at 1906, outputting aviation flight information via the one or more docks for display on the one or more eyepieces at 1908, performing speech recognition to identify at least one ATC command to climb, descend, or maintain at least one specified altitude at 1910, detecting at least one discrepancy involving altitude when at least one altitude value is not consistent with the at least one ATC command to climb, descend or maintain the at least one specified altitude at 1912. As another specific example of this operation, the processor can detect and recognize a speech command to maintain level 9000 indicated altitude for November 104 Zulu Uniform, the specific tail number that corresponds to the aircraft. Upon recognizing the tail number and the level 9000 altitude command, the processor can monitor the altitude output in the aviation flight information of the synthetic goggles and determine whether the altitude deviates from 9000 by more than a specified threshold amount. The threshold amount can be user defined or automatically selected, such as not to exceed 100 feet deviation. Upon detecting any such deviation beyond the threshold, the synthetic vision goggles can display a notification indication. In certain embodiments, a further request can be provided to switch to autopilot mode and if accepted and instruction can be transmitted to the navigation system of the aircraft to make the correction in altitude.

Figure 20:
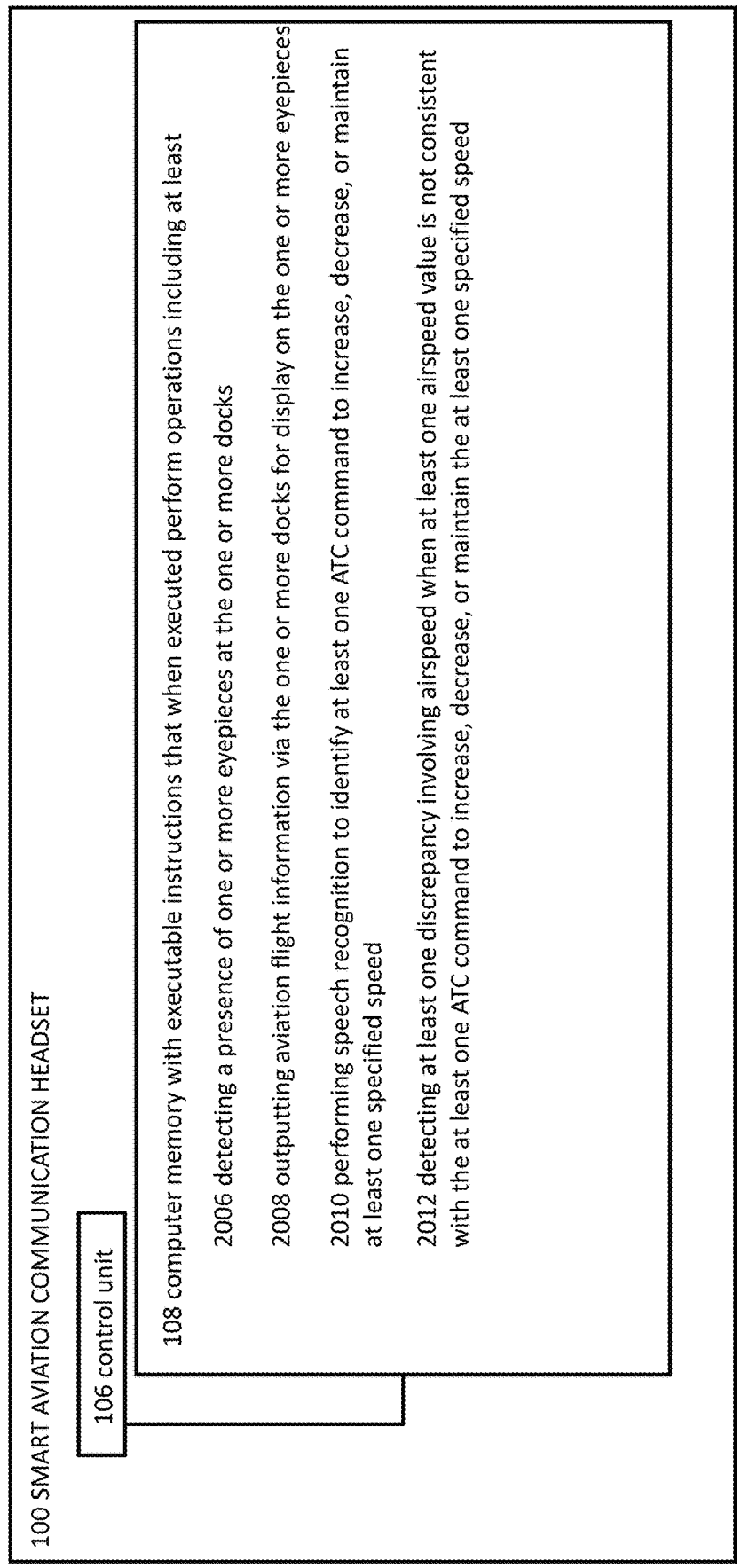

FIG. 20 is a system diagram of a smart aviation communication headset 100, in accordance with an embodiment of the invention. In one embodiment, an aviation communication headset 100 includes, but is not limited to, at least one microphone 114; one or more speakers 112; one or more docks 123 configured to interface with one or more eyepieces 120/121; and at least one control unit 106 configured by one or more executable instructions stored on computer memory 108 to perform operations including at least: detecting a presence of one or more eyepieces at the one or more docks at 2006; outputting aviation flight information via the one or more docks for display on the one or more eyepieces at 2008; performing speech recognition to identify at least one ATC command to increase, decrease, or maintain at least one specified speed at 2010; and detecting at least one discrepancy involving airspeed when at least one airspeed value is not consistent with the at least one ATC command to increase, decrease, or maintain the at least one specified speed at 2012. For example, a detected and recognized ATC instruction may be to slow to 200 knots indicated. The processor component can then determine whether the displayed aviation information in the synthetic vision goggles is consistent with this instruction within 10 seconds of receipt. In the event not, the airspeed bug can blink or flash or move to provide a reminder regarding the command for airspeed. In one particular embodiment, the airspeed bug displayed on the synthetic vision goggles can be moved to the ATC commanded airspeed to further assist in compliance of the command.

Figure 21:
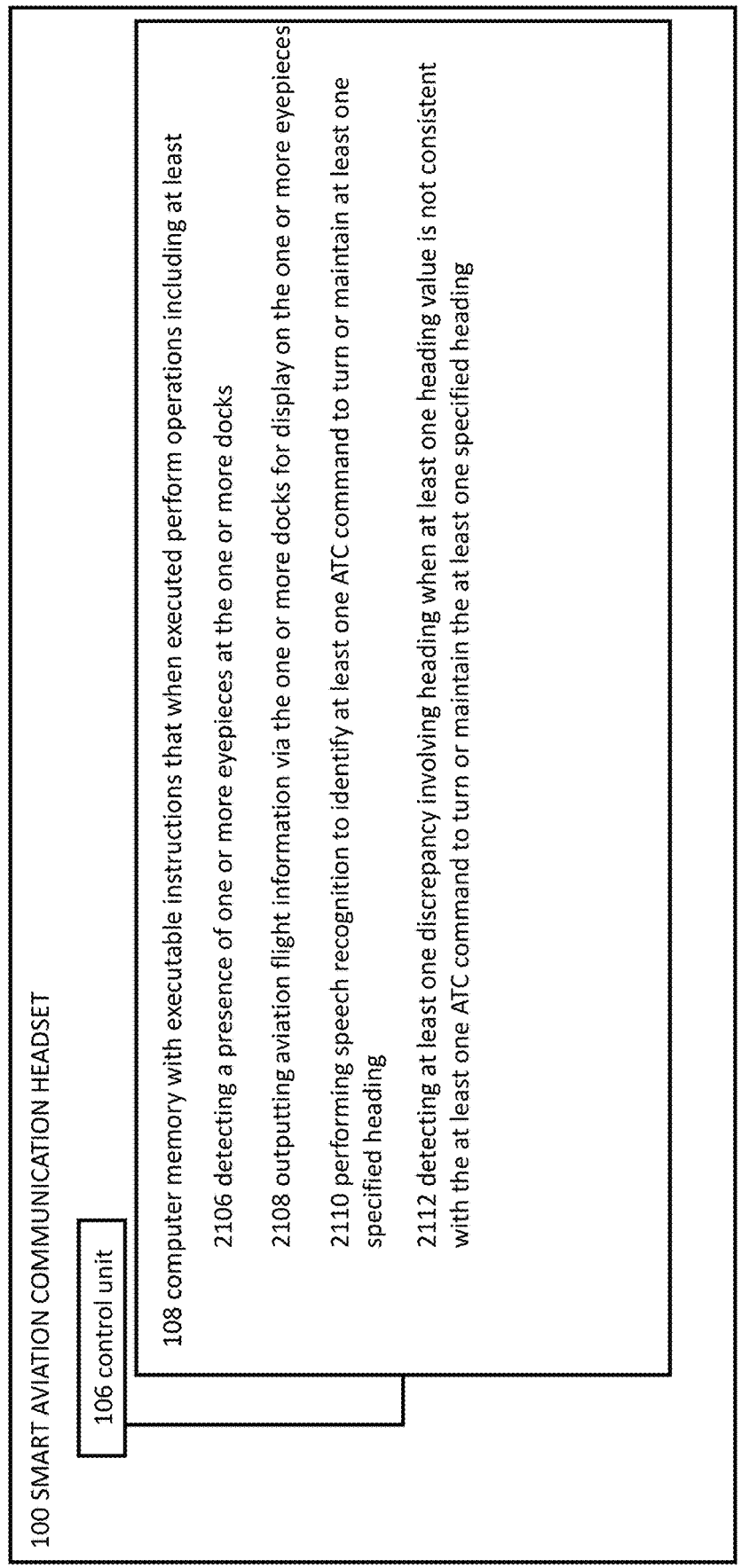

FIG. 21 is a system diagram of a smart aviation communication headset 100, in accordance with an embodiment of the invention. In one embodiment, an aviation communication headset 100 includes, but is not limited to, at least one microphone 114; one or more speakers 112; one or more docks 123 configured to interface with one or more eyepieces 120/121; and at least one control unit 106 configured by one or more executable instructions stored on computer memory 108 to perform operations including at least: detecting a presence of one or more eyepieces at the one or more docks at 2106; outputting aviation flight information via the one or more docks for display on the one or more eyepieces at 2108; performing speech recognition to identify at least one ATC command to turn or maintain at least one specified heading at 2110; and detecting at least one discrepancy involving heading when at least one heading value is not consistent with the at least one ATC command to turn or maintain the at least one specified heading at 2112. For example, a ATC command for N104ZU to turn right 10 degrees can be detected and recognized through speech recognition. The processor can adjust the heading bug automatically to move 10 degrees right of the current heading (e.g., 90 degrees if currently at an 80 degree heading). Furthermore, the processor can determine if after 5 seconds whether a turn to the heading is being conducted or whether a turn to the heading has been accomplished using the flight information of the synthetic vision goggles. In the event not, the heading bug may flash or a warning indication may be output via the speakers or the display of the synthetic vision goggles. For instance, a voice output via the headset speakers may state that a turn to the right 10 degrees should be performed.

Figure 22:
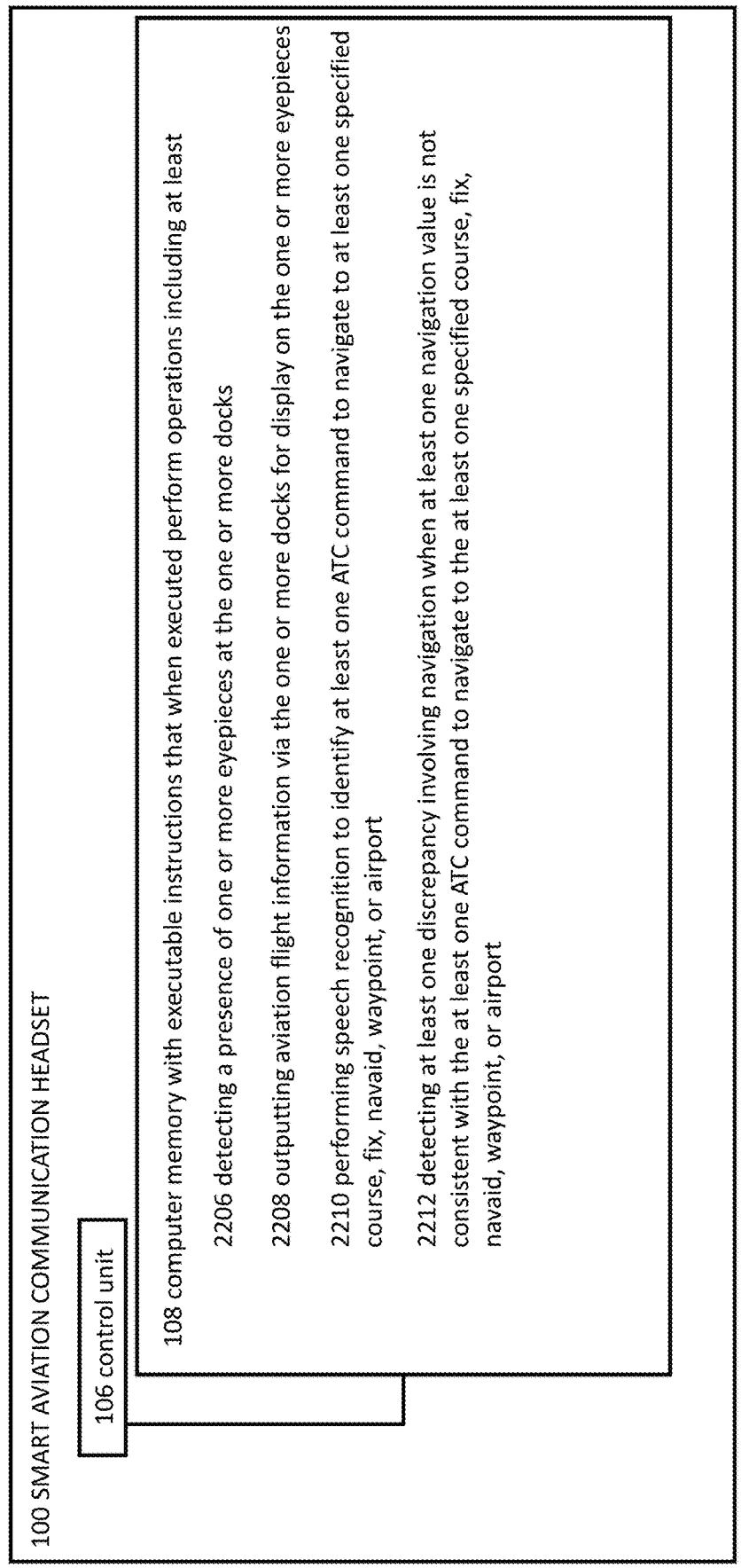

FIG. 22 is a system diagram of a smart aviation communication headset 100, in accordance with an embodiment of the invention. In one embodiment, an aviation communication headset 100 includes, but is not limited to, at least one microphone 114; one or more speakers 112; one or more docks 123 configured to interface with one or more eyepieces 120/121; and at least one control unit 106 configured by one or more executable instructions stored on computer memory 108 to perform operations including at least: detecting a presence of one or more eyepieces at the one or more docks at 2206; outputting aviation flight information via the one or more docks for display on the one or more eyepieces at 2208; performing speech recognition to identify at least one ATC command to navigate to at least one specified course, fix, navaid, waypoint, or airport at 2210; and detecting at least one discrepancy involving navigation when at least one navigation value is not consistent with the at least one ATC command to navigate to the at least one specified course, fix, navaid, waypoint, or airport at 2212. For example, the ATC command may include an instruction of cleared direct to ZOLGI intersection and then hold. The processor can detect and recognize this instruction as applicable and determine whether the instruction is being complied with by monitoring the flight information of the synthetic vision goggles. For instance, a turn in the wrong direction away from ZOLGI or a hold in the wrong direction upon crossing ZOLGI can trigger a warning indication on the display of the synthetic vision goggles or via the audio output of speakers of the aviation communication headset. For instance, the warning indication can be an arrow or directional indication on the display or an audible warning that a right turn is recommend if a left turn is away from the fix or navigational path.

Figure 23:
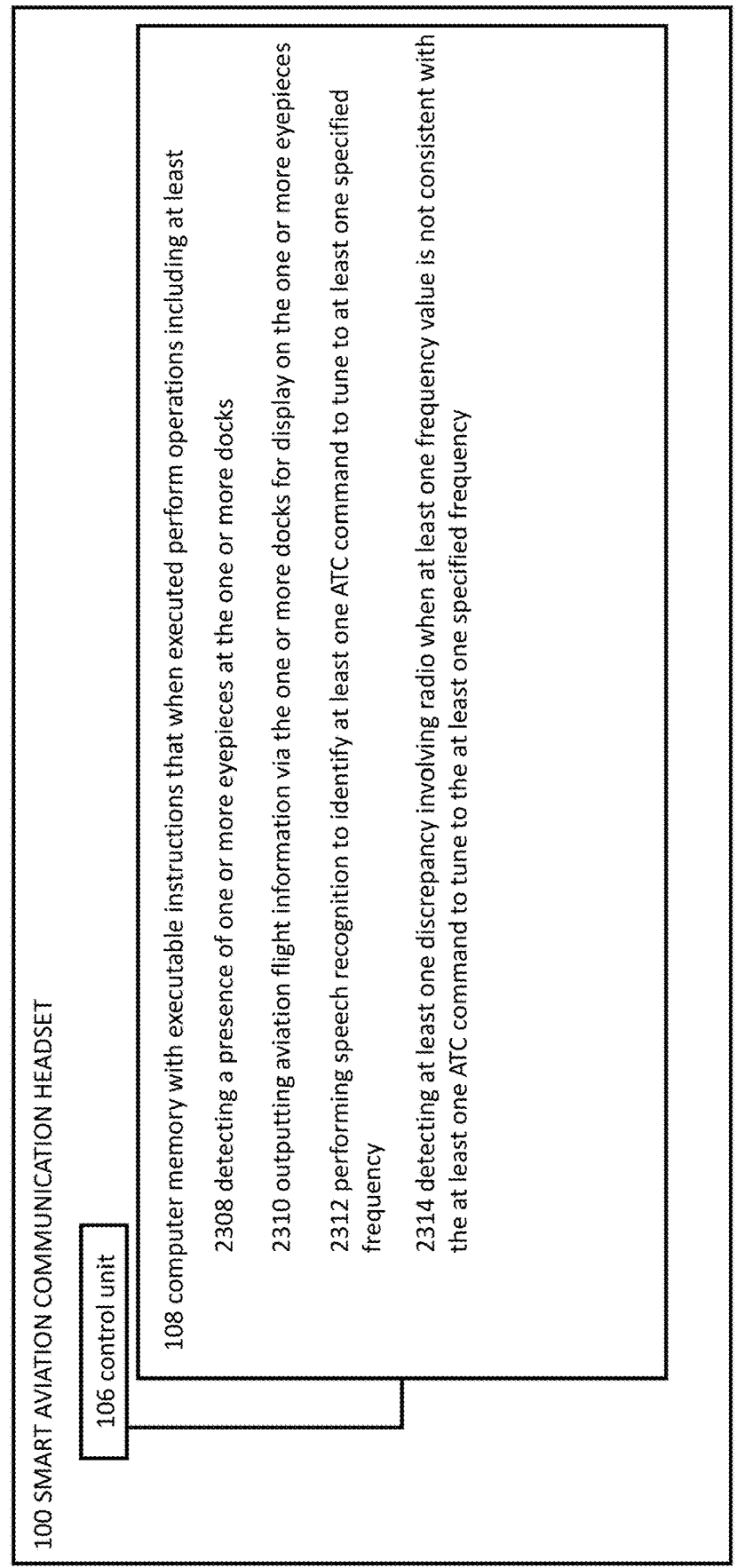

FIG. 23 is a system diagram of a smart aviation communication headset 100, in accordance with an embodiment of the invention. In one embodiment, an aviation communication headset 100 includes, but is not limited to, at least one microphone 114; one or more speakers 112; one or more docks 123 configured to interface with one or more eyepieces 120/121; and at least one control unit 106 configured by one or more executable instructions stored on computer memory 108 to perform operations including at least: detecting a presence of one or more eyepieces at the one or more docks at 2308; outputting aviation flight information via the one or more docks for display on the one or more eyepieces at 2310; performing speech recognition to identify at least one ATC command to tune to at least one specified frequency at 2312; and detecting at least one discrepancy involving radio when at least one frequency value is not consistent with the at least one ATC command to tune to the at least one specified frequency at 2314. For example, an ATC instruction may be to contact Seattle Center on 127.1. Upon detection and recognition of the radio frequency command received and determined applicable to the aircraft, the processor can determine whether the radio frequency has been tuned to 127.1 within a specified time period using the flight information associated with the one or more eyepieces. In the event not, the radio frequency can be auto-tuned or an indication can be made to correct the issue.

Figure 24:
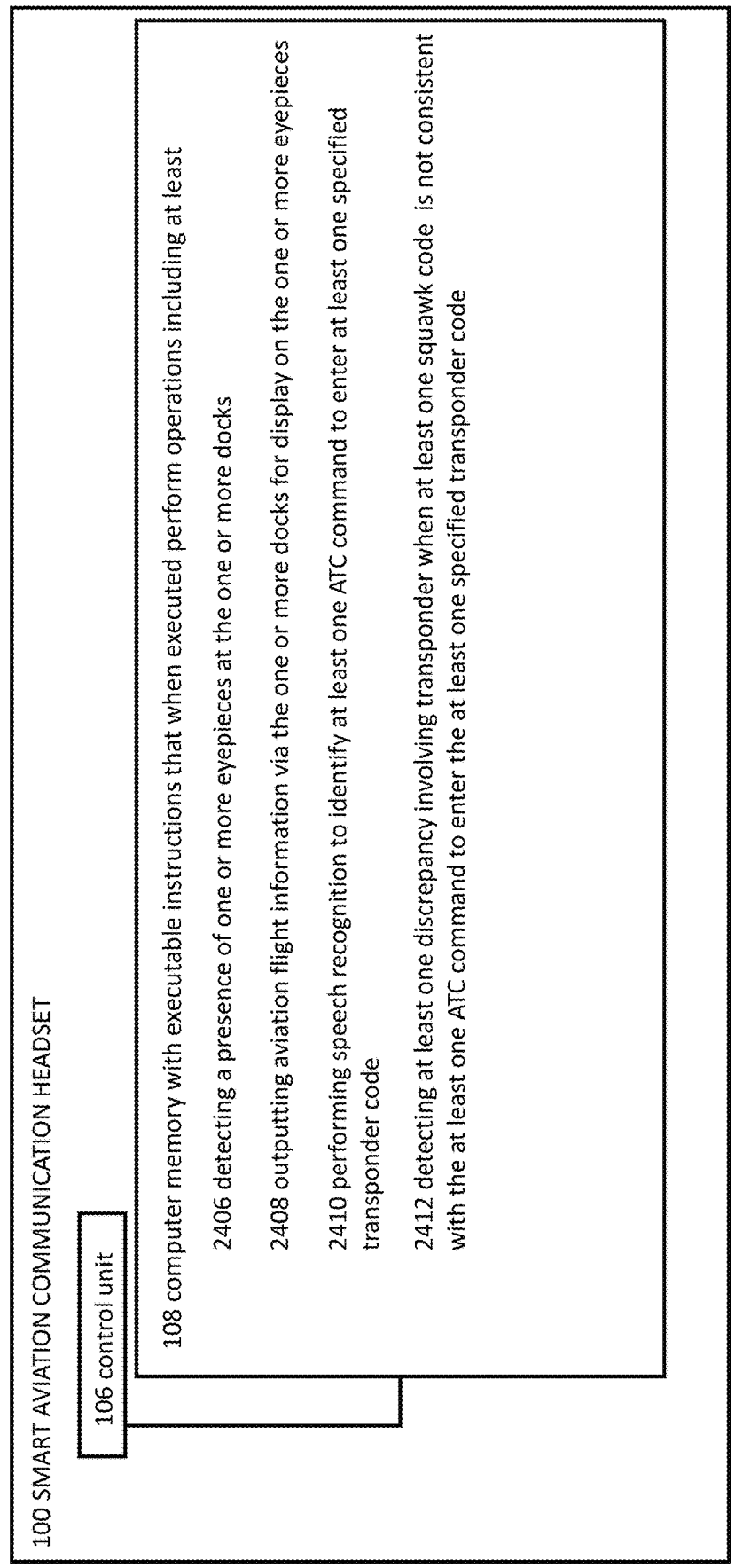

FIG. 24 is a system diagram of a smart aviation communication headset 100, in accordance with an embodiment of the invention. In one embodiment, an aviation communication headset 100 includes, but is not limited to, at least one microphone 114; one or more speakers 112; one or more docks 123 configured to interface with one or more eyepieces 120/121; and at least one control unit 106 configured by one or more executable instructions stored on computer memory 108 to perform operations including at least: detecting a presence of one or more eyepieces at the one or more docks at 2406; outputting aviation flight information via the one or more docks for display on the one or more eyepieces at 2408; performing speech recognition to identify at least one ATC command to enter at least one specified transponder code at 2410; and detecting at least one discrepancy involving transponder when at least one squawk code is not consistent with the at least one ATC command to enter the at least one specified transponder code at 2412. For instance, upon recognition and determined applicability of an ATC command to squawk 6312, the processor can determine using the flight information of the synthetic vision goggles whether the transponder has been switched to the appropriate code of 6312. If an ident request is made, the processor can further determine whether the ident indication has been activated. In the event not, the transponder can be autotuned to 6312 and the ident request satisfied.

Note that in FIGS. 18-24, a camera of the aviation communication headset or the synthetic vision goggles can be used to scan the instruments of the aircraft, such as the panel mounted instruments. The instruments may be digital or analog and the values can be monitored to determine whether or not compliance with an ATC command is satisfied.

Figure 25:
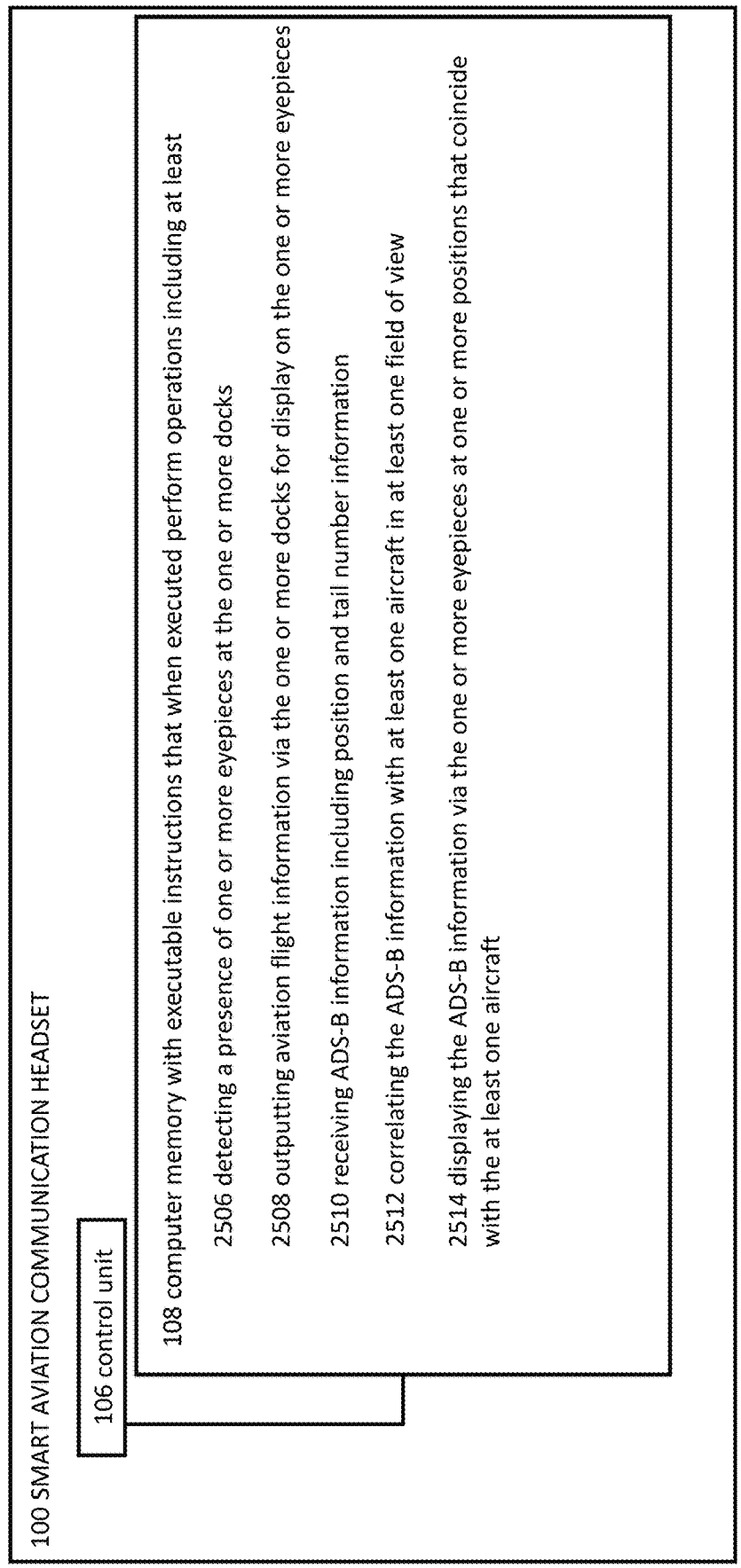

FIG. 25 is a system diagram of a smart aviation communication headset 100, in accordance with an embodiment of the invention. In one embodiment, an aviation communication headset 100 includes, but is not limited to, at least one microphone 114; one or more speakers 112; one or more docks 123 configured to interface with one or more eyepieces 120/121; and at least one control unit 106 configured by one or more executable instructions stored on computer memory 108 to perform operations including at least: detecting a presence of one or more eyepieces at the one or more docks at 2506; outputting aviation flight information via the one or more docks for display on the one or more eyepieces at 2508; receiving ADS-B information including position and tail number information at 2510; correlating the ADS-B information with at least one aircraft in at least one field of view at 2512; and displaying the ADS-B information via the one or more eyepieces at one or more positions that coincide with the at least one aircraft at 2514. The synthetic vision goggles are operable to display a synthetic view of reality, including representations of aircraft within the apparent field of view of the synthetic vision goggles. A processor associated with the headset or the synthetic vision goggles receives ADS-B information including tail number and position information for aircraft in the vicinity. The tail number and position information are then displayed within the synthetic vision goggles at a position that corresponds to the actual position in reality of the aircraft.

Figure 26:
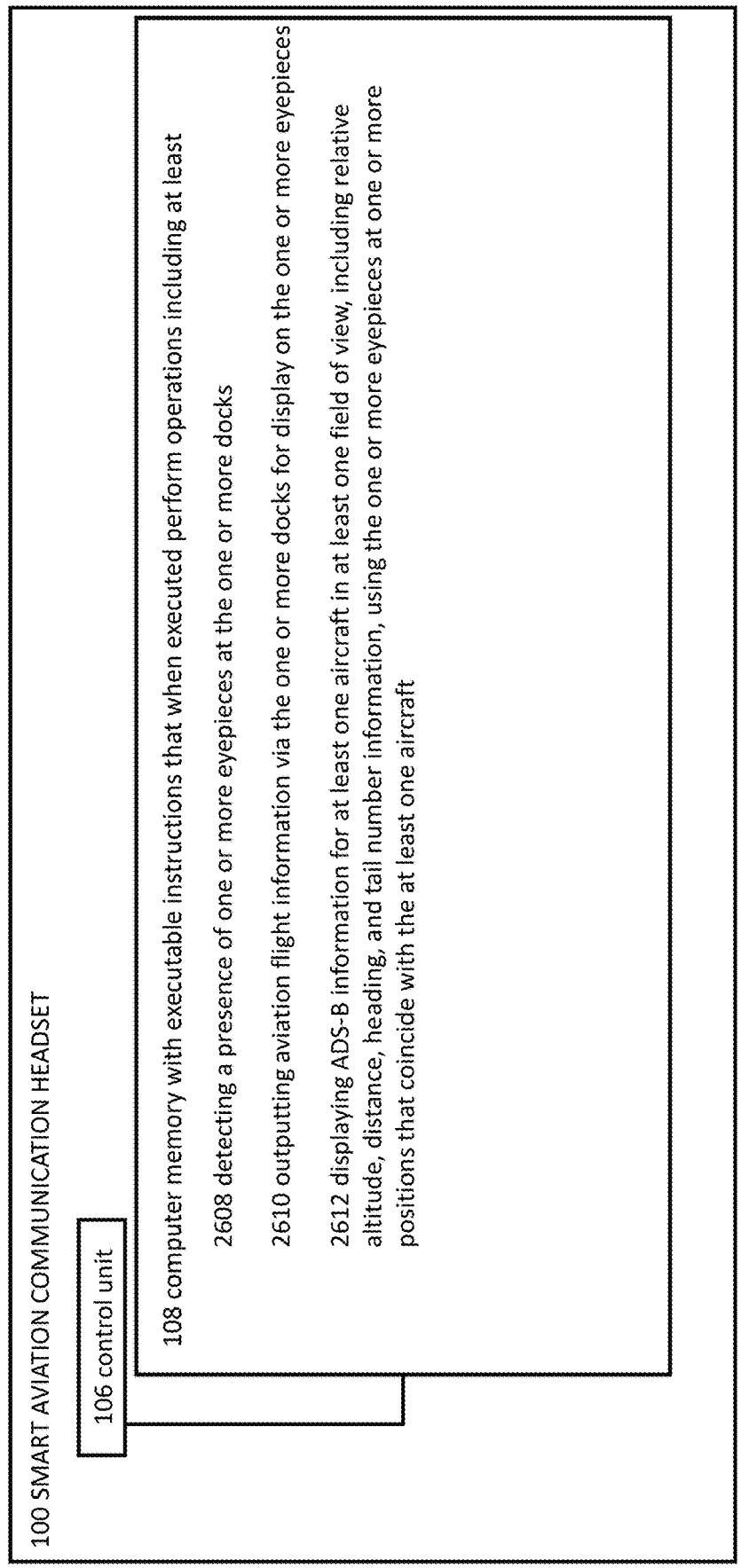

FIG. 26 is a system diagram of a smart aviation communication headset 100, in accordance with an embodiment of the invention. In one embodiment, an aviation communication headset 100 includes, but is not limited to, at least one microphone 114; one or more speakers 112; one or more docks 123 configured to interface with one or more eyepieces 120/121; and at least one control unit 106 configured by one or more executable instructions stored on computer memory 108 to perform operations including at least: detecting a presence of one or more eyepieces at the one or more docks at 2608; outputting aviation flight information via the one or more docks for display on the one or more eyepieces at 2610; and displaying ADS-B information for at least one aircraft in at least one field of view, including relative altitude, distance, heading, and tail number information, using the one or more eyepieces at one or more positions that coincide with the at least one aircraft at 2612. For example, the synthetic vision goggles can display at a position in the synthetic vision that corresponds to an actual location or position of an aircraft in reality, the tail number and altitude the aircraft as well as direction of flight or distance away information for the aircraft.

Figure 27:
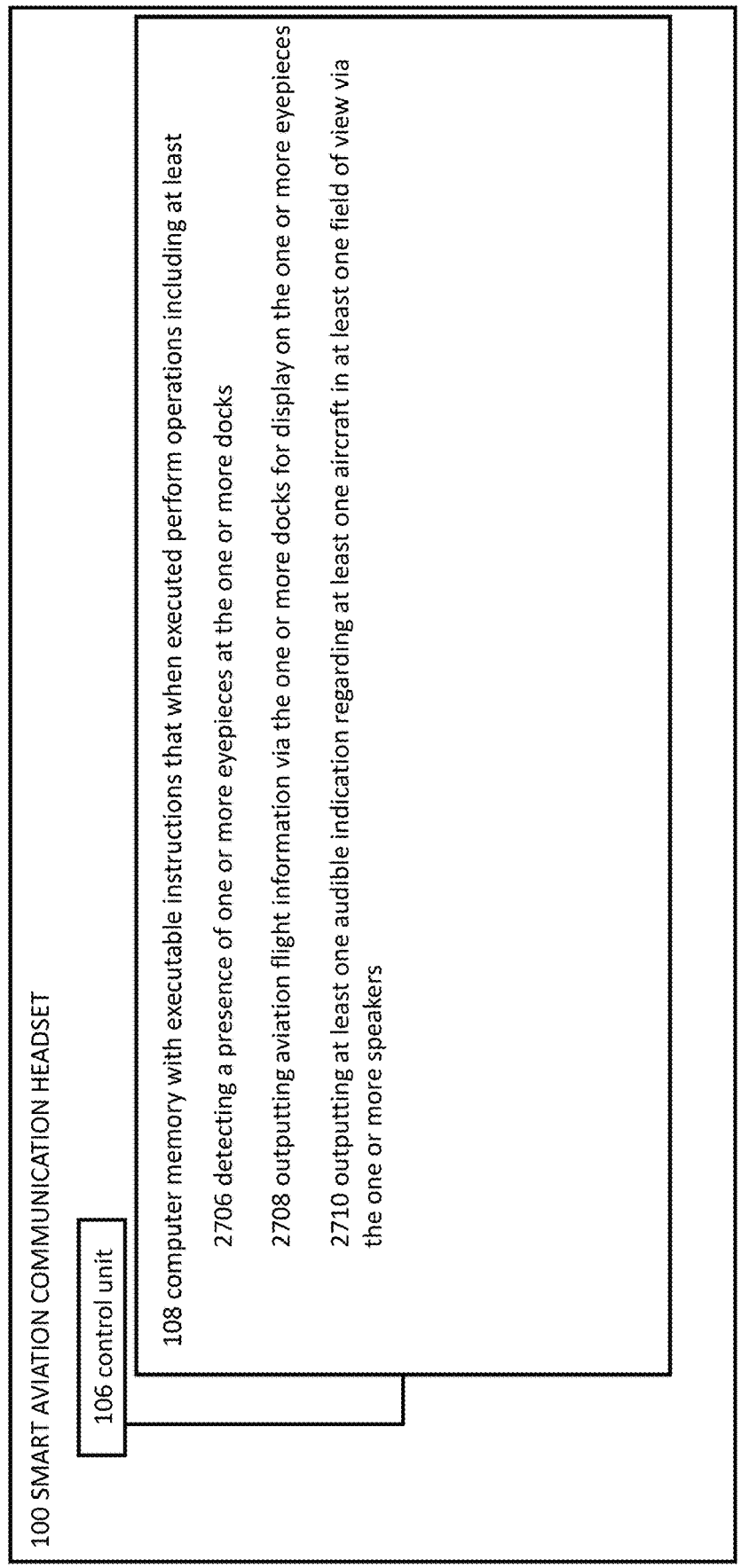

FIG. 27 is a system diagram of a smart aviation communication headset 100, in accordance with an embodiment of the invention. In one embodiment, an aviation communication headset 100 includes, but is not limited to, at least one microphone 114; one or more speakers 112; one or more docks 123 configured to interface with one or more eyepieces 120/121; and at least one control unit 106 configured by one or more executable instructions stored on computer memory 108 to perform operations including at least: detecting a presence of one or more eyepieces at the one or more docks at 2706; outputting aviation flight information via the one or more docks for display on the one or more eyepieces at 2708; and outputting at least one audible indication regarding at least one aircraft in at least one field of view via the one or more speakers at 2710. For example, a processor can obtain information from a camera associated with the headset or synthetic vision goggles regarding aircraft within the field of view. The camera can include very high resolution image capture capabilities to enable discrimination of aircraft that are difficult to see with the naked eye. Upon detecting an aircraft within the field of view, an audible indication can be provided via the speakers of the aviation communication headset. For example, if a plane is detected by the camera, the speakers can state a warning that there exists an aircraft at 2 o'clock, five miles, opposite direction, 500 feet below. This information can further or alternatively be displayed via the synthetic vision goggles.

Figure 28:
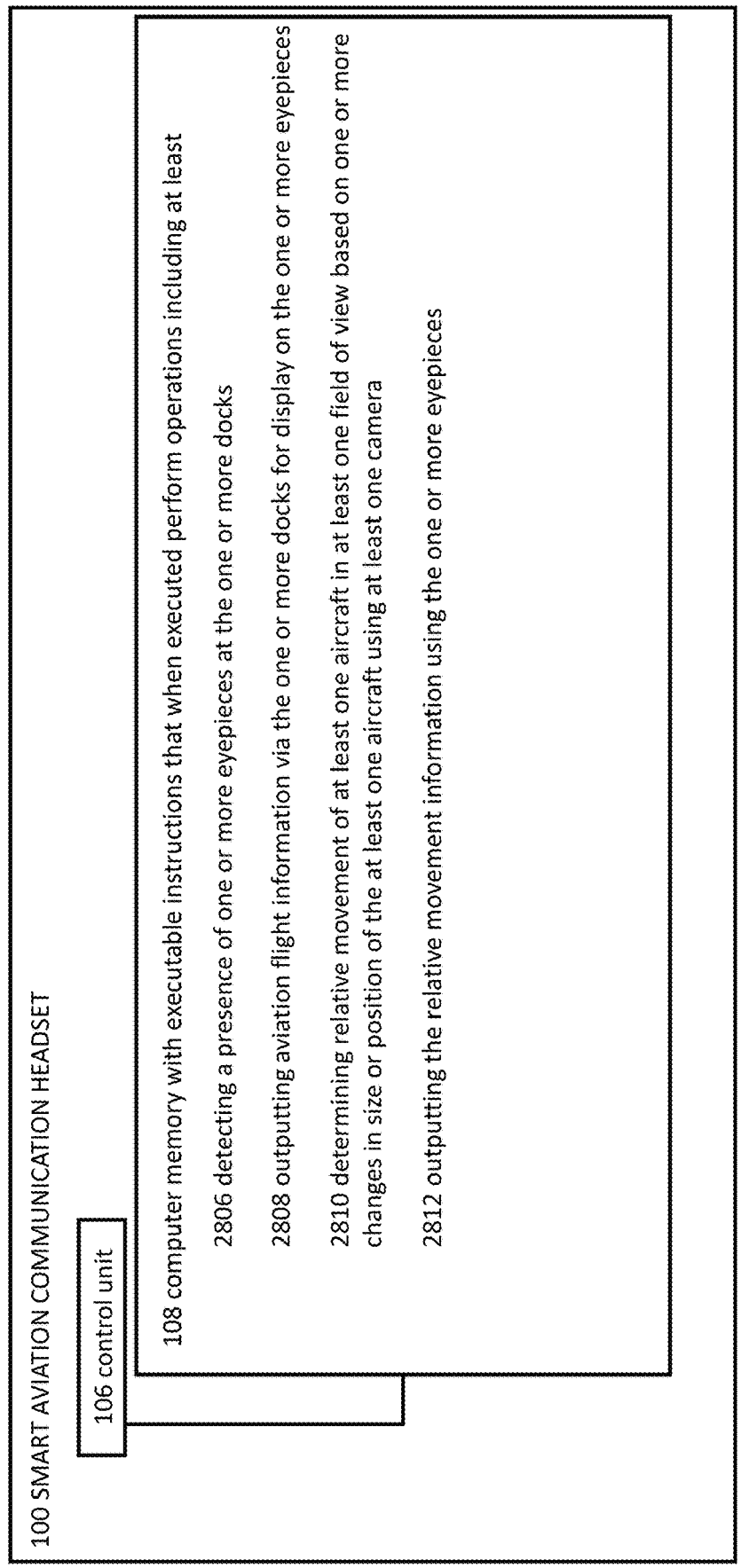

FIG. 28 is a system diagram of a smart aviation communication headset 100, in accordance with an embodiment of the invention. In one embodiment, an aviation communication headset 100 includes, but is not limited to, at least one microphone 114; one or more speakers 112; one or more docks 123 configured to interface with one or more eyepieces 120/121; and at least one control unit 106 configured by one or more executable instructions stored on computer memory 108 to perform operations including at least: detecting a presence of one or more eyepieces at the one or more docks at 2806; outputting aviation flight information via the one or more docks for display on the one or more eyepieces at 2808; determining relative movement of at least one aircraft in at least one field of view based on one or more changes in size or position of the at least one aircraft using at least one camera at 2810; and outputting the relative movement information using the one or more eyepieces at 2812. For example, a camera on the synthetic vision goggles can be used to detect movement from left to right or right to left or up or down in combination with increases or decreases in size. The processor can then use this information to determine the distance, direction, and speed of the aircraft and then output the information for display on the synthetic vision goggles. Thus, ADS-B information can be supplemented with visual field information that is actually detected using the camera. Further the ADS-B information can be confirmed against what is actually detected. The camera can include both normal spectrum and infrared spectrum detection capabilities to permit other aircraft to be identified during either VMC or IMC conditions.

Figure 29:
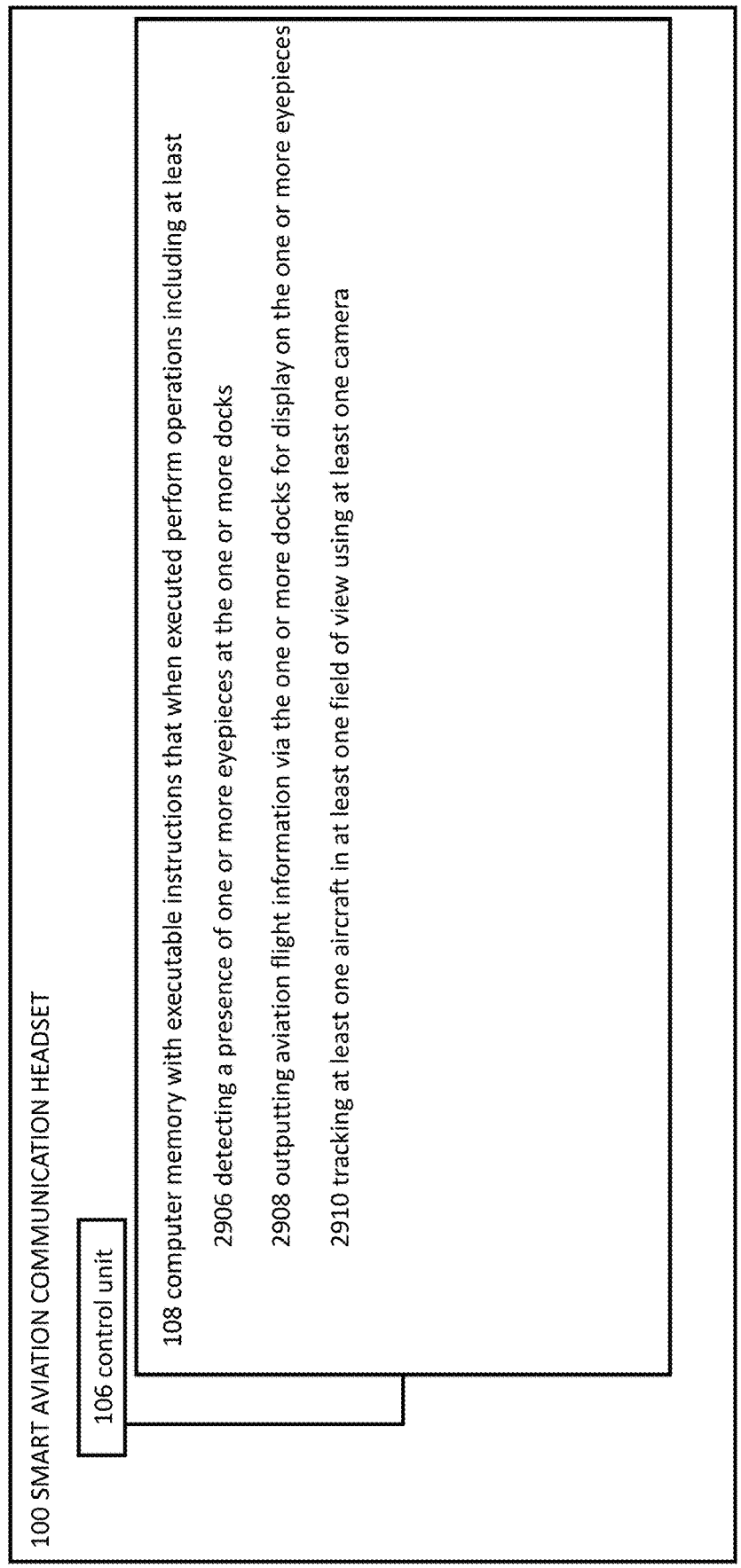

FIG. 29 is a system diagram of a smart aviation communication headset 100, in accordance with an embodiment of the invention. In one embodiment, an aviation communication headset 100 includes, but is not limited to, at least one microphone 114; one or more speakers 112; one or more docks 123 configured to interface with one or more eyepieces 120/121; and at least one control unit 106 configured by one or more executable instructions stored on computer memory 108 to perform operations including at least: detecting a presence of one or more eyepieces at the one or more docks at 2906; outputting aviation flight information via the one or more docks for display on the one or more eyepieces at 2908; and tracking at least one aircraft in at least one field of view using at least one camera at 2910. The processor can use the information from the camera of the headset or synthetic vision goggles to monitor and track movement of aircraft in reality while the synthetic vision headset is being worn. The tracked movement of any aircraft can be displayed using the synthetic vision goggles.

Figure 30:
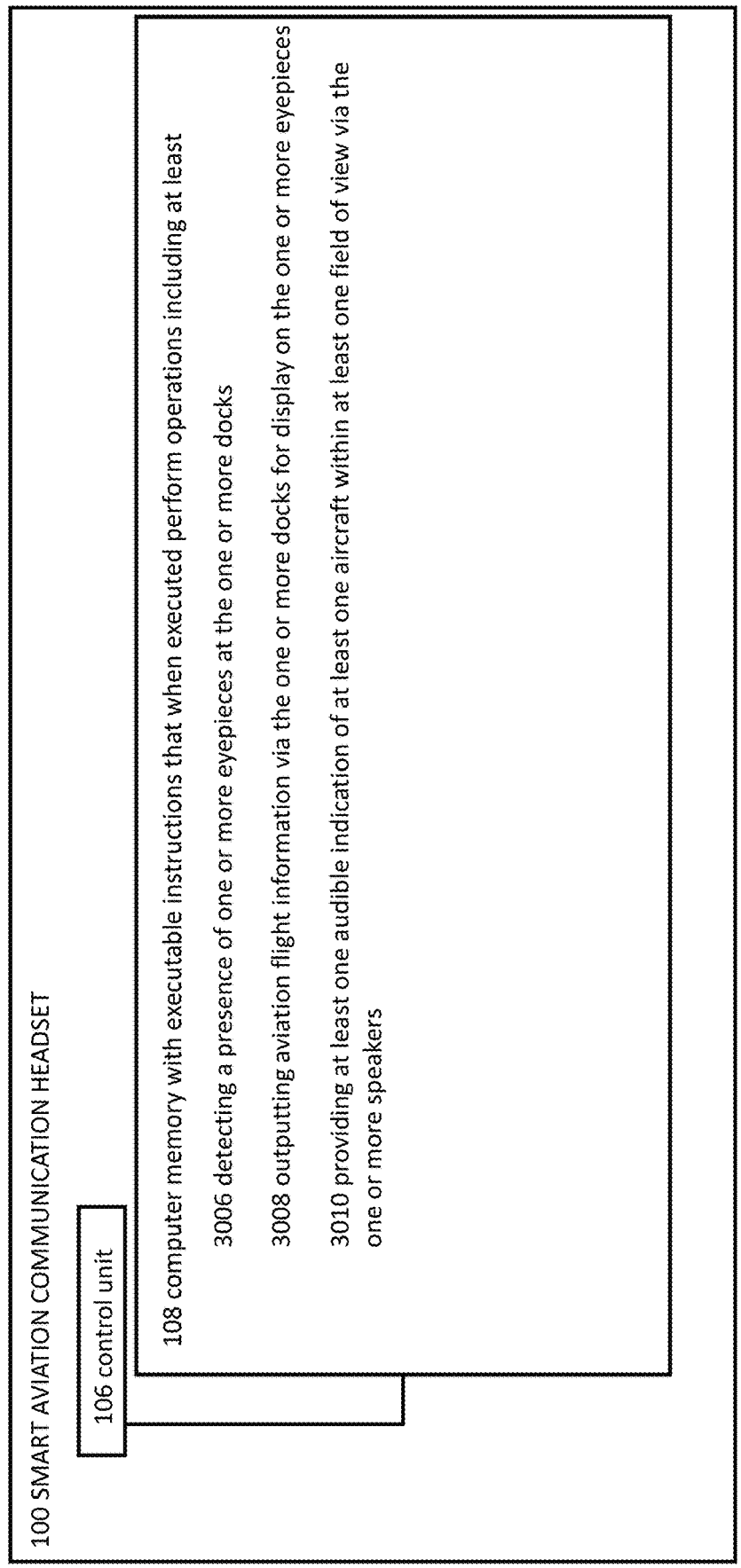

FIG. 30 is a system diagram of a smart aviation communication headset 100, in accordance with an embodiment of the invention. In one embodiment, an aviation communication headset 100 includes, but is not limited to, at least one microphone 114; one or more speakers 112; one or more docks 123 configured to interface with one or more eyepieces 120/121; and at least one control unit 106 configured by one or more executable instructions stored on computer memory 108 to perform operations including at least: detecting a presence of one or more eyepieces at the one or more docks at 3006; outputting aviation flight information via the one or more docks for display on the one or more eyepieces at 3008; and providing at least one audible indication of at least one aircraft within at least one field of view via the one or more speakers at 3010. The audible indication can include output via the speakers of the aviation communication headset that there exists an aircraft within the field of view. A specified distance or direction or altitude threshold can be defined, which then is used to filter out notifications for only those aircraft that satisfy the conditions specified.

Figure 31:
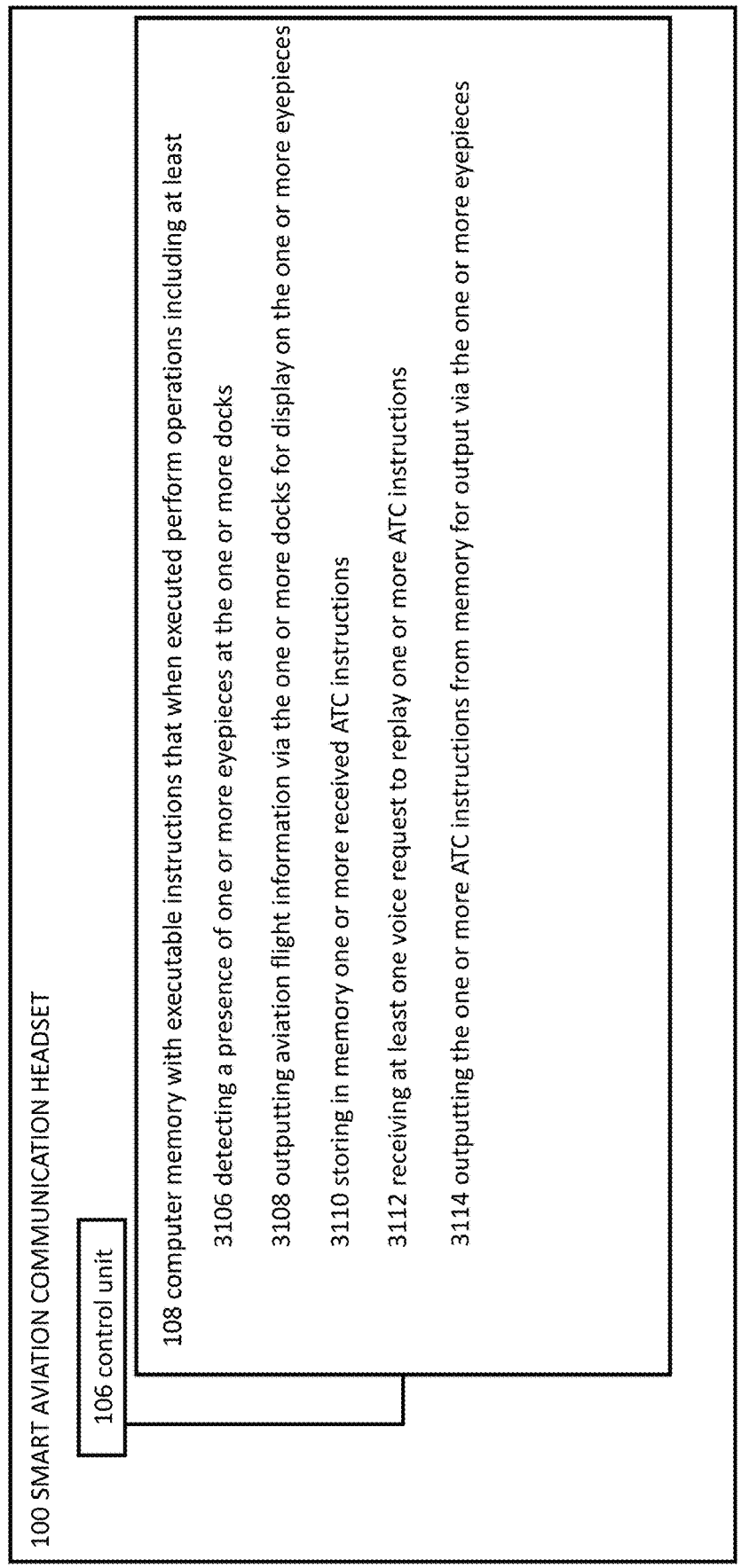

FIG. 31 is a system diagram of a smart aviation communication headset 100, in accordance with an embodiment of the invention. In one embodiment, an aviation communication headset 100 includes, but is not limited to, at least one microphone 114; one or more speakers 112; one or more docks 123 configured to interface with one or more eyepieces 120/121; and at least one control unit 106 configured by one or more executable instructions stored on computer memory 108 to perform operations including at least: detecting a presence of one or more eyepieces at the one or more docks at 3106; outputting aviation flight information via the one or more docks for display on the one or more eyepieces at 3108; storing in memory one or more received ATC instructions at 3110; receiving at least one voice request to replay one or more ATC instructions at 3112; and outputting the one or more ATC instructions from memory for output via the one or more eyepieces 3114. For example, ATC communication may be received to descend to 3500 feet and reset transponder to 6464 and contact Center on 125.7. This audio can be stored in memory and then recalled by speaking into the microphone of the aviation communication headset. For instance, a command of 'AITHRE play back ATC'. Upon receiving this command, the processor component of the aviation communication headset or the synthetic vision goggles can obtain the last ATC instruction from memory and output the instruction as visual text information or as indicators such as flashing heading bugs via the synthetic vision goggles. Optionally, the ATC command may also be output audibly via the speakers of the aviation communication headset.

Figure 32:
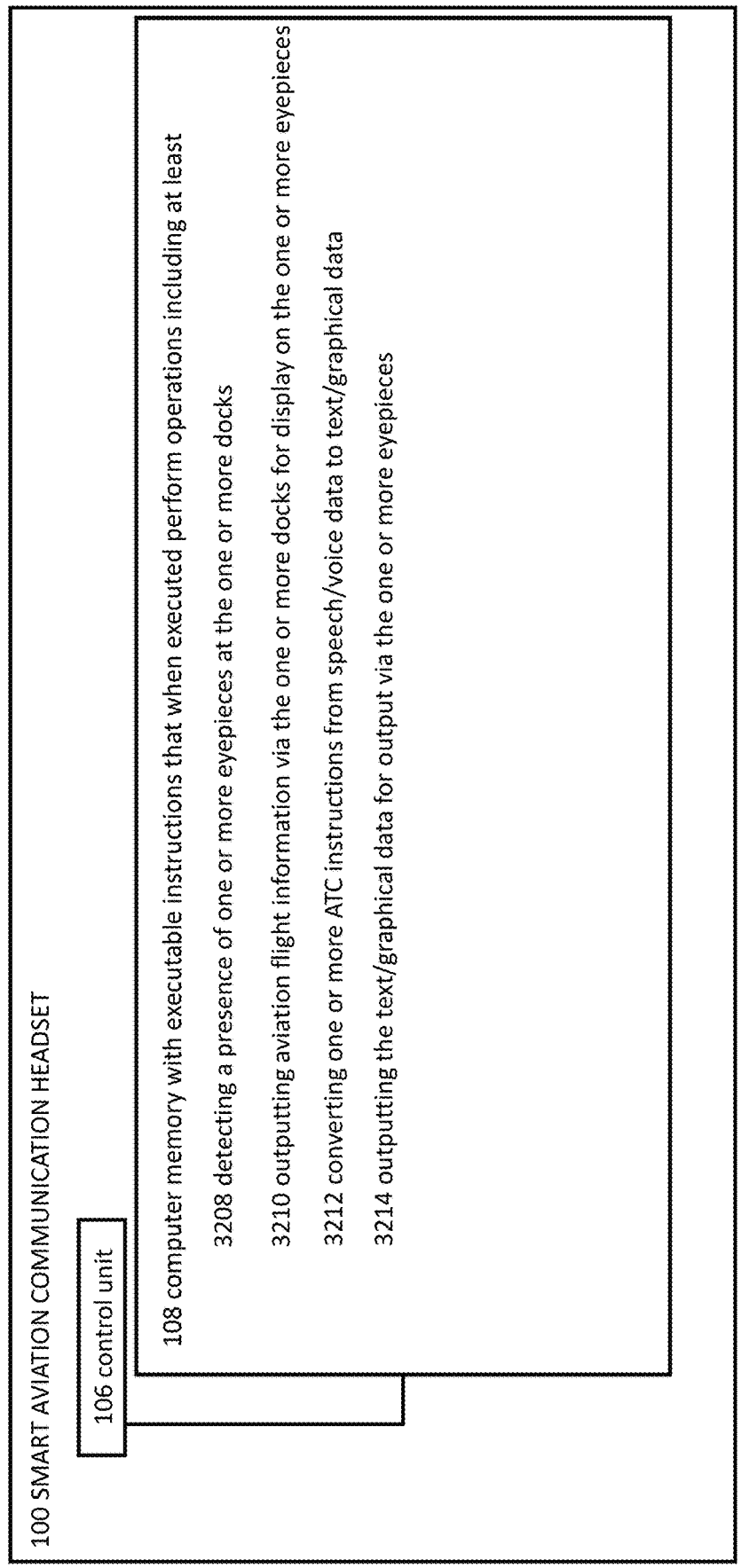

FIG. 32 is a system diagram of a smart aviation communication headset 100, in accordance with an embodiment of the invention. In one embodiment, an aviation communication headset 100 includes, but is not limited to, at least one microphone 114; one or more speakers 112; one or more docks 123 configured to interface with one or more eyepieces 120/121; and at least one control unit 106 configured by one or more executable instructions stored on computer memory 108 to perform operations including at least: detecting a presence of one or more eyepieces at the one or more docks at 3208; outputting aviation flight information via the one or more docks for display on the one or more eyepieces at 3210; converting one or more ATC instructions from speech/voice data to text/graphical data at 3212; and outputting the text/graphical data for output via the one or more eyepieces at 3214. For example, ATC communication can be received by the aviation communication headset to proceed direct to the ZOLGI fix and maintain 4000. The ATC instruction can be stored in memory and then recalled via the microphone of the aviation communication headset with a playback request. Upon receiving the playback request, the processor component of the aviation communication headset or the synthetic vision goggles the obtains the ATC instruction from memory and coverts the instruction to visual data that is output via the synthetic vision goggles. For instance, the digital HSI indicator can display relative to the ZOLGI fix and the altitude bug can flash or pulse at 4000 feet MSL.

Figure 33:
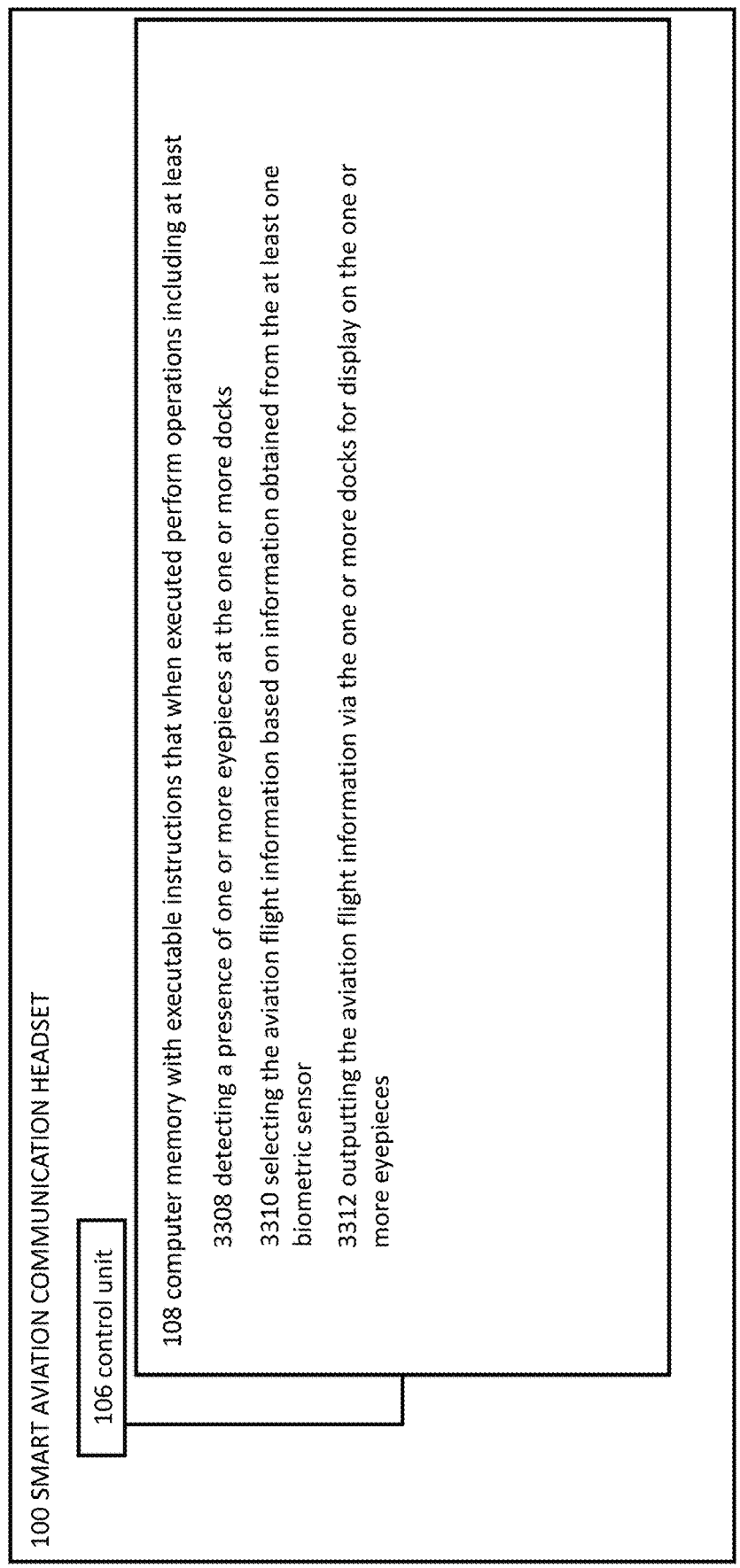

FIG. 33 is a system diagram of a smart aviation communication headset 100, in accordance with an embodiment of the invention. In one embodiment, an aviation communication headset 100 includes, but is not limited to, at least one microphone 114; one or more speakers 112; one or more docks 123 configured to interface with one or more eyepieces 120/121; and at least one control unit 106 configured by one or more executable instructions stored on computer memory 108 to perform operations including at least: detecting a presence of one or more eyepieces at the one or more docks at 3308; selecting the aviation flight information based on information obtained from the at least one biometric sensor at 3310; and outputting the aviation flight information via the one or more docks for display on the one or more eyepieces at 3312. Different individuals may use or share the synthetic vision goggles. For example, in a flight training environment there may be many different students that can dock the synthetic vision goggles. Additionally, in a commercial flight environment, the synthetic vision goggles may stay with the plane as different pilots transition between flights. Furthermore, in a pilot or co-pilot situation there may be sharing of the synthetic vision goggles. The synthetic vision goggles include a biometric sensor that detects fingerprint or iris information to identify the wearer. Upon identifying the wearer the settings for that particular individual can be loaded and assumed in the synthetic vision environment. For instance, a pilot may be a VFR only pilot so the processor component can remove any IFR related information that may be unnecessary or confusing to the pilot, such as HIS, approach or departure procedure information, or glideslope information. Alternatively, a passenger may not be a pilot and the processor can tune the settings of the synthetic vision goggles to provide interesting non-flight information about towns, airports, or other features of interest.

Figure 34:
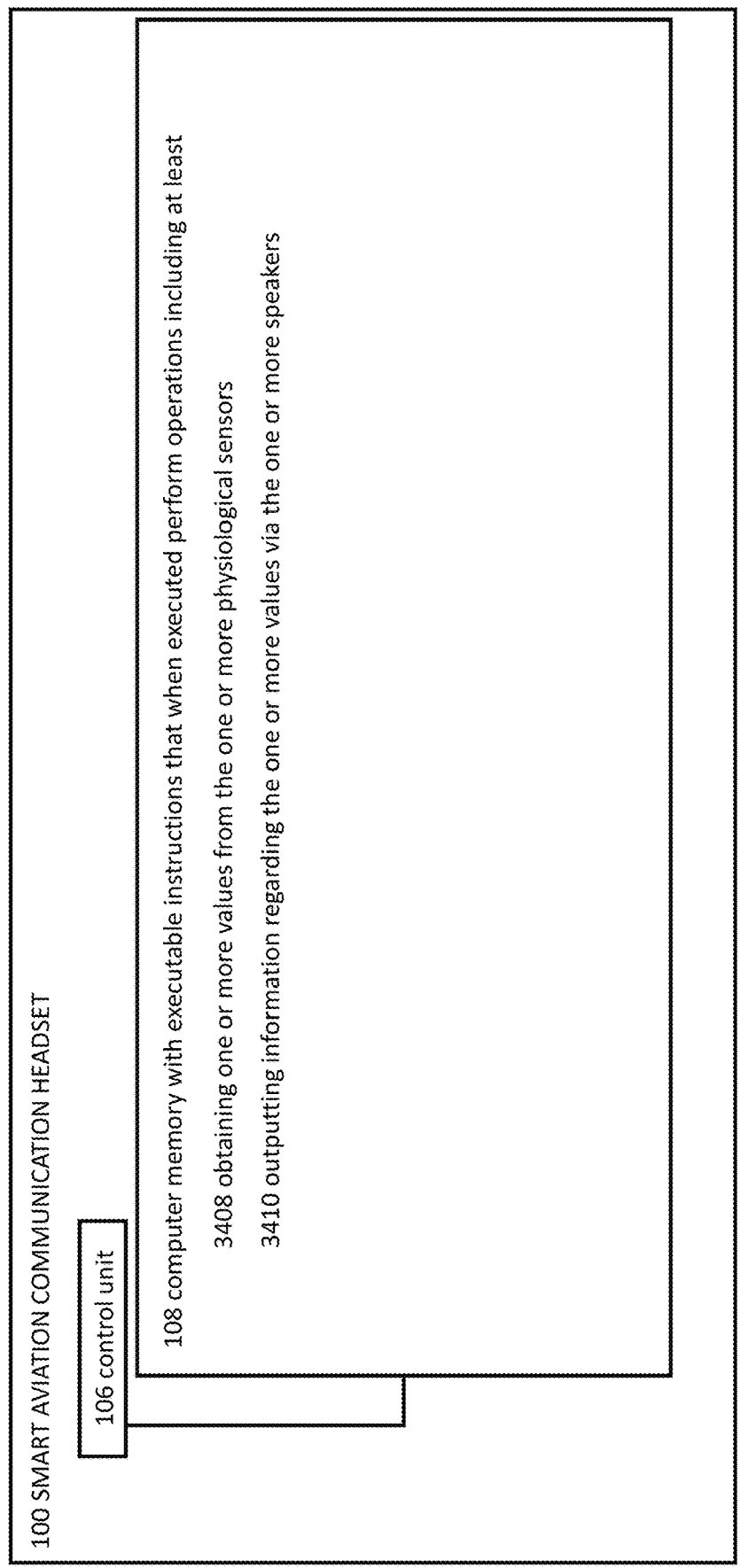

FIG. 34 is a system diagram of a smart aviation communication headset 100, in accordance with an embodiment of the invention. In one embodiment, an aviation communication headset 100 includes, but is not limited to, at least one microphone 114; one or more speakers 112; one or more physiological sensors 118; and at least one control unit 106 configured by one or more executable instructions stored on computer memory 108 to perform operations including at least: obtaining one or more values from the one or more physiological sensors; and outputting information regarding the one or more values via the one or more speakers. The one or more physiological sensors 118 can include a blood oxygen level sensor; a pulse rate sensor; a temperature sensor; a perspiration sensor; chemical sensor; or a coloration sensor. The one or more physiological sensors 118 can be incorporated on any of a headband, ear cushion, or within an ear cup of the headset. An earlobe receptacle may be incorporated within an ear cup of the headset, wherein the one or more physiological sensors are included within the earlobe receptacle for obtaining one or more physiological measurements from an earlobe of an individual when the headset is being worn. The earlobe receptacle may be movable. For instance, the physiological sensor may monitor blood oxygen level by emitting an alternating red and infrared light and determining an intensity of absorbed or reflected light. The blood oxygen level can then be audibly output via the speakers of the aviation communication headset, such as outputting that your blood oxygen level is good or normal.

Figure 35:
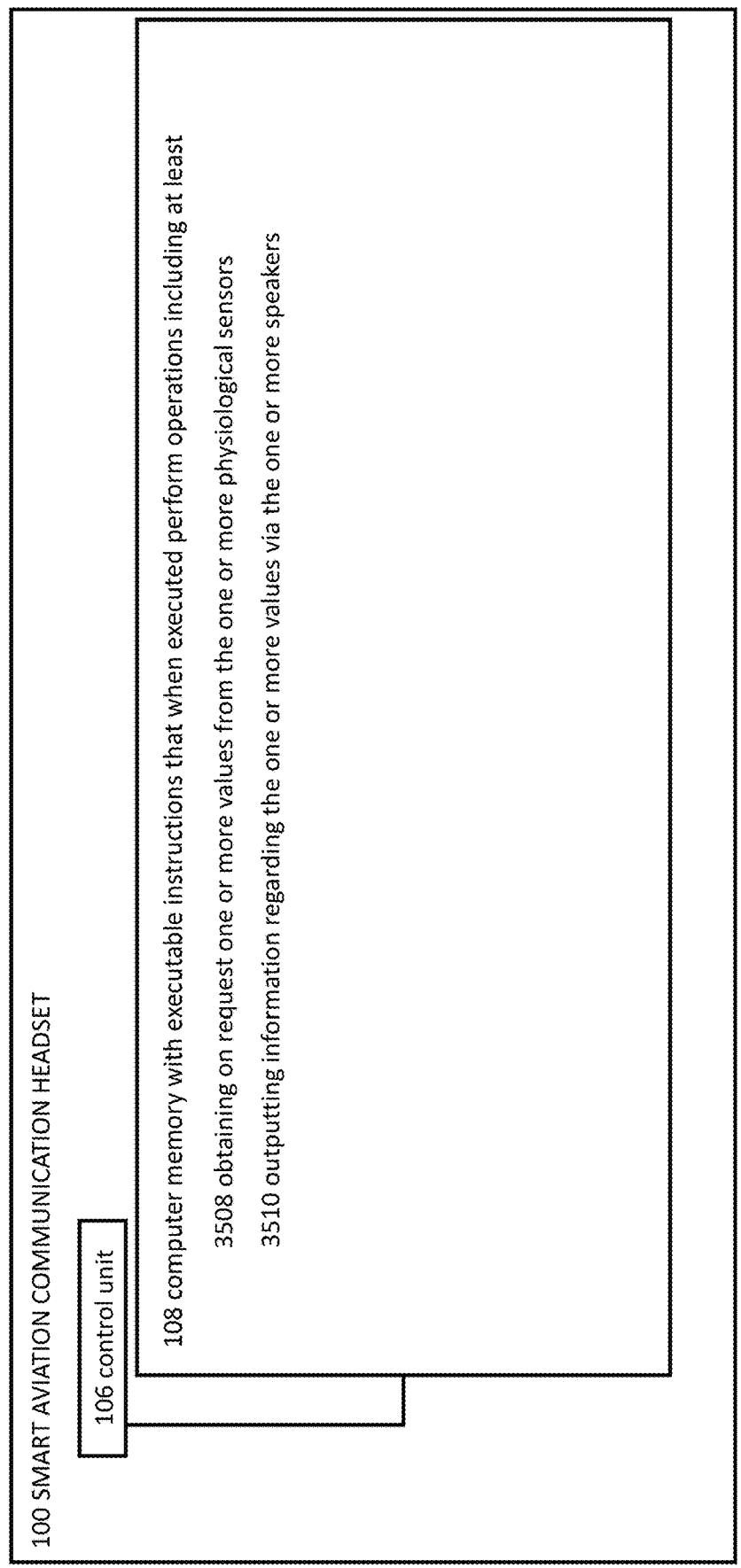

FIG. 35 is a system diagram of a smart aviation communication headset 100, in accordance with an embodiment of the invention. In one embodiment, an aviation communication headset 100 includes, but is not limited to, at least one microphone 114; one or more speakers 112; one or more physiological sensors 118; and at least one control unit 106 configured by one or more executable instructions stored on computer memory 108 to perform operations including at least: obtaining on request one or more values from the one or more physiological sensors at 3508; and outputting information regarding the one or more values via the one or more speakers at 3510. For example, a speech request can be received by the processor component via the microphone of the aviation communication headset for an update on a panel of health parameters. Upon receiving the speech request, the processor can obtain from memory or in real-time from the physiological sensor information to satisfy the request. The panel of health information can then be output via the speakers of the aviation communication headset. For instance, audible information can be output via the speakers regarding the blood pressure, heart rate, blood oxygen level, and carbon monoxide information.

Figure 36:
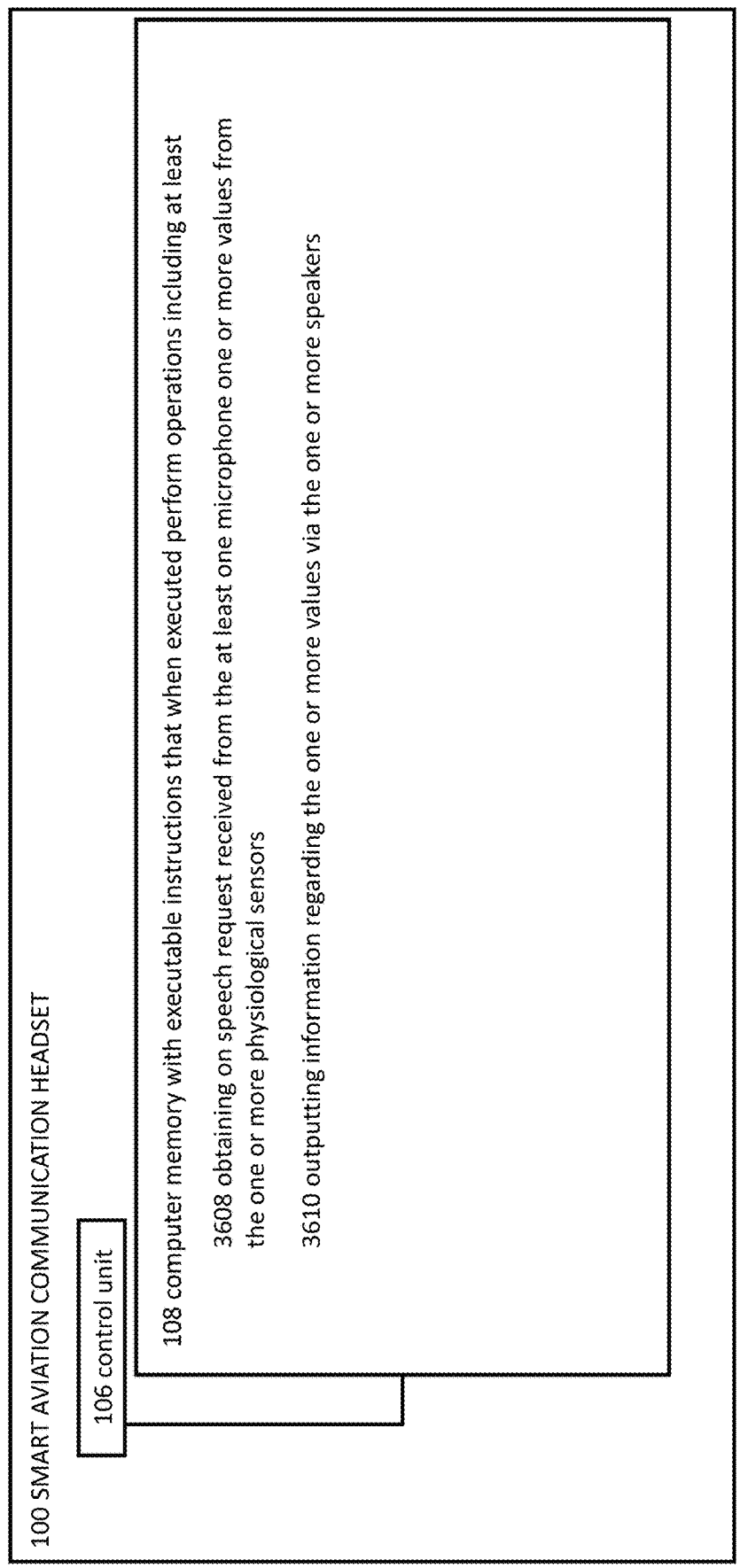

FIG. 36 is a system diagram of a smart aviation communication headset 100, in accordance with an embodiment of the invention. In one embodiment, an aviation communication headset 100 includes, but is not limited to, at least one microphone 114; one or more speakers 112; one or more physiological sensors 118; and at least one control unit 106 configured by one or more executable instructions stored on computer memory 108 to perform operations including at least: obtaining on speech request received from the at least one microphone one or more values from the one or more physiological sensors at 3608; and outputting information regarding the one or more values via the one or more speakers at 3610. For example, the processor can obtain a speech command from the microphone of the aviation communication headset such as "AITHRE tell me my pulse and blood pressure". The processor can use the physiological sensor to obtain the pulse and blood pressure information and then output the values audibly via the speakers of the aviation communication headset.

Figure 37:
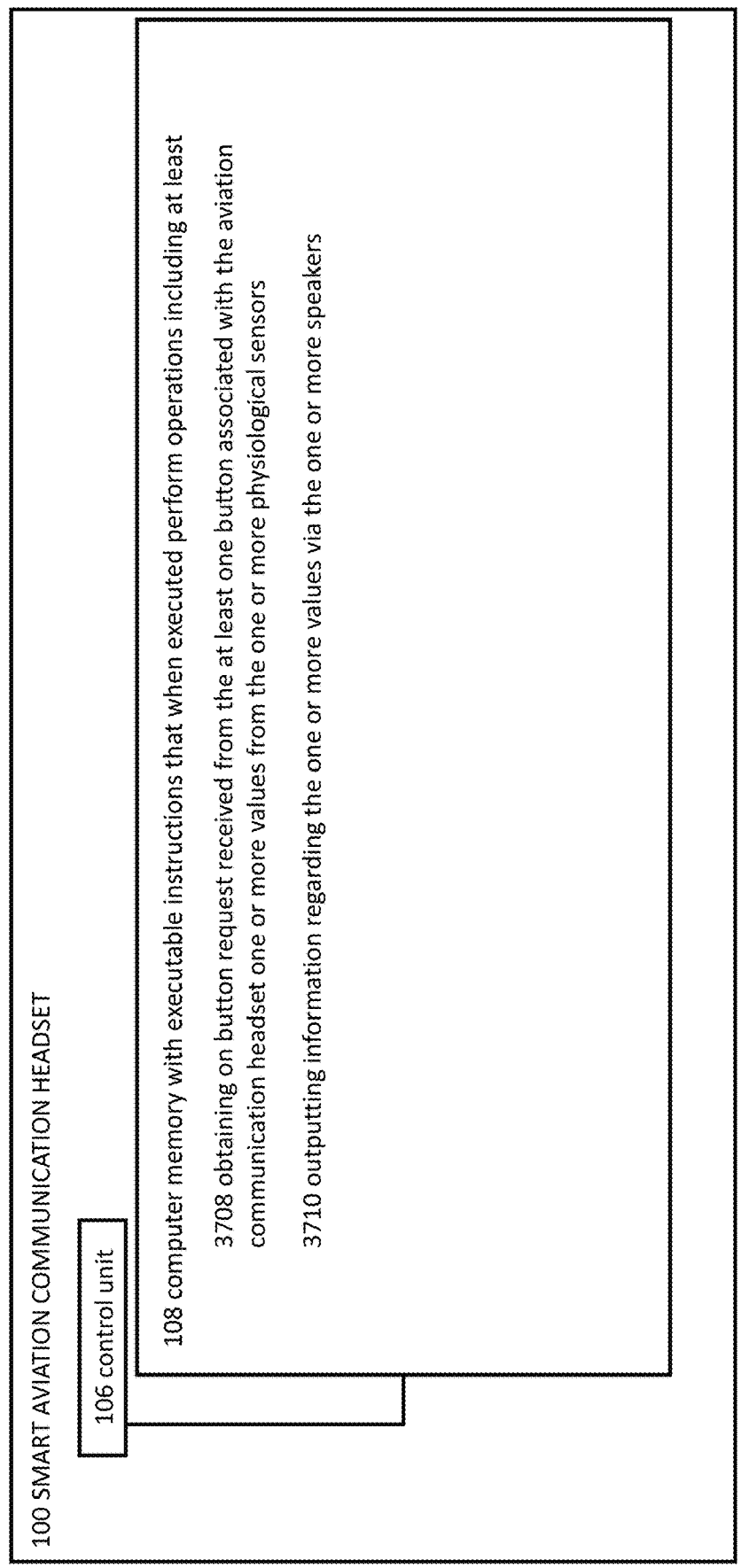

FIG. 37 is a system diagram of a smart aviation communication headset 100, in accordance with an embodiment of the invention. In one embodiment, an aviation communication headset 100 includes, but is not limited to, at least one microphone 114; one or more speakers 112; one or more physiological sensors 118; and at least one control unit 106 configured by one or more executable instructions stored on computer memory 108 to perform operations including at least: obtaining on button request received from the at least one button associated with the aviation communication headset one or more values from the one or more physiological sensors at 3708; and outputting information regarding the one or more values via the one or more speakers at 3710. For instance, the processor component can detect that a button on the earcup of the headset has been depressed. Upon detecting the button press, the processor component can signal and output information via the speakers regarding the health parameters.

Figure 38:
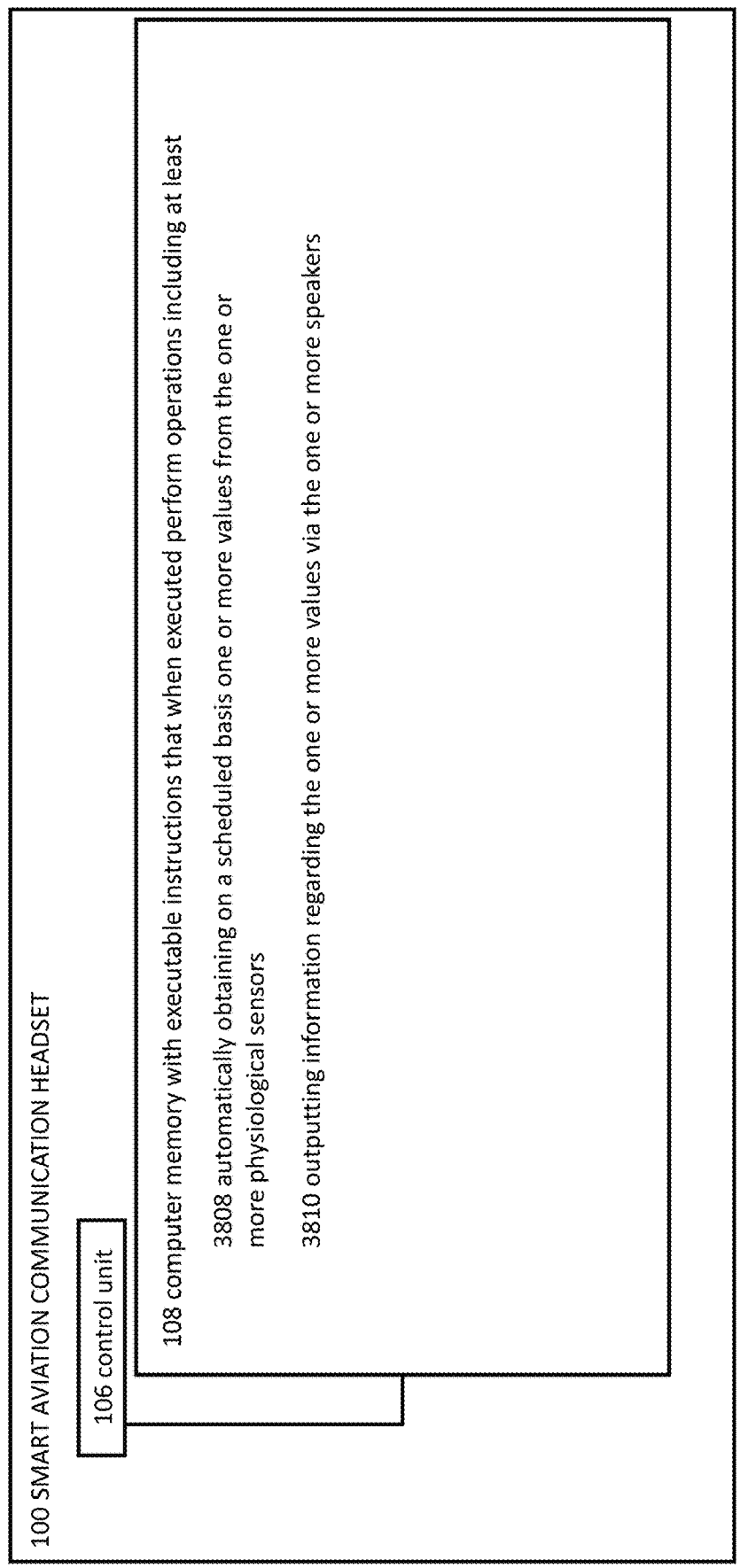

FIG. 38 is a system diagram of a smart aviation communication headset 100, in accordance with an embodiment of the invention. In one embodiment, an aviation communication headset 100 includes, but is not limited to, at least one microphone 114; one or more speakers 112; one or more physiological sensors 118; and at least one control unit 106 configured by one or more executable instructions stored on computer memory 108 to perform operations including at least: automatically obtaining on a scheduled basis one or more values from the one or more physiological sensors at 3808; and outputting information regarding the one or more values via the one or more speakers at 3810. The processor component can intermittently determine the value of one or more health parameters, such as breathing rate, skin coloration, or hearing levels, and output information on the one or more health parameters via the speakers of the aviation communication headset. The intervals of monitoring can be user defined or default values and may increase or decrease automatically. For instance, the interval may begin at every 5 minutes, but shorten to every minute in an event of a health parameters being outside a defined or specified normal range.

Figure 39:
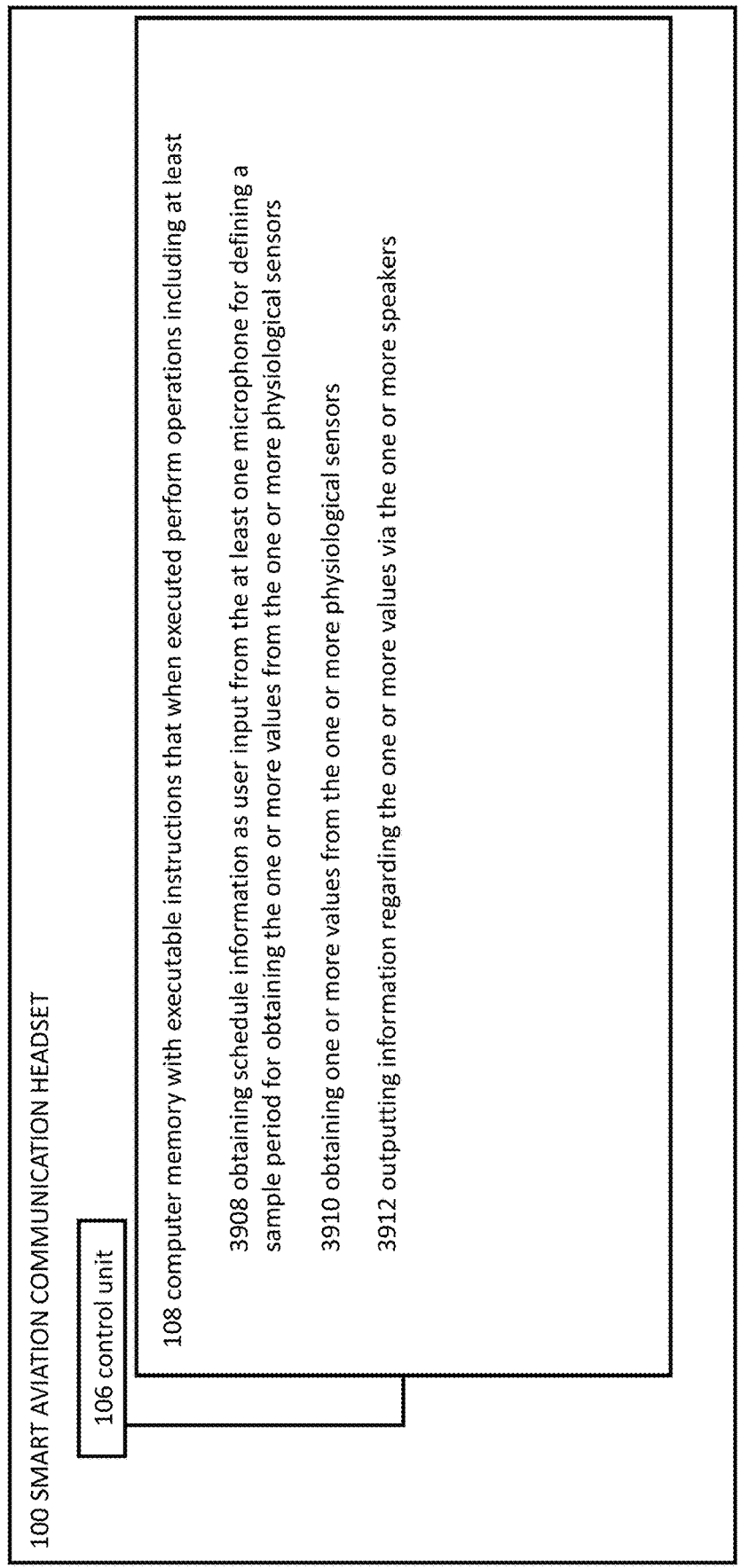

FIG. 39 is a system diagram of a smart aviation communication headset 100, in accordance with an embodiment of the invention. In one embodiment, an aviation communication headset 100 includes, but is not limited to, at least one microphone 114; one or more speakers 112; one or more physiological sensors 118; and at least one control unit 106 configured by one or more executable instructions stored on computer memory 108 to perform operations including at least: obtaining schedule information as user input from the at least one microphone for defining a sample period for obtaining the one or more values from the one or more physiological sensors at 3908; obtaining one or more values from the one or more physiological sensors at 3910; and outputting information regarding the one or more values via the one or more speakers and 3912. For example, a processor component can detect a speech command such as "AITHRE output carbon monoxide and blood oxygen levels above 10000 feet and every minute." The processor component can then establish those parameters and output the blood oxygen and carbon monoxide levels beginning at 10000 feet every minute via the speakers of the aviation communication headset.

Figure 40:
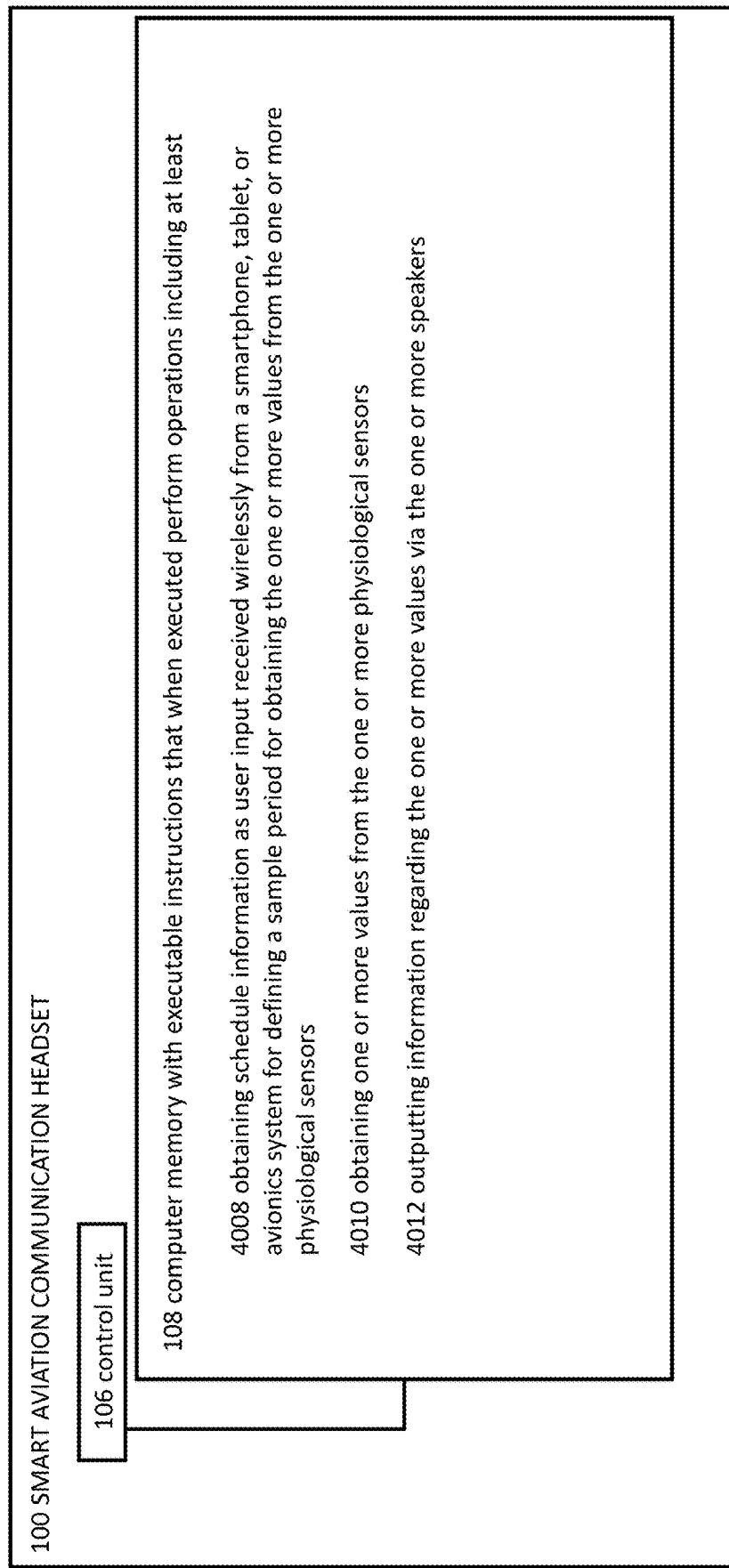

FIG. 40 is a system diagram of a smart aviation communication headset 100, in accordance with an embodiment of the invention. In one embodiment, an aviation communication headset 100 includes, but is not limited to, at least one microphone 114; one or more speakers 112; one or more physiological sensors 118; and at least one control unit 106 configured by one or more executable instructions stored on computer memory 108 to perform operations including at least: obtaining schedule information as user input received wirelessly from a smartphone, tablet, or avionics system for defining a sample period for obtaining the one or more values from the one or more physiological sensors at 4008; obtaining one or more values from the one or more physiological sensors at 4010; and outputting information regarding the one or more values via the one or more speakers at 4012. For example, a wireless receiver of the aviation communication headset can receive a wireless communication from a tablet computer that includes a defined schedule information for health parameter output. The schedule information can be time based or need based, such as when a health parameter is above or below a specified threshold, altitude based, and may be changed based on circumstances, such as quicker or slower based on values of the health parameter. The health parameter can be output audibly via the speakers of the aviation communication headset or can be output visually via the tablet, phone, watch, avionics system, or heads up display.

Figure 41:
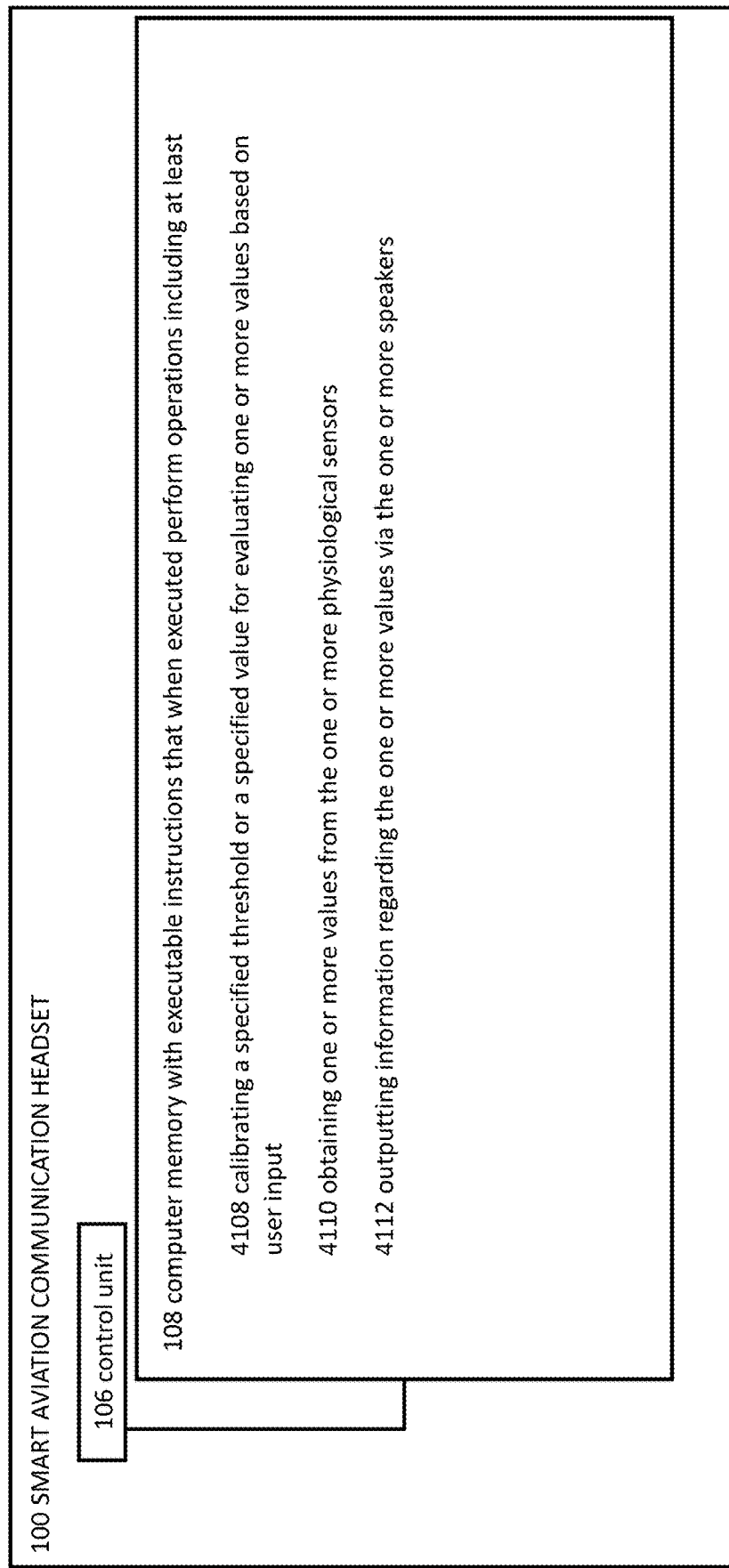

FIG. 41 is a system diagram of a smart aviation communication headset 100, in accordance with an embodiment of the invention. In one embodiment, an aviation communication headset 100 includes, but is not limited to, at least one microphone 114; one or more speakers 112; one or more physiological sensors 118; and at least one control unit 106 configured by one or more executable instructions stored on computer memory 108 to perform operations including at least: calibrating a specified threshold or a specified value for evaluating one or more values based on user input at 4108; obtaining one or more values from the one or more physiological sensors at 4110; and outputting information regarding the one or more values via the one or more speakers at 4112. For example, the processor component can receive an audible command received via the microphone of the aviation communication headset, such as "AITHRE set carbon monoxide threshold to 10 PPM." The processor component can then store the threshold in memory for use in determining when one or more physiological values is outside normal values. The input can alternatively be received as one or more wireless signals from an avionics system or from a portable electronic device.

Figure 42:
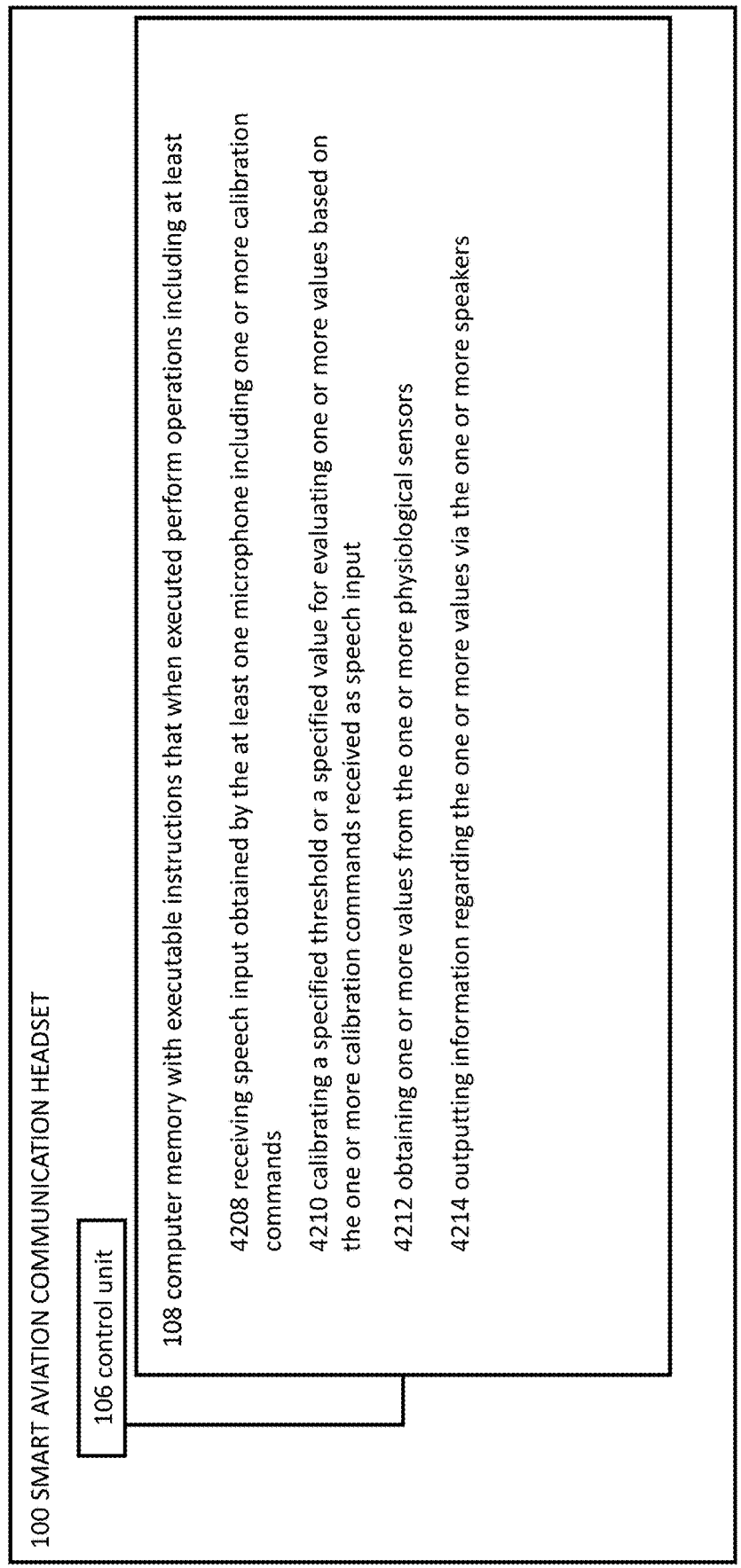

FIG. 42 is a system diagram of a smart aviation communication headset 100, in accordance with an embodiment of the invention. In one embodiment, an aviation communication headset 100 includes, but is not limited to, at least one microphone 114; one or more speakers 112; one or more physiological sensors 118; and at least one control unit 106 configured by one or more executable instructions stored on computer memory 108 to perform operations including at least: receiving speech input obtained by the at least one microphone including one or more calibration commands at 4208; calibrating a specified threshold or a specified value for evaluating one or more values based on the one or more calibration commands received as speech input at 4210; obtaining one or more values from the one or more physiological sensors at 4212; and outputting information regarding the one or more values via the one or more speakers at 4214. For example, the processor component can receive one or more speech signals received via wireless communication with a mobile phone device. The speech signals can include a command to set the blood oxygen threshold to 90 percent. The threshold can be stored in memory and then used to determine whether the blood oxygen level should be output via the speakers of the aviation communication headset.

Figure 43:
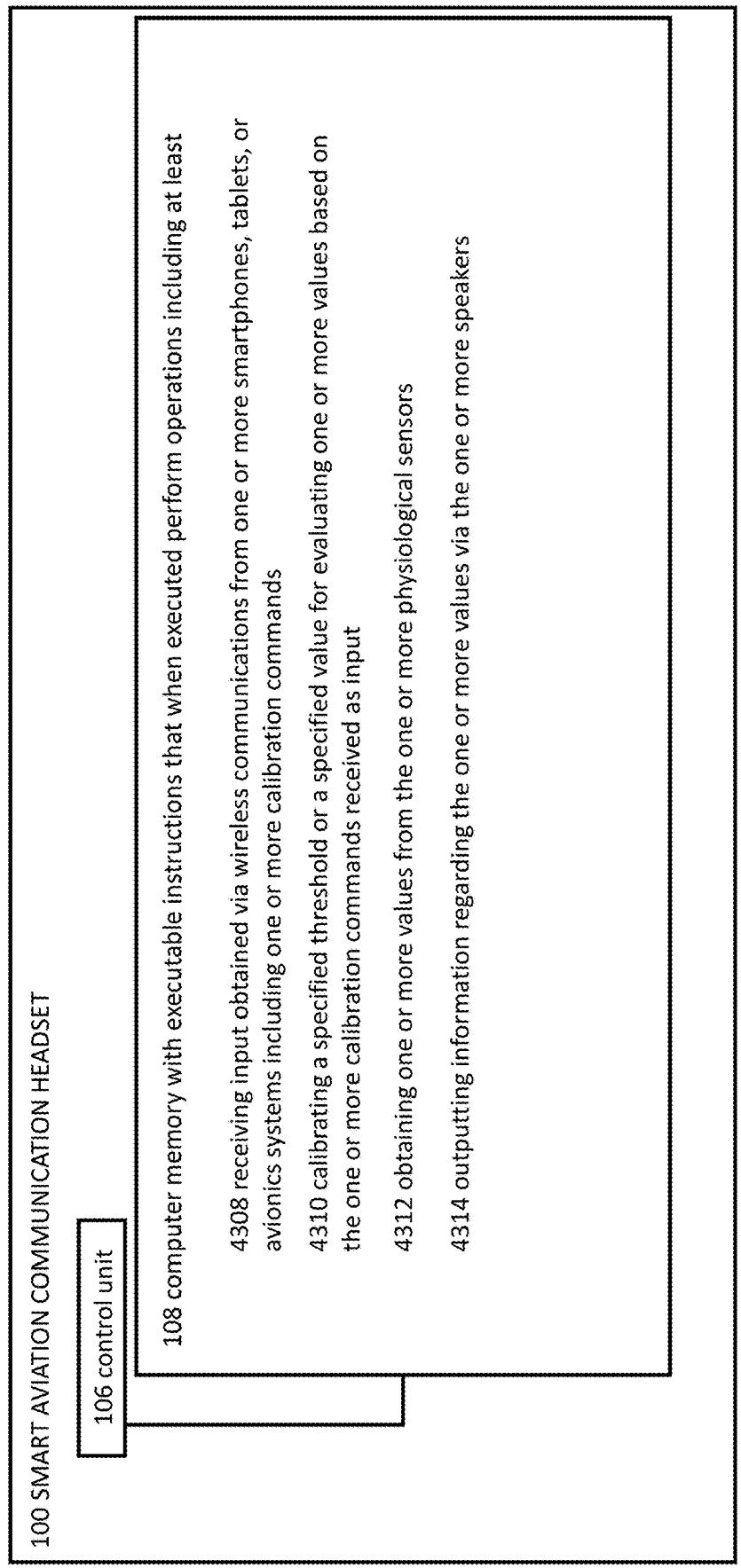

FIG. 43 is a system diagram of a smart aviation communication headset 100, in accordance with an embodiment of the invention. In one embodiment, an aviation communication headset 100 includes, but is not limited to, at least one microphone 114; one or more speakers 112; one or more physiological sensors 118; and at least one control unit 106 configured by one or more executable instructions stored on computer memory 108 to perform operations including at least: receiving input obtained via wireless communications from one or more smartphones, tablets, or avionics systems including one or more calibration commands at 4308; calibrating a specified threshold or a specified value for evaluating one or more values based on the one or more calibration commands received as input at 4310; obtaining one or more values from the one or more physiological sensors at 4312; and outputting information regarding the one or more values via the one or more speakers at 4314. For example, the processor component can receive one or more BLUETOOTH or WIFI signals from a tablet computer, such as an IPAD MINI that is running an aviation health application. The application can provide a sliding bar scale for each of one or more measurable parameters, wherein the position of the sliding bar on the scale defines where to trigger warnings. The application can include customization or individualization, such as for each of the passengers. For instance, a child can be more closely monitored with tighter tolerances than an adult. The processor then receives the communications via a receiver and then stores the thresholds for comparison with measured parameters.

Figure 44:
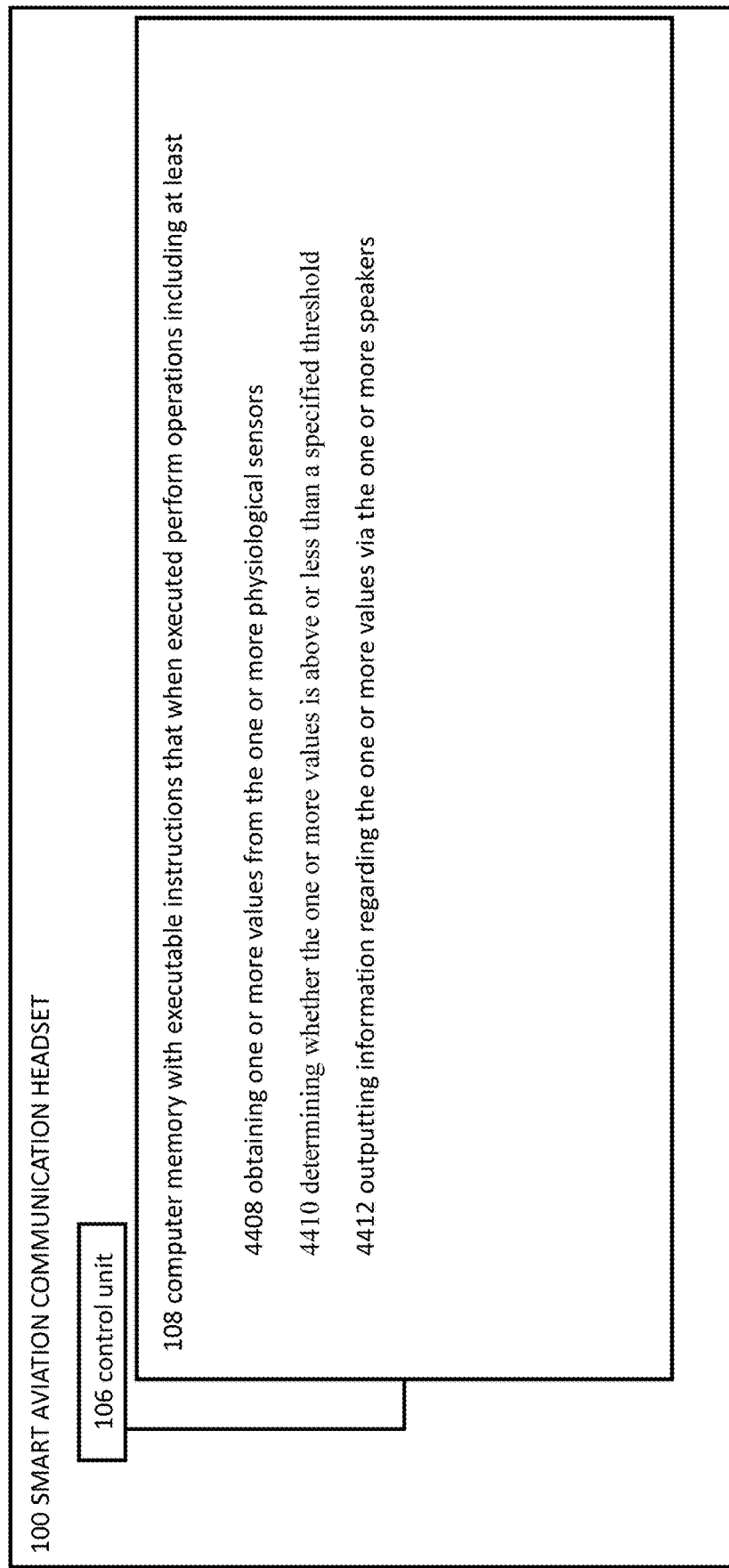

FIG. 44 is a system diagram of a smart aviation communication headset 100, in accordance with an embodiment of the invention. In one embodiment, an aviation communication headset 100 includes, but is not limited to, at least one microphone 114; one or more speakers 112; one or more physiological sensors 118; and at least one control unit 106 configured by one or more executable instructions stored on computer memory 108 to perform operations including at least: obtaining one or more values from the one or more physiological sensors at 4408; determining whether the one or more values is above or less than a specified threshold at 4410; and outputting information regarding the one or more values via the one or more speakers at 4412. For example, the processor component can receive heart rate, blood pressure, perspiration, breathing rate, coloration, blood oxygen, carbon monoxide, pupil dilation, hearing test, chemical measurements, or the like from the one or more physiological sensors. The processor then obtains from memory the one or more thresholds for each of the various parameters and then determines which, if any, are above or below the specified thresholds. A warning can then be provided as audible output via the speakers of the aviation communication headset. For instance, the speakers can output an indication that skin coloration is indicating paleness and sweat is above normal and suggest air or hydration. The output can also indicate that any or all parameters are within normal range.

Figure 45:
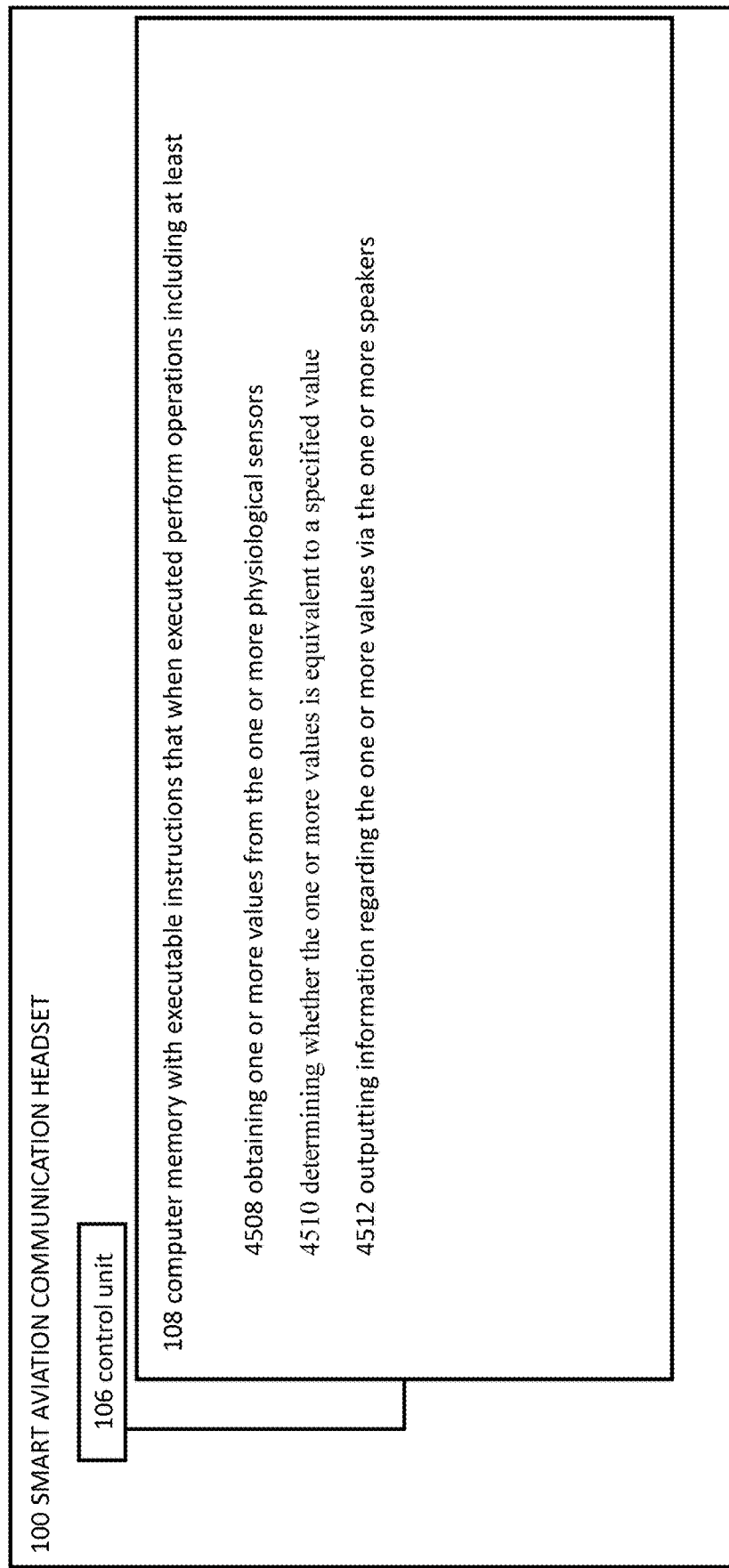

FIG. 45 is a system diagram of a smart aviation communication headset 100, in accordance with an embodiment of the invention. In one embodiment, an aviation communication headset 100 includes, but is not limited to, at least one microphone 114; one or more speakers 112; one or more physiological sensors 118; and at least one control unit 106 configured by one or more executable instructions stored on computer memory 108 to perform operations including at least: obtaining one or more values from the one or more physiological sensors at 4508; determining whether the one or more values is equivalent to a specified value at 4510; and outputting information regarding the one or more values via the one or more speakers at 4512. For example, the threshold value can be an equivalency test such as a subjective or objective value. The test can be binary, Boolean, or a test of a specific number or percentage.

Figure 46:
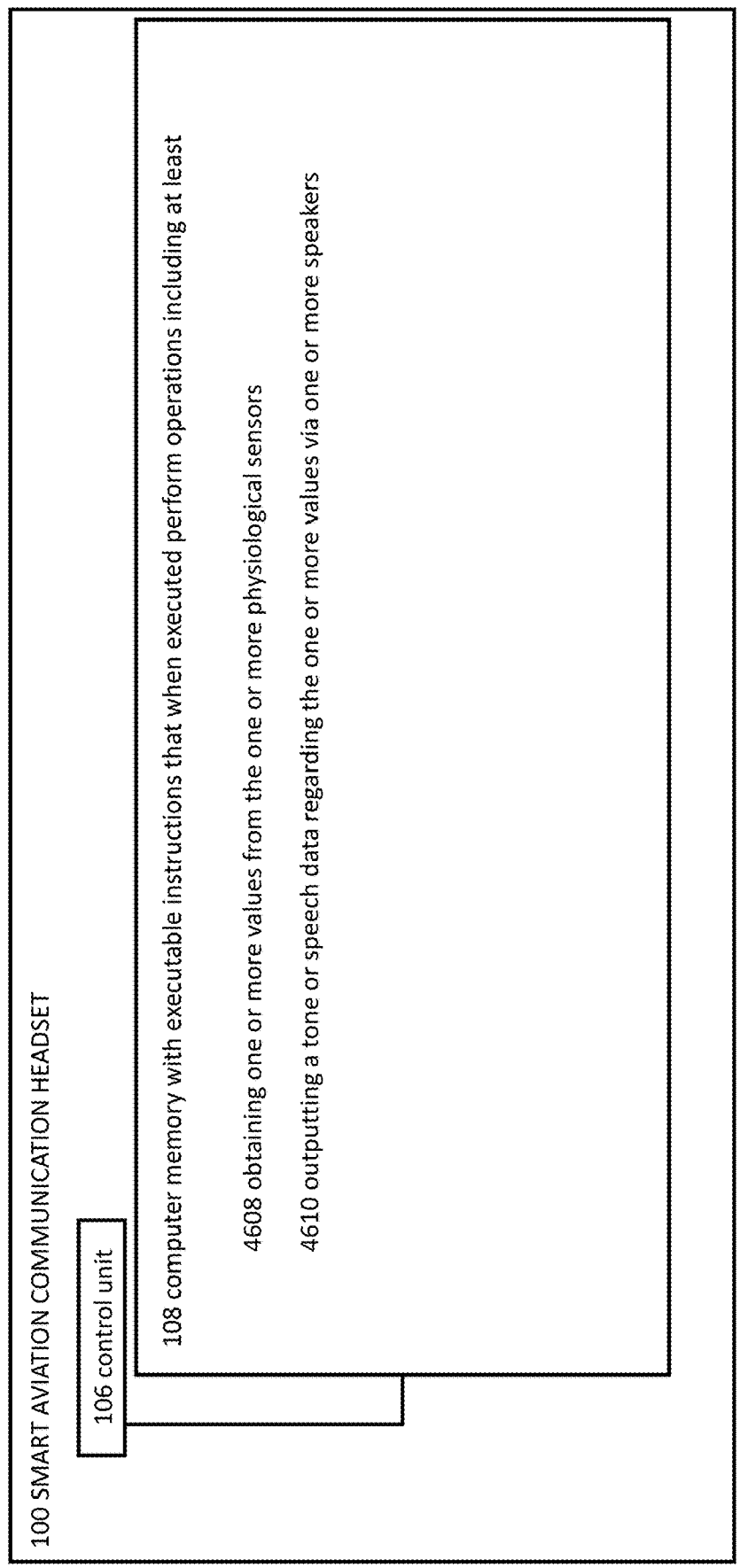

FIG. 46 is a system diagram of a smart aviation communication headset 100, in accordance with an embodiment of the invention. In one embodiment, an aviation communication headset 100 includes, but is not limited to, at least one microphone 114; one or more speakers 112; one or more physiological sensors 118; and at least one control unit 106 configured by one or more executable instructions stored on computer memory 108 to perform operations including at least: obtaining one or more values from the one or more physiological sensors at 4608; and outputting a tone or speech data regarding the one or more values via one or more speakers at 4610. For example, the speech output can be a voice output via the speakers of the aviation communication headset, such as "Jim your blood pressure appears to be falling". Alternatively, a tone can be emitted such as a single tone for normal parameter values and a dual tone for abnormal parameter values. The frequency of the speech or tone output can be adjusted by the processor component according to a user specification or according to a severity level of the deviance from the threshold. For instance, the processor component can signal for the emission of one or more sounds every minute during normal parameter values but then quicken the emissions to every 15 seconds for deviant situations. The processor component can then shift back to more periodic emissions upon recovery of the parameter value toward the normal level.

Figure 47:
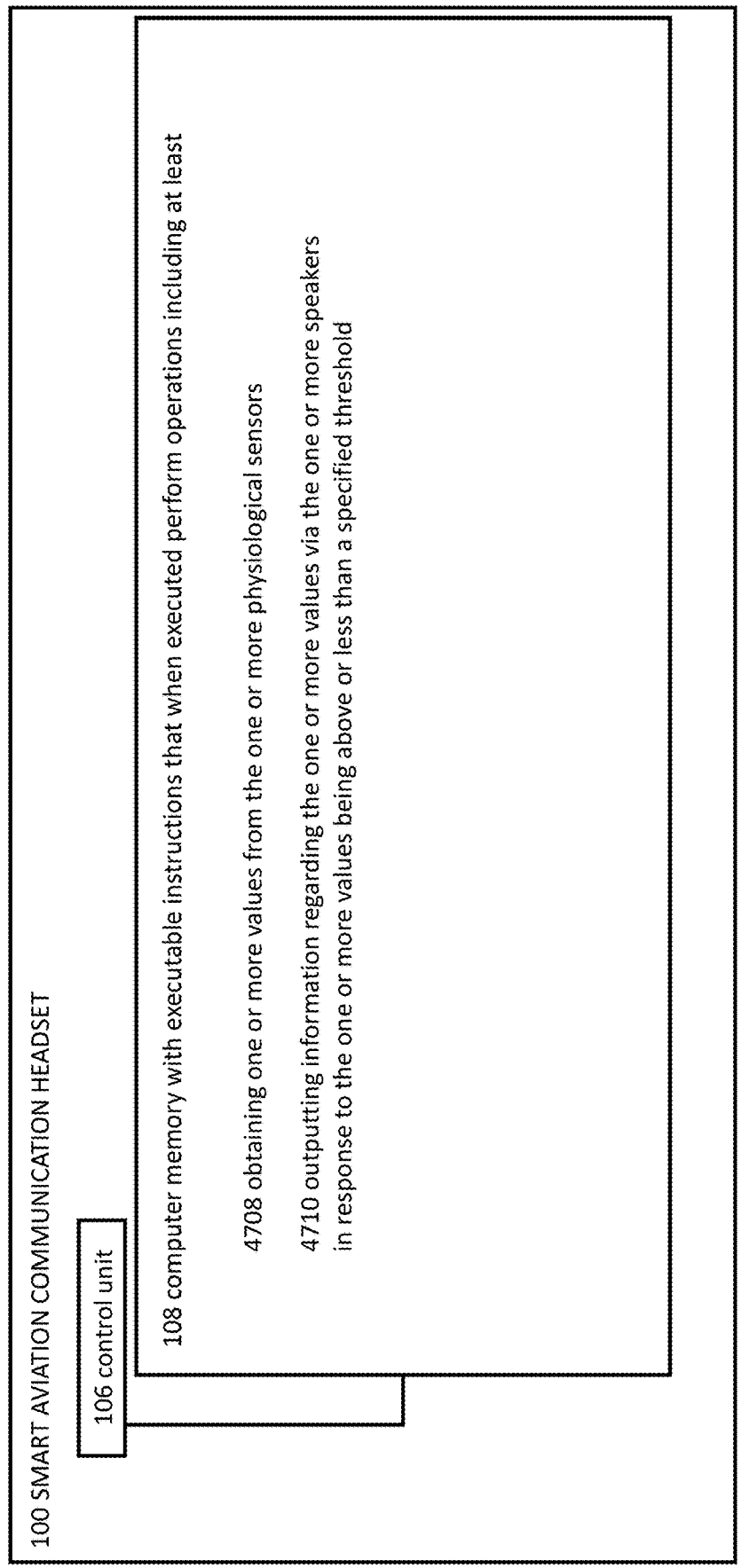

FIG. 47 is a system diagram of a smart aviation communication headset 100, in accordance with an embodiment of the invention. In one embodiment, an aviation communication headset 100 includes, but is not limited to, at least one microphone 114; one or more speakers 112; one or more physiological sensors 118; and at least one control unit 106 configured by one or more executable instructions stored on computer memory 108 to perform operations including at least: obtaining one or more values from the one or more physiological sensors at 4708; and outputting information regarding the one or more values via the one or more speakers in response to the one or more values being above or less than a specified threshold at 4710. For example, the processor component can obtain from memory the stored threshold value of 90 beats per minute. The processor can compare heart rate values to the 90 beats per minute and upon surpassing that rate, emit an audio signal for output via the speakers of the aviation communication headset.

FIG. 48 is a system diagram of a smart aviation communication headset 100, in accordance with an embodiment of the invention. In one embodiment, an aviation communication headset 100 includes, but is not limited to, at least one microphone 114; one or more speakers 112; one or more physiological sensors 118; and at least one control unit 106 configured by one or more executable instructions stored on computer memory 108 to perform operations including at least: obtaining one or more values from the one or more physiological sensors at 4808 and outputting information regarding the one or more values via the one or more speakers in response to the one or more values being a specified amount at 4810. For example, the processor can obtain from memory a stored value of 50 ppm for carbon monoxide. Upon receiving analog input signals from a carbon monoxide sensor that are indicative of 50 ppm, the processor component can signal for the output of a series of tones via the speaker of the aviation communication headset.

Figure 49:
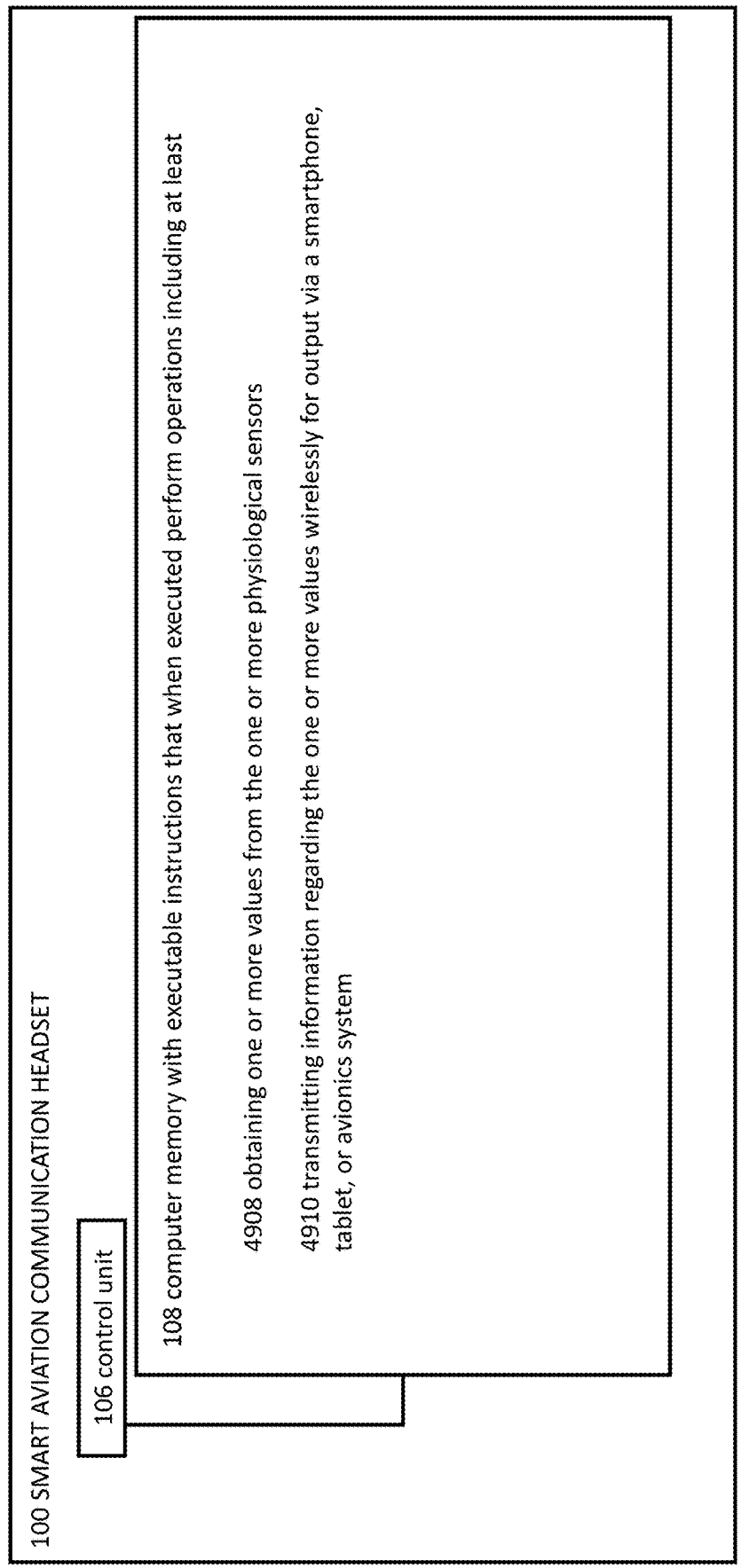

FIG. 49 is a system diagram of a smart aviation communication headset 100, in accordance with an embodiment of the invention. In one embodiment, an aviation communication headset 100 includes, but is not limited to, at least one microphone 114; one or more speakers 112; one or more physiological sensors 118; and at least one control unit 106 configured by one or more executable instructions stored on computer memory 108 to perform operations including at least: obtaining one or more values from the one or more physiological sensors at 4908; and transmitting information regarding the one or more values wirelessly for output via a smartphone, tablet, or avionics system. For example, upon a determination that a physiological parameter is at, above, or below a specified value, the processor component can signal for wireless transmission via BLUETOOTH or WIFI, which signal is readable by a smartwatch, smartphone, or tablet computer. The processor can also communicate with these devices all parameter values even when not in an alarm or warning situation. In one particular embodiment, a panel of health parameters can be communicated to an avionics system of the aircraft for output, such as adjacent to the engine monitoring instruments. All passenger health information can be transmitted and selectable or expandable as desired on any one of these electronic devices or avionics systems.

Figure 50:
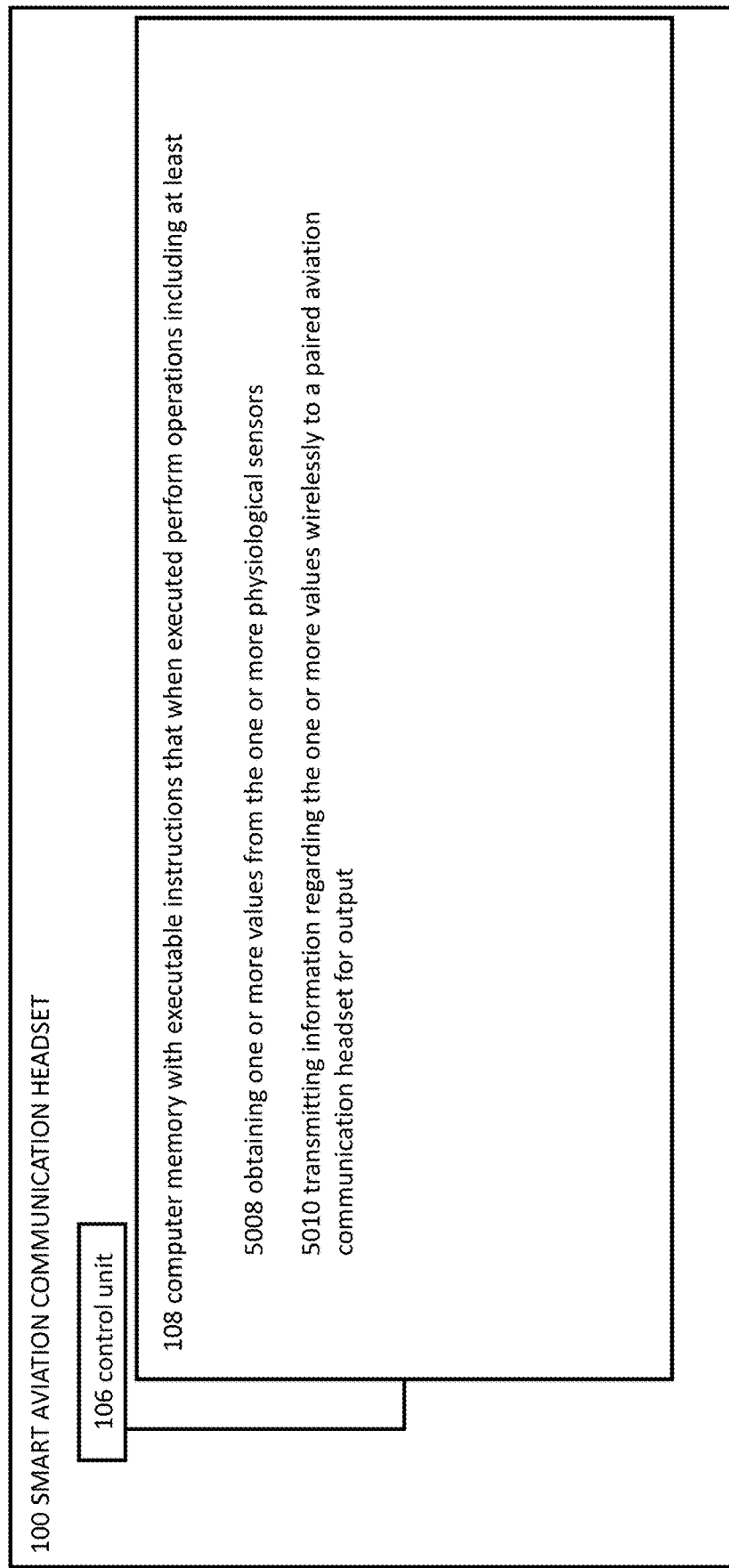

FIG. 50 is a system diagram of a smart aviation communication headset 100, in accordance with an embodiment of the invention. In one embodiment, an aviation communication headset 100 includes, but is not limited to, at least one microphone 114; one or more speakers 112; one or more physiological sensors 118; and at least one control unit 106 configured by one or more executable instructions stored on computer memory 108 to perform operations including at least: obtaining one or more values from the one or more physiological sensors at 5008 and transmitting information regarding the one or more values wirelessly to a paired aviation communication headset for output at 5010. For example, the processor component can through WIFI or BLUETOOTH communications pair with one or more other processor components of another aviation communication headset. The processor component can then receive the wireless signals containing health parameters sampled from physiological sensors of the other aviation communication headsets. This enables the physiological parameters from multiple headsets to be consolidated and monitored by the processor component and warning signals associated with the multiple headsets to be output via the speakers. For instance, a pilot can monitor passenger physiological values with or without passenger knowledge through use of the paired aviation headsets as described herein.

Figure 51:
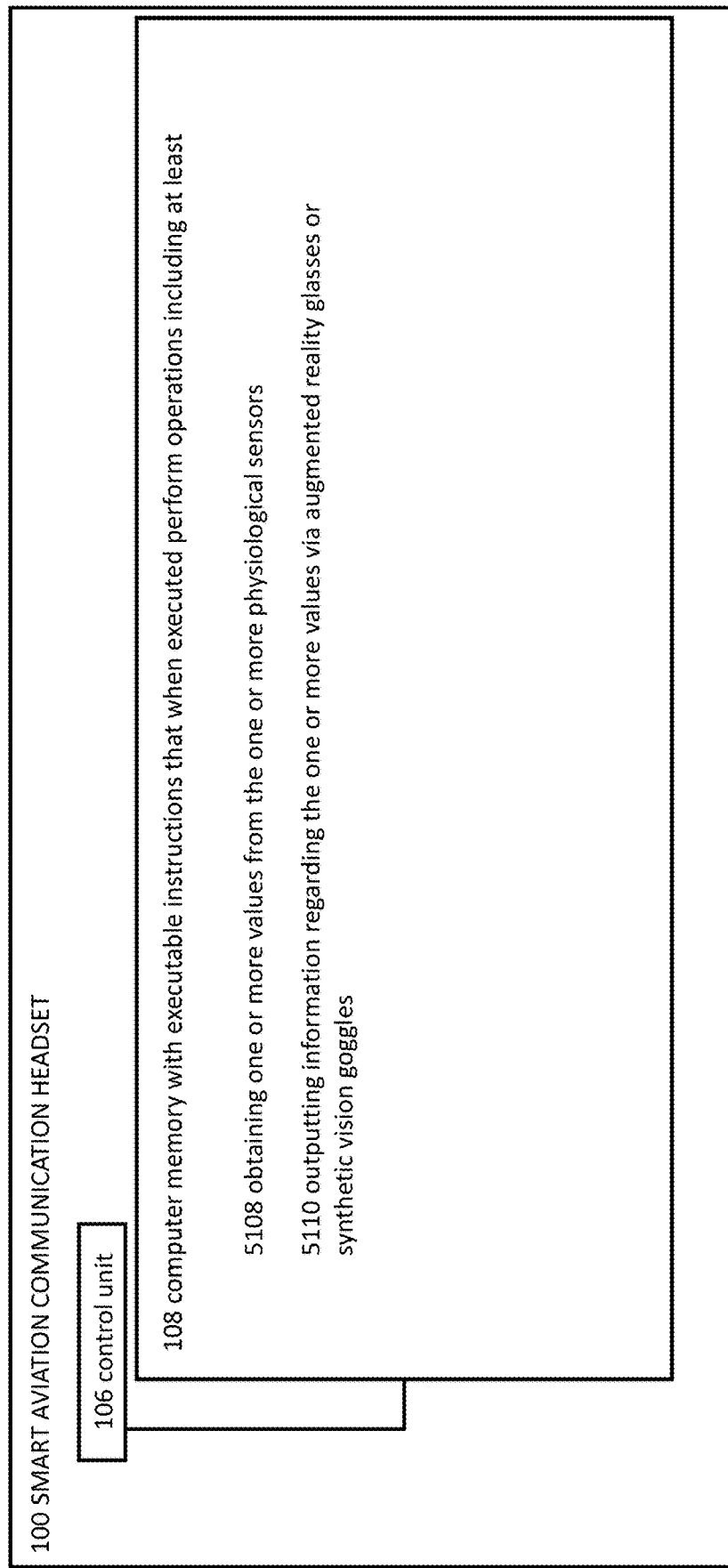

FIG. 51 is a system diagram of a smart aviation communication headset 100, in accordance with an embodiment of the invention. In one embodiment, an aviation communication headset 100 includes, but is not limited to, at least one microphone 114; one or more speakers 112; one or more physiological sensors 118; and at least one control unit 106 configured by one or more executable instructions stored on computer memory 108 to perform operations including at least: obtaining one or more values from the one or more physiological sensors at 5108 and outputting information regarding the one or more values via augmented reality glasses or synthetic vision goggles at 5110. For example, the processor can obtain health parameter values from the physiological sensors and then communicate those values to the synthetic vision goggles or augmented reality goggles for display. The display of the values can be a moving bar on a scale, which scale can include color variations corresponding to normal, abnormal, and high risk situations. For instance, parameters such as breathing rate, oxygen levels, carbon monoxide values, heart rate, and others from one or multiple different aviation communications headsets (e.g., passenger headsets) can be displayed for monitoring. The health parameter data can be hidden from view and then displayed upon detection of an abnormal condition or high risk condition.

FIG. 52 is a system diagram of a smart aviation communication headset 100, in accordance with an embodiment of the invention. In one embodiment, an aviation communication headset 100 includes, but is not limited to, at least one microphone 114; one or more speakers 112; one or more physiological sensors 118; and at least one control unit 106 configured by one or more executable instructions stored on computer memory 108 to perform operations including at least: pairing the aviation communication headset with at least one other aviation communication headset to transmit or receive one or more values of one or more physiological sensors to or from the at least one other aviation communication headset at 5208; obtaining one or more values from the one or more physiological sensors at 5210; and outputting information regarding the one or more values via the one or more speakers at 5212. For example, the processor of a pilot headset can pair via BLUETOOTH or WIFI with a copilot or passenger headset. The pairing can be initiated by the processor based on received instructions, which can be based on proximity to the other aviation communication headsets, a button, or based on speech commands received via the microphone of the aviation communication headset. Once paired, the processor component can receive and transmit instructions with the paired aviation communication headset. For instance, speech commands can be received via the microphone of the pilot aviation communication headset to control sampling and transmission of health data from the copilot aviation communication headset or the passenger aviation communication headset. A speech command processed by the processor could be, for example, "AITHRE tell me 'PASSENGER'S NAME' blood oxygen level". In response to this command, the processor can obtain the parameter value and provide a speaker output of the value via the speakers of the pilot's aviation communication headset.

Figure 53:
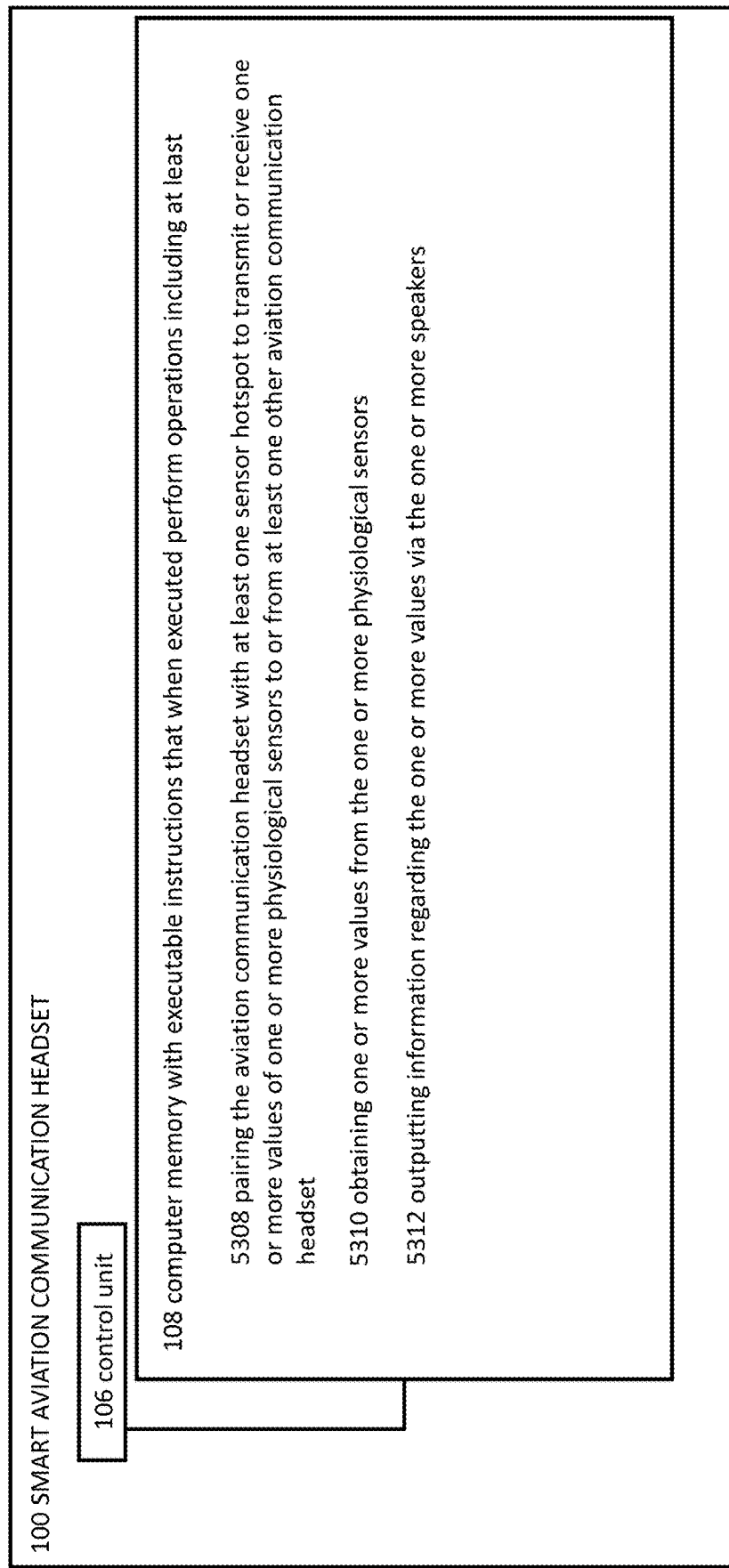

FIG. 53 is a system diagram of a smart aviation communication headset 100, in accordance with an embodiment of the invention. In one embodiment, an aviation communication headset 100 includes, but is not limited to, at least one microphone 114; one or more speakers 112; one or more physiological sensors 118; and at least one control unit 106 configured by one or more executable instructions stored on computer memory 108 to perform operations including at least: pairing the aviation communication headset with at least one sensor hotspot to transmit or receive one or more values of one or more physiological sensors to or from at least one other aviation communication headset at 5308; obtaining one or more values from the one or more physiological sensors at 5310; and outputting information regarding the one or more values via the one or more speakers at 5312. For example, a processor of a master aviation communication headset can pair via BLUETOOTH or WIFI with a hotspot that is located in the aircraft. The hotspot can include a processor, memory, a communication antenna, and instructions that configure the processor to pair with a plurality of slave aviation communication headsets to receive and collect health parameter data. The collected health parameter data obtained from the plurality of slave aviation communication headsets can be funneled to the processor of the master aviation communication headset for output via the speakers, synthetic vision goggles, or augmented reality glasses.

Figure 54:
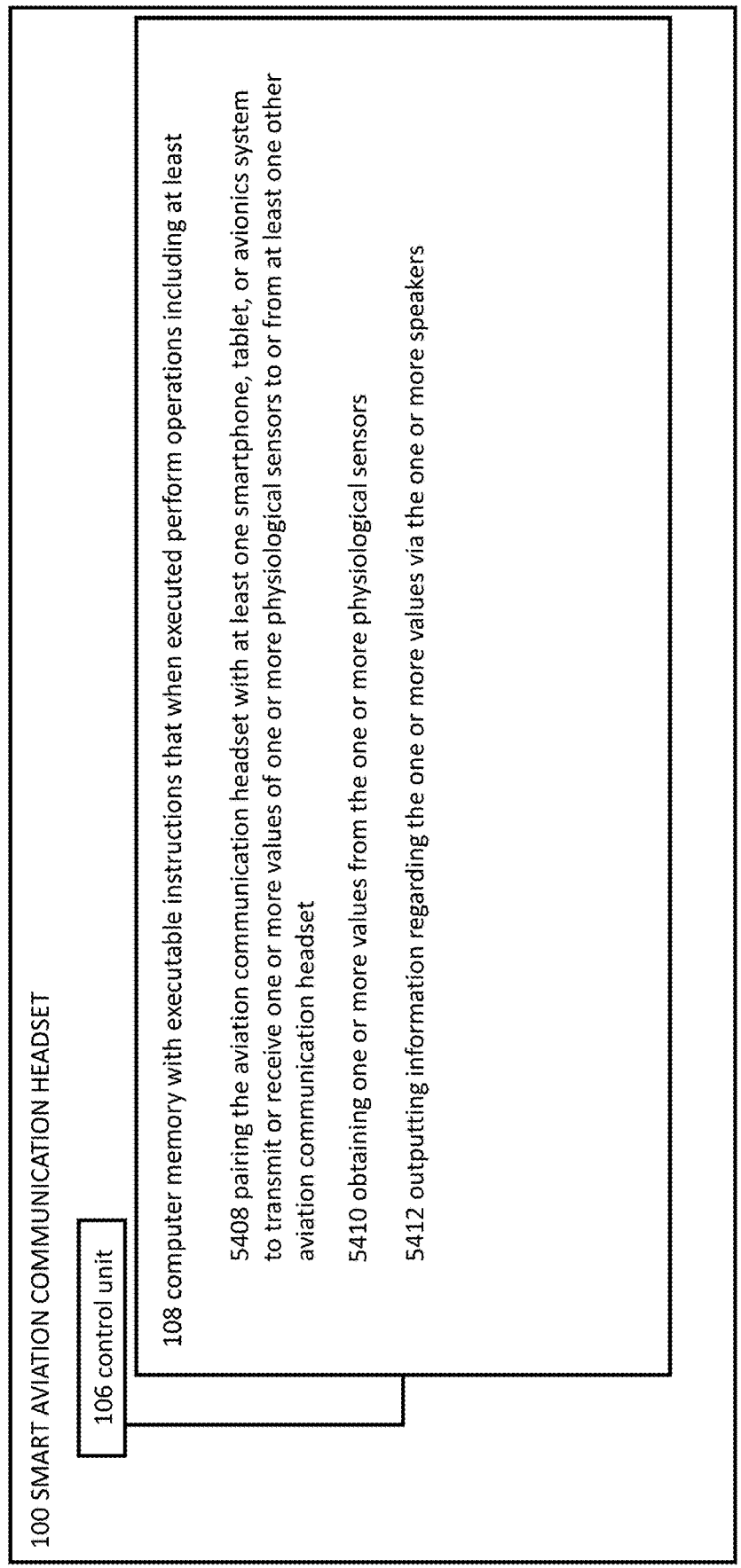

FIG. 54 is a system diagram of a smart aviation communication headset 100, in accordance with an embodiment of the invention. In one embodiment, an aviation communication headset 100 includes, but is not limited to, at least one microphone 114; one or more speakers 112; one or more physiological sensors 118; and at least one control unit 106 configured by one or more executable instructions stored on computer memory 108 to perform operations including at least: pairing the aviation communication headset with at least one smartphone, tablet, or avionics system to transmit or receive one or more values of one or more physiological sensors to or from at least one other aviation communication headset at 5408; obtaining one or more values from the one or more physiological sensors at 5410; and outputting information regarding the one or more values via the one or more speakers at 5412. For example, a mobile phone device can operate as a hotspot to pair with and communicate with a plurality of aviation communication headsets for collecting health parameter data. The mobile phone device can include an application that presents the collected health parameter data, which may be standalone or be included with a navigation software application, such as that provided by FOREFLIGHT or GARMIN. The processor of the aviation communication headset can communicate with the mobile phone device to obtain and output one or more health parameter values via the speakers of the aviation communication headset.

Figure 55:
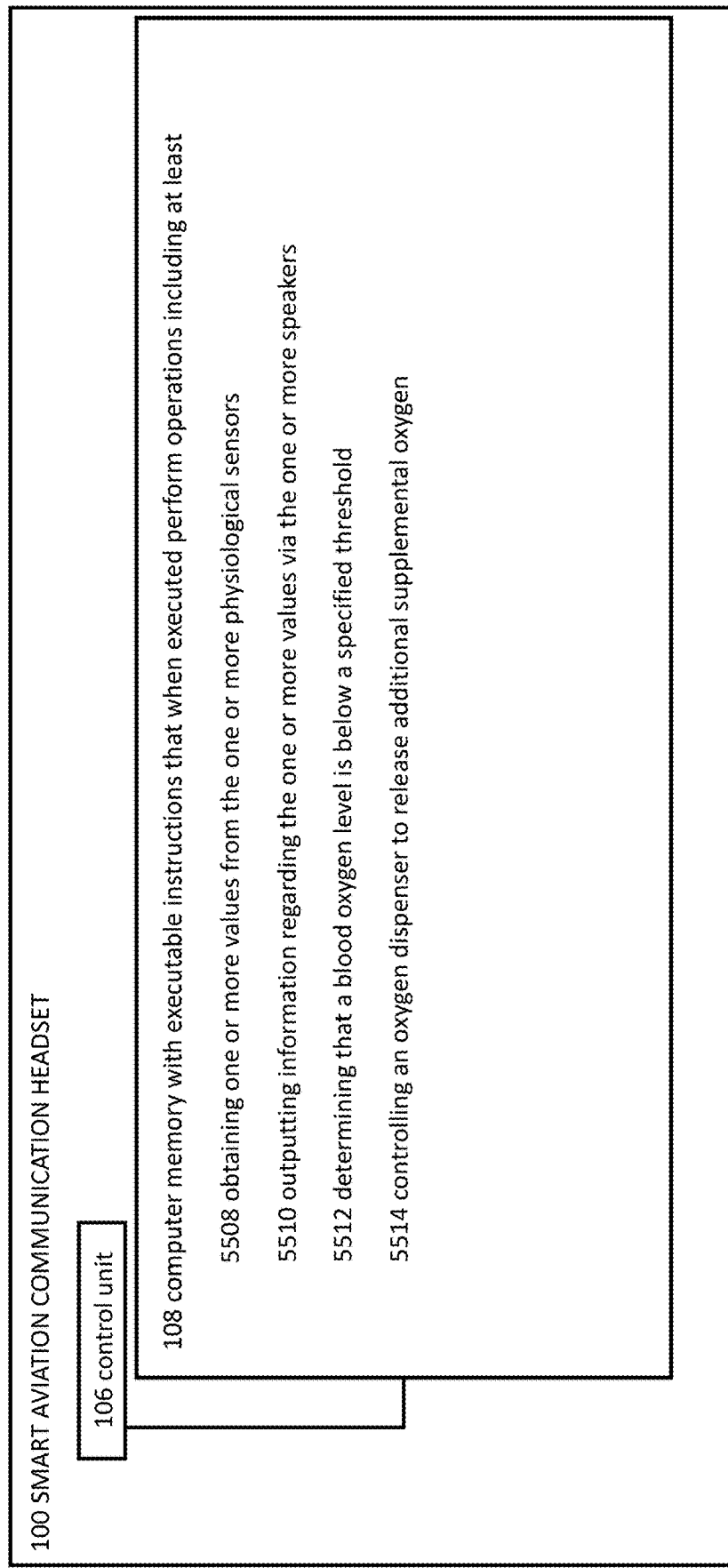

FIG. 55 is a system diagram of a smart aviation communication headset 100, in accordance with an embodiment of the invention. In one embodiment, an aviation communication headset 100 includes, but is not limited to, at least one microphone 114; one or more speakers 112; one or more physiological sensors 118; and at least one control unit 106 configured by one or more executable instructions stored on computer memory 108 to perform operations including at least: obtaining one or more values from the one or more physiological sensors at 5508; outputting information regarding the one or more values via the one or more speakers at 5510; determining that a blood oxygen level is below a specified threshold at 5512; and controlling an oxygen dispenser to release additional supplemental oxygen at 5514. For example, the processor can obtain blood oxygen levels using red and infrared light and corresponding sensors that are positioned within an earcup of the aviation communication headset using a earlobe. The values obtained by the processor can be compared with acceptable values for blood oxygen. Upon determining that the blood oxygen level is low, the processor can signal for opening of a valve of an oxygen dispenser coupled to the headband of the aviation communication headset. The degree of valve opening can be correlated to the severity of hypoxic conditions as detected by the processor using the sensors. That is, a slightly low oxygen level may result in only a small amount of oxygen being released. A more severe hypoxic condition can result in full valve opening. Feedback from the blood oxygen sensor can result in the processor continuously or intermittently adjusting the valve to ensure that the blood oxygen level remains sufficient without unnecessarily wasting available oxygen for dispensation.

FIG. 56 is a system diagram of a smart aviation communication headset 100, in accordance with an embodiment of the invention. In one embodiment, an aviation communication headset 100 includes, but is not limited to, at least one microphone 114; one or more speakers 112; one or more physiological sensors 118; and at least one control unit 106 configured by one or more executable instructions stored on computer memory 108 to perform operations including at least: obtaining one or more values from the one or more physiological sensors at 5608; outputting information regarding the one or more values via the one or more speakers at 5610; determining that a blood oxygen level is below a specified threshold at 5612; and controlling an autopilot of an avionics system to descend to a lower altitude at 5614. For example, the processor component can detect that blood oxygen has fallen below a critical threshold value, such as 70%. At this trigger value, the processor component can transmit to a navigation system or avionics system or autopilot unit via a communication link an instruction to initiate a descent to a lower altitude. This functionality can ensure that in an event of low blood oxygen, which may lead to unresponsiveness in a pilot or copilot, the plane can automatically descend to a safer altitude where oxygen is more abundant.

Figure 57:
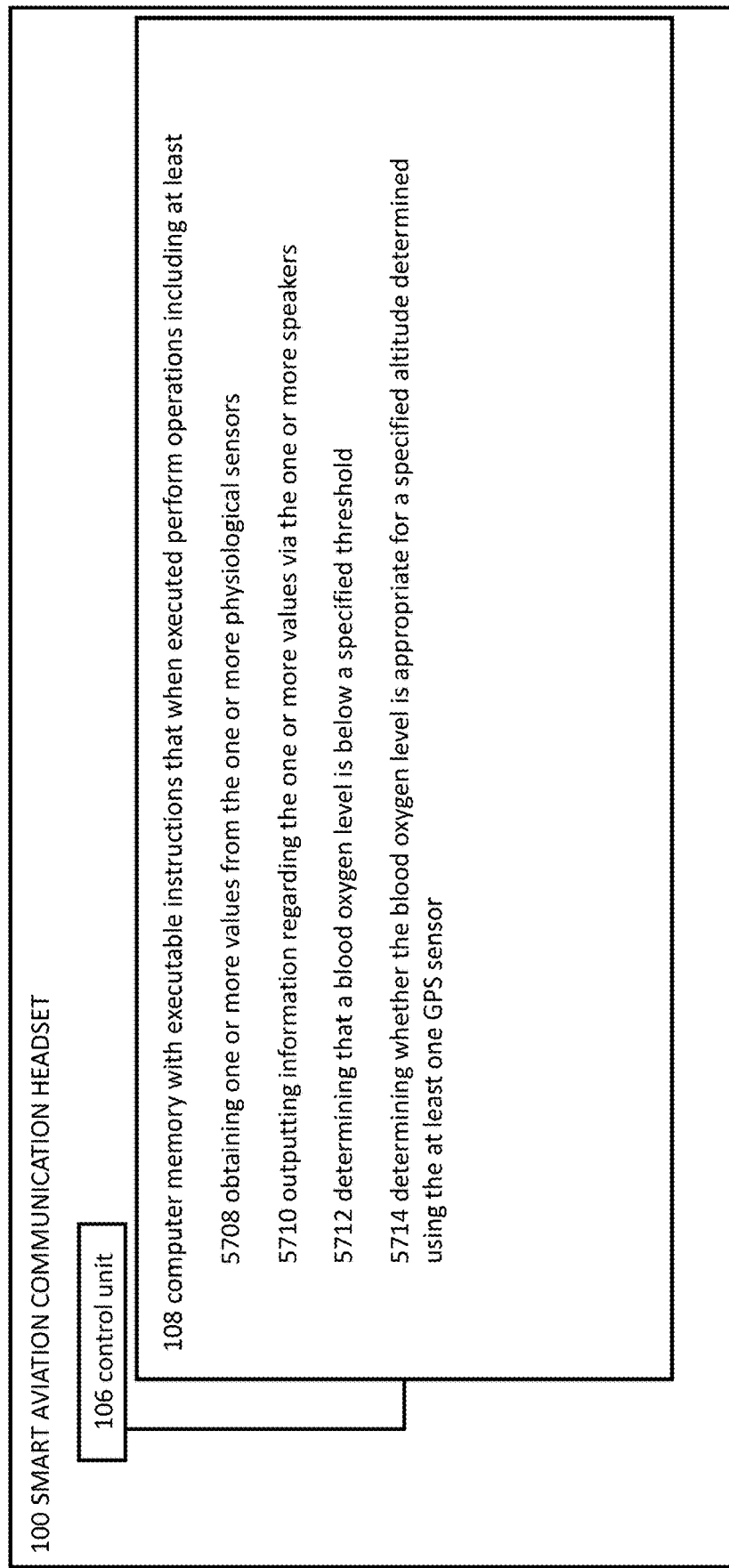

FIG. 57 is a system diagram of a smart aviation communication headset 100, in accordance with an embodiment of the invention. In one embodiment, an aviation communication headset 100 includes, but is not limited to, at least one microphone 114; one or more speakers 112; one or more physiological sensors 118; and at least one control unit 106 configured by one or more executable instructions stored on computer memory 108 to perform operations including at least: obtaining one or more values from the one or more physiological sensors at 5708; outputting information regarding the one or more values via the one or more speakers at 5710; determining that a blood oxygen level is below a specified threshold at 5712; and determining whether the blood oxygen level is appropriate for a specified altitude determined using the at least one GPS sensor at 5714. For example, the processor component can obtain the blood oxygen level parameter value from the sensor and a GPS altitude, which can be adjusted for pressure and temperature to density altitude. The GPS or density altitude can be used by the processor to obtain the expected range of blood oxygen levels, which can be calibrated to a person's age. The processor can then compare the blood oxygen level measured to the expected blood oxygen level to determine if either the reading is not accurate or the blood oxygen level is being affected by something other than altitude. For instance, the processor component can output a warning to adjust the sensor with respect to the earlobe to ensure a better reading. In an event that a more accurate reading cannot be obtained, the processor component can output a warning to double check the blood oxygen with an alternative measurement tool, such as a finger blood oxygen reader. In an event that the blood oxygen level remains inconsistent with altitude expected values, the processor component can provide an output of a health issue that may be affecting the values independently of altitude. Additional actions that the processor may execute are fully opening an oxygen dispenser valve, descending to a lower altitude, turning the transponder to 7700, broadcasting a message via a communication radio on the emergency 121.5 frequency regarding the situation, or prompting an emergency checklist.

Figure 58:
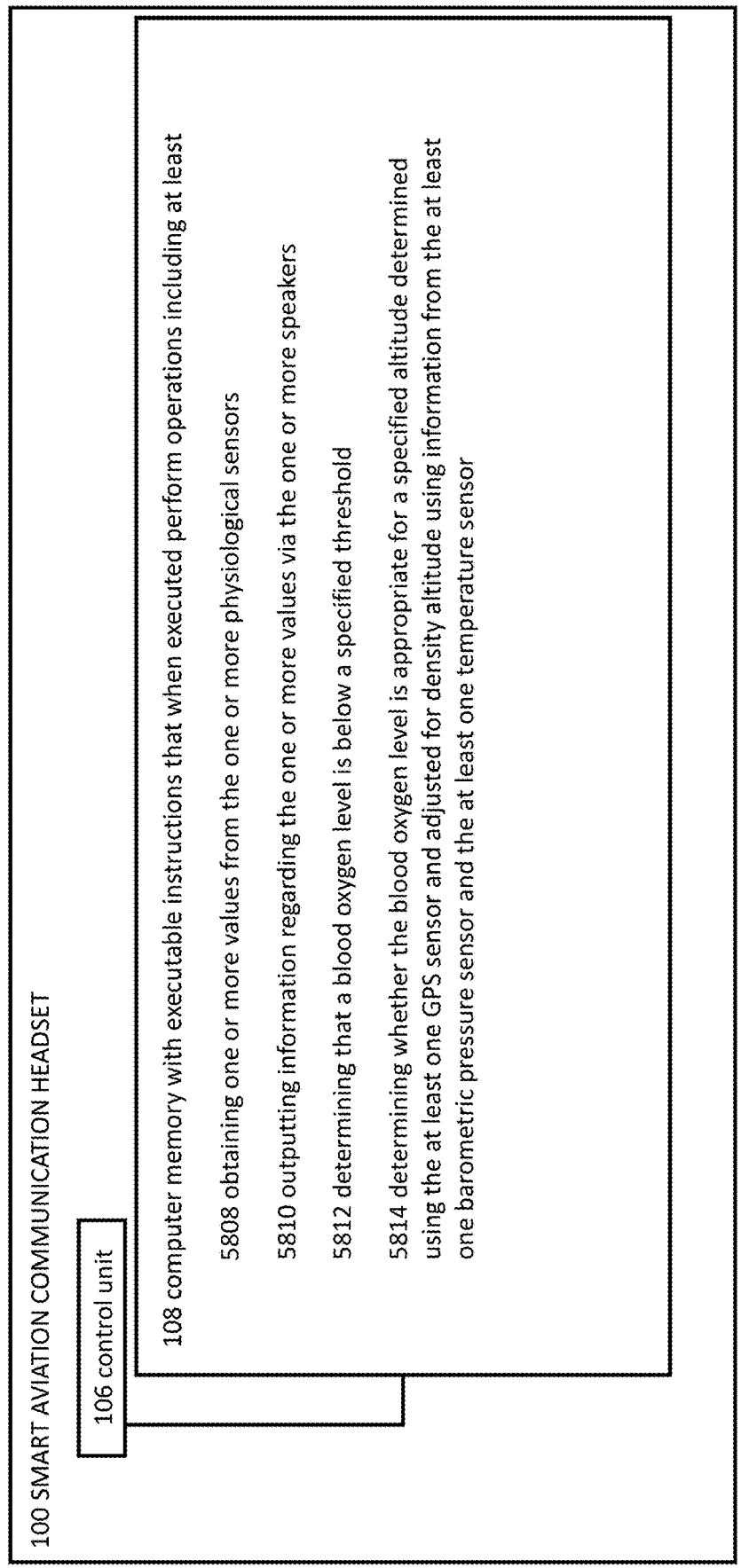

FIG. 58 is a system diagram of a smart aviation communication headset 100, in accordance with an embodiment of the invention. In one embodiment, an aviation communication headset 100 includes, but is not limited to, at least one microphone 114; one or more speakers 112; one or more physiological sensors 118; and at least one control unit 106 configured by one or more executable instructions stored on computer memory 108 to perform operations including at least: obtaining one or more values from the one or more physiological sensors at 5808; outputting information regarding the one or more values via the one or more speakers at 5810; determining that a blood oxygen level is below a specified threshold at 5812; and determining whether the blood oxygen level is appropriate for a specified altitude determined using the at least one GPS sensor and adjusted for density altitude using information from the at least one barometric pressure sensor and the at least one temperature sensor at 5814. The processor component can use real-time measurements of barometric pressure and temperature to calibrate a GPS altitude to obtain actual density altitude values. These sensors can be incorporated into the aviation communication headset to enable the processor component to more accurately determine an expected blood oxygen level for a particular altitude MSL.

Figure 59:
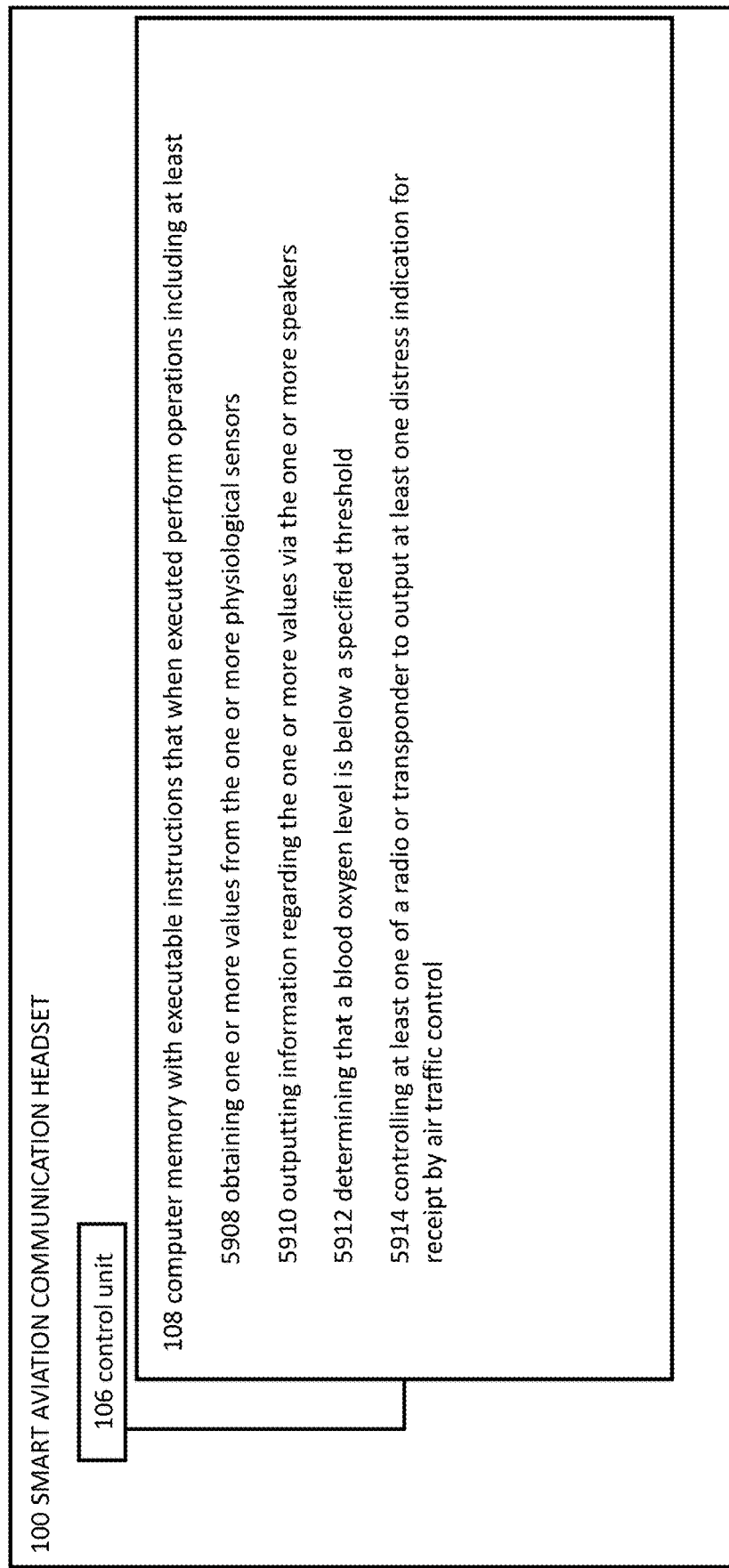

FIG. 59 is a system diagram of a smart aviation communication headset 100, in accordance with an embodiment of the invention. In one embodiment, an aviation communication headset 100 includes, but is not limited to, at least one microphone 114; one or more speakers 112; one or more physiological sensors 118; and at least one control unit 106 configured by one or more executable instructions stored on computer memory 108 to perform operations including at least: obtaining one or more values from the one or more physiological sensors at 5908; outputting information regarding the one or more values via the one or more speakers at 5910; determining that a blood oxygen level is below a specified threshold at 5912; and controlling at least one of a radio or transponder to output at least one distress indication for receipt by air traffic control at 5914. For example, the processor component can upon determining that a blood oxygen level is below a specified threshold, or that any other physiological value is outside a normal range (including carbon monoxide values), transmit an instruction to squawk 7700 on the transponder, initiate an ident command, tune a communication radio to 121.5, and transmit an emergency broadcast on the frequency. For instance, the processor can request response from a pilot regarding a warning level of low blood oxygen. Upon not receiving an adequate response or an incoherent response, the processor can initiate the emergency sequence to obtain assistance from air traffic control and emergency personnel.

Figure 60:
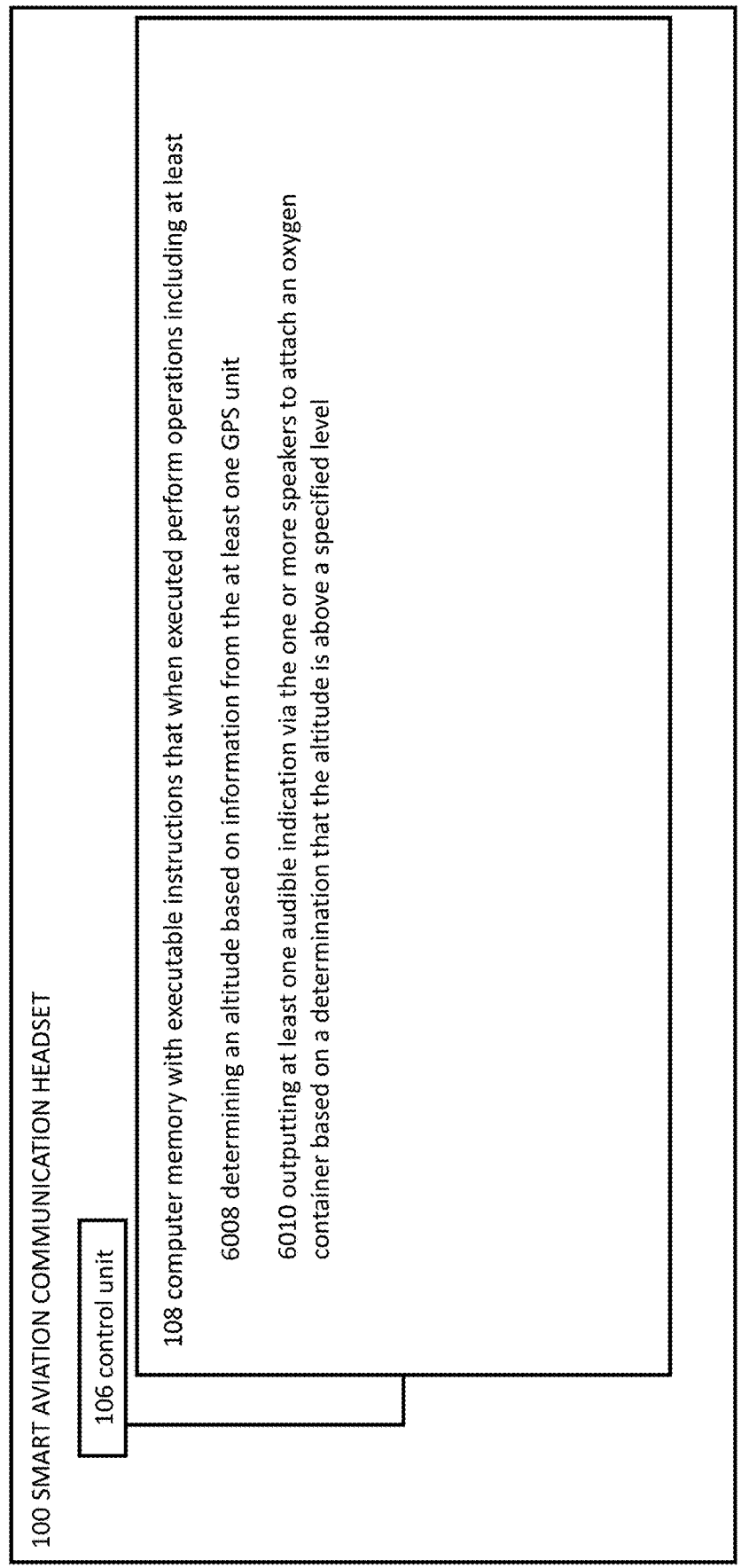

FIG. 60 is a system diagram of a smart aviation communication headset 100, in accordance with an embodiment of the invention. In one embodiment, an aviation communication headset 100 includes, but is not limited to, at least one microphone 114; one or more speakers 112; an oxygen dispenser receptacle 115; a cannula 117; an oxygen container 172; an oxygen regulator 119; a GPS unit 134; and at least one control unit 106 configured by one or more executable instructions stored on computer memory 108 to perform operations including at least: determining an altitude based on information from the at least one GPS unit at 6008; and outputting at least one audible indication via the one or more speakers to attach an oxygen container based on a determination that the altitude is above a specified level at 6010. For example, the processor component can obtain GPS altitude information from the GPS unit and upon reaching a certain altitude can output an audible reminder via the speakers of the aviation communication headset to dispense oxygen. The reminder can specify the level of oxygen per minute to initiate based on the altitude. For instance, upon reaching 5000 feet at night the processor component can provide the audible reminder to begin dispensing oxygen. Alternatively, upon determining that an altitude of 12,500 has been reached during the day the processor component can provide the audible reminder via the speakers. A light sensor can be integrated into the aviation communication headset to adjust the trigger values based on the different requirements of oxygen during the day and night due to the requirement for greater oxygen for night vision.

Figure 61:
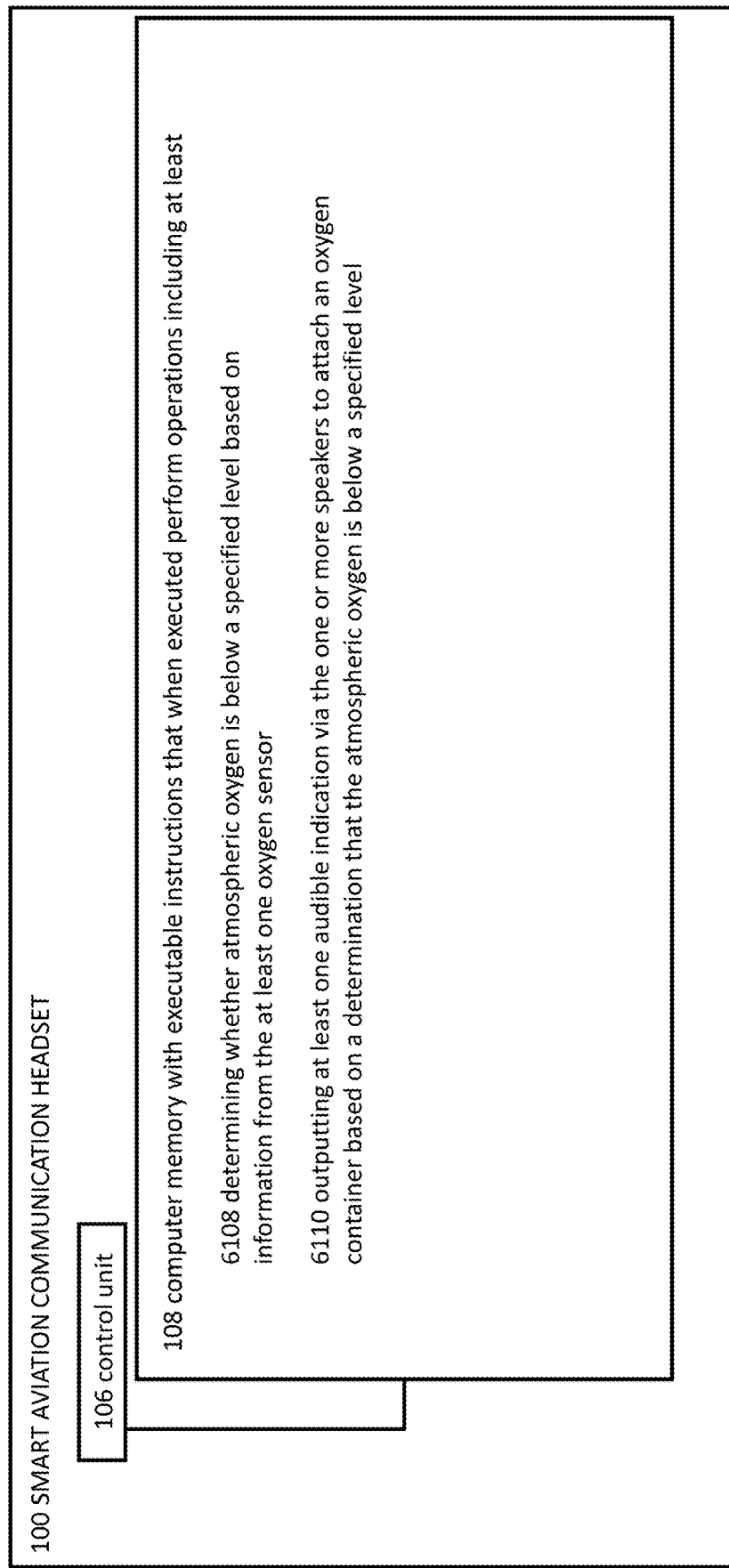

FIG. 61 is a system diagram of a smart aviation communication headset 100, in accordance with an embodiment of the invention. In one embodiment, an aviation communication headset 100 includes, but is not limited to, at least one microphone 114; one or more speakers 112; an oxygen dispenser receptacle 115; a cannula 117; an oxygen container 172; an oxygen regulator 119; a GPS unit 134; and at least one control unit 106 configured by one or more executable instructions stored on computer memory 108 to perform operations including at least: determining whether atmospheric oxygen is below a specified level based on information from the at least one oxygen sensor at 6108; and outputting at least one audible indication via the one or more speakers to attach an oxygen container based on a determination that the atmospheric oxygen is below a specified level at 6110. For example, the processor component can alternatively obtain actual oxygen level measurements using an oxygen sensor integrated with the aviation communication headset. Based on oxygen level measurements, the processor component can initiate the audible reminder to initiate oxygen dispensation. In certain embodiments, the actual oxygen level measured can be used to compare with GPS or density altitude based estimates of oxygen levels. The comparison can be used to calibrate the GPS and density values.

Figure 62:
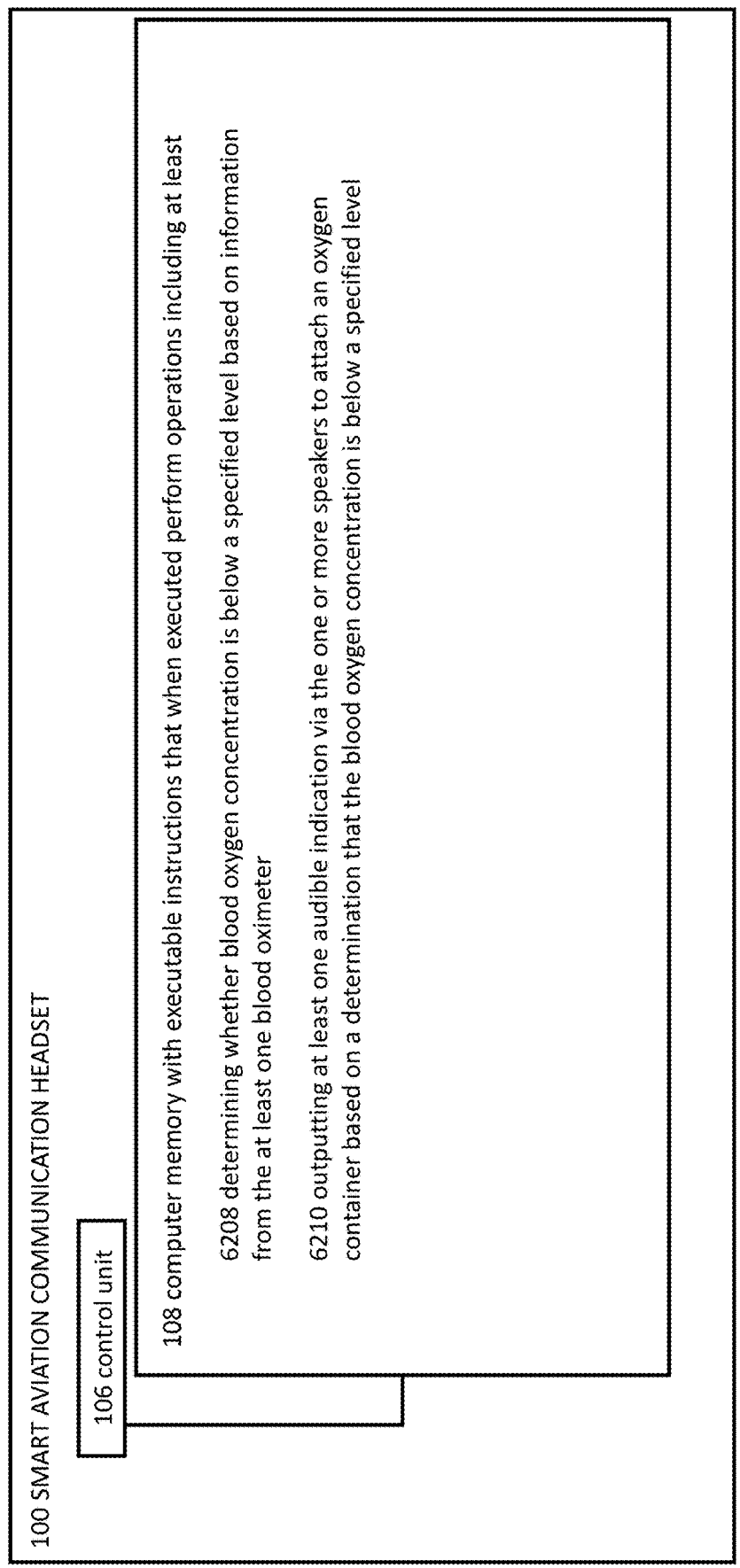

FIG. 62 is a system diagram of a smart aviation communication headset 100, in accordance with an embodiment of the invention. In one embodiment, an aviation communication headset 100 includes, but is not limited to, at least one microphone 114; one or more speakers 112; an oxygen dispenser receptacle 115; a cannula 117; an oxygen container 172; an oxygen regulator 119; a GPS unit 134; and at least one control unit 106 configured by one or more executable instructions stored on computer memory 108 to perform operations including at least: determining whether blood oxygen concentration is below a specified level based on information from the at least one blood oximeter at 6208; and outputting at least one audible indication via the one or more speakers to attach an oxygen container based on a determination that the blood oxygen concentration is below a specified level at 6210. For example, the processor component can provide a reminder to attach the oxygen dispenser based on a measured blood oxygen level using earlobe sensors disposed within an earcup of the aviation communication headset.

Figure 63:
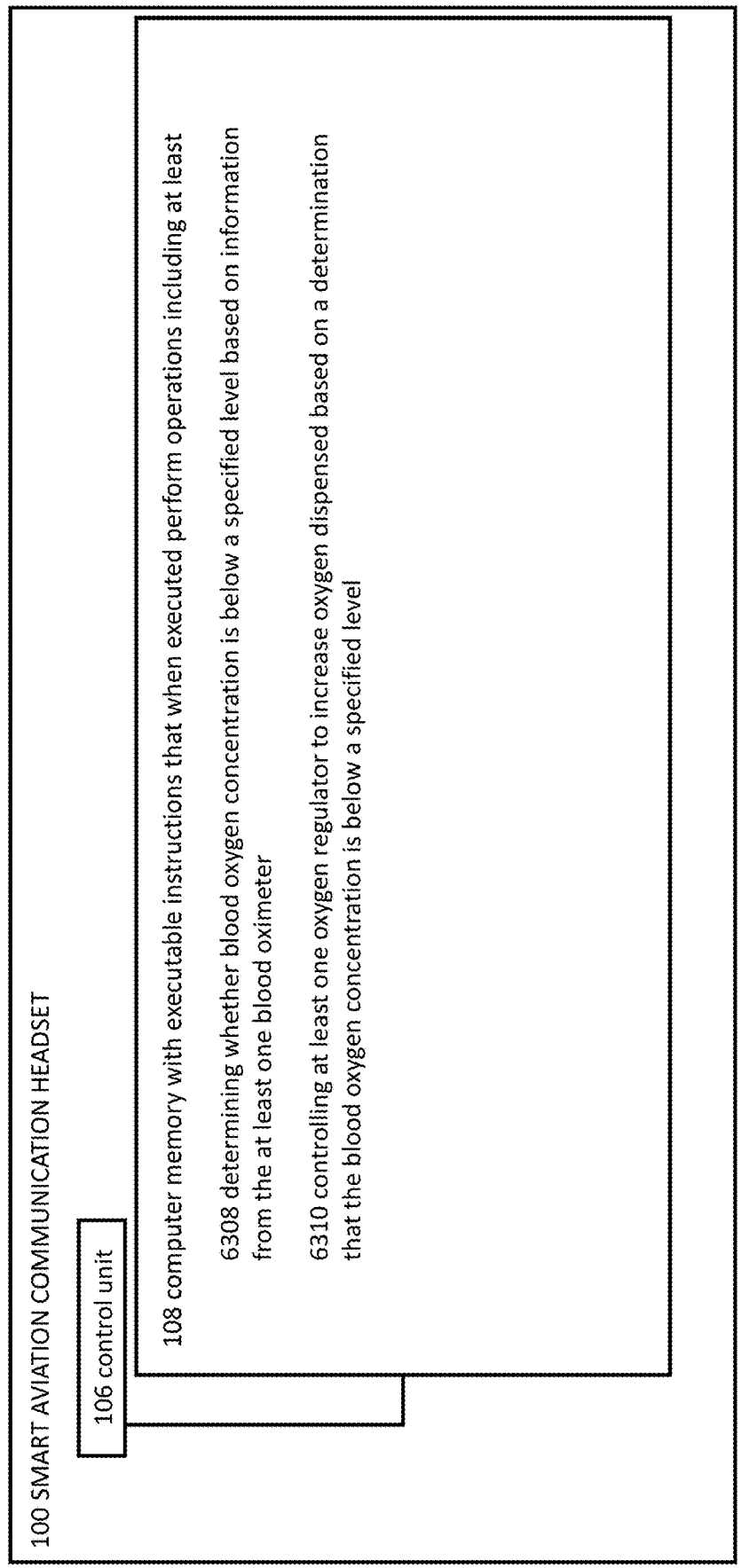

FIG. 63 is a system diagram of a smart aviation communication headset 100, in accordance with an embodiment of the invention. In one embodiment, an aviation communication headset 100 includes, but is not limited to, at least one microphone 114; one or more speakers 112; an oxygen dispenser receptacle 115; a cannula 117; an oxygen container 172; an oxygen regulator 119; a GPS unit 134; and at least one control unit 106 configured by one or more executable instructions stored on computer memory 108 to perform operations including at least: determining whether blood oxygen concentration is below a specified level based on information from the at least one blood oximeter at 6308; and controlling at least one oxygen regulator to increase oxygen dispensed based on a determination that the blood oxygen concentration is below a specified level at 6310. For example, the processor can provide an output via the speakers to attach an oxygen cylinder upon reaching 10,000 MSL density altitude. The blood oxygen level can be obtained from one or more sensors by the processor component thereafter to adjust a valve or control a regulator to dispense the minimum necessary oxygen required to maintain a specified blood oxygen value, such as over 85 percent or over 90 percent blood oxygen.

Figure 64:
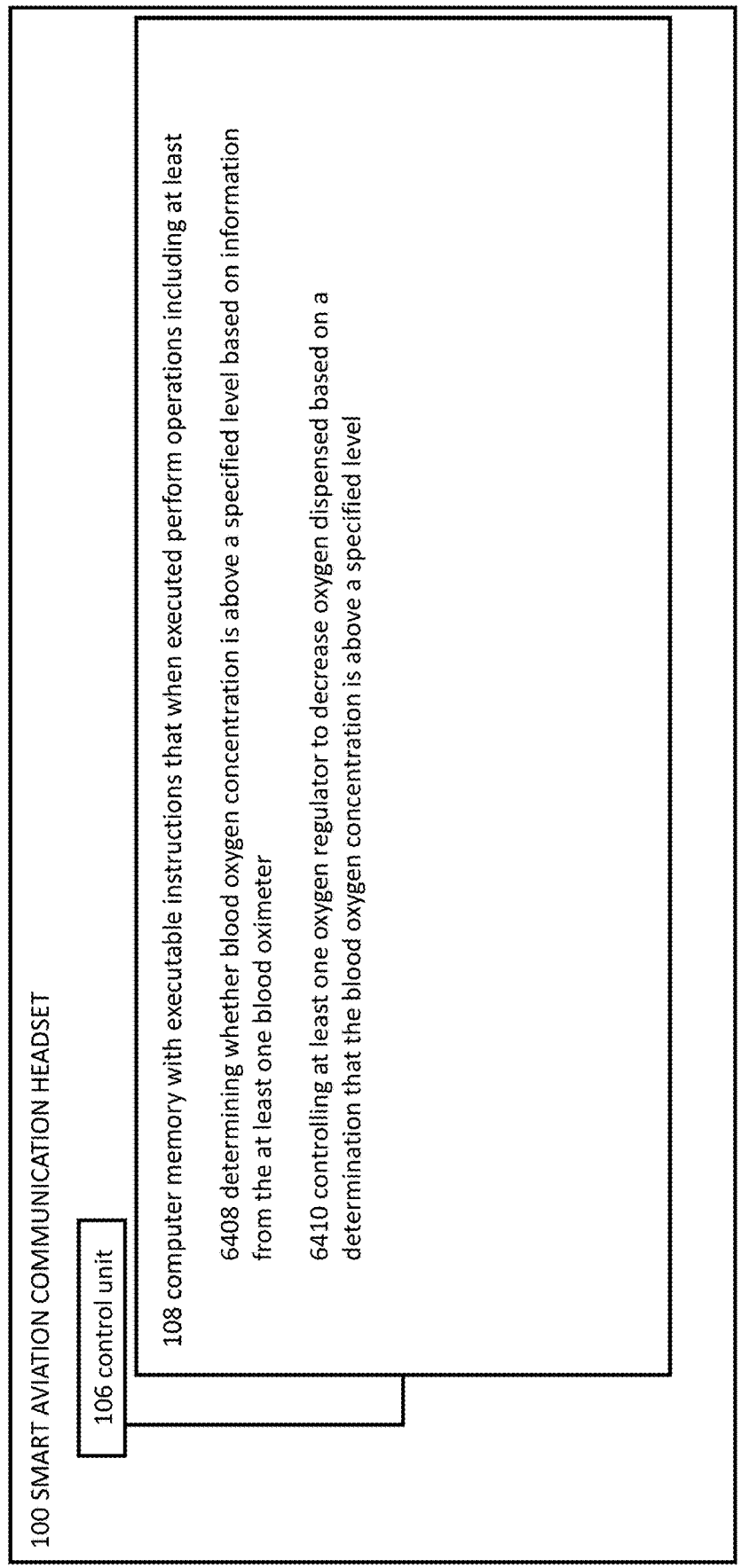

FIG. 64 is a system diagram of a smart aviation communication headset 100, in accordance with an embodiment of the invention. In one embodiment, an aviation communication headset 100 includes, but is not limited to, at least one microphone 114; one or more speakers 112; an oxygen dispenser receptacle 115; a cannula 117; an oxygen container 172; an oxygen regulator 119; a GPS unit 134; and at least one control unit 106 configured by one or more executable instructions stored on computer memory 108 to perform operations including at least: determining whether blood oxygen concentration is above a specified level based on information from the at least one blood oximeter at 6408; and controlling at least one oxygen regulator to decrease oxygen dispensed based on a determination that the blood oxygen concentration is above a specified level at 6410. For example, upon detecting that the blood oxygen level is above 95%, the processor component can control a regulator of an oxygen container to incrementally reduce the flow of oxygen until the blood oxygen level stabilizes at a specified value, such as 90%. This incremental adjustment by the processor can maximize the duration of available oxygen and minimize waste.

Figure 65:
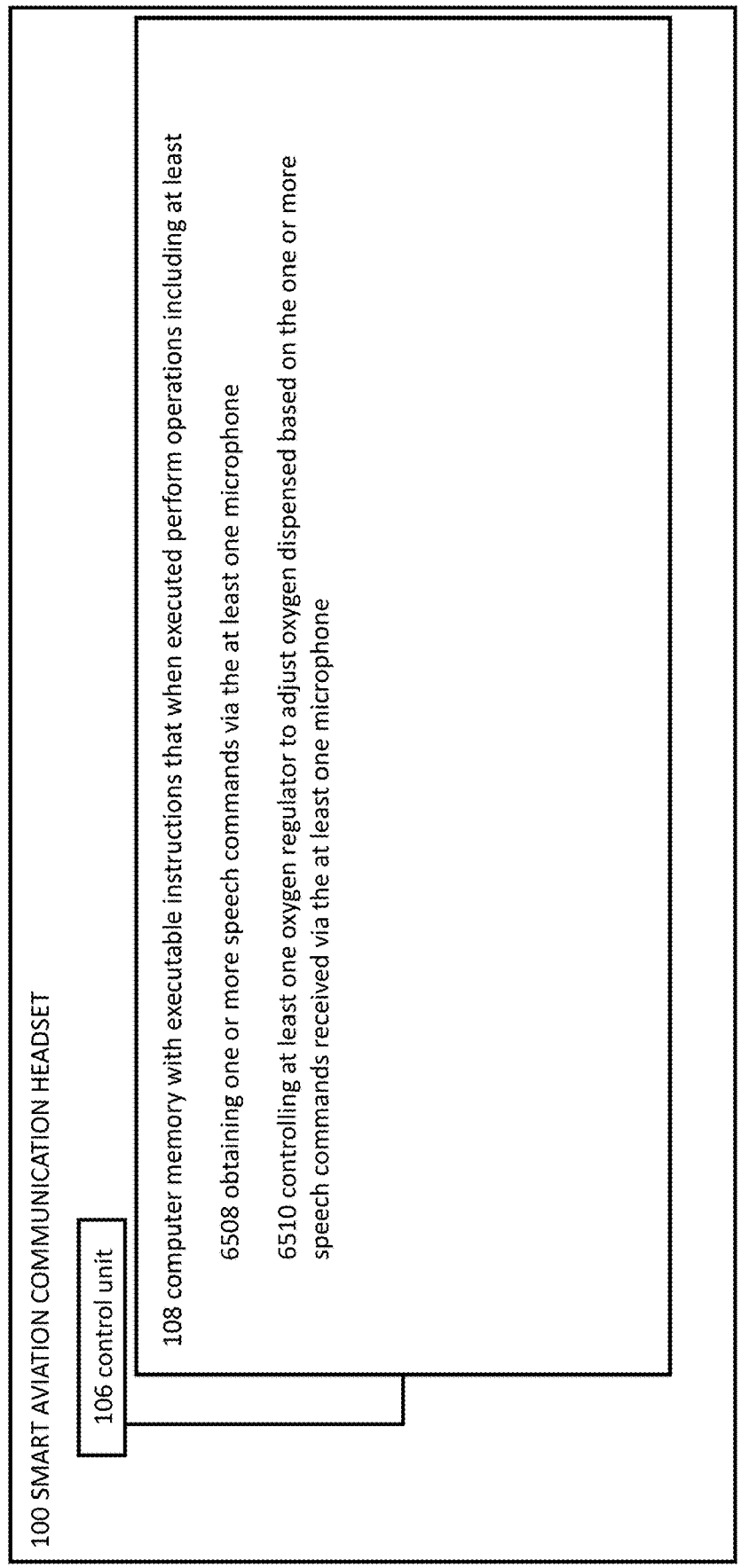

FIG. 65 is a system diagram of a smart aviation communication headset 100, in accordance with an embodiment of the invention. In one embodiment, an aviation communication headset 100 includes, but is not limited to, at least one microphone 114; one or more speakers 112; an oxygen dispenser receptacle 115; a cannula 117; an oxygen container 172; an oxygen regulator 119; a GPS unit 134; and at least one control unit 106 configured by one or more executable instructions stored on computer memory 108 to perform operations including at least: obtaining one or more speech commands via the at least one microphone at 6508; and controlling at least one oxygen regulator to adjust oxygen dispensed based on the one or more speech commands received via the at least one microphone at 6510. The processor of the aviation communication headset can receive speech commands via the microphone of the aviation communication headset. The processor can perform speech recognition on the speech commands and convert those speech commands into control signals of the oxygen regulator. For instance, the processor can receive a speech command to increase the flow of oxygen by 0.1 L per hour. The processor can then control the oxygen regulator to result in flow of 0.1 L per hour.

Figure 66:
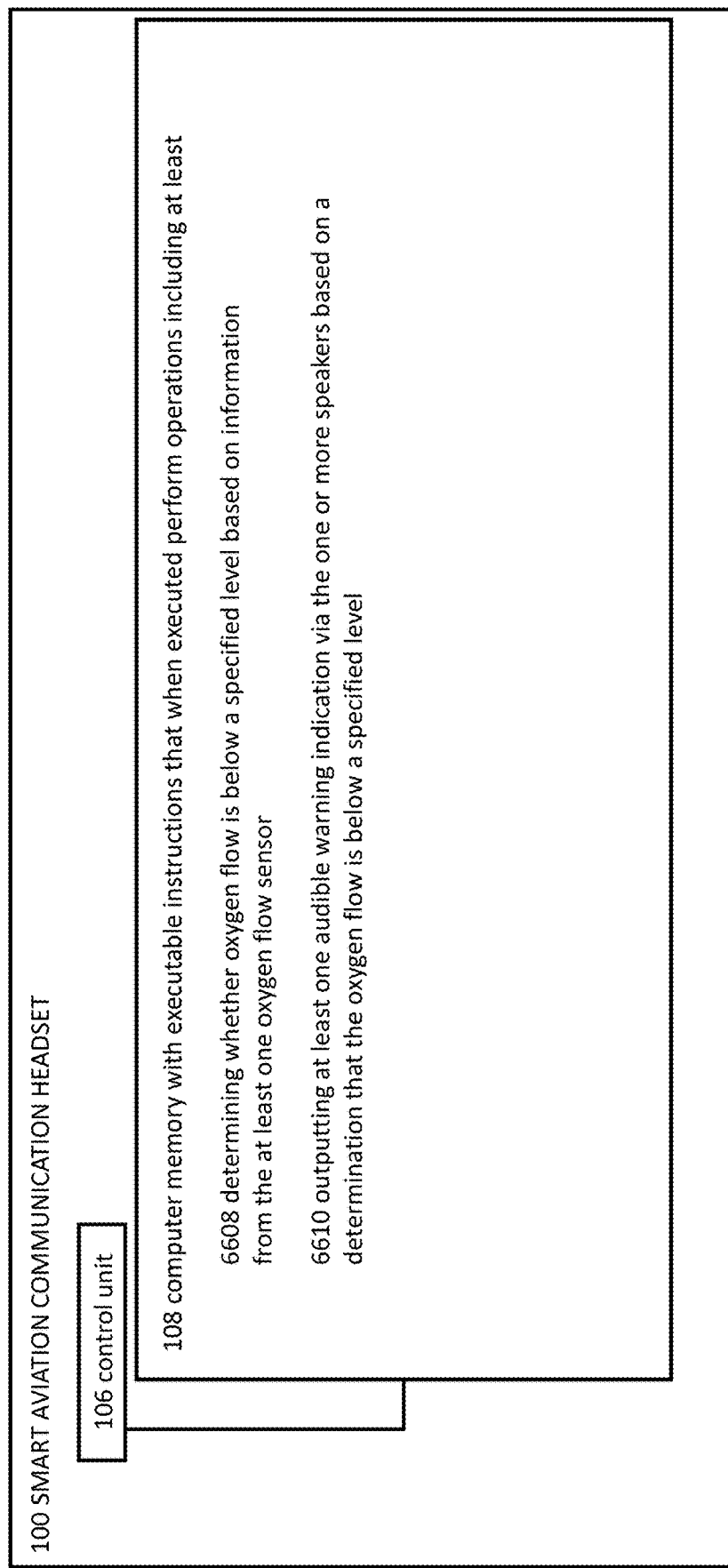

FIG. 66 is a system diagram of a smart aviation communication headset 100, in accordance with an embodiment of the invention. In one embodiment, an aviation communication headset 100 includes, but is not limited to, at least one microphone 114; one or more speakers 112; an oxygen dispenser receptacle 115; a cannula 117; an oxygen container 172; an oxygen regulator 119; a GPS unit 134; and at least one control unit 106 configured by one or more executable instructions stored on computer memory 108 to perform operations including at least: determining whether oxygen flow is below a specified level based on information from the at least one oxygen flow sensor at 6608; and outputting at least one audible warning indication via the one or more speakers based on a determination that the oxygen flow is below a specified level at 6610. The processor component can receive flow rate signals from an oxygen flow sensor or meter that is associated with the cannula. Upon detecting a flow rate that is less than an expected amount, such as when the oxygen container is almost depleted or when the regulator is not properly functioning, the processor component can output an audible warning via the speakers of the aviation communication headset. The warning can include an indication to replace the oxygen container. The processor component can also adjust the regulator dynamically based on the actual flow rate of oxygen to ensure the desired amount of oxygen is dispensed.

Figure 67:
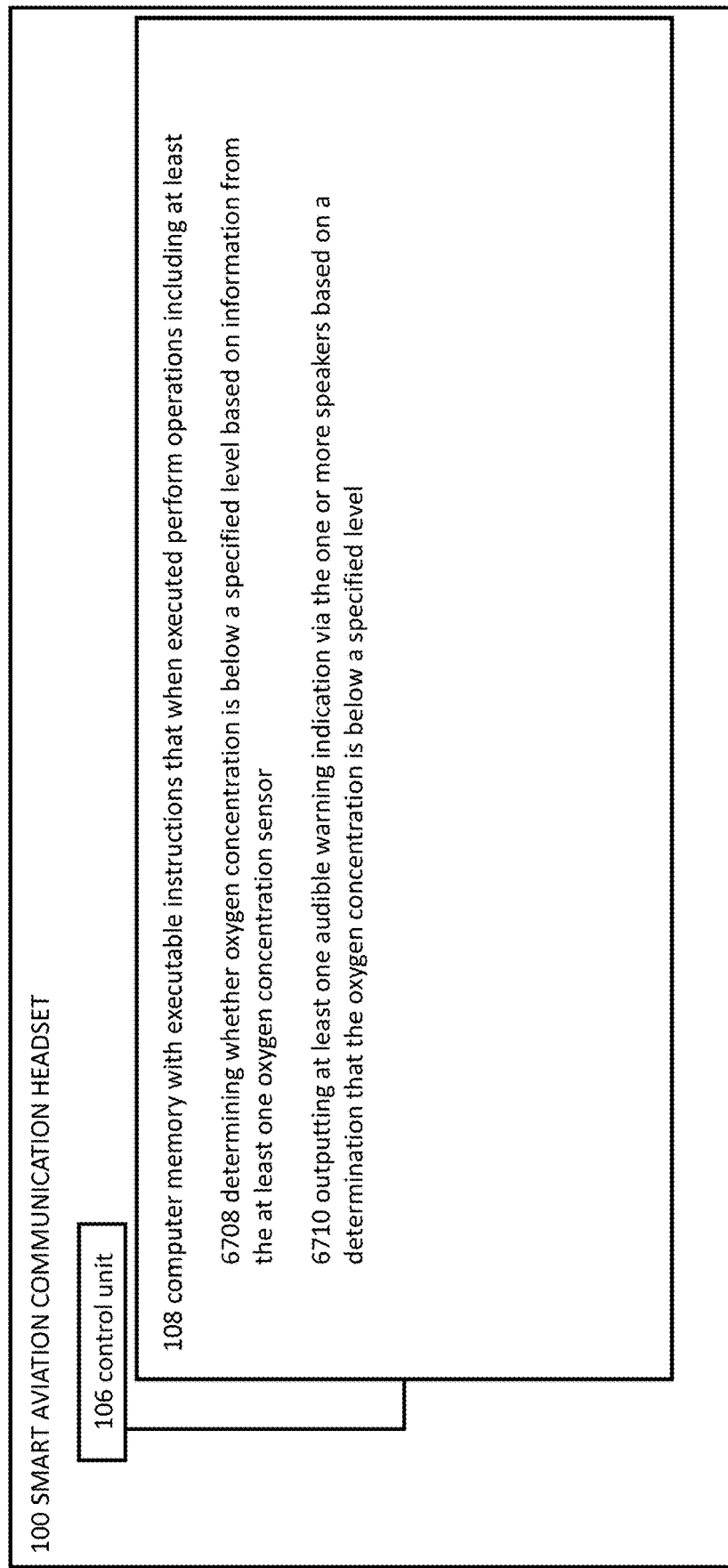
Figure 68:
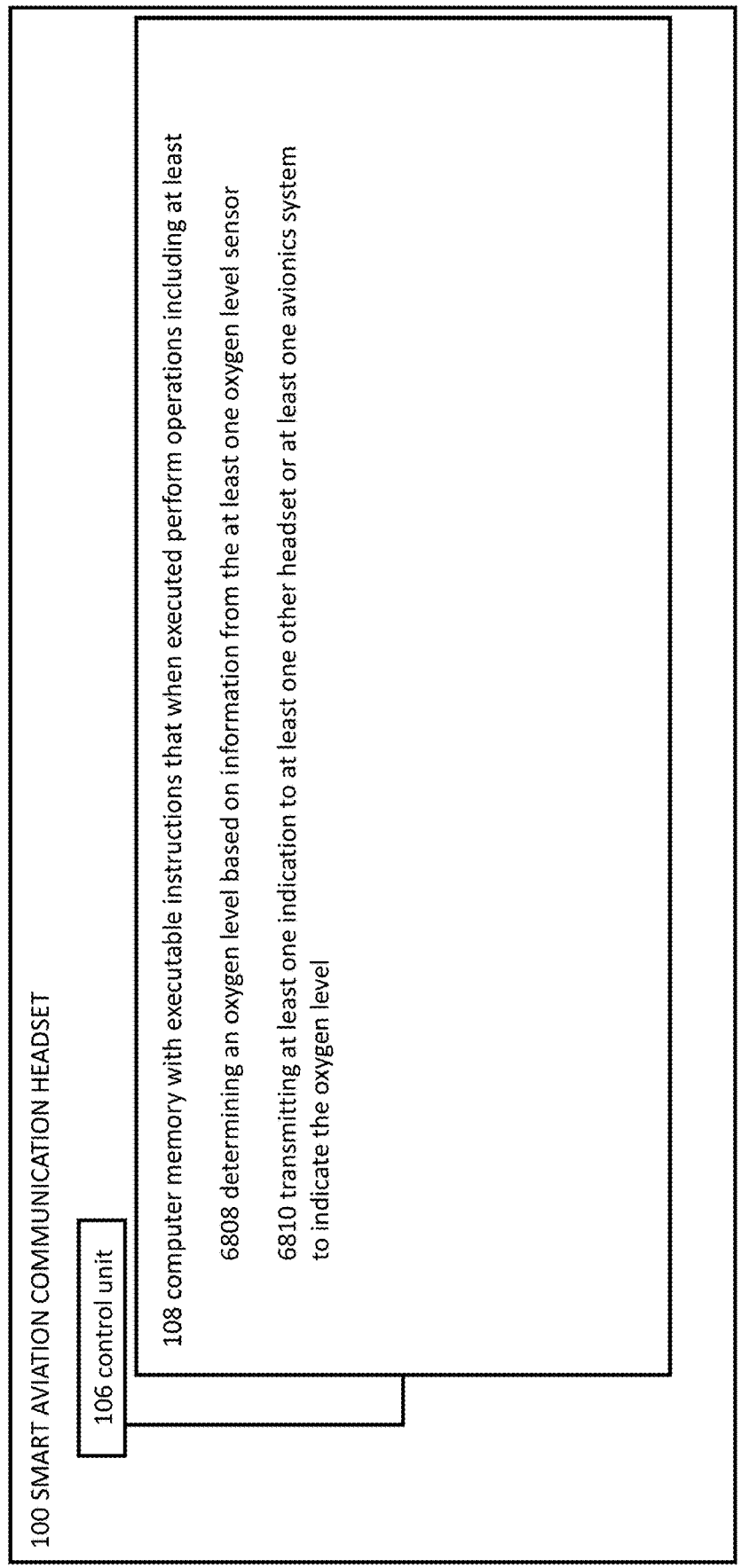
Figure 69:
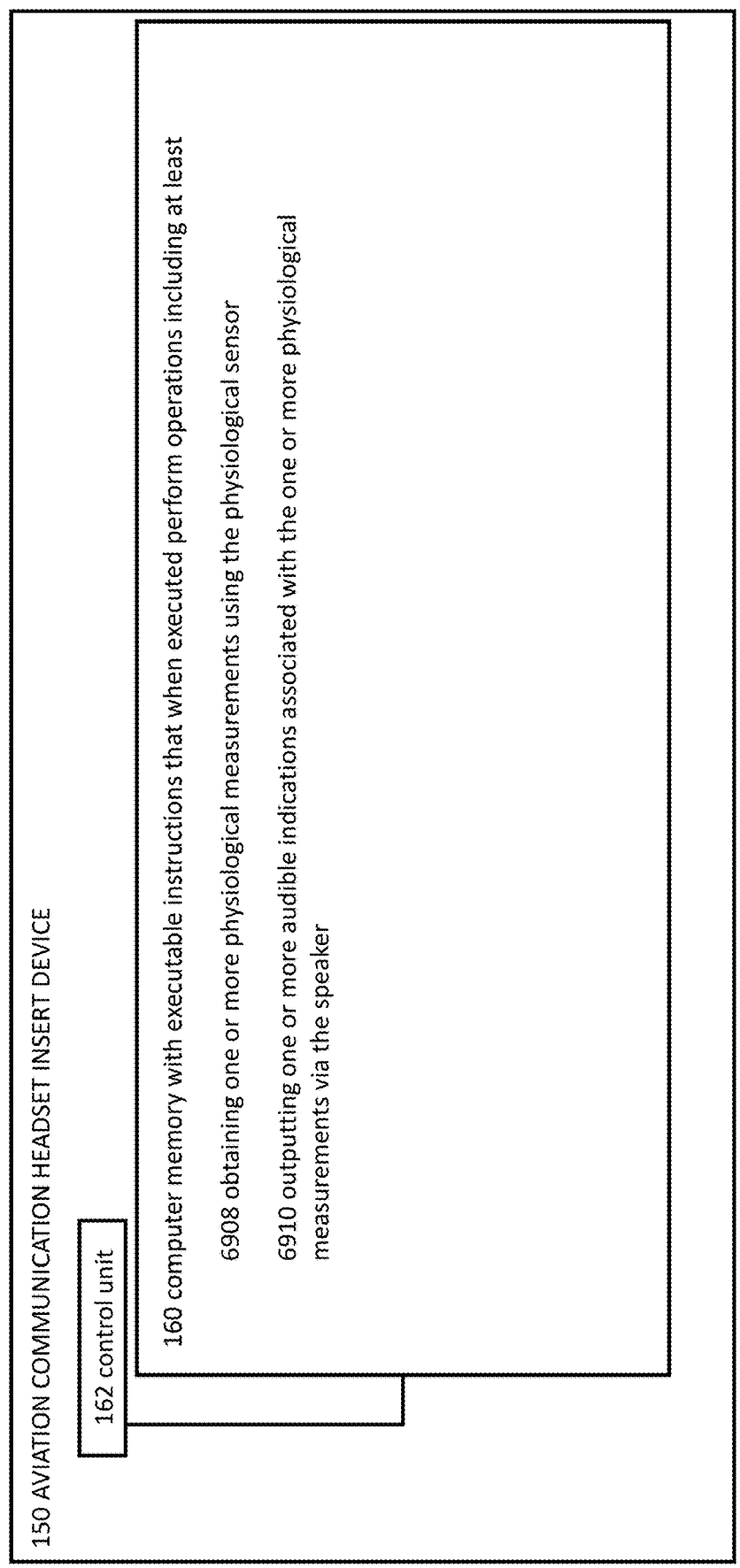
Figure 70:
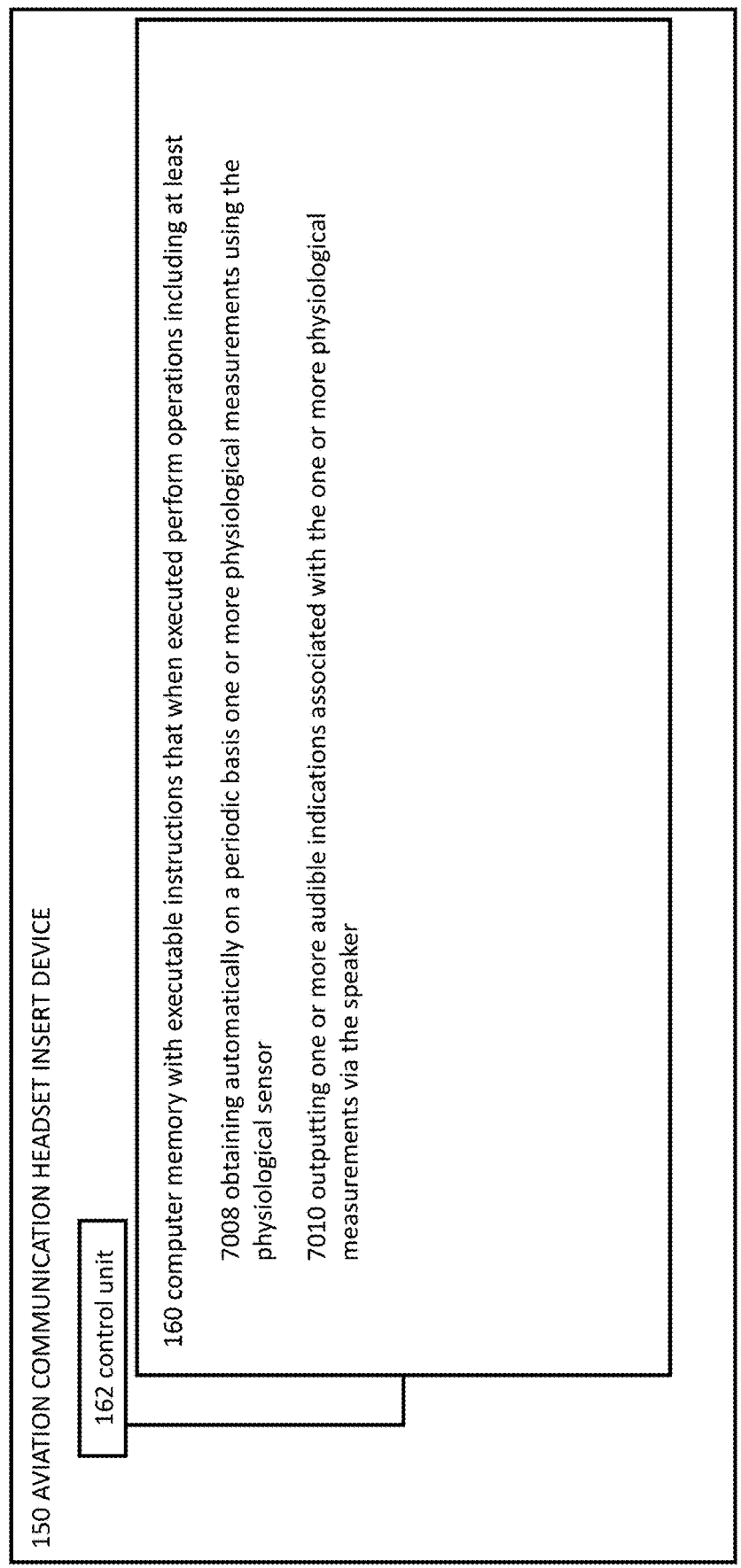
Figure 71:
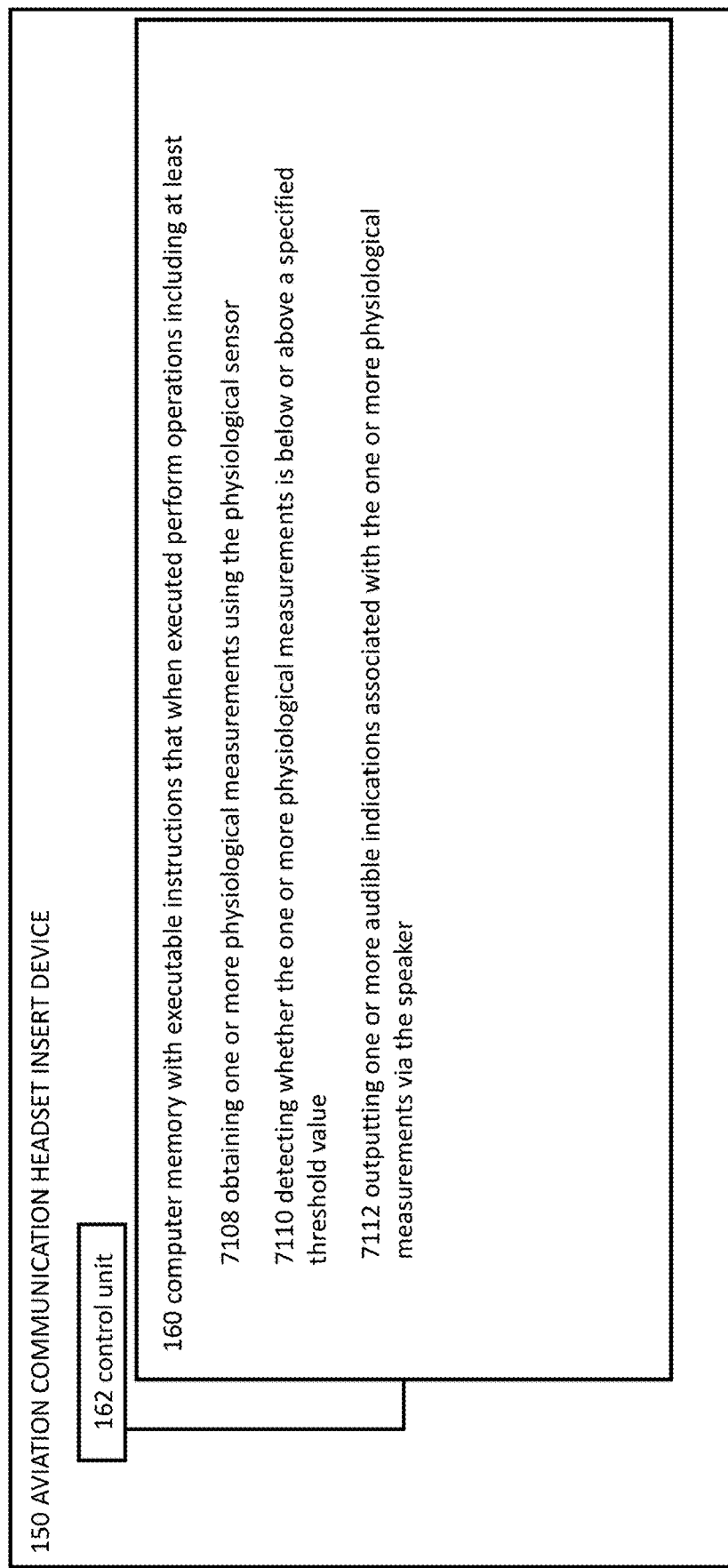
Figure 72:
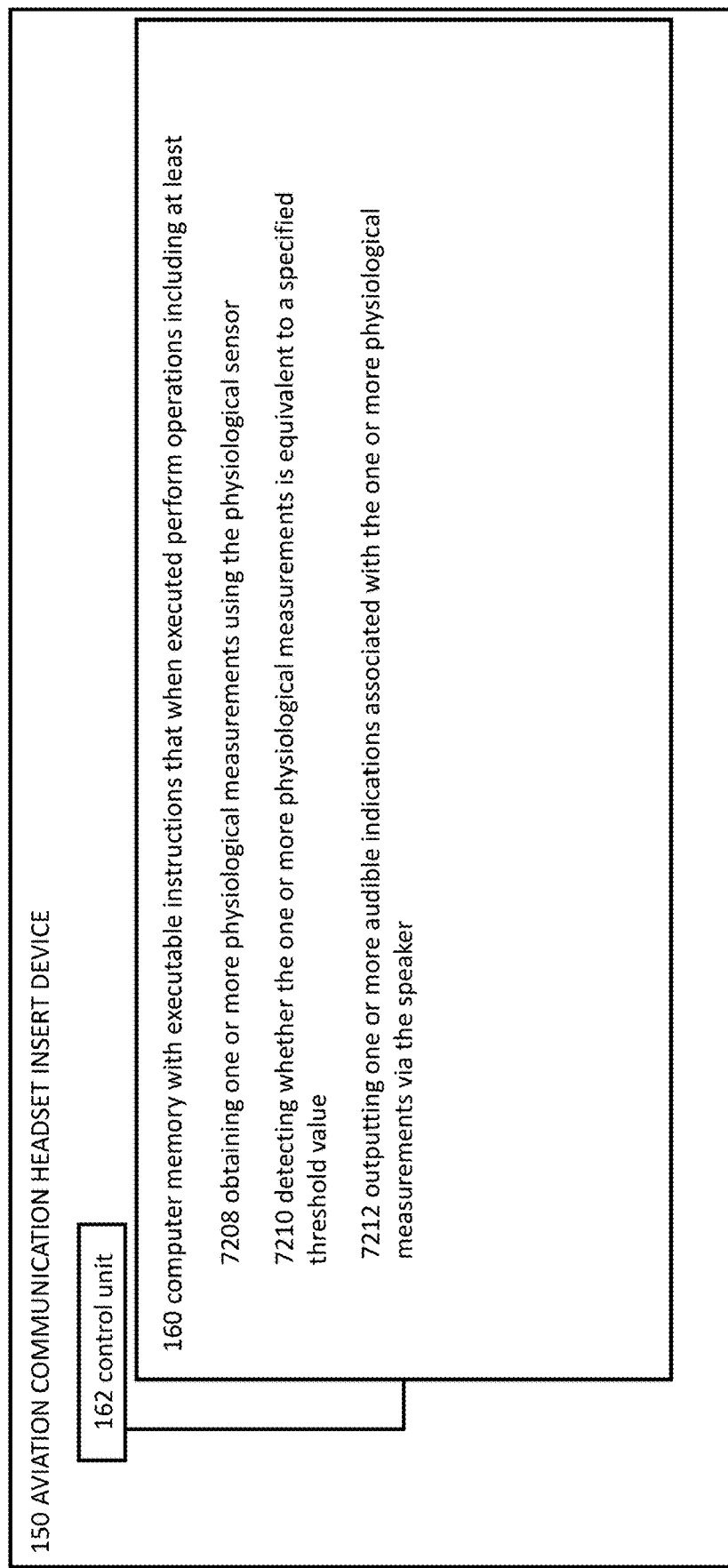
Figure 73:
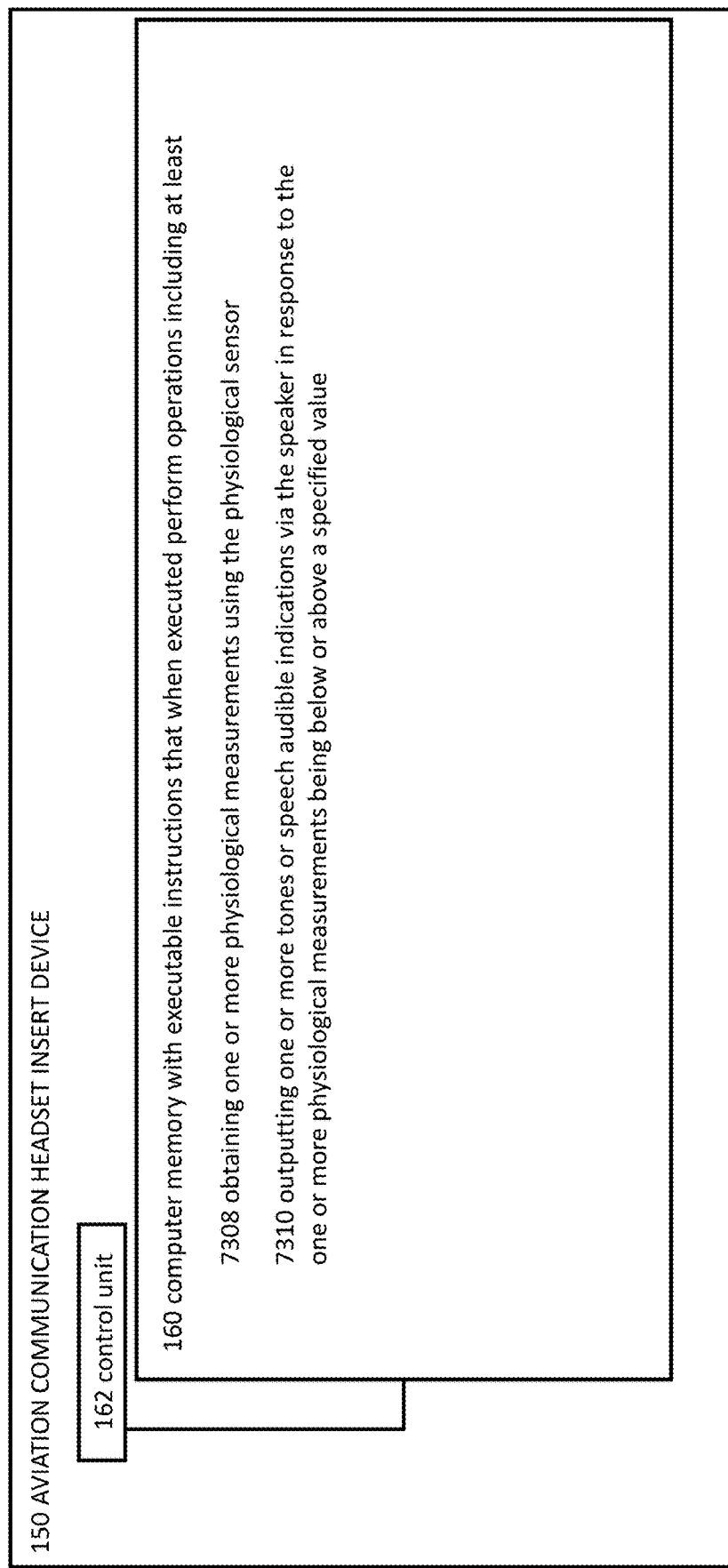
Figure 74:
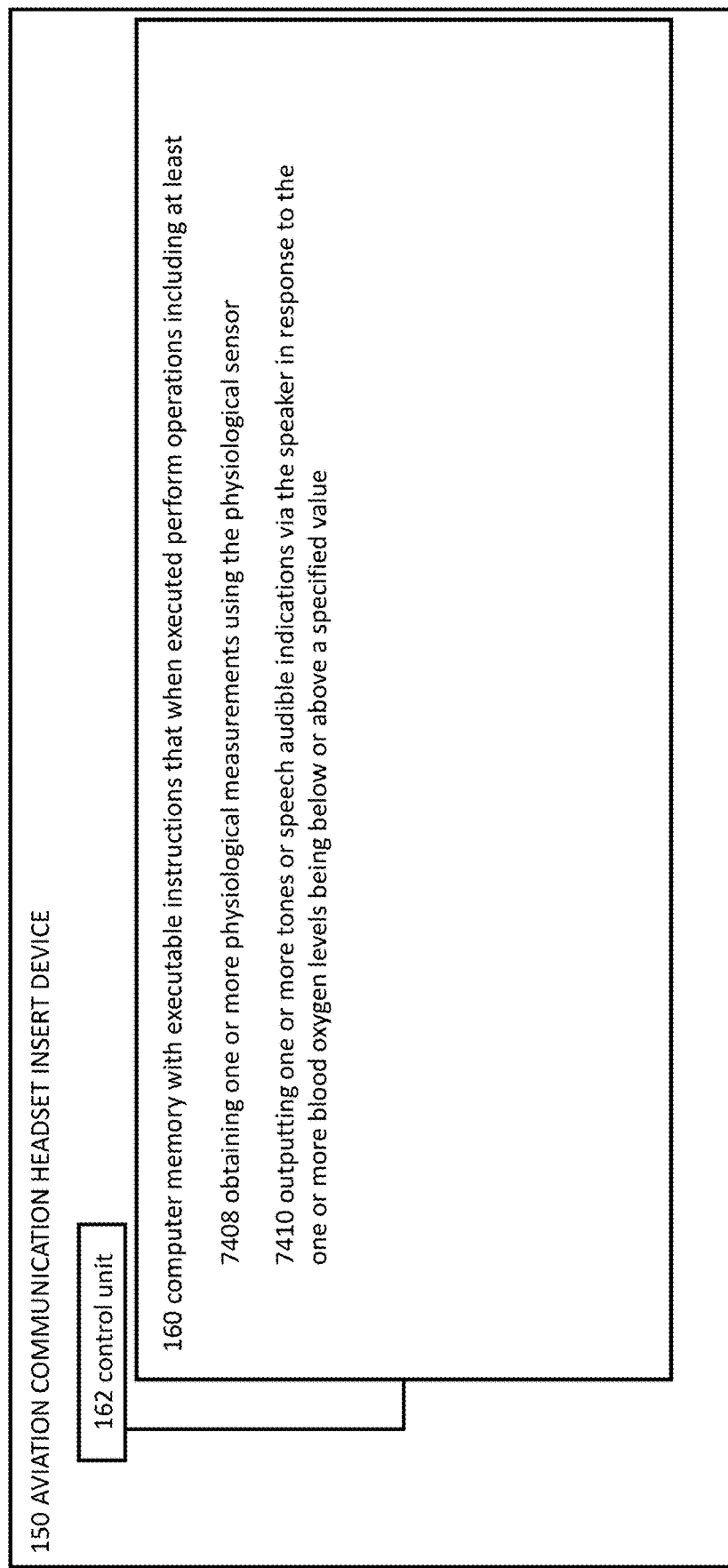
Figure 75:
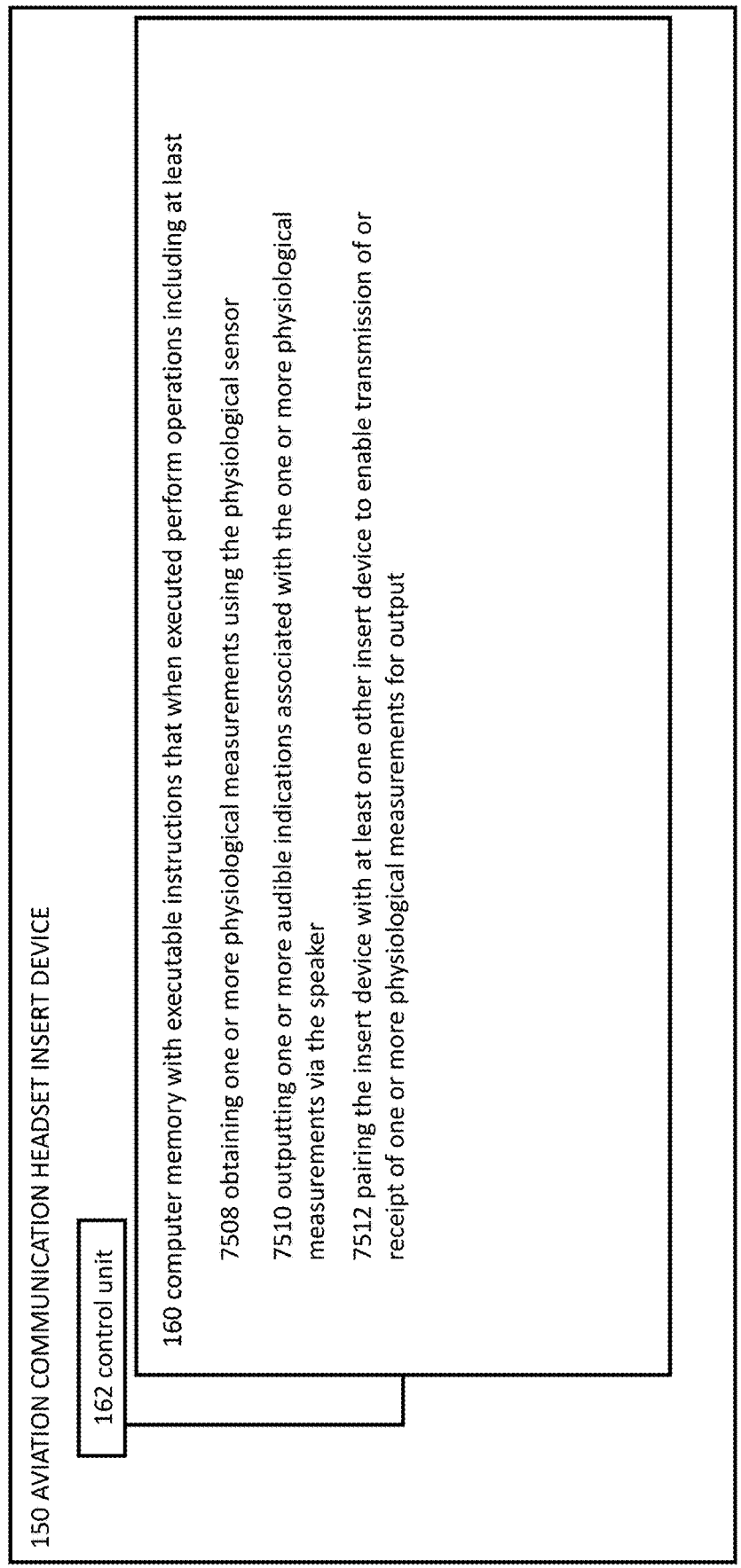
Figure 76:
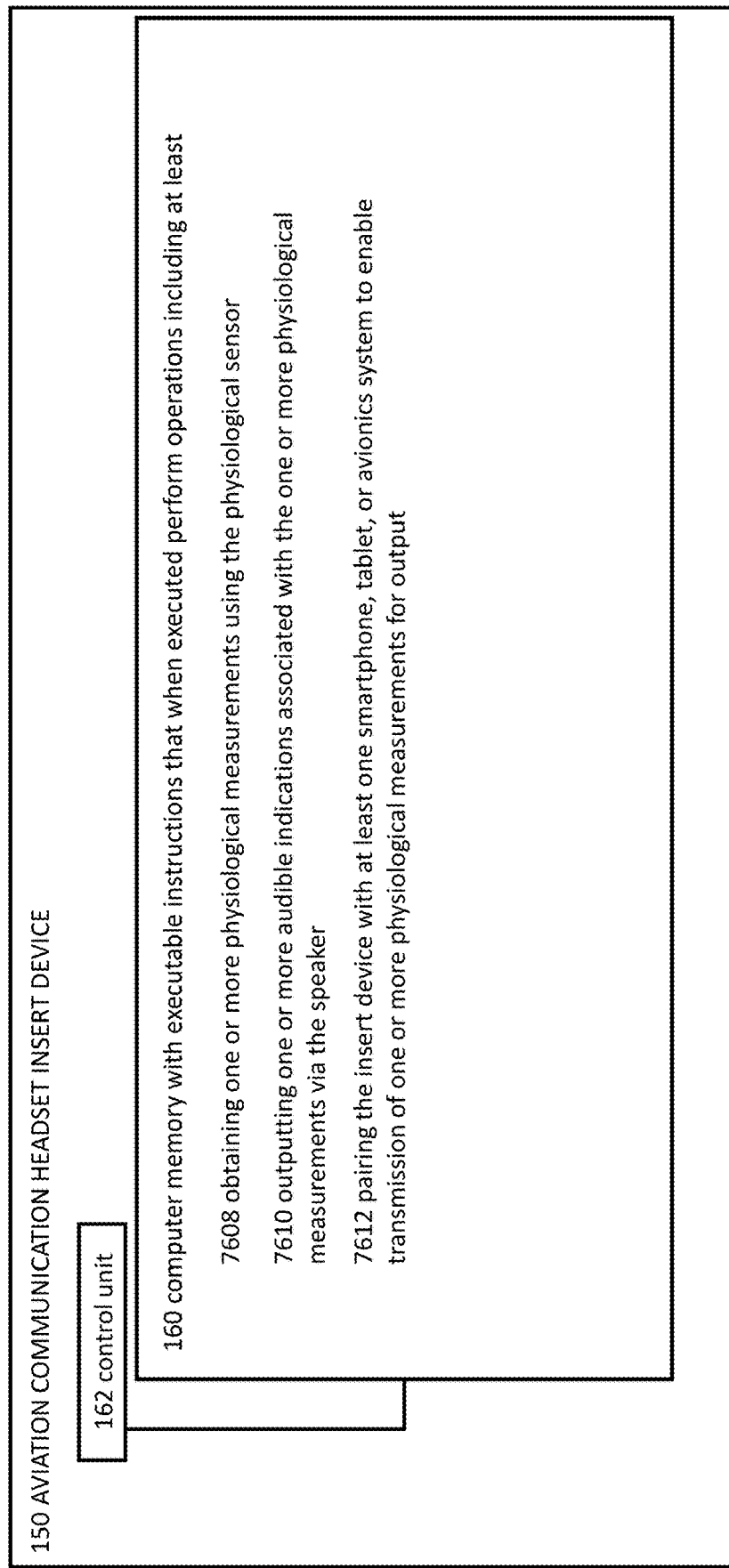
Figure 77:
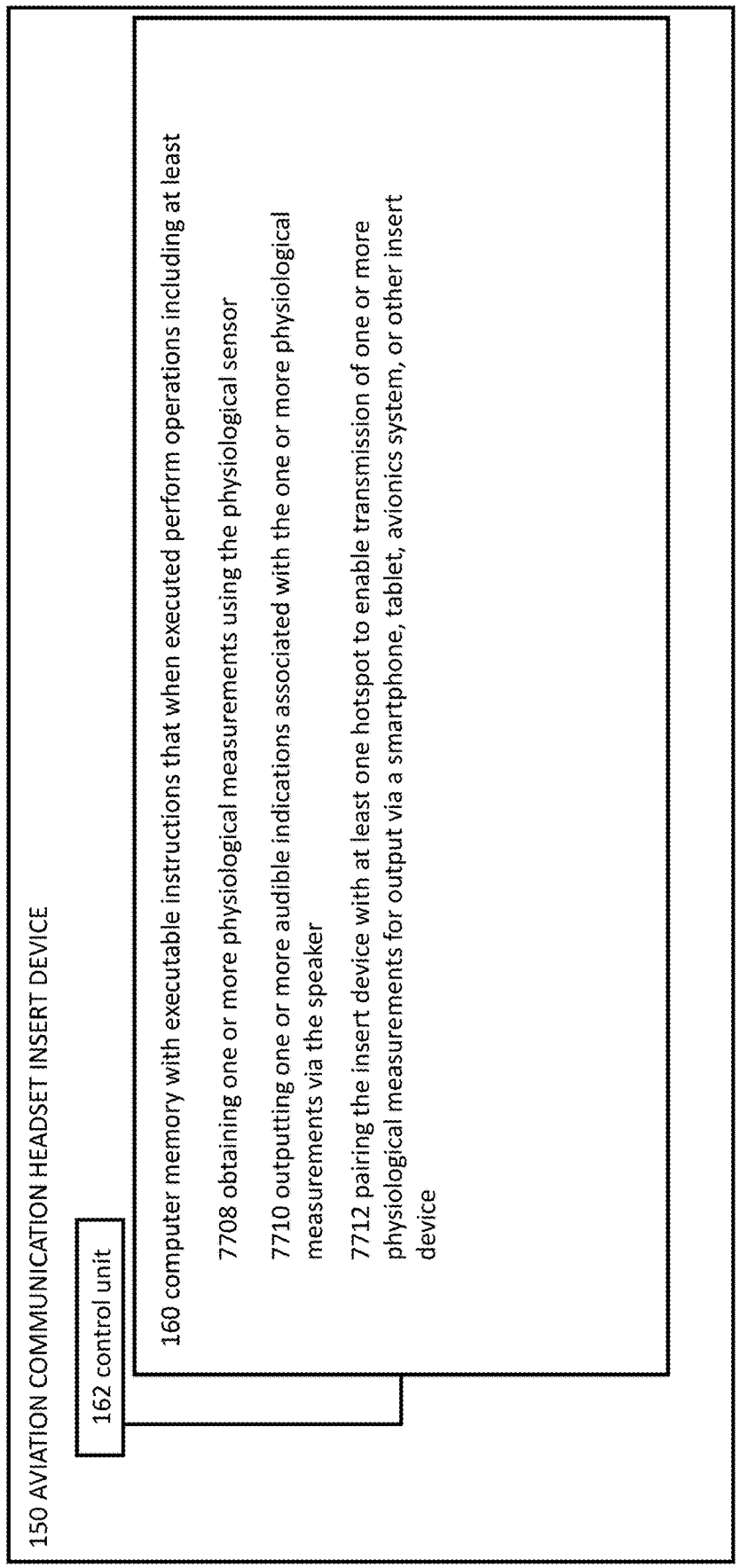
Figure 78:
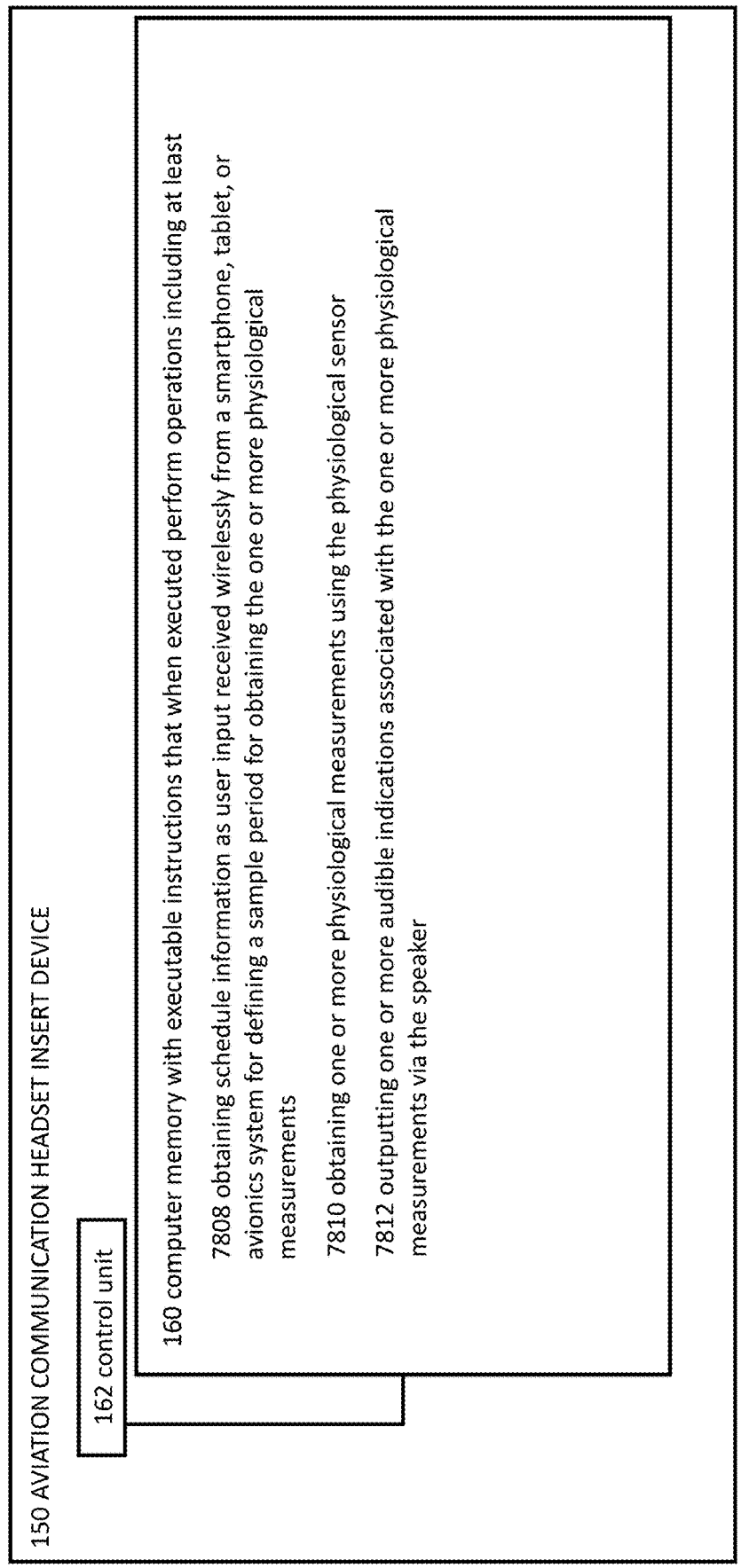
Figure 79:
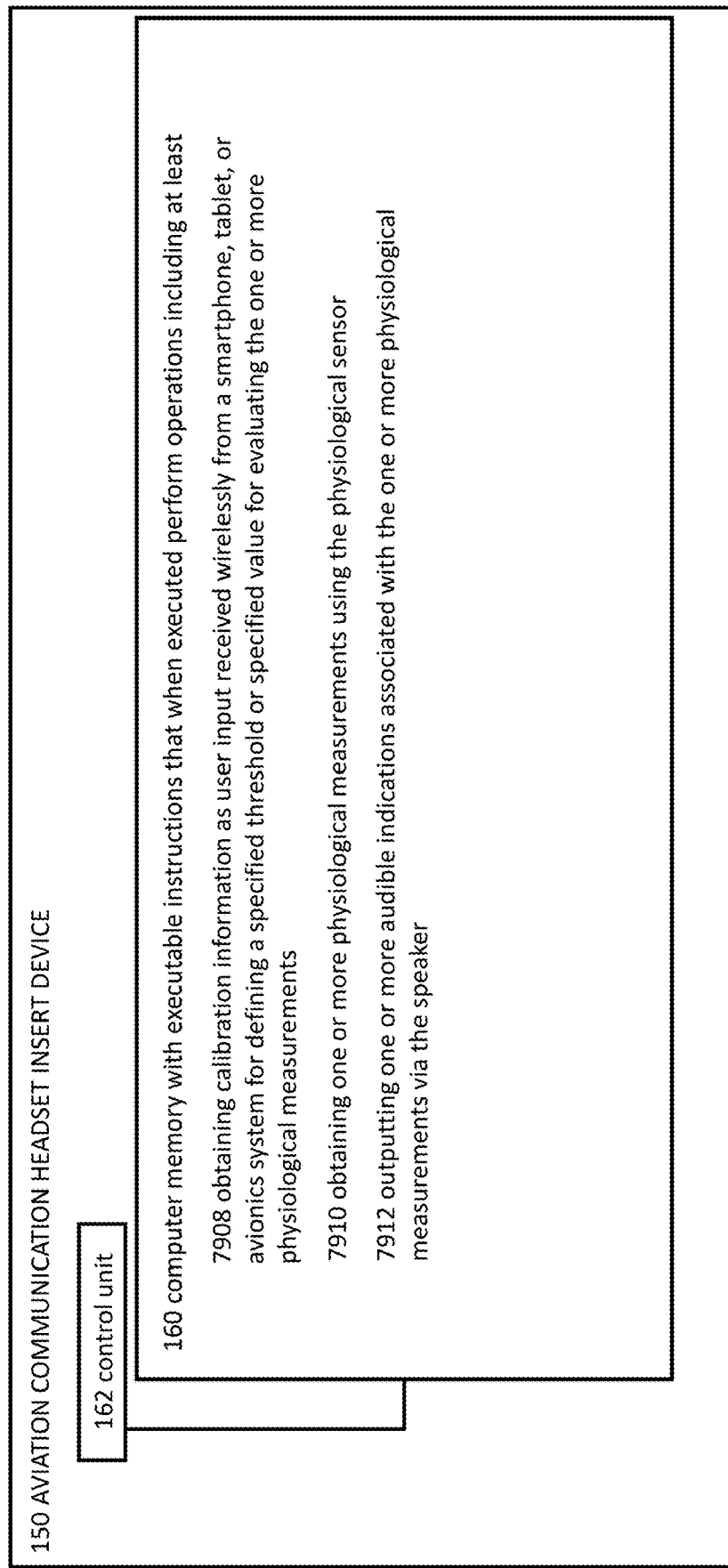
Figure 80:
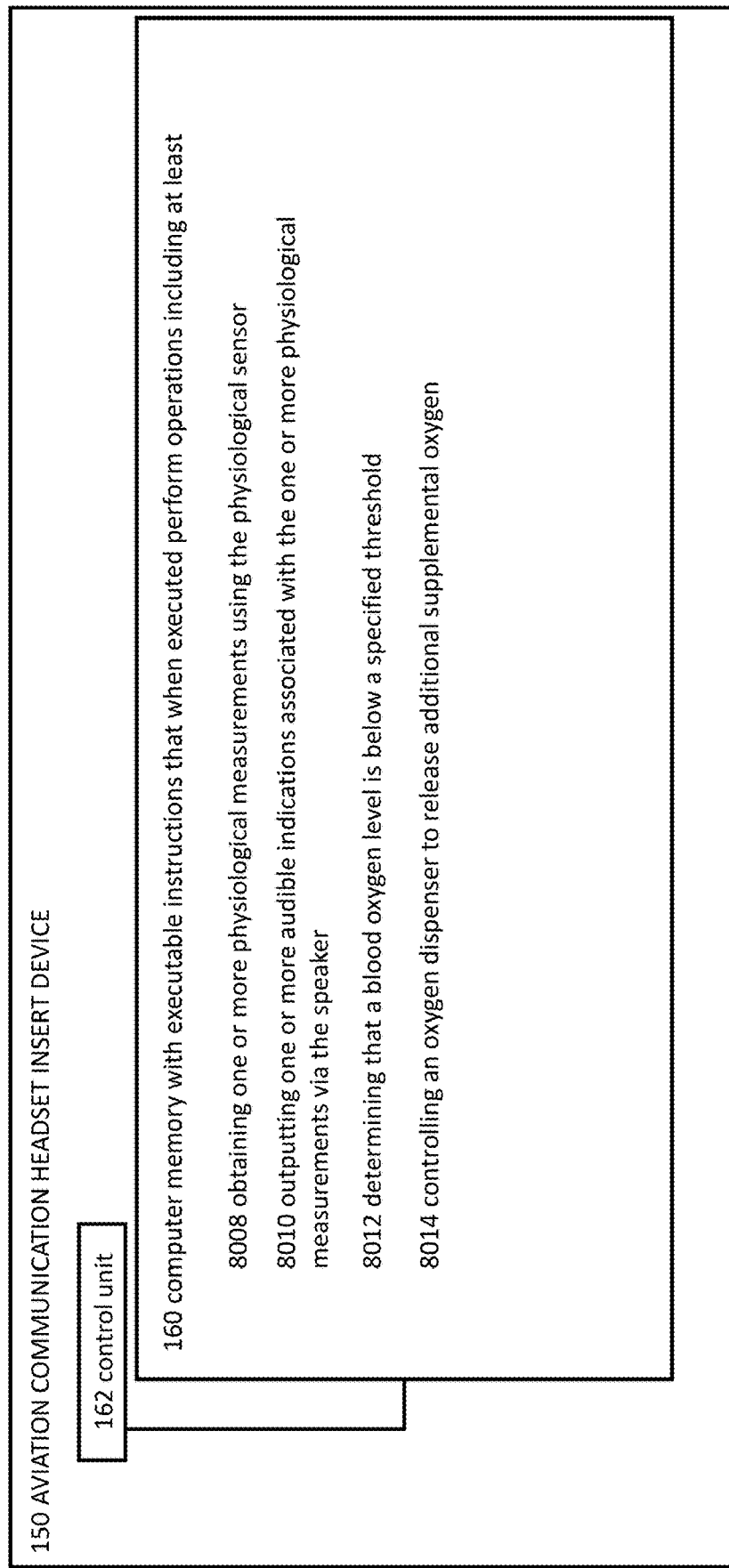
Figure 81:
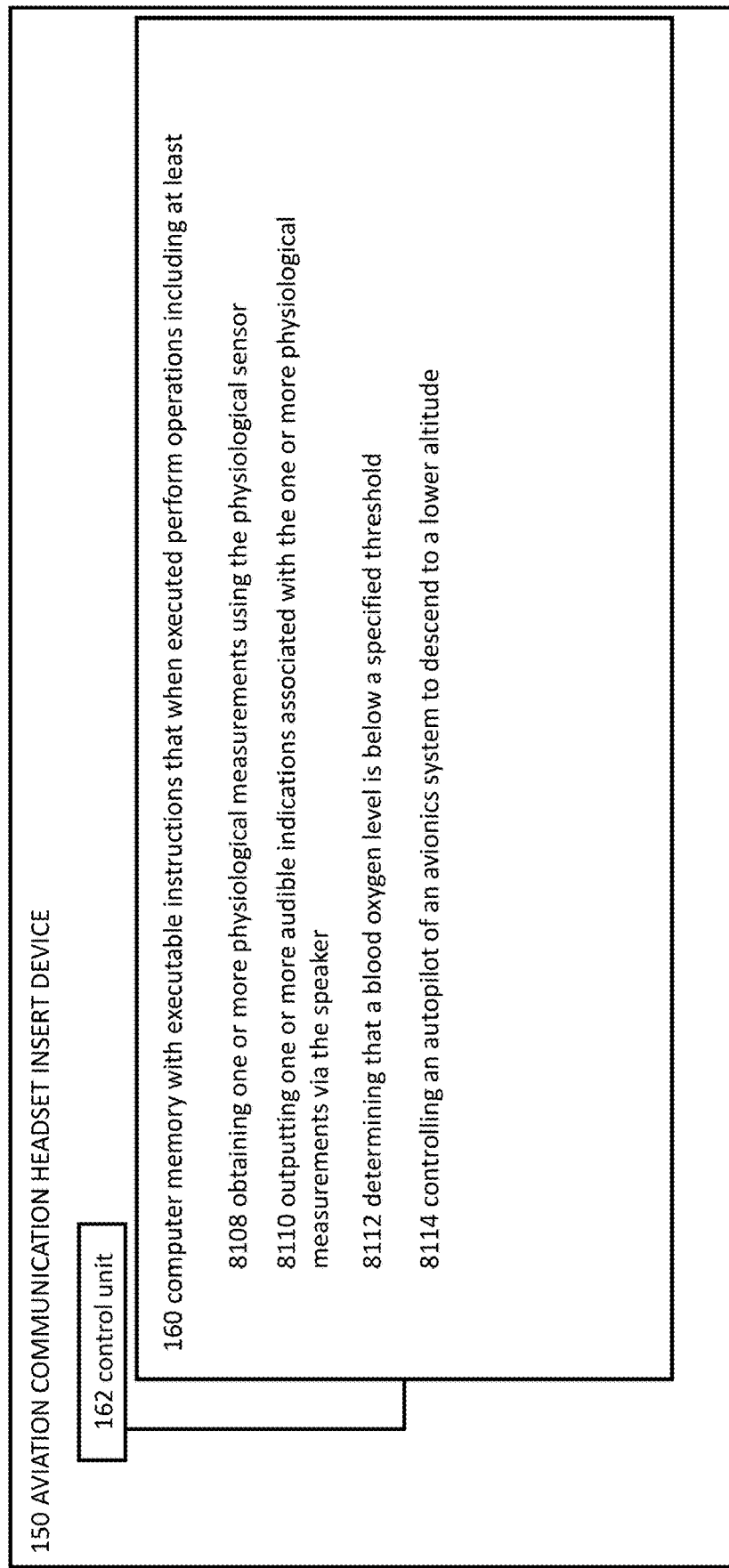
Figure 82:
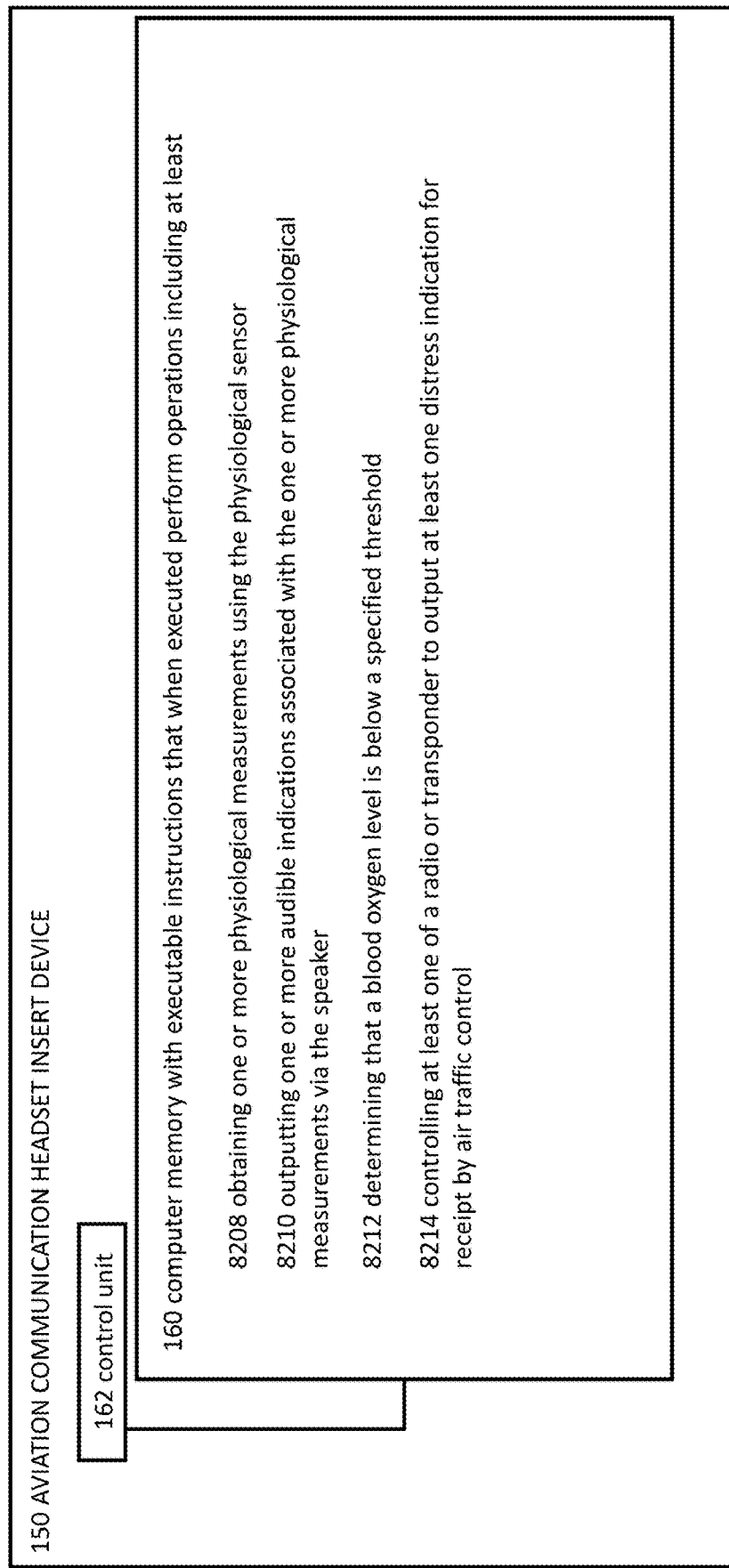
Figure 83:
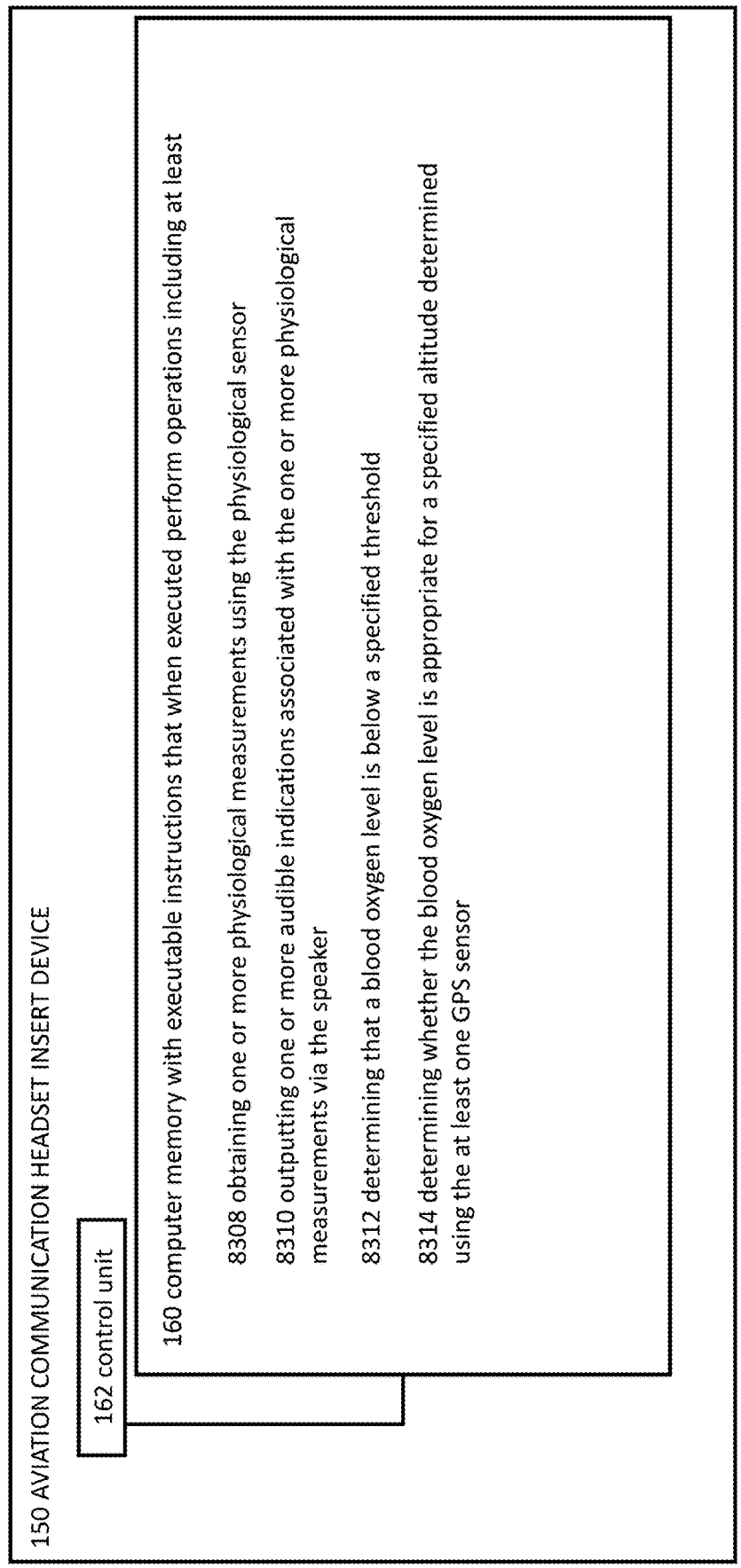
Figure 84:
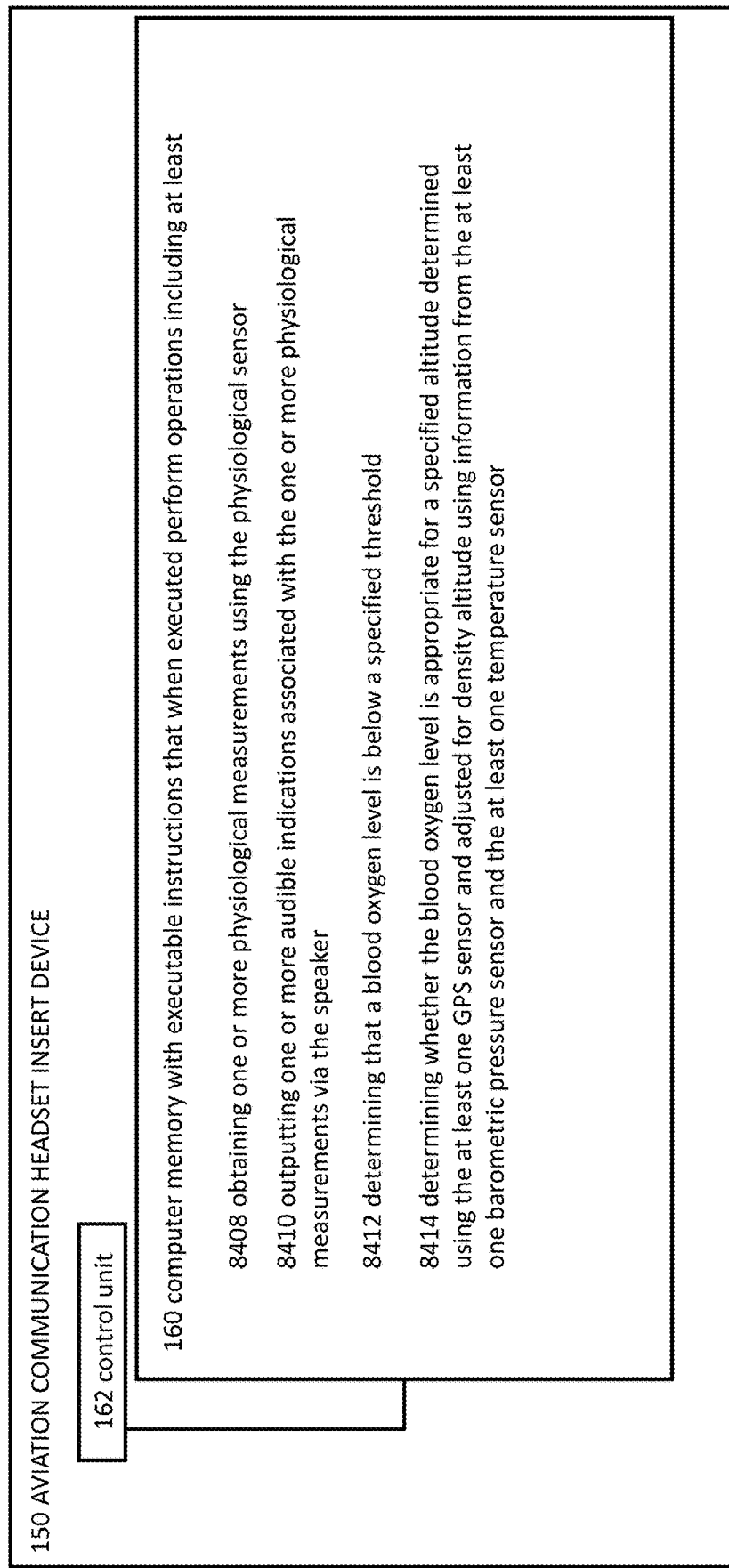

FIG. 67 is a system diagram of a smart aviation communication headset 100, in accordance with an embodiment of the invention. In one embodiment, an aviation communication headset 100 includes, but is not limited to, at least one microphone 114; one or more speakers 112; an oxygen dispenser receptacle 115; a cannula 117; an oxygen container 172; an oxygen regulator 119; a GPS unit 134; and at least one control unit 106 configured by one or more executable instructions stored on computer memory 108 to perform operations including at least:

FIG. 68 is a system diagram of a smart aviation communication headset 100, in accordance with an embodiment of the invention. In one embodiment, an aviation communication headset 100 includes, but is not limited to, at least one microphone 114; one or more speakers 112; an oxygen dispenser receptacle 115; a cannula 117; an oxygen container 172; an oxygen regulator 119; a GPS unit 134; and at least one control unit 106 configured by one or more executable instructions stored on computer memory 108 to perform operations including at least: determining whether oxygen concentration is below a specified level based on information from the at least one oxygen concentration sensor at 6708; and outputting at least one audible warning indication via the one or more speakers based on a determination that the oxygen concentration is below a specified level at 6710. For example, the processor component can, periodically or on demand, obtain pressure readouts from an oxygen concentration or pressure sensor associated with the regulator or the dispenser container. Upon the pressure or concentration of oxygen falling below a specified value, the processor component can output an audible warning, such as an indication to replace the oxygen container or an indication that there remains a specified number of minutes remaining of oxygen. The processor can also control the regulator in an emergency mode to conserve as much oxygen as possible by lowering the dispensation to the minimum threshold for cognitive functioning.

FIGS. 69-84 are system diagrams of an aviation communication headset insert device 150, in accordance with various embodiments of the invention. In these embodiments, an aviation communication headset insert device 150 may include, but is not limited to, an earlobe receptacle 154; tension members 152 extending from opposing ends of the earlobe receptacle to tensionally brace the insert device 150 within an ear cup of an aviation headset; a physiological sensor 156 incorporated into the earlobe receptacle; a speaker 158; and at least one control unit 162 configured by one or more executable instructions stored on computer memory 160 to perform specified operations. The specified operations are similar or equivalent to those discussed in reference to FIGS. 34-59, with the exception that the insert device is self-contained and performs the operations independent of the aviation communication headset, thereby enabling similar functionality to be introduced to legacy aviation communication headsets.

Figure 85:
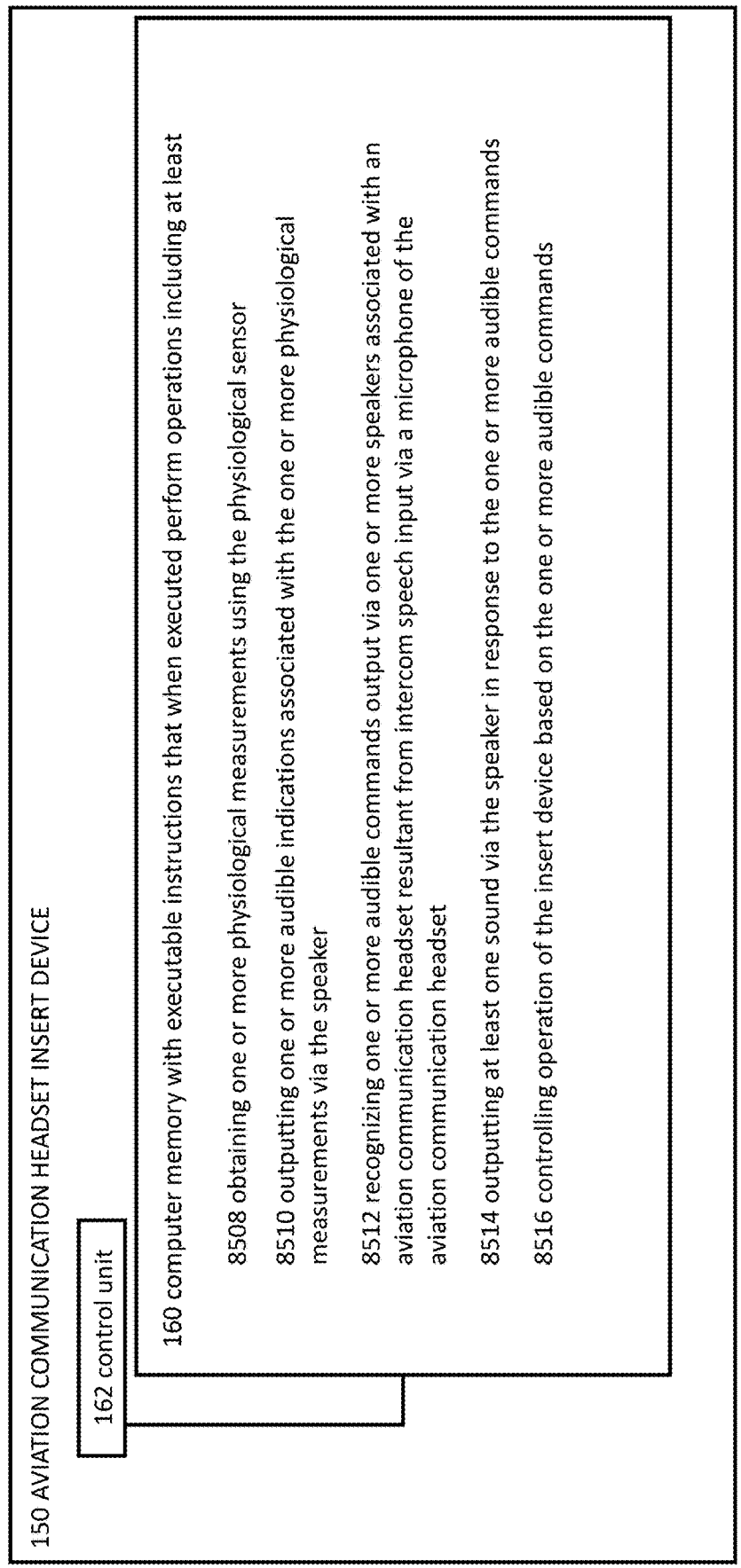

FIG. 85 is a system diagram of an aviation communication headset insert device 150, in accordance with an embodiment of the invention. In this embodiment, an aviation communication headset insert device 150 includes, but is not limited to, an earlobe receptacle 154; tension members 152 extending from opposing ends of the earlobe receptacle to tensionally brace the insert device 150 within an ear cup of an aviation headset; a physiological sensor 156 incorporated into the earlobe receptacle; a speaker 158; a microphone 173, and at least one control unit 162 configured by one or more executable instructions stored on computer memory 160 to perform operations of: obtaining one or more physiological measurements using the physiological sensor at 8508; outputting one or more audible indications associated with the one or more physiological measurements via the speaker at 8510; recognizing one or more audible commands output via one or more speakers associated with an aviation communication headset resultant from intercom speech input via a microphone of the aviation communication headset at 8512; outputting at least one sound via the speaker in response to the one or more audible commands at 8514; and controlling operation of the insert device based on the one or more audible commands at 8516. For example, the microphone of the insert device can detect speech signals output from a speaker of an aviation communication headset due to the placement of the insert device within the acoustically isolated environment. Thus, a microphone of the aviation communication headset can be used to communicate with the insert device due to the output via speakers of an earcup which are detected by the microphone of the insert device. The processor of the insert device can recognize the speech signals detected using speech recognition and convert the speech signals into commands that are usable to control the insert device. No wiring between the insert device and an aviation communication headset is required. The speaker of the insert device can output audible sound based on signals from the processor of the insert device, which sounds are again within the acoustically isolated earcup of the aviation communication headset. For instance, the processor of the insert device can detect and recognize a speech command of "AITHRE tell me my blood oxygen level", which speech command originates from a microphone of an aviation communication headset and is output via a speaker of the aviation communication headset where the insert device is positioned and where the microphone of the insert device detects such. The processor of the insert device can obtain the current or recent blood oxygen level and output that value via a speaker of the insert device, such that the readout of the blood oxygen level can be heard by a wearer of the aviation communication headset.

Figure 86:
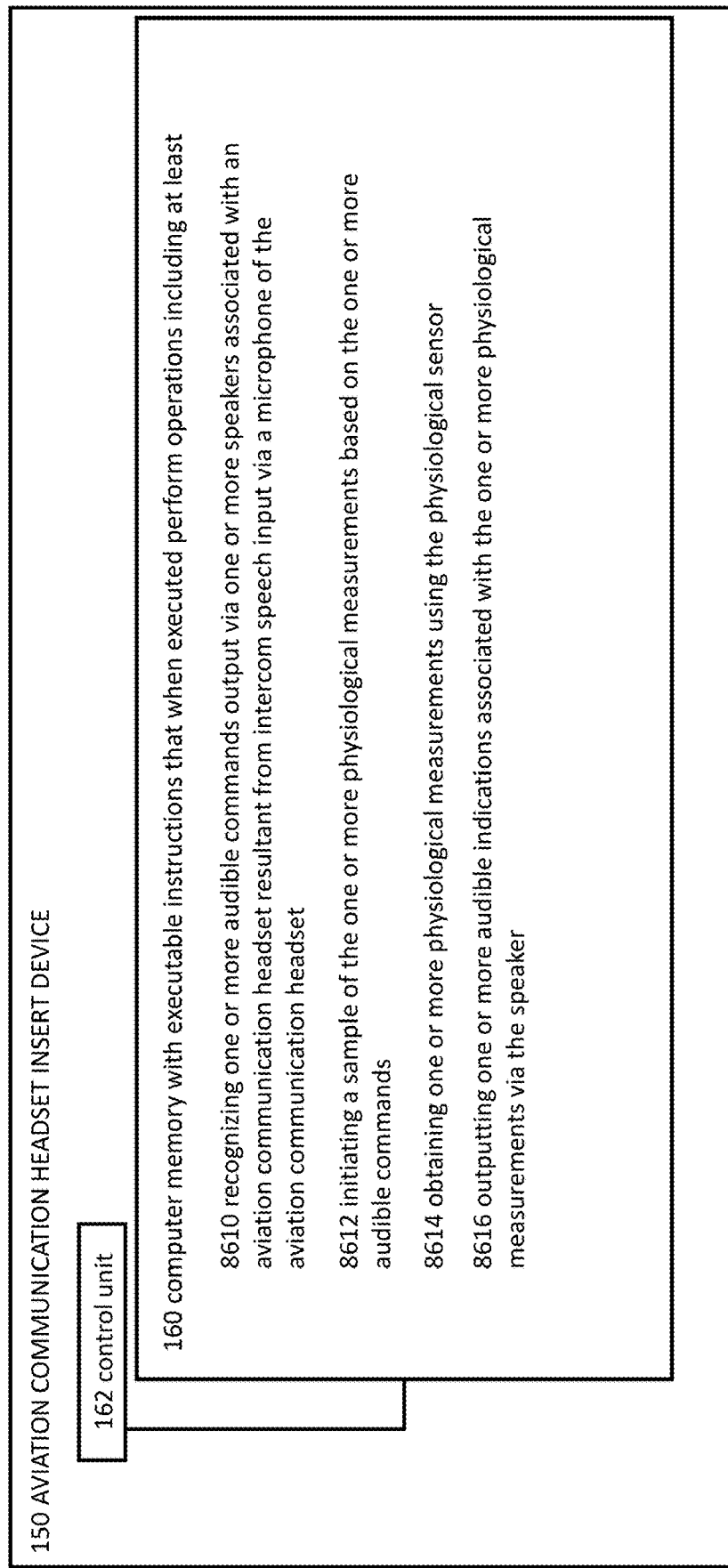

FIG. 86 is a system diagram of an aviation communication headset insert device 150, in accordance with an embodiment of the invention. In this embodiment, an aviation communication headset insert device 150 includes, but is not limited to, an earlobe receptacle 154; tension members 152 extending from opposing ends of the earlobe receptacle to tensionally brace the insert device 150 within an ear cup of an aviation headset; a physiological sensor 156 incorporated into the earlobe receptacle; a speaker 158; a microphone 173, and at least one control unit 162 configured by one or more executable instructions stored on computer memory 160 to perform operations of: recognizing one or more audible commands output via one or more speakers associated with an aviation communication headset resultant from intercom speech input via a microphone of the aviation communication headset at 8610; initiating a sample of the one or more physiological measurements based on the one or more audible commands at 8612; obtaining one or more physiological measurements using the physiological sensor at 8614; and outputting one or more audible indications associated with the one or more physiological measurements via the speaker at 8616. For example, the processor of the insert device can recognize a command received via a microphone of the insert device, which command was spoken into a microphone of an aviation communication headset and reproduced into the acoustically isolated environment of the earcup of the aviation headset via the speaker of the aviation headset. The recognized command can include initiating a sample of pulse rate. The processor executes the recognized command and obtains the pulse rate using the physiological sensor of the insert device. The processor of the insert device then outputs via a speaker of the insert device the pulse rate, such as 70 beats per minute.

Figure 87:
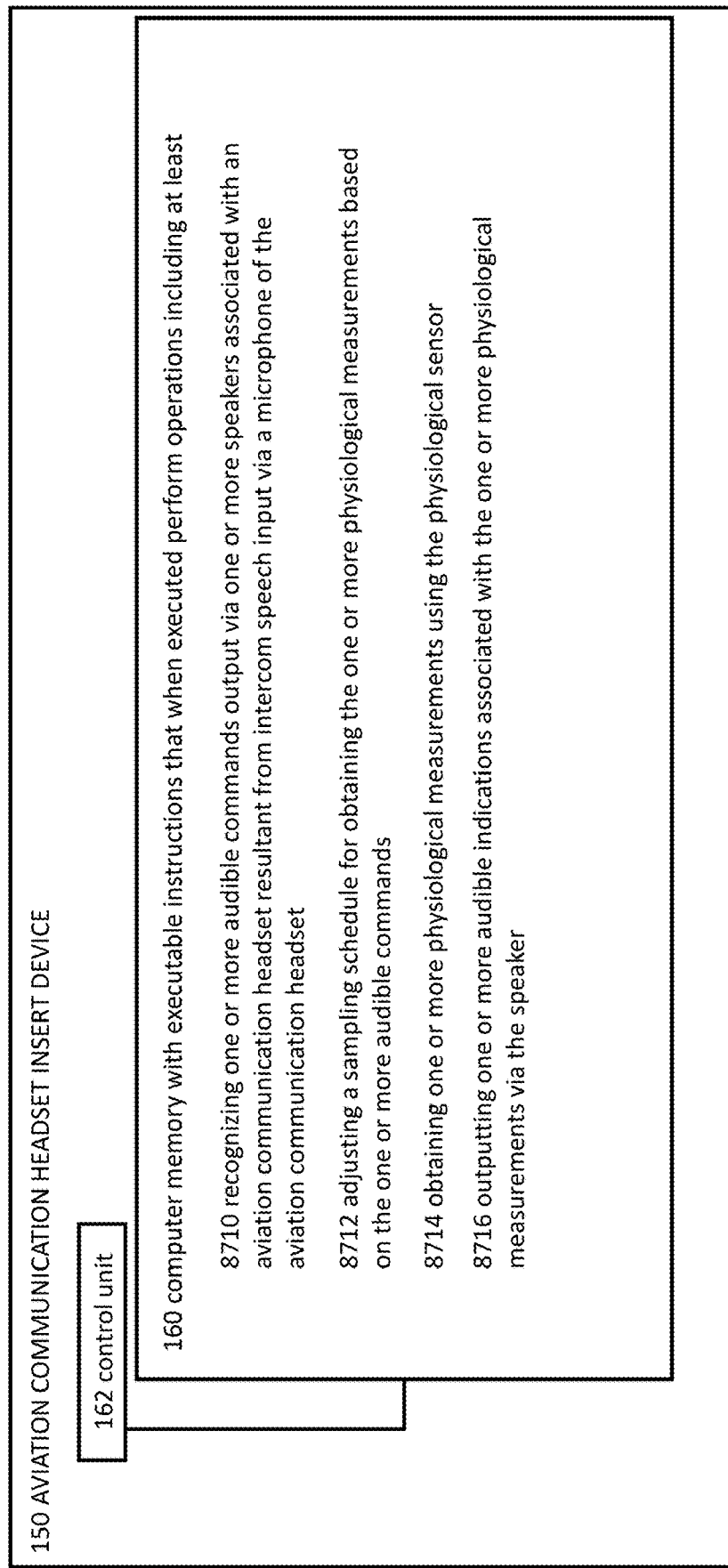

FIG. 87 is a system diagram of an aviation communication headset insert device 150, in accordance with an embodiment of the invention. In this embodiment, an aviation communication headset insert device 150 includes, but is not limited to, an earlobe receptacle 154; tension members 152 extending from opposing ends of the earlobe receptacle to tensionally brace the insert device 150 within an ear cup of an aviation headset; a physiological sensor 156 incorporated into the earlobe receptacle; a speaker 158; a microphone 173, and at least one control unit 162 configured by one or more executable instructions stored on computer memory 160 to perform operations of: recognizing one or more audible commands output via one or more speakers associated with an aviation communication headset resultant from intercom speech input via a microphone of the aviation communication headset at 8710; adjusting a sampling schedule for obtaining the one or more physiological measurements based on the one or more audible commands at 8712; obtaining one or more physiological measurements using the physiological sensor at 8714; and outputting one or more audible indications associated with the one or more physiological measurements via the speaker at 8716. For example, the processor of the insert device can recognize an audible command to sample blood oxygen every minute when over 10,000 feet MSL. The processor can then adjust the sample rate in accordance of the command and initiate sampling and output of the blood oxygen values determined using the sensors of the insert device.

Figure 88:
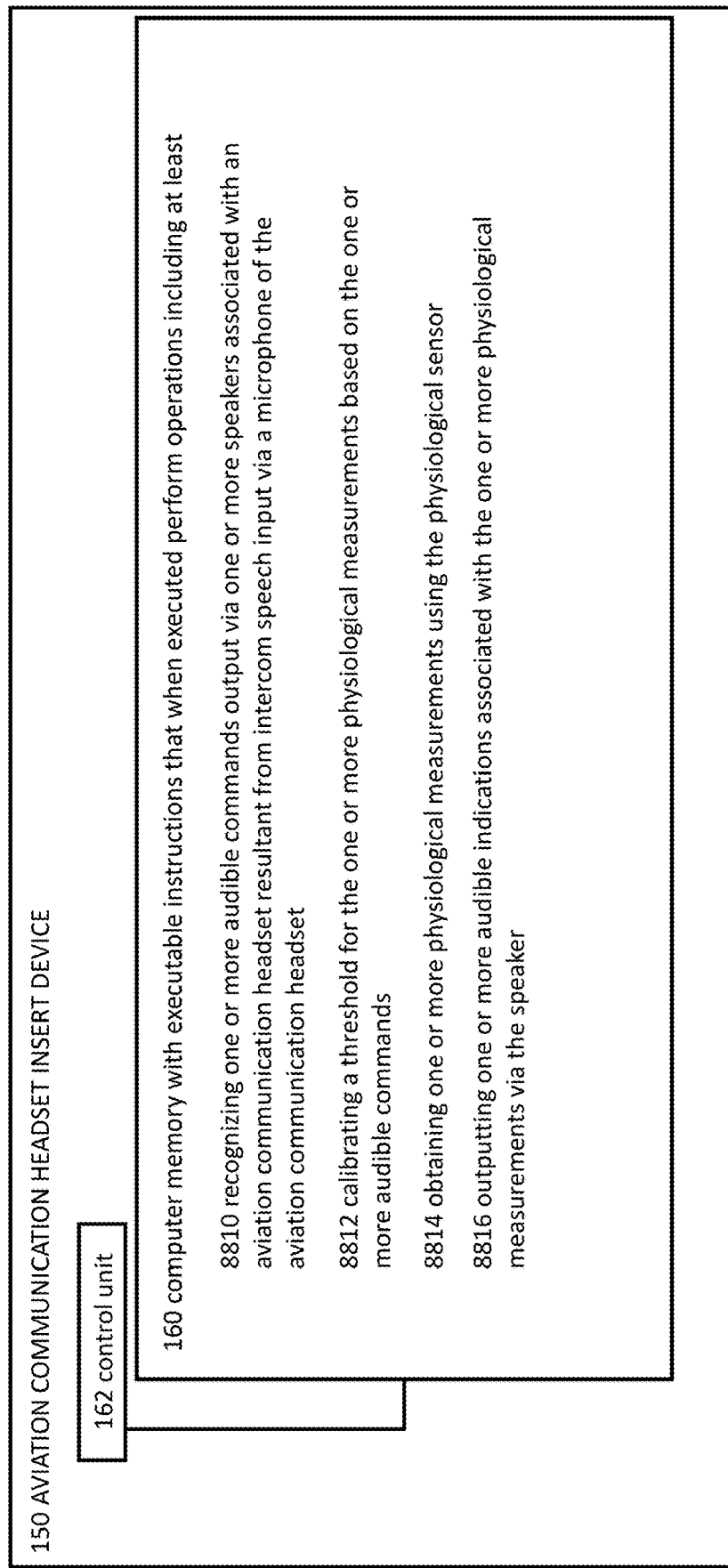

FIG. 88 is a system diagram of an aviation communication headset insert device 150, in accordance with an embodiment of the invention. In this embodiment, an aviation communication headset insert device 150 includes, but is not limited to, an earlobe receptacle 154; tension members 152 extending from opposing ends of the earlobe receptacle to tensionally brace the insert device 150 within an ear cup of an aviation headset; a physiological sensor 156 incorporated into the earlobe receptacle; a speaker 158; a microphone 173, and at least one control unit 162 configured by one or more executable instructions stored on computer memory 160 to perform operations of: recognizing one or more audible commands output via one or more speakers associated with an aviation communication headset resultant from intercom speech input via a microphone of the aviation communication headset at 8810; calibrating a threshold for the one or more physiological measurements based on the one or more audible commands at 8812; obtaining one or more physiological measurements using the physiological sensor at 8814; and outputting one or more audible indications associated with the one or more physiological measurements via the speaker at 8816. For example, the processor of the insert device can recognize a command received via the microphone of the insert device to set the blood oxygen warning threshold to 90 percent. The processor of the insert device can then establish the threshold and compare sampled blood oxygen levels to the threshold. In an event that the blood oxygen level falls below percent, the processor of the insert device can output an indication of such via the speaker of the insert device.

Figure 89:
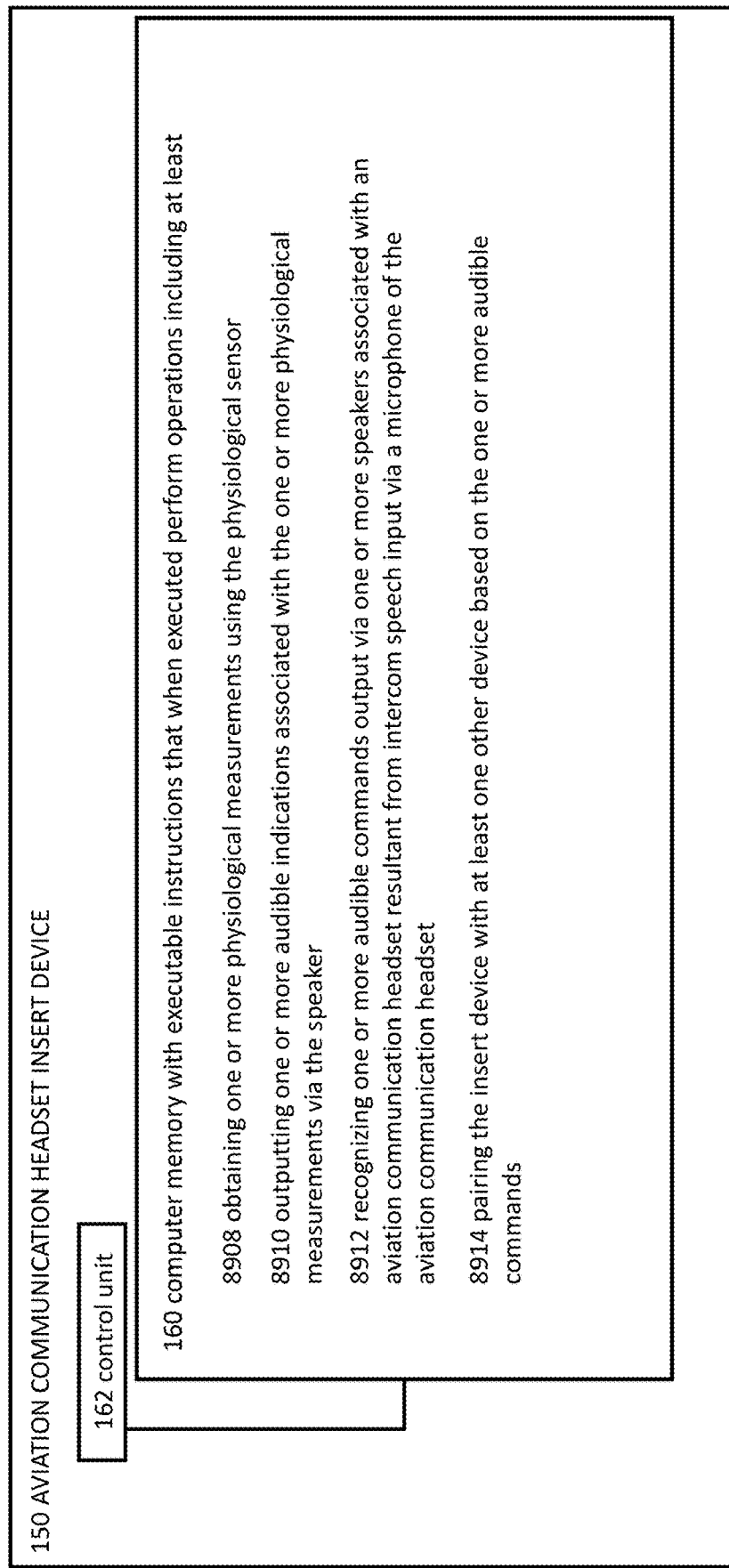

FIG. 89 is a system diagram of an aviation communication headset insert device 150, in accordance with an embodiment of the invention. In this embodiment, an aviation communication headset insert device 150 includes, but is not limited to, an earlobe receptacle 154; tension members 152 extending from opposing ends of the earlobe receptacle to tensionally brace the insert device 150 within an ear cup of an aviation headset; a physiological sensor 156 incorporated into the earlobe receptacle; a speaker 158; a microphone 173, and at least one control unit 162 configured by one or more executable instructions stored on computer memory 160 to perform operations of: obtaining one or more physiological measurements using the physiological sensor at 8908; outputting one or more audible indications associated with the one or more physiological measurements via the speaker at 8910; recognizing one or more audible commands output via one or more speakers associated with an aviation communication headset resultant from intercom speech input via a microphone of the aviation communication headset at 8912; and pairing the insert device with at least one other device based on the one or more audible commands at 8914. The processor of the insert device may be paired via BLUETOOTH or WIFI with another insert device, a mobile computing device, or with an avionics system of an aircraft. The processor can initiate pairing based on proximity, recognition of a prior paired device, or based on speech commands recognized and received via a microphone of the insert device. For instance, the processor of the insert device can receive a command of "AITHRE begin pairing with all other insert devices." This command can be provided via a microphone of an aviation headset and output via a speaker of the aviation headset where it is detected by the microphone and processor of the insert device. Upon recognition of the pairing command, the processor of the insert device can initiate and complete pairing and provide an audible indicator of the status of the pairing via the speaker of the insert device. Pairing of the insert device can enable communications to flow therebetween. One specific embodiment would be for the processor of the insert device to act as a master for other slave insert devices, to collect and output physiological parameter values, such as those for co-pilots or passengers. Another specific embodiment would be for the processor of the insert device to transmit physiological parameter values to a mobile device or avionics system to output the parameter values, such as in a panel of digital instruments adjacent to engine monitoring instruments.

Figure 90:
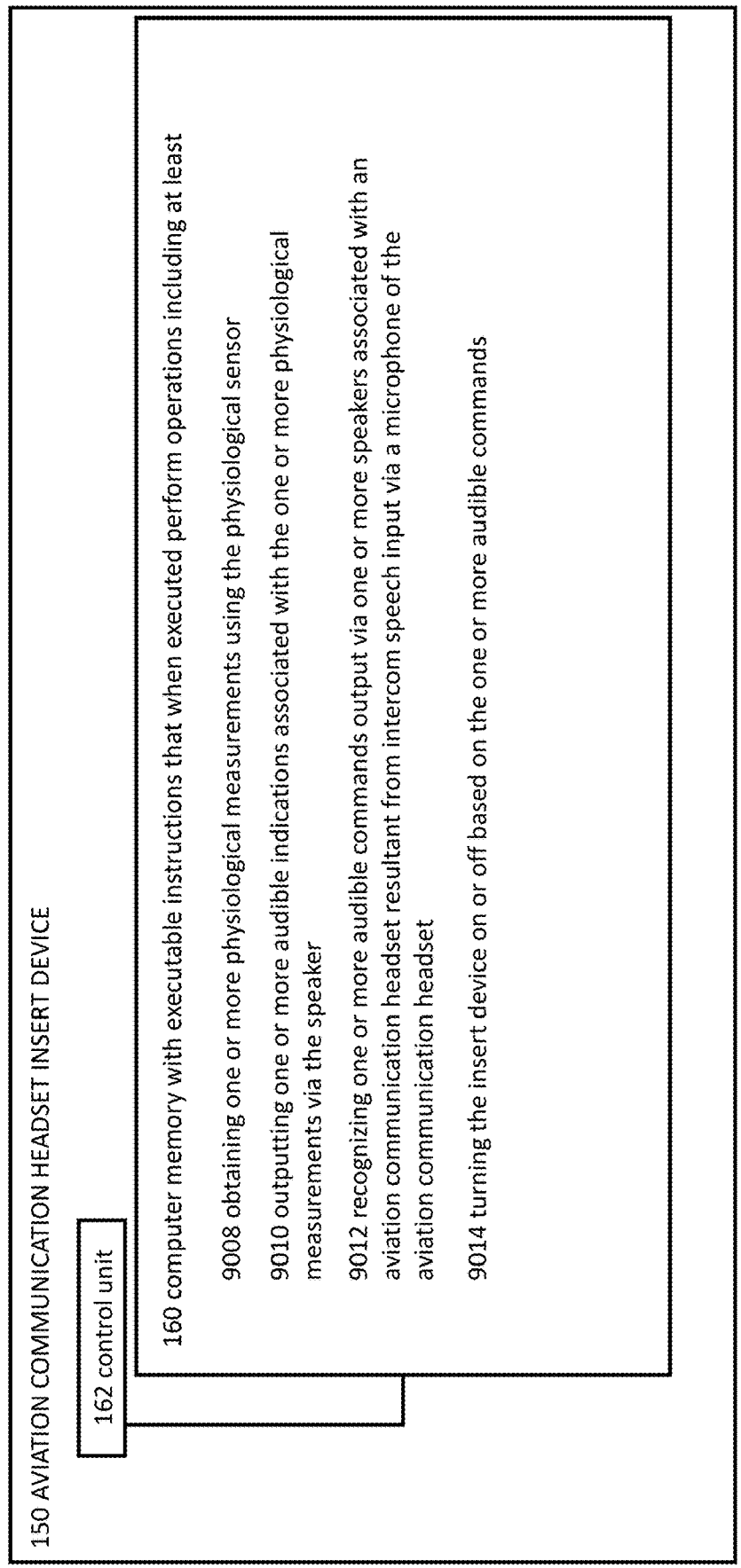

FIG. 90 is a system diagram of an aviation communication headset insert device 150, in accordance with an embodiment of the invention. In this embodiment, an aviation communication headset insert device 150 includes, but is not limited to, an earlobe receptacle 154; tension members 152 extending from opposing ends of the earlobe receptacle to tensionally brace the insert device 150 within an ear cup of an aviation headset; a physiological sensor 156 incorporated into the earlobe receptacle; a speaker 158; a microphone 173, and at least one control unit 162 configured by one or more executable instructions stored on computer memory 160 to perform operations of: obtaining one or more physiological measurements using the physiological sensor at 9008; outputting one or more audible indications associated with the one or more physiological measurements via the speaker at 9010; recognizing one or more audible commands output via one or more speakers associated with an aviation communication headset resultant from intercom speech input via a microphone of the aviation communication headset at 9012; and turning the insert device on or off based on the one or more audible commands at 9014. For example, the processor of the insert device can recognize a speech command received via the microphone of the insert device to power down or enter a low power non-detecting state. The processor can, upon recognizing the command, enter the low power or off state. Similar functionality can be provided by the processor of the insert device to power on from a low power state.

Note that any of the embodiments or operations discussed in reference to the insert device can similarly be present or apply in the context of the replacement cushion device 164 or the ear clip 184 or the earcup attachment device 202 or the replacement cushion device 216.

Figure 91:
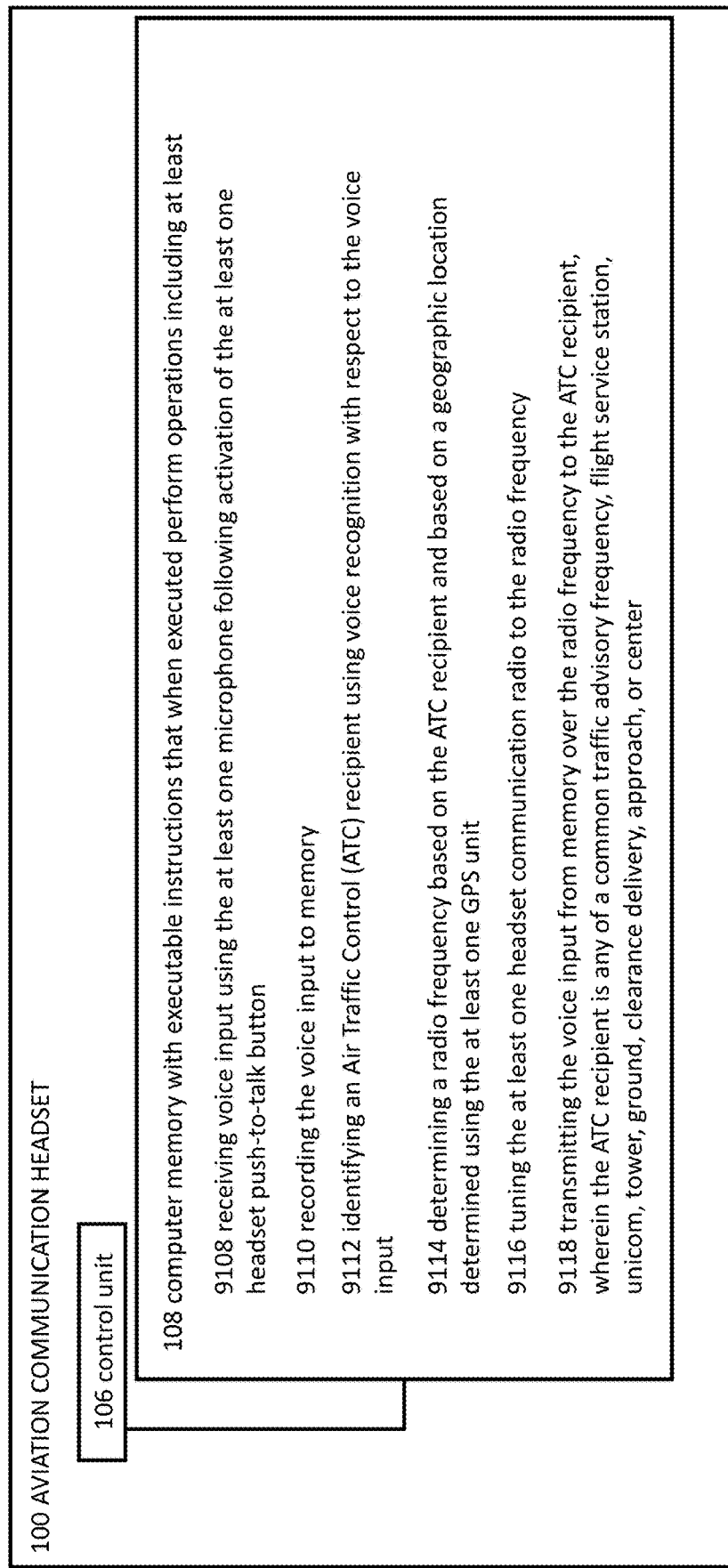

FIG. 91 is a system diagram of a smart aviation communication headset 100, in accordance with an embodiment of the invention. In one embodiment, an aviation communication headset 100 includes, but is not limited to, at least one microphone 114; one or more speakers 112; at least one global positioning system (GPS) 134, at least one panel communication link 137 operable to interface with a panel-mounted communication system of an aircraft; at least one headset communication radio 138; at least one headset push-to-talk button 122 that when activated causes bypass of the at least one panel communication link 137 to transmit one or more radio broadcasts using the at least one headset communication radio 138; and at least one control unit 106 configured by one or more executable instructions stored on computer memory 108 to perform operations including at least: receiving voice input using the at least one microphone following activation of the at least one headset push-to-talk button at 9108; recording the voice input to memory at 9110; identifying an Air Traffic Control (ATC) recipient using voice recognition with respect to the voice input at 9112; determining a radio frequency based on the ATC recipient and based on a geographic location determined using the at least one GPS unit at 9114; tuning the at least one headset communication radio to the radio frequency at 9116; transmitting the voice input from memory over the radio frequency to the ATC recipient, wherein the ATC recipient is any of a common traffic advisory frequency, flight service station, unicom, tower, ground, clearance delivery, approach, or center at 9118. For example, a processor component of the aviation communication headset can receive the audio of "Seattle Center N104ZU level 5000 VFR Bremerton" following activation of the auxiliary push to talk (PTT) button. The received audio can be buffered to memory and the processor can recognize that the radio transmission as being intended for Seattle Center based on speech recognition performed with respect to the audio. There being multiple possible Seattle Center radio frequencies, the processor component can determine the appropriate radio frequency based on position and altitude information determined from the GPS unit. For instance, the radio frequency of 127.05 can be identified by the processor component as being applicable to Seattle Center for the current GPS location and altitude. The processor component can then tune the auxiliary communication radio to 127.05 and transmit the audio from memory over 127.05 using the auxiliary radio. Thus, the pilot no longer requires knowledge of the appropriate radio frequency and no longer must tune the radio frequency manually prior to transmission. Furthermore, no modifications to aircraft avionics systems or aircraft radios are required as the auxiliary PTT of the aviation communication headset enables the radio transmission to bypass the aircraft communication radios in favor of the functionally advanced auxiliary communication radio associated with the aviation communication headset.

Figure 92:
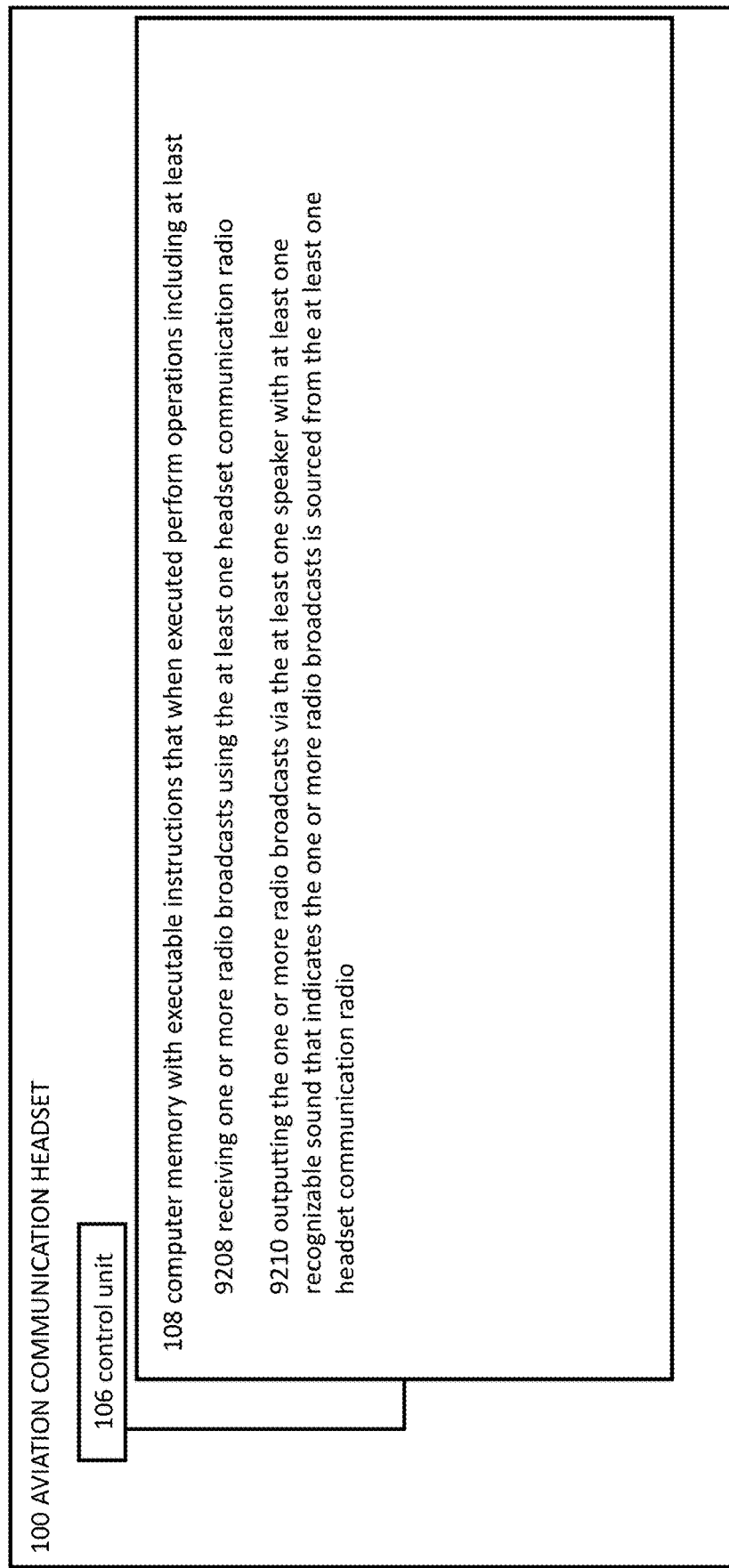

FIG. 92 is a system diagram of a smart aviation communication headset 100, in accordance with an embodiment of the invention. In one embodiment, an aviation communication headset 100 includes, but is not limited to, at least one microphone 114; one or more speakers 112; at least one global positioning system (GPS) 134, at least one panel communication link 137 operable to interface with a panel-mounted communication system of an aircraft; at least one headset communication radio 138; at least one headset push-to-talk button 122 that when activated causes bypass of the at least one panel communication link 137 to transmit one or more radio broadcasts using the at least one headset communication radio 138; and at least one control unit 106 configured by one or more executable instructions stored on computer memory 108 to perform operations including at least: receiving one or more radio broadcasts using the at least one headset communication radio at 9208; and outputting the one or more radio broadcasts via the at least one speaker with at least one recognizable sound that indicates the one or more radio broadcasts is sourced from the at least one headset communication radio at 9210. For example, the processor component can receive one or more incoming radio transmissions via the auxiliary radio and output those radio transmissions via the speakers of the aviation communication headset. The aviation communication headset can also simultaneously receive incoming radio transmissions via any one or more aircraft communication radios via the standard panel link. Due to the multitude of incoming radio transmissions and sources, the processor component can provide a recognizable phrase or tone in association with the output of audio sourced from the auxiliary communication radio. Alternatively, the processor component can modify the voice to assume a certain quality or characteristic (e.g., accent, male, female) when the audio is sourced from the auxiliary communication radio. The additional tone or phrase or modification to the voice by the processor component enables a pilot to distinguish between radio broadcasts that originate from the auxiliary radio. For instance, the processor component can add a beep to an incoming auxiliary radio transmission such that the output via the speakers sounds as "BEEP N104ZU Seattle Center descend maintain 3000."

Figure 93:
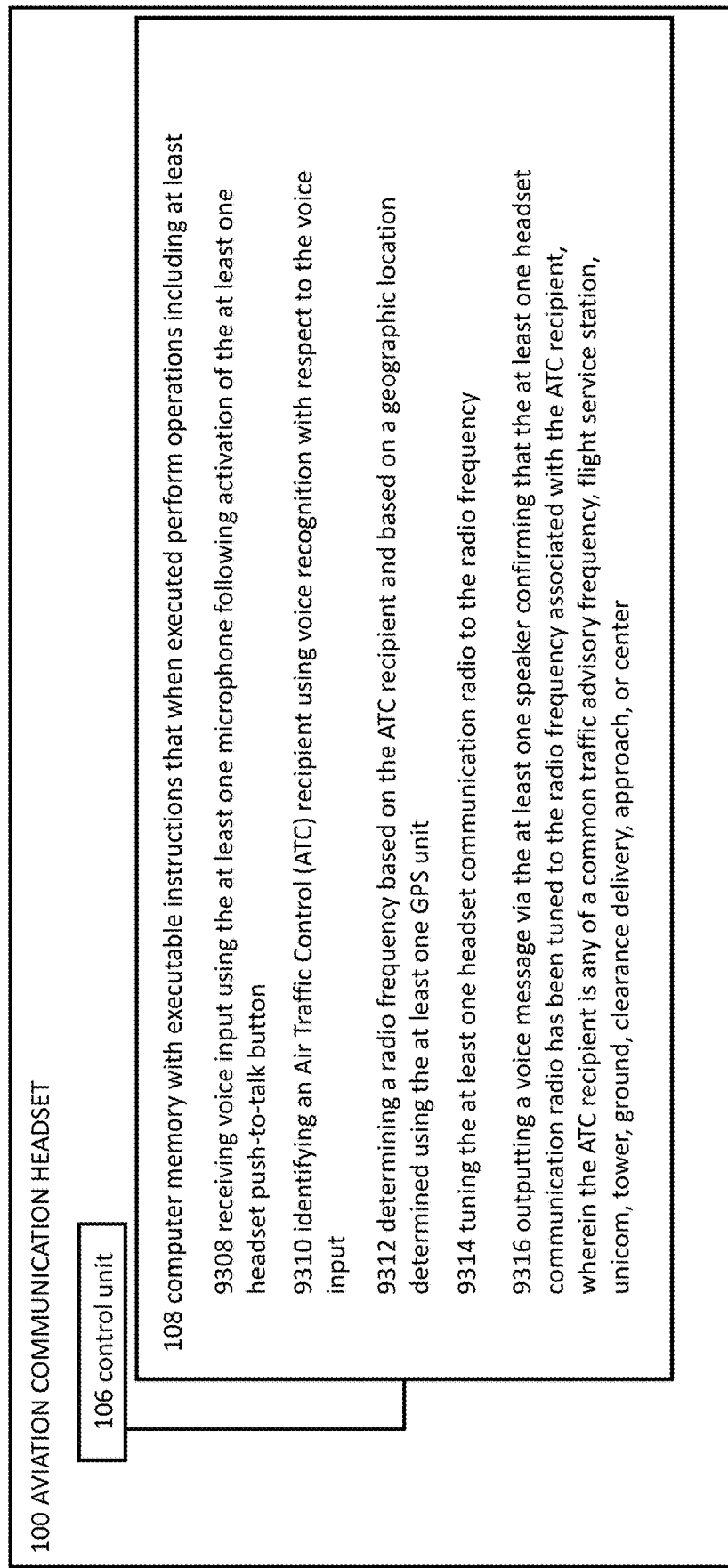

FIG. 93 is a system diagram of a smart aviation communication headset 100, in accordance with an embodiment of the invention. In one embodiment, an aviation communication headset 100 includes, but is not limited to, at least one microphone 114; one or more speakers 112; at least one global positioning system (GPS) 134, at least one panel communication link 137 operable to interface with a panel-mounted communication system of an aircraft; at least one headset communication radio 138; at least one headset push-to-talk button 122 that when activated causes bypass of the at least one panel communication link 137 to transmit one or more radio broadcasts using the at least one headset communication radio 138; and at least one control unit 106 configured by one or more executable instructions stored on computer memory 108 to perform operations including at least: receiving voice input using the at least one microphone following activation of the at least one headset push-to-talk button at 9308; identifying an Air Traffic Control (ATC) recipient using voice recognition with respect to the voice input at 9310; determining a radio frequency based on the ATC recipient and based on a geographic location determined using the at least one GPS unit at 9312; at 9314; and outputting a voice message via the at least one speaker confirming that the at least one headset communication radio has been tuned to the radio frequency associated with the ATC recipient, wherein the ATC recipient is any of a common traffic advisory frequency, flight service station, unicom, tower, ground, clearance delivery, approach, or center at 9316. For example, the processor component can recognize a target recipient from audio obtained via the microphone of the aviation communication headset, identify the frequency of the target recipient based on the current geographic location, and then tune the auxiliary radio. The processor can provide an output via the speakers of the aviation communication headset to indicate that the auxiliary radio has been tuned to the appropriate frequency and is ready for transmission or receipt of broadcasts. For instance, the processor component can receive audio of "Boeing Tower" upon detection of the auxiliary PTT. The processor component can recognize Boeing Tower and determine the appropriate frequency based on the GPS position and altitude information, such as 118.3. The processor component can then control the auxiliary radio to turn to 118.3 and then output the audio of "Boeing Tower Tuned." The auxiliary radio can then receive and transmit broadcasts using the 118.3 without the pilot ever needing to know the appropriate frequency or manually tune to the frequency.

Figure 94:
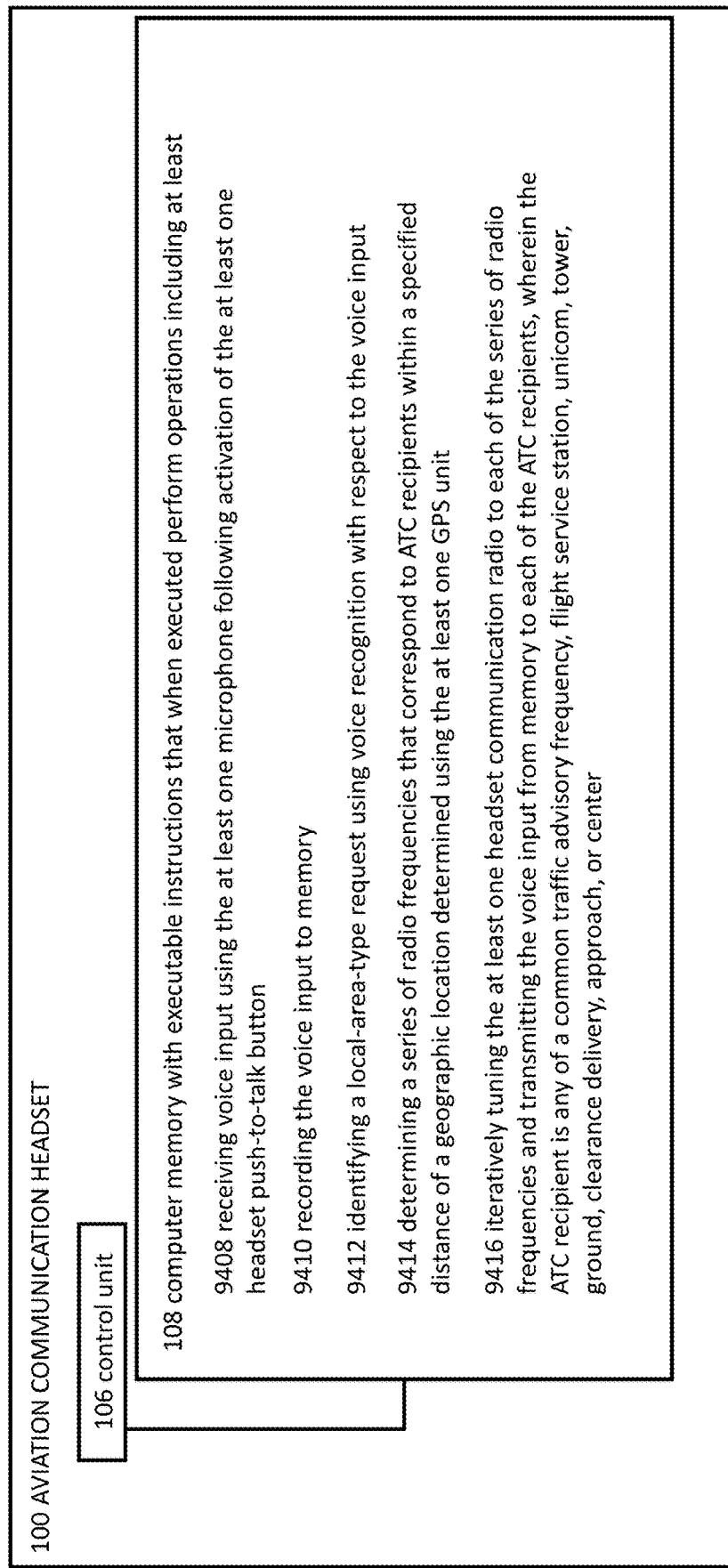

FIG. 94 is a system diagram of a smart aviation communication headset 100, in accordance with an embodiment of the invention. In one embodiment, an aviation communication headset 100 includes, but is not limited to, at least one microphone 114; one or more speakers 112; at least one global positioning system (GPS) 134, at least one panel communication link 137 operable to interface with a panel-mounted communication system of an aircraft; at least one headset communication radio 138; at least one headset push-to-talk button 122 that when activated causes bypass of the at least one panel communication link 137 to transmit one or more radio broadcasts using the at least one headset communication radio 138; and at least one control unit 106 configured by one or more executable instructions stored on computer memory 108 to perform operations including at least: receiving voice input using the at least one microphone following activation of the at least one headset push-to-talk button at 9408; recording the voice input to memory at 9410; identifying a local-area-type request using voice recognition with respect to the voice input at 9412; determining a series of radio frequencies that correspond to ATC recipients within a specified distance of a geographic location determined using the at least one GPS unit at 9414; and iteratively tuning the at least one headset communication radio to each of the series of radio frequencies and transmitting the voice input from memory to each of the ATC recipients, wherein the ATC recipient is any of a common traffic advisory frequency, flight service station, unicom, tower, ground, clearance delivery, approach, or center at 9416. For example, due to the overlap of radio frequencies associated with various uncontrolled areas, the processor component can recognize a speech command of "Local Area" or the like contained in audio received from the microphone of the aviation communication headset following activation of the auxiliary PTT. Based on recognition of this command, the processor component can identify the area frequencies based on the GPS position information and iteratively broadcast the message using the auxiliary radio to each of the identified frequencies. For instance, a processor component can obtain the audio of "Local Area N104ZU 7 North 3500 Inbound Full Stop Bremerton". Based on recognition of the Local Area type command and the GPS position information, the processor component can identify the Apex Airport CTAF 122.8 and the Bremerton Airport CTAF 123.05. The processor can transmit the audio via the 122.8 and then via the 123.05 frequencies using the auxiliary radio, thereby enabling the audio to be broadcast on all local and proximate frequencies to alert other aircraft of the intentions. The pilot is not required to know the frequencies of any of the local area airports or to tune to any of the frequencies manually. Note that the processor component can cycle between the identified local frequencies rapidly to identify any responsive radio transmissions. The processor component can also following the local area transmission tune to the radio frequency closest to the geographic area based on the received GPS information, with changes in the tuning triggered upon updated GPS information. That is, following the local area transmission to Apex and Bremerton, the processor component can tune the auxiliary radio to Apex until the GPS indicates 5 miles to Bremerton whereby the processor component tunes the auxiliary radio to Bremerton.

Figure 95:
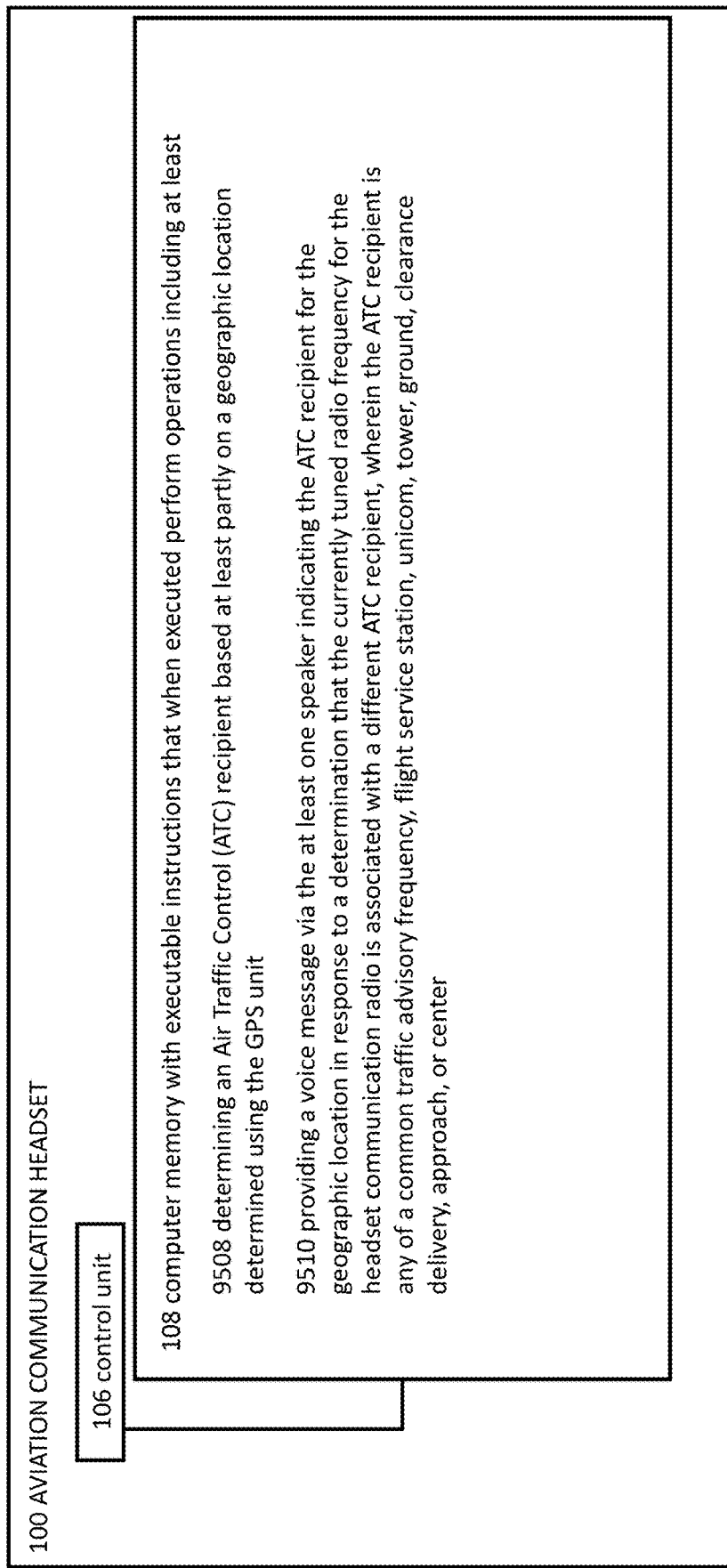

FIG. 95 is a system diagram of a smart aviation communication headset 100, in accordance with an embodiment of the invention. In one embodiment, an aviation communication headset 100 includes, but is not limited to, at least one microphone 114; one or more speakers 112; at least one global positioning system (GPS) 134, at least one panel communication link 137 operable to interface with a panel-mounted communication system of an aircraft; at least one headset communication radio 138; at least one headset push-to-talk button 122 that when activated causes bypass of the at least one panel communication link 137 to transmit one or more radio broadcasts using the at least one headset communication radio 138; and at least one control unit 106 configured by one or more executable instructions stored on computer memory 108 to perform operations including at least: determining an Air Traffic Control (ATC) recipient based at least partly on a geographic location determined using the GPS unit at 9508; and providing a voice message via the at least one speaker indicating the ATC recipient for the geographic location in response to a determination that the currently tuned radio frequency for the headset communication radio is associated with a different ATC recipient, wherein the ATC recipient is any of a common traffic advisory frequency, flight service station, unicom, tower, ground, clearance delivery, approach, or center at 9510. For example, the processor component can constantly monitor the GPS location and the tuned frequency of the auxiliary communication radio. Upon detection of a mismatch, the processor component can output an alert, reminder, or notification via the speakers that the auxiliary radio may not be properly tuned for the geographic area. For instance, enroute from Seattle to Portland, the processor component can determine that the auxiliary radio is tuned to Seattle Approach 126.5, but based on the GPS position the processor component can determine that the appropriate frequency is Seattle Center on 120.3. The processor component can output a notification to change to Seattle Center on 120.3 via the speakers or can request permission to change to Seattle Center on 120.3. The processor component can recognize speech received from the microphone of the aviation headset and control the auxiliary radio accordingly, such as to initiate the tuning change.

Figure 96:
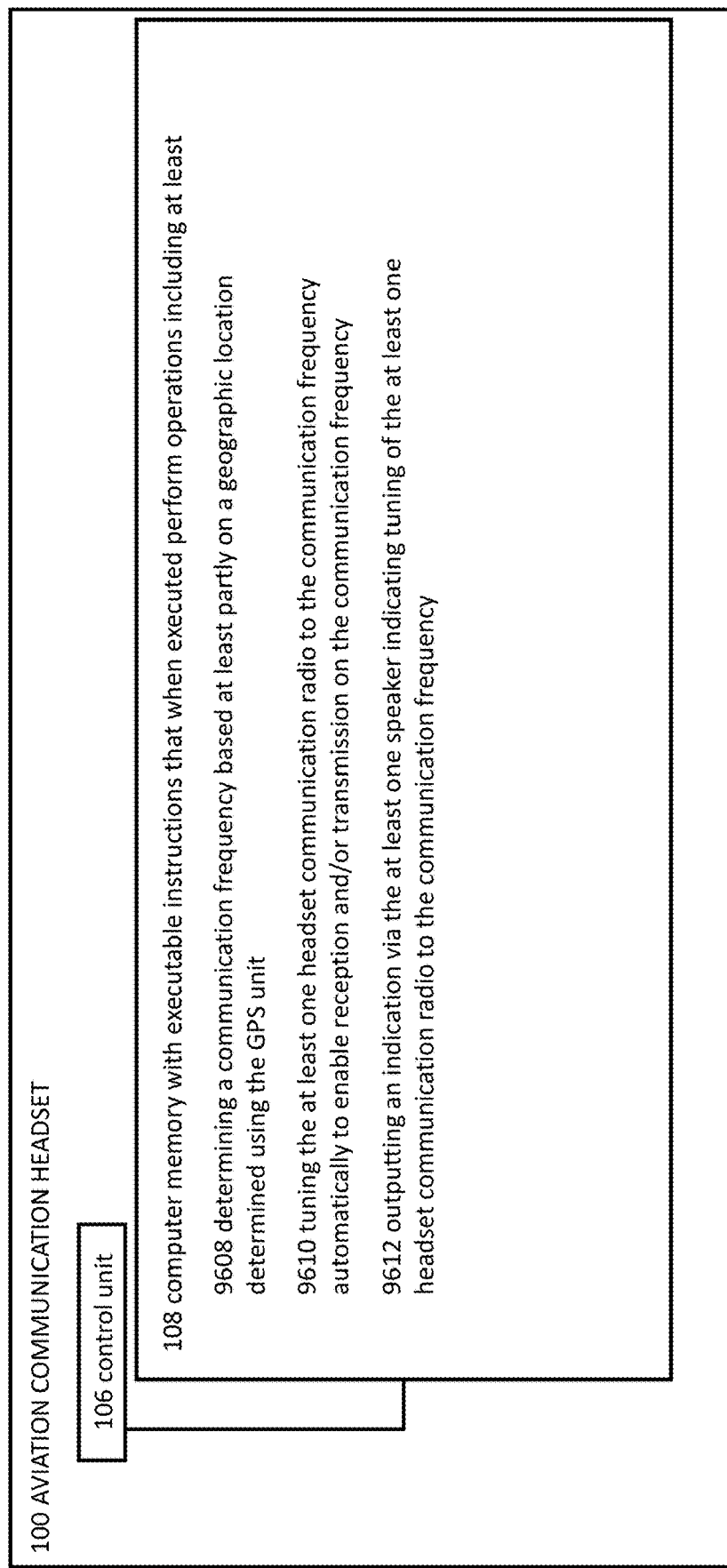

FIG. 96 is a system diagram of a smart aviation communication headset 100, in accordance with an embodiment of the invention. In one embodiment, an aviation communication headset 100 includes, but is not limited to, at least one microphone 114; one or more speakers 112; at least one global positioning system (GPS) 134, at least one panel communication link 137 operable to interface with a panel-mounted communication system of an aircraft; at least one headset communication radio 138; at least one headset push-to-talk button 122 that when activated causes bypass of the at least one panel communication link 137 to transmit one or more radio broadcasts using the at least one headset communication radio 138; and at least one control unit 106 configured by one or more executable instructions stored on computer memory 108 to perform operations including at least: determining a communication frequency based at least partly on a geographic location determined using the GPS unit at 9608; tuning the at least one headset communication radio to the communication frequency automatically to enable reception and/or transmission on the communication frequency at 9610; and outputting an indication via the at least one speaker indicating tuning of the at least one headset communication radio to the communication frequency at 9612. For example, the processor component can continuously monitor the GPS position information during a cross country flight and automatically tune the auxiliary radio to the closest airport frequency or the closest approach or center frequency to enable reception and/or broadcast. For instance, passing through Central Washington near Snoqualmie Pass, the auxiliary communication radio can be tuned by the processor to 122.9 when in proximity of Cle Elum airport, 123.0 when in proximity to Bowers Field, and 118.25 when in proximity to Grant Count Airport, thereby enabling fluid communication with the most proximate airport and traffic. No knowledge of the local frequencies is required nor is any manual tuning of the auxiliary radio.

Figure 97:
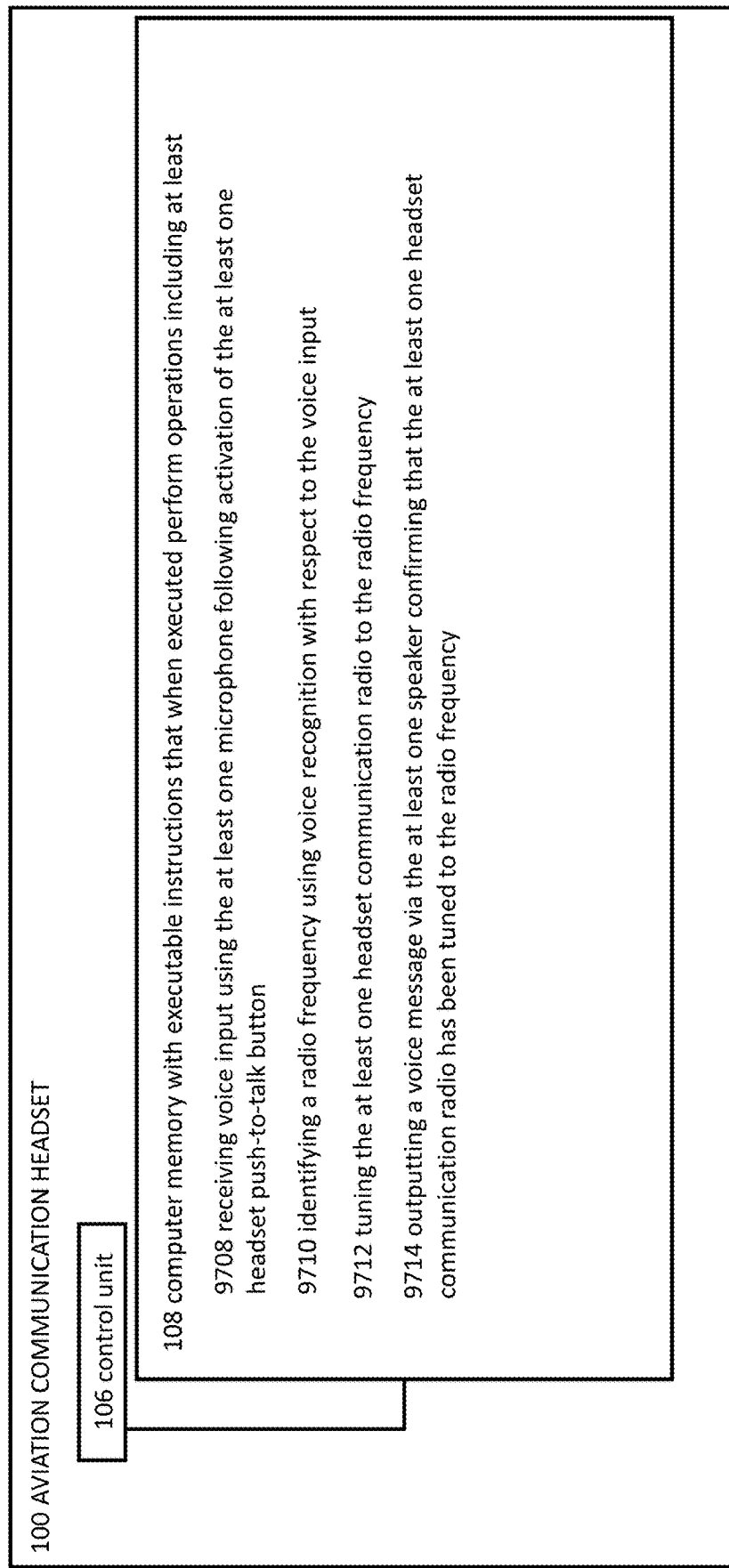

FIG. 97 is a system diagram of a smart aviation communication headset 100, in accordance with an embodiment of the invention. In one embodiment, an aviation communication headset 100 includes, but is not limited to, at least one microphone 114; one or more speakers 112; at least one global positioning system (GPS) 134, at least one panel communication link 137 operable to interface with a panel-mounted communication system of an aircraft; at least one headset communication radio 138; at least one headset push-to-talk button 122 that when activated causes bypass of the at least one panel communication link 137 to transmit one or more radio broadcasts using the at least one headset communication radio 138; and at least one control unit 106 configured by one or more executable instructions stored on computer memory 108 to perform operations including at least: receiving voice input using the at least one microphone following activation of the at least one headset push-to-talk button at 9708; identifying a radio frequency using voice recognition with respect to the voice input at 9710; tuning the at least one headset communication radio to the radio frequency at 9712; and outputting a voice message via the at least one speaker confirming that the at least one headset communication radio has been tuned to the radio frequency at 9714. For instance, the processor can receive audio via the microphone of the aviation communication headset of "Bremerton Weather" following activation of the auxiliary PTT button. The processor component can determine the frequency of 121.2 for Bremerton AWOS based on speech recognition performed with respect to the audio and retrieval of the frequency from memory. The processor component can then control the auxiliary communication radio by tuning such to 121.2 and outputting an indication via the speakers of the aviation communication headset that the Bremerton Weather frequency 121.1 has been tuned.

Figure 98:
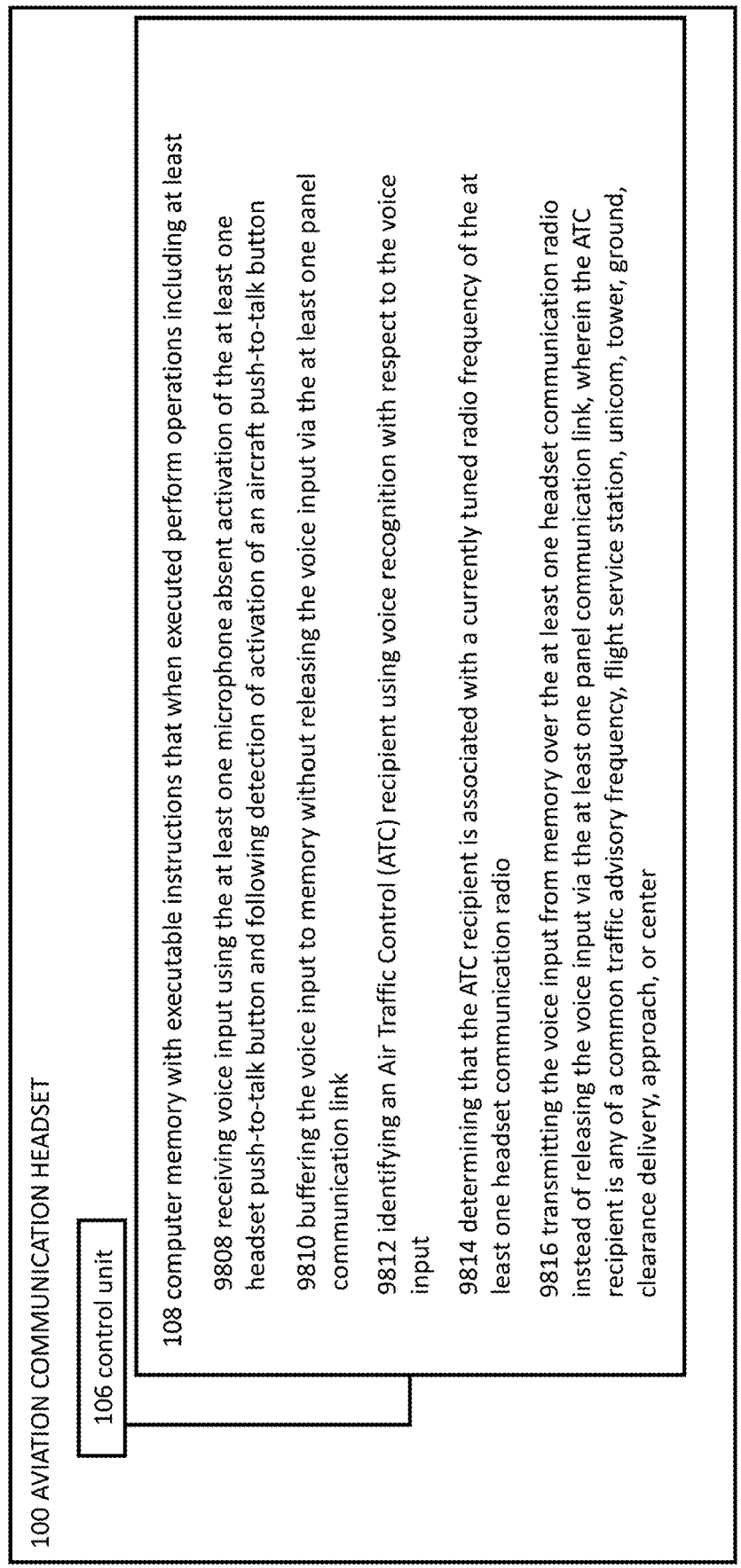

FIG. 98 is a system diagram of a smart aviation communication headset 100, in accordance with an embodiment of the invention. In one embodiment, an aviation communication headset 100 includes, but is not limited to, at least one microphone 114; one or more speakers 112; at least one global positioning system (GPS) 134, at least one panel communication link 137 operable to interface with a panel-mounted communication system of an aircraft; at least one headset communication radio 138; at least one headset push-to-talk button 122 that when activated causes bypass of the at least one panel communication link 137 to transmit one or more radio broadcasts using the at least one headset communication radio 138; and at least one control unit 106 configured by one or more executable instructions stored on computer memory 108 to perform operations including at least: receiving voice input using the at least one microphone absent activation of the at least one headset push-to-talk button and following detection of activation of an aircraft push-to-talk button at 9808; buffering the voice input to memory without releasing the voice input via the at least one panel communication link at 9810; identifying an Air Traffic Control (ATC) recipient using voice recognition with respect to the voice input at 9812; determining that the ATC recipient is associated with a currently tuned radio frequency of the at least one headset communication radio at 9814; and transmitting the voice input from memory over the at least one headset communication radio instead of releasing the voice input via the at least one panel communication link, wherein the ATC recipient is any of a common traffic advisory frequency, flight service station, unicom, tower, ground, clearance delivery, approach, or center at 9816. With the introduction of an auxiliary PTT button associated with an additional auxiliary communication radio, it is possible for a pilot to get confused and depress an aircraft PTT button for a radio transmission that should be broadcast via the auxiliary radio. In such circumstances, the processor component receives and buffers into memory audio received via the microphone of the aviation communication headset following detection of activation of an aircraft PTT. The processor component performs speech recognition on the audio to determine the intended recipient before releasing the audio for broadcast on either the auxiliary communication radio of from the aircraft panel communication radio. Upon identifying the intended recipient, the processor component determines whether the auxiliary communication radio is tuned to a frequency for the intended recipient. If so, the processor component redirects the audio to be broadcast over the auxiliary communication radio instead of the panel mounted communication radio as requested based on the activation of the aircraft PTT button. For instance, the auxiliary communication radio may be tuned to Boeing Tower and the aircraft communication radio may be tuned to Bremerton CTAF. The processor component can receive audio of "Boeing Tower N104ZU North Vashon 1500 inbound with Whiskey" without detecting any activation of the auxiliary PTT button (e.g., the pilot accidentally activated the aircraft PTT button to transmit this radio broadcast, but the radio broadcast would go to Bremerton and not Boeing). Accordingly, the processor component can hold the radio broadcast and determine that the auxiliary communication radio is tuned to Boeing Tower. Upon this determination, the processor component can redirect the audio to be broadcast over the auxiliary communication radio instead of releasing the audio for transmission via the panel mounted communication radio, even without any activation of the auxiliary PTT button.

Figure 99:
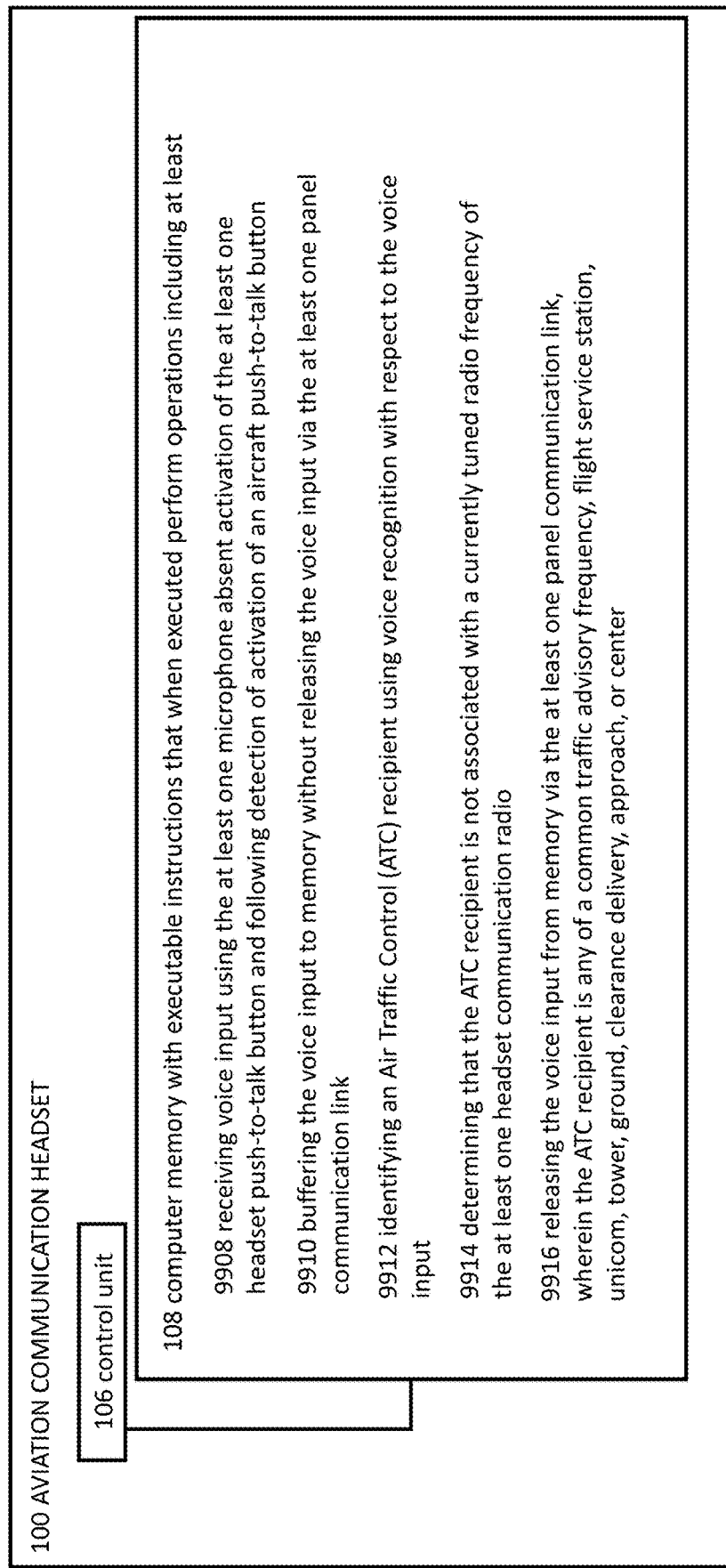

FIG. 99 is a system diagram of a smart aviation communication headset 100, in accordance with an embodiment of the invention. In one embodiment, an aviation communication headset 100 includes, but is not limited to, at least one microphone 114; one or more speakers 112; at least one global positioning system (GPS) 134, at least one panel communication link 137 operable to interface with a panel-mounted communication system of an aircraft; at least one headset communication radio 138; at least one headset push-to-talk button 122 that when activated causes bypass of the at least one panel communication link 137 to transmit one or more radio broadcasts using the at least one headset communication radio 138; and at least one control unit 106 configured by one or more executable instructions stored on computer memory 108 to perform operations including at least: receiving voice input using the at least one microphone absent activation of the at least one headset push-to-talk button and following detection of activation of an aircraft push-to-talk button at 9908; buffering the voice input to memory without releasing the voice input via the at least one panel communication link at 9910; identifying an Air Traffic Control (ATC) recipient using voice recognition with respect to the voice input at 9912; determining that the ATC recipient is not associated with a currently tuned radio frequency of the at least one headset communication radio at 9914; and releasing the voice input from memory via the at least one panel communication link, wherein the ATC recipient is any of a common traffic advisory frequency, flight service station, unicom, tower, ground, clearance delivery, approach, or center at 9916. For example, the processor component can obtain audio from the microphone of the aviation communication headset of "Bremerton N104ZU 5 East 2000 inbound planning left 45 runway 20" following activation of the aircraft PTT button. The processor component can hold the audio and confirm that the Bremerton frequency is not tuned in the auxiliary communication radio before releasing the audio via the link to the aircraft communication radio for broadcast as requested.

Figure 100:
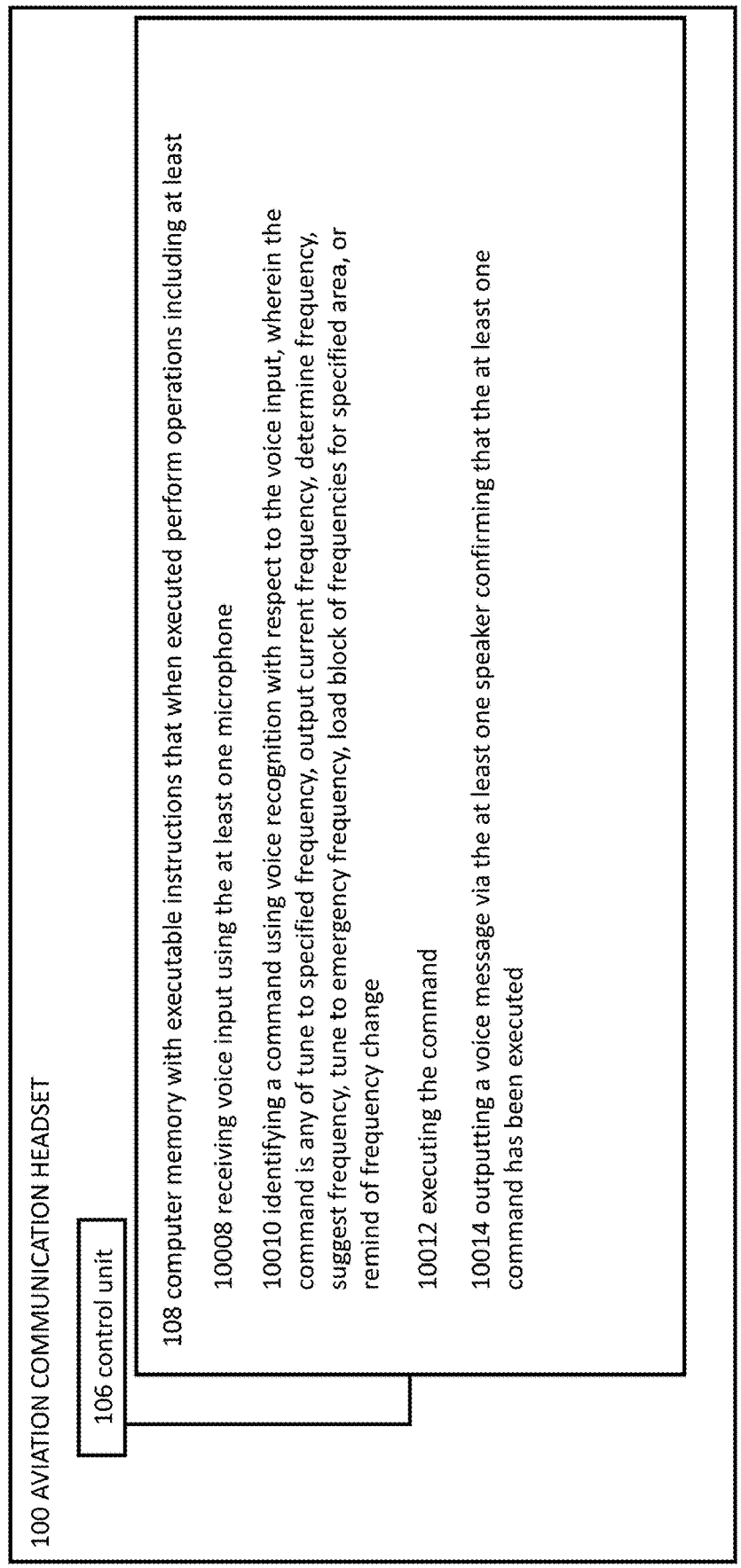

FIG. 100 is a system diagram of a smart aviation communication headset 100, in accordance with an embodiment of the invention. In one embodiment, an aviation communication headset 100 includes, but is not limited to, at least one microphone 114; one or more speakers 112; at least one global positioning system (GPS) 134, at least one panel communication link 137 operable to interface with a panel-mounted communication system of an aircraft; at least one headset communication radio 138; at least one headset push-to-talk button 122 that when activated causes bypass of the at least one panel communication link 137 to transmit one or more radio broadcasts using the at least one headset communication radio 138; and at least one control unit 106 configured by one or more executable instructions stored on computer memory 108 to perform operations including at least: receiving voice input using the at least one microphone at 10008; identifying a command using voice recognition with respect to the voice input, wherein the command is any of tune to specified frequency, output current frequency, determine frequency, suggest frequency, tune to emergency frequency, load block of frequencies for specified area, or remind of frequency change at 10010; executing the command at 10012; and outputting a voice message via the at least one speaker confirming that the at least one command has been executed at 10014.

FIG. 101 is a system diagram of a smart aviation communication headset 100, in accordance with an embodiment of the invention. In one embodiment, an aviation communication headset 100 includes, but is not limited to, at least one microphone 114; one or more speakers 112; at least one global positioning system (GPS) 134, at least one panel communication link 137 operable to interface with a panel-mounted communication system of an aircraft; at least one headset communication radio 138; at least one headset push-to-talk button 122 that when activated causes bypass of the at least one panel communication link 137 to transmit one or more radio broadcasts using the at least one headset communication radio 138; and at least one control unit 106 configured by one or more executable instructions stored on computer memory 108 to perform operations including at least: receiving at least one digital relay request contained in at least one radio transmission received from another aircraft radio via the at least one headset communication radio at 10108; tuning the at least one headset communication radio to a communication frequency encoded in the at least one relay request at 10110; and transmitting at least one message encoded in the at least one relay request over the communication frequency on behalf of the other aircraft radio to enable the other aircraft radio to communicate indirectly over the communication frequency using the at least one headset communication radio without redundant audio broadcasts at 10112. Due to line of sight limitations of radio broadcasts, it may be difficult for an aircraft on the ground to reach air traffic control (ATC). Similarly, due to range limitations on radio broadcasts, it may be difficult for an aircraft and ATC to communicate. Accordingly, the processor component of the aviation communication headset can relay radio broadcasts using the auxiliary communication radio on behalf of another aircraft. For example, the processor component can receive a digital relay request using the auxiliary communication radio, which digital relay request can originate from another aircraft radio (e.g., an aircraft on the ground or further out from an aircraft in the air). The digital relay request can include the message and the frequency for transmission, and is digitally encoded and not detectable by standard communication radios. Upon receiving the digital relay request, the processor component can determine the transmission frequency and decode the audio message. The processor component can then transmit the audio message over the transmission frequency using the auxiliary communication radio. For instance, an aircraft on the ground may not be able to reach ATC for an instrument flight rules (IFR) clearance despite there being many aircraft in the air above the airport with easy radio access to ATC. The ground aircraft communication radio can transmit a relay request with the message and transmission frequency to an airborne aircraft, which can decode the message and forward the broadcast over the transmission frequency as described herein. This enables the ground aircraft to reach ATC without having to use a mobile phone in the aircraft or rush to make a clearance void time after receiving the clearance on a landline. Similarly, ATC may have difficulty reaching a pilot under radar coverage despite the pilot being in line of sight with another above radar coverage aircraft. ATC can transmit a relay request, which can be decoded and rebroadcast by the communication radio of the above radar coverage aircraft to the below radar coverage aircraft.

Figure 102:
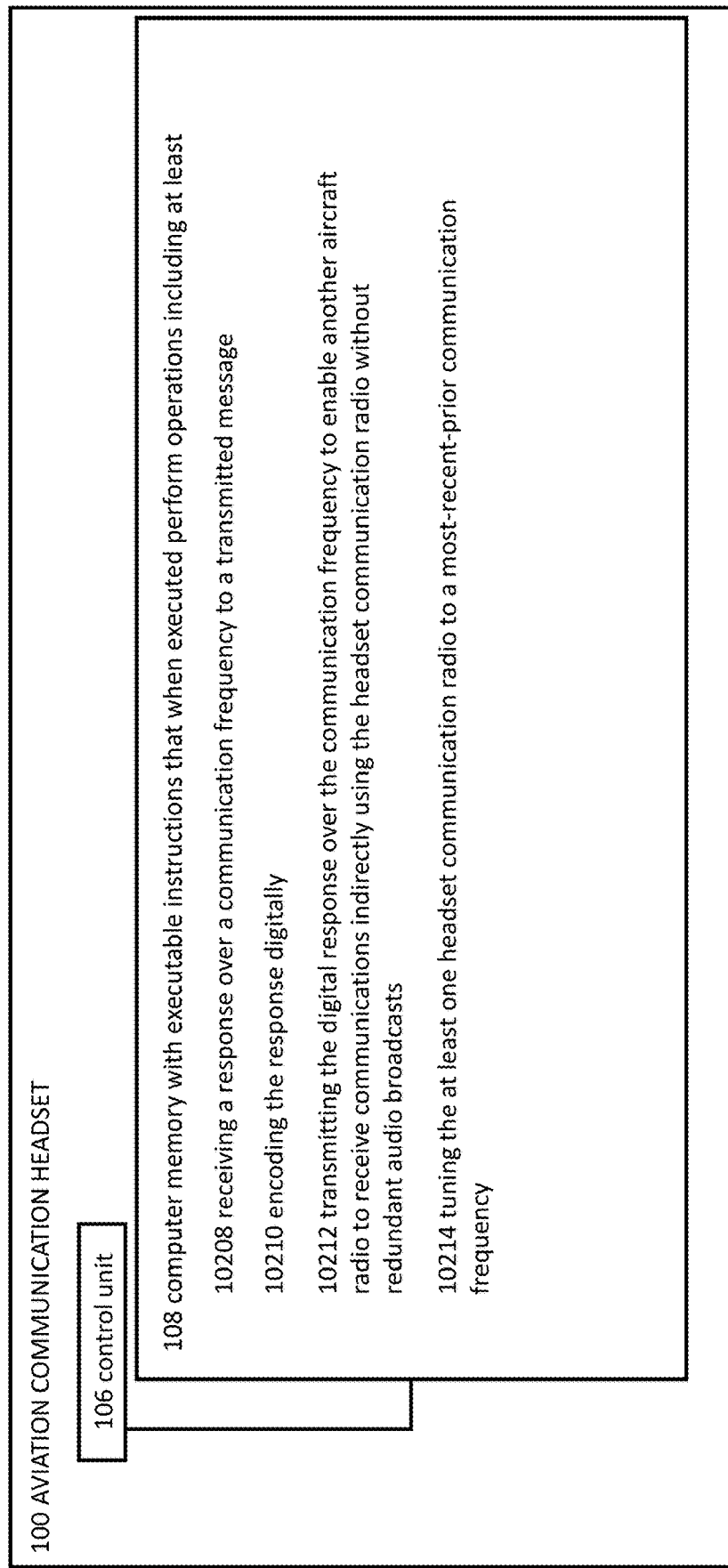

FIG. 102 is a system diagram of a smart aviation communication headset 100, in accordance with an embodiment of the invention. In one embodiment, an aviation communication headset 100 includes, but is not limited to, at least one microphone 114; one or more speakers 112; at least one global positioning system (GPS) 134, at least one panel communication link 137 operable to interface with a panel-mounted communication system of an aircraft; at least one headset communication radio 138; at least one headset push-to-talk button 122 that when activated causes bypass of the at least one panel communication link 137 to transmit one or more radio broadcasts using the at least one headset communication radio 138; and at least one control unit 106 configured by one or more executable instructions stored on computer memory 108 to perform operations including at least: receiving a response over a communication frequency to a transmitted message at 10208; encoding the response digitally at 10210; transmitting the digital response over the communication frequency to enable another aircraft radio to receive communications indirectly using the headset communication radio without redundant audio broadcasts at 10212; and tuning the at least one headset communication radio to a most-recent-prior communication frequency at 10214. Following transmission of a radio broadcast, the processor component can await a response on the transmitted frequency using the auxiliary communication radio. Upon receiving the response, the processor component can digitally encode the response and transmit such to the aircraft requesting the relay. For instance, upon receiving a relay request for an aircraft on the ground and transmitting the message associated with the relay request on the specified frequency to Seattle Center, the processor component can monitor the frequency of Seattle Center for a response referencing the aircraft on the ground. Upon receiving the response from Seattle Center, the processor component can digitally encode the message and forward it to the aircraft on the ground for replay.

FIG. 103 is a system diagram of a smart aviation communication headset 100, in accordance with an embodiment of the invention. In one embodiment, an aviation communication headset 100 includes, but is not limited to, at least one microphone 114; one or more speakers 112; at least one global positioning system (GPS) 134, at least one panel communication link 137 operable to interface with a panel-mounted communication system of an aircraft; at least one headset communication radio 138; at least one headset push-to-talk button 122 that when activated causes bypass of the at least one panel communication link 137 to transmit one or more radio broadcasts using the at least one headset communication radio 138; and at least one control unit 106 configured by one or more executable instructions stored on computer memory 108 to perform operations including at least: receiving voice data following activation of the at least one headset push-to-talk button at 10308; recognizing at least one relay request, communication frequency, and message based at least partly on speech recognition performed on the voice data at 10310; digitally encoding the at least one relay request and message for transmission at 10312; and transmitting a digital relay request and message over a communication frequency to enable the at least one headset communication radio to extend or modify communication range through another aircraft radio without redundant audio broadcasts at 10314. For example, the processor component can receive audio such as "Relay Request Seattle Center 104ZU on the ground Hoquiam and requesting IFR clearance" received using the microphone of the aviation communication headset. The processor component can perform speech recognition on the audio to identify the relay request nature of the audio and can determine Seattle Center's radio frequency based on GPS position information received. The processor component can thereafter digitally encode the message and frequency and transmit the message via the auxiliary communication radio for receipt and relay by another aircraft communication radio.

Figure 104:
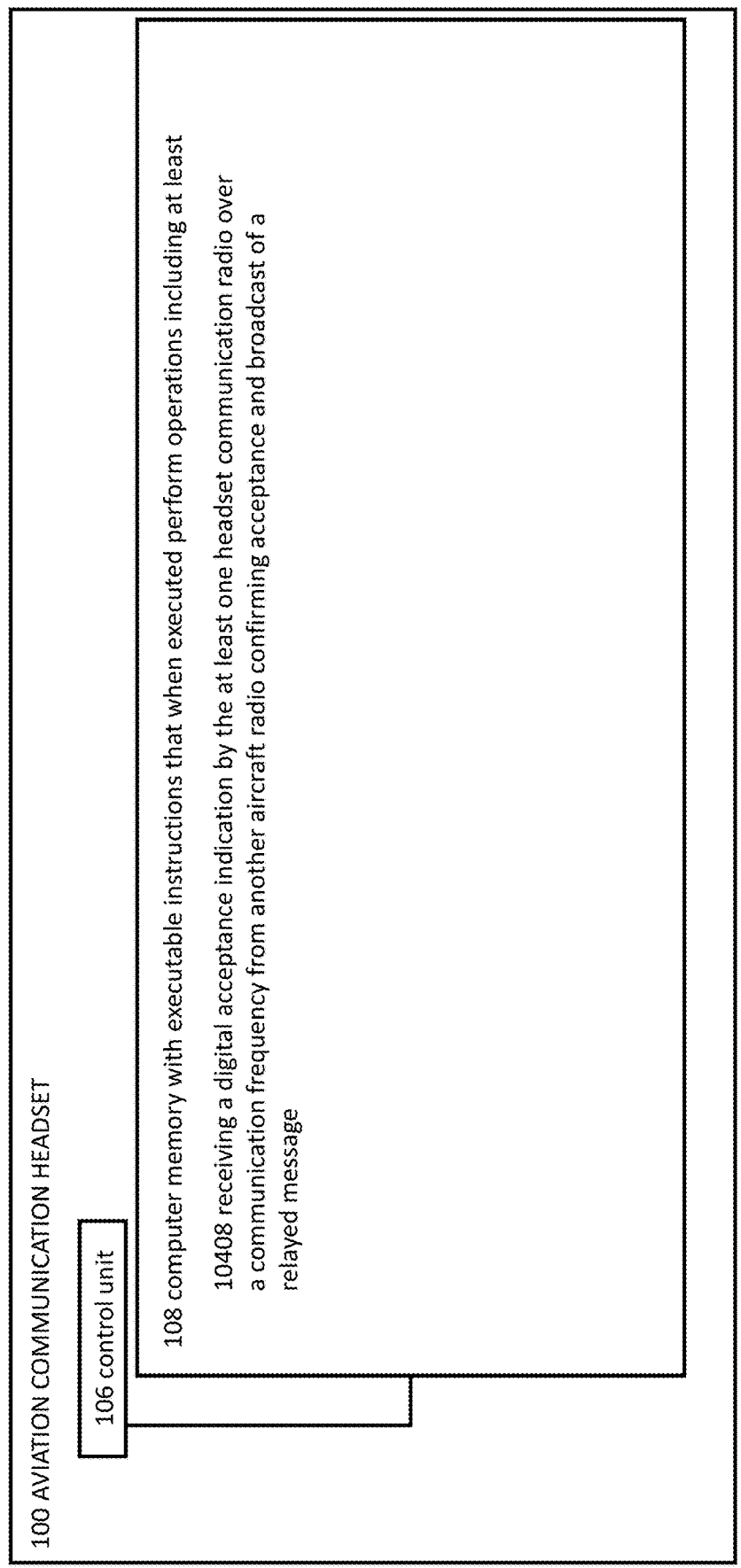

FIG. 104 is a system diagram of a smart aviation communication headset 100, in accordance with an embodiment of the invention. In one embodiment, an aviation communication headset 100 includes, but is not limited to, at least one microphone 114; one or more speakers 112; at least one global positioning system (GPS) 134, at least one panel communication link 137 operable to interface with a panel-mounted communication system of an aircraft; at least one headset communication radio 138; at least one headset push-to-talk button 122 that when activated causes bypass of the at least one panel communication link 137 to transmit one or more radio broadcasts using the at least one headset communication radio 138; and at least one control unit 106 configured by one or more executable instructions stored on computer memory 108 to perform operations including at least: receiving a digital acceptance indication by the at least one headset communication radio over a communication frequency from another aircraft radio confirming acceptance and broadcast of a relayed message at 10408. For example, the processor component can determine whether a relay request has been satisfied by monitoring for one or more handshake or confirmation messages received via the auxiliary communication radio indicating that a relay request has been received and satisfied. In the event, no handshake or confirmation indication is received, the processor component can retransmit the relay request periodically until confirmation is received.

Figure 105:
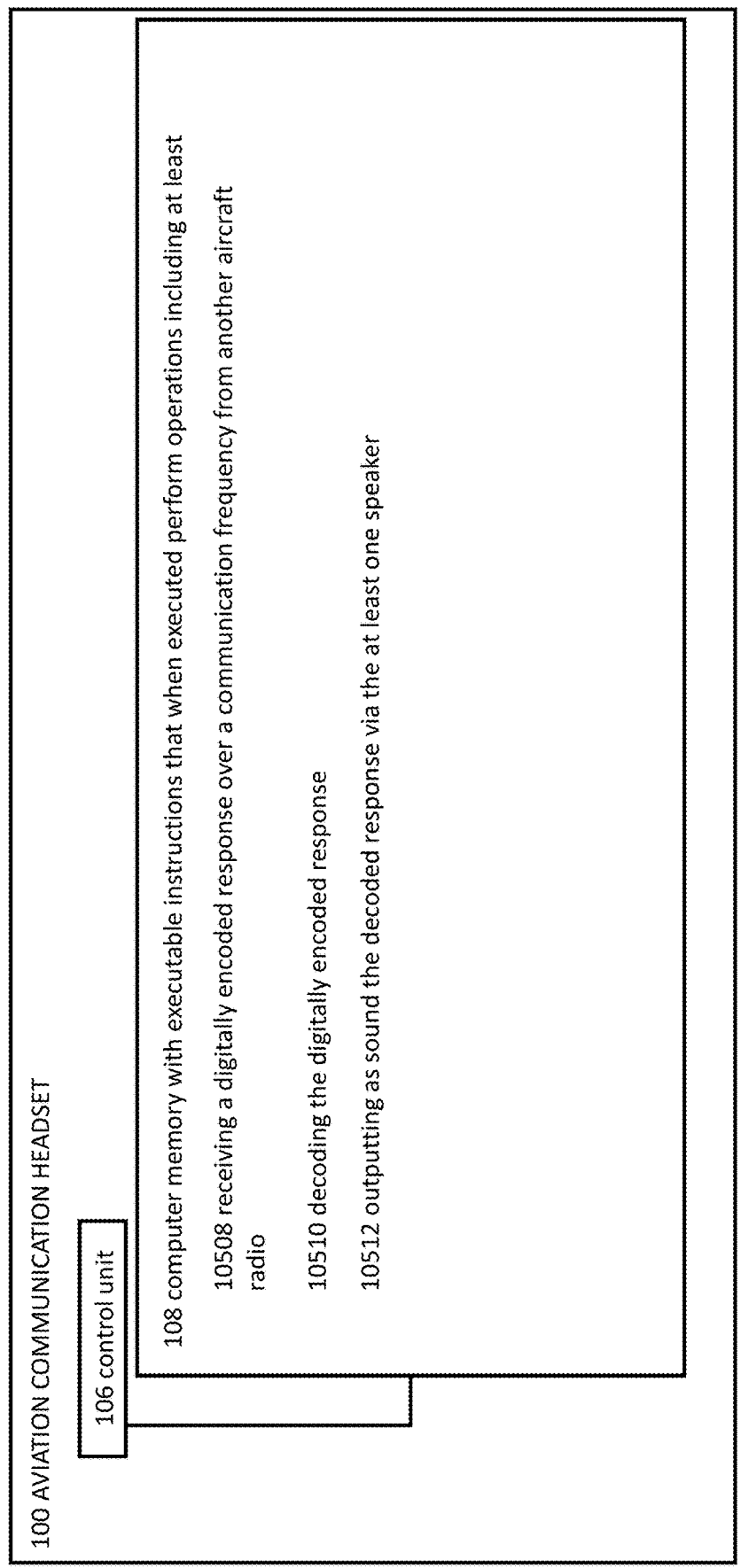

FIG. 105 is a system diagram of a smart aviation communication headset 100, in accordance with an embodiment of the invention. In one embodiment, an aviation communication headset 100 includes, but is not limited to, at least one microphone 114; one or more speakers 112; at least one global positioning system (GPS) 134, at least one panel communication link 137 operable to interface with a panel-mounted communication system of an aircraft; at least one headset communication radio 138; at least one headset push-to-talk button 122 that when activated causes bypass of the at least one panel communication link 137 to transmit one or more radio broadcasts using the at least one headset communication radio 138; and at least one control unit 106 configured by one or more executable instructions stored on computer memory 108 to perform operations including at least: receiving a digitally encoded response over a communication frequency from another aircraft radio at 10508; decoding the digitally encoded response at 10510; and outputting as sound the decoded response via the at least one speaker at 10512. For example, the processor component can receive a responsive encoded digital message to a relay request. The encoded digital message can be decoded into audio signals and output by the processor component via the speakers of the aviation communication headset. For instance, an aircraft outside of radar coverage can communicate with ATC via another aircraft that is within radar coverage. The ATC response can be received by the processor component, decoded, and output permitting a expanded communication range.

Figure 106:
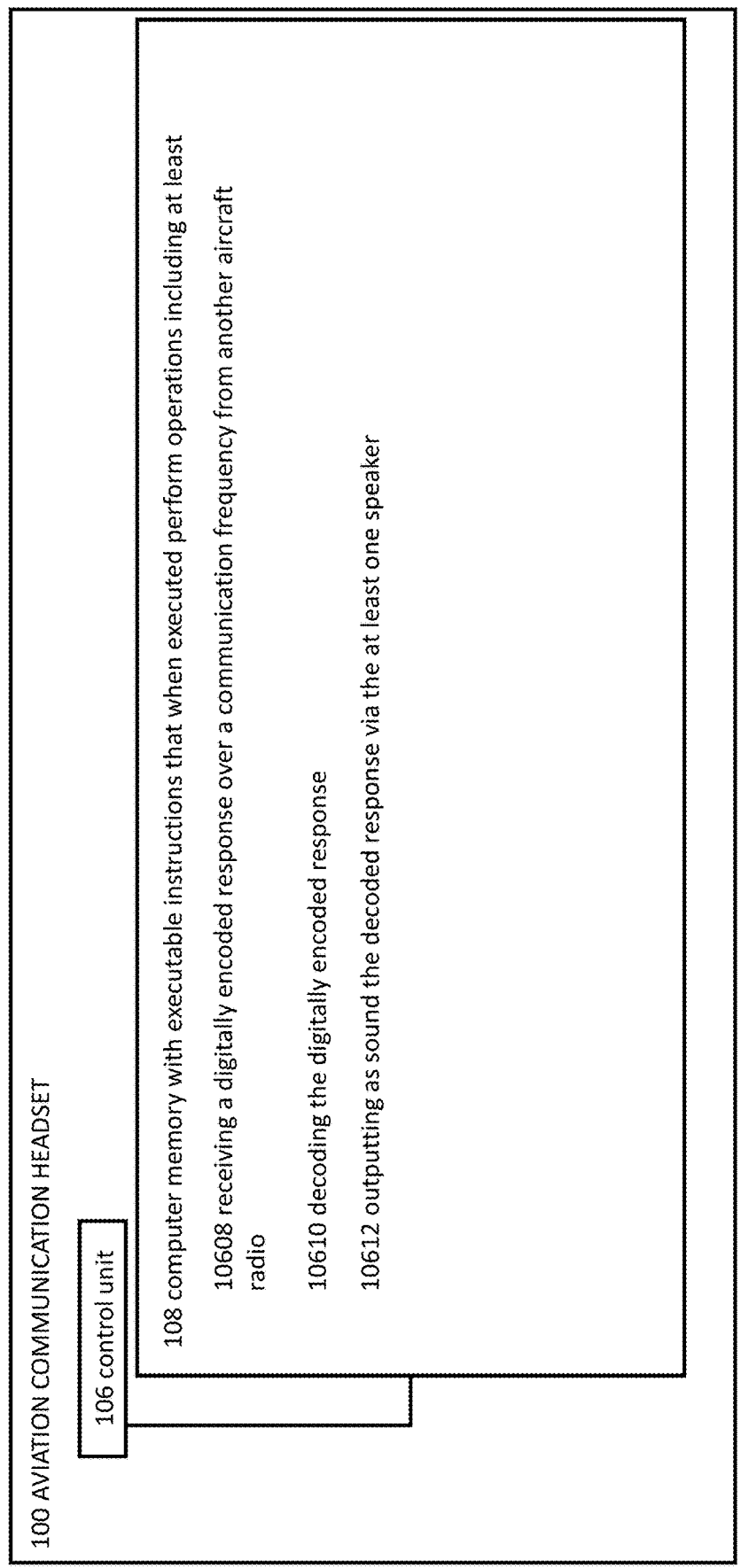

FIG. 106 is a system diagram of a smart aviation communication headset 100, in accordance with an embodiment of the invention. In one embodiment, an aviation communication headset 100 includes, but is not limited to, at least one microphone 114; one or more speakers 112; at least one global positioning system (GPS) 134, at least one panel communication link 137 operable to interface with a panel-mounted communication system of an aircraft; at least one headset communication radio 138; at least one headset push-to-talk button 122 that when activated causes bypass of the at least one panel communication link 137 to transmit one or more radio broadcasts using the at least one headset communication radio 138; and at least one control unit 106 configured by one or more executable instructions stored on computer memory 108 to perform operations including at least: receiving a digitally encoded response over a communication frequency from another aircraft radio at 10608; decoding the digitally encoded response at 10610; outputting as sound the decoded response via the at least one speaker at 10612.

Figure 107:
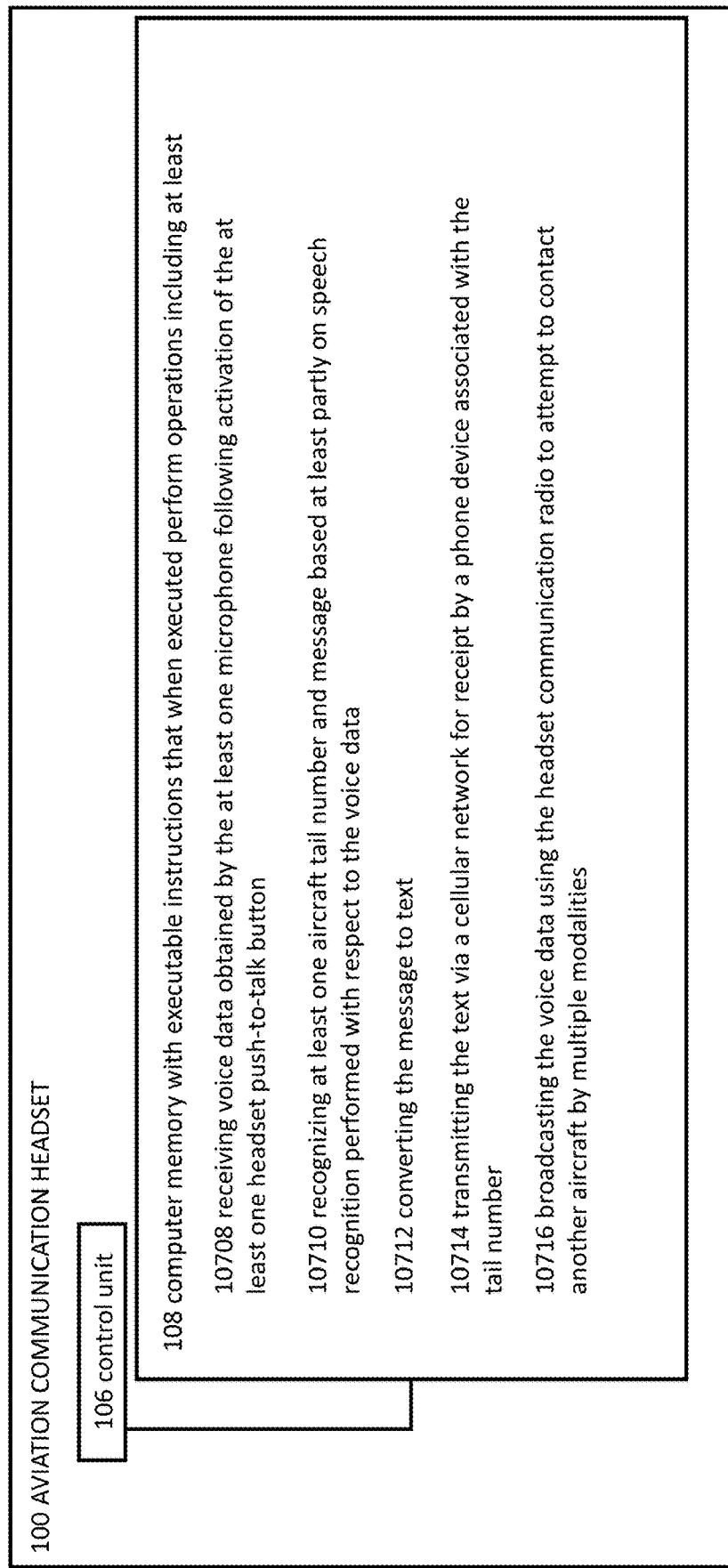

FIG. 107 is a system diagram of a smart aviation communication headset 100, in accordance with an embodiment of the invention. In one embodiment, an aviation communication headset 100 includes, but is not limited to, at least one microphone 114; one or more speakers 112; at least one global positioning system (GPS) 134, at least one panel communication link 137 operable to interface with a panel-mounted communication system of an aircraft; at least one headset communication radio 138; at least one headset push-to-talk button 122 that when activated causes bypass of the at least one panel communication link 137 to transmit one or more radio broadcasts using the at least one headset communication radio 138; and at least one control unit 106 configured by one or more executable instructions stored on computer memory 108 to perform operations including at least: receiving voice data obtained by the at least one microphone following activation of the at least one headset push-to-talk button at 10708; recognizing at least one aircraft tail number and message based at least partly on speech recognition performed with respect to the voice data at 10710; converting the message to text at 10712; transmitting the text via a cellular network for receipt by a phone device associated with the tail number at 10714; and broadcasting the voice data using the headset communication radio to attempt to contact another aircraft by multiple modalities at 10716. ADS-B traffic information provides information on proximate aircraft, including tail number information. However, communicating with identified aircraft can be difficult or impossible since there is no way to know which radio frequency is being monitored by the identified aircraft. Accordingly, the processor component can receive audio from the microphone of the aviation communication headset and recognize a plane-to-plane communication request following activation of the auxiliary PTT. For instance, "N7963G this is N104ZU state your intentions." The processor component can broadcast the message over the currently tuned frequency of the auxiliary radio. However, the processor component can also recognize the intended recipient by the tail number, such as N7963G, and obtain the mobile phone number for the recipient from a pilot database. The processor component can convert the speech or audio to text and transmit the text message to the phone number associated with the recipient using the auxiliary communication radio or BLUETOOTH or physically coupled mobile device. This functionality enables enhanced pilot-to-pilot communication in instances outside of airport airspace, such as during cross-country trips.

Figure 108:
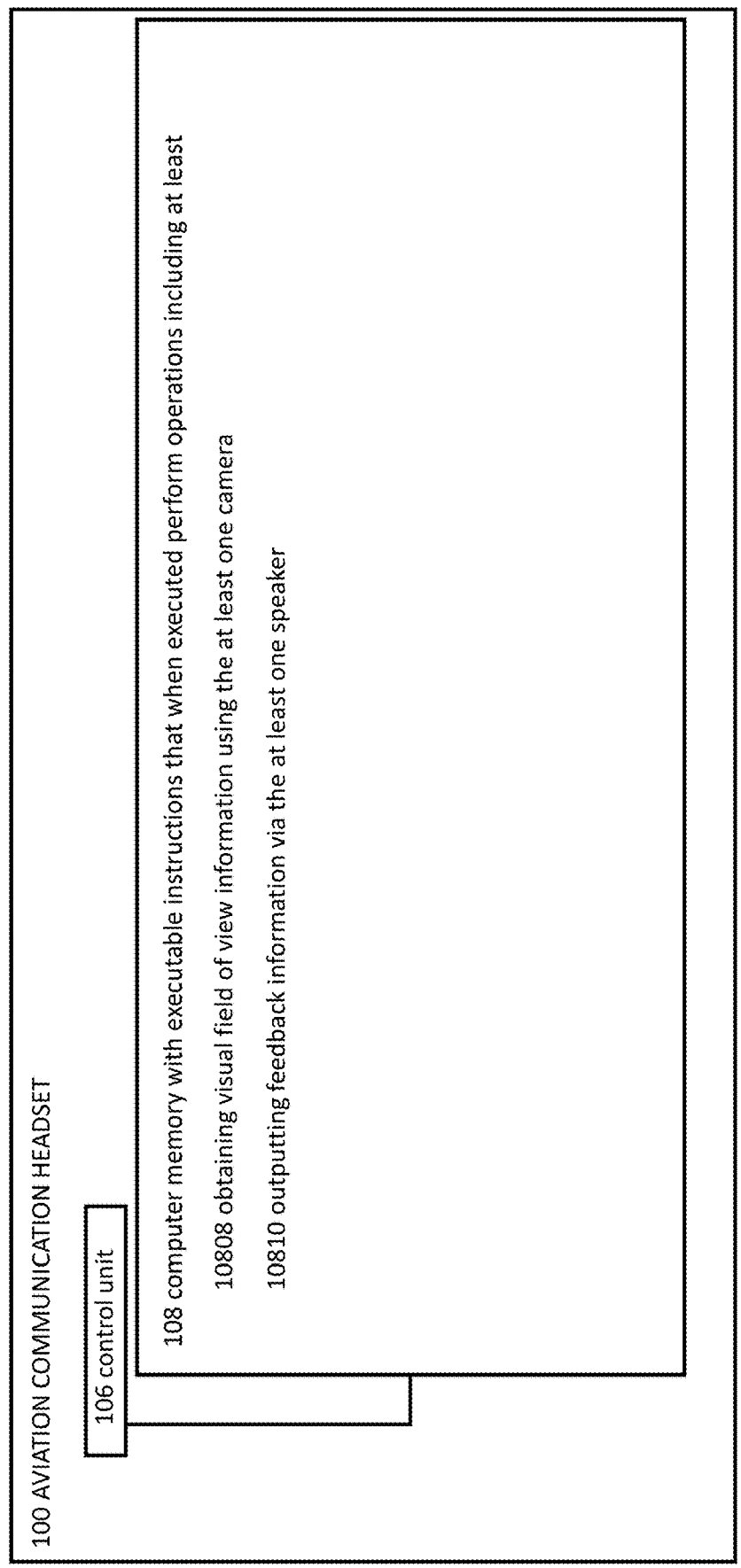

FIG. 108 is a system diagram of a smart aviation communication headset 100, in accordance with an embodiment of the invention. In one embodiment, an aviation communication headset 100 includes, but is not limited to, at least one microphone 114; one or more speakers 112; at least one camera 170 for capturing one or more images in a field of view; and at least one control unit 106 configured by one or more executable instructions stored on computer memory 108 to perform operations including at least: obtaining visual field of view information using the at least one camera at 10808; and outputting feedback information via the at least one speaker at 10810. For example, the processor of the smart aviation communication headset can receive image data from the camera of the smart aviation communication headset. The camera is positioned to provide a forward facing field of view that corresponds with the pilot's field of view when wearing the smart aviation communication headset. The processor analyzes the image data to identify potential issues with instrument readings, radio settings, transponder or ELT settings, navigation or avionics settings, weather, engine readings, and/or health status outputs. The processor component controls output to the speakers of the smart aviation communication headset to provide an audible indication of any issues identified using the camera image data.

Figure 109:
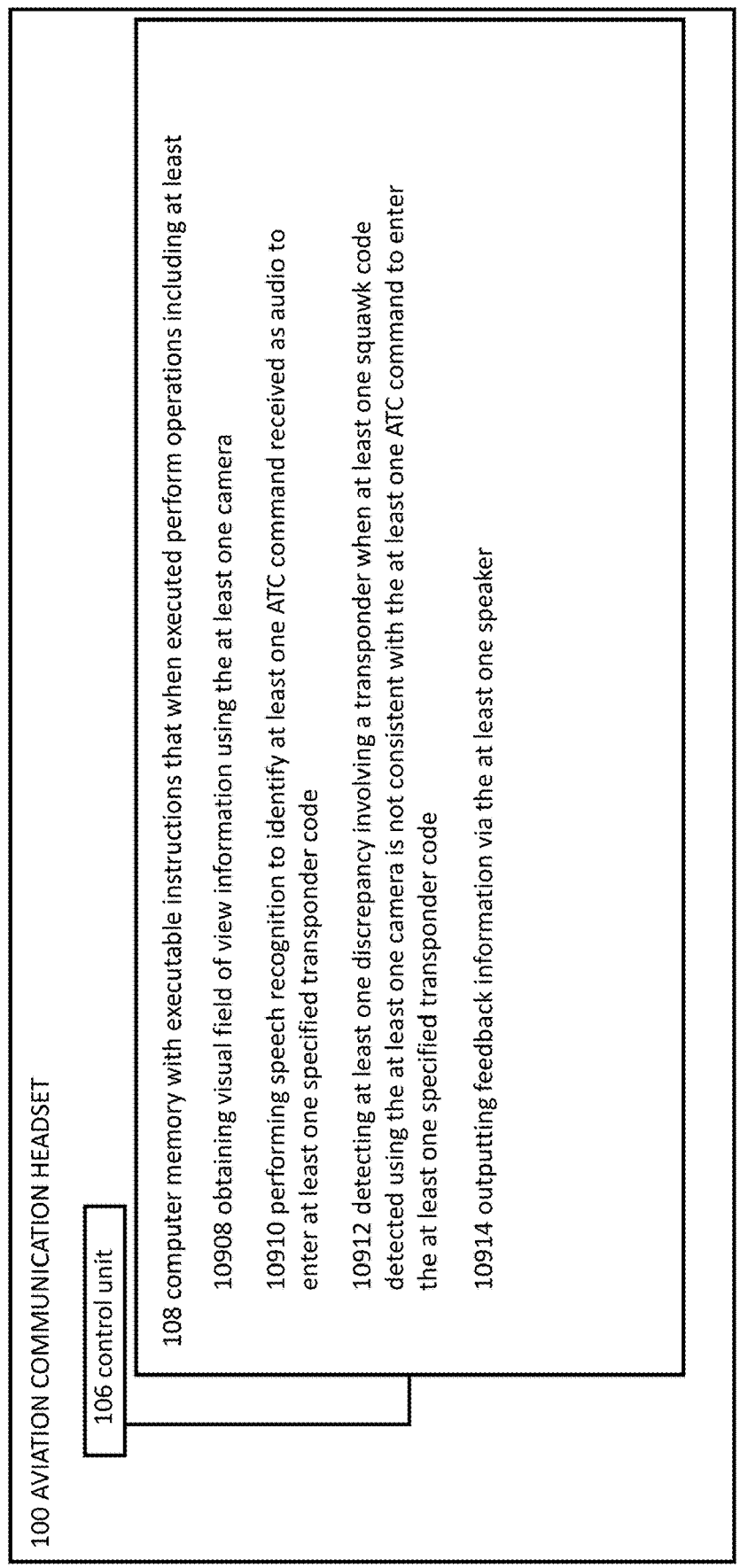

FIG. 109 is a system diagram of a smart aviation communication headset 100, in accordance with an embodiment of the invention. In one embodiment, an aviation communication headset 100 includes, but is not limited to, at least one microphone 114; one or more speakers 112; at least one camera 170 for capturing one or more images in a field of view; and at least one control unit 106 configured by one or more executable instructions stored on computer memory 108 to perform operations including at least: obtaining visual field of view information using the at least one camera at 10908; performing speech recognition to identify at least one ATC command received as audio to enter at least one specified transponder code 10910; detecting at least one discrepancy involving a transponder when at least one squawk code detected using the at least one camera is not consistent with the at least one ATC command to enter the at least one specified transponder code at 10912; and outputting feedback information via the at least one speaker at 10914. For example, the processor component can receive audio data from one or more radio outputs by using a microphone or intercepting the electronic signals. The processor can perform speech recognition on the audio data received to determine a transponder code for the aircraft, such as recognizing the ATC instruction of "N104ZU Squawk 6134". Upon identifying the transponder code, the processor component can monitor the visual field information using the camera of the smart aviation communication hedset. Specifically, the processor component can analyze the display imagery of the transponder unit or portion of the avionics system to determine whether 6134 has been entered. In an even that 6134 is not entered or is entered incorrectly as evidenced by the imagery of the field of view, the processor component can control an output signal via the speakers to provide a warning. For instance, the processor can output the audio of "Warning Transponder Code Mismatch—squawk 6134". The audio output is via the speakers of the aviation communication headset.

Figure 110:
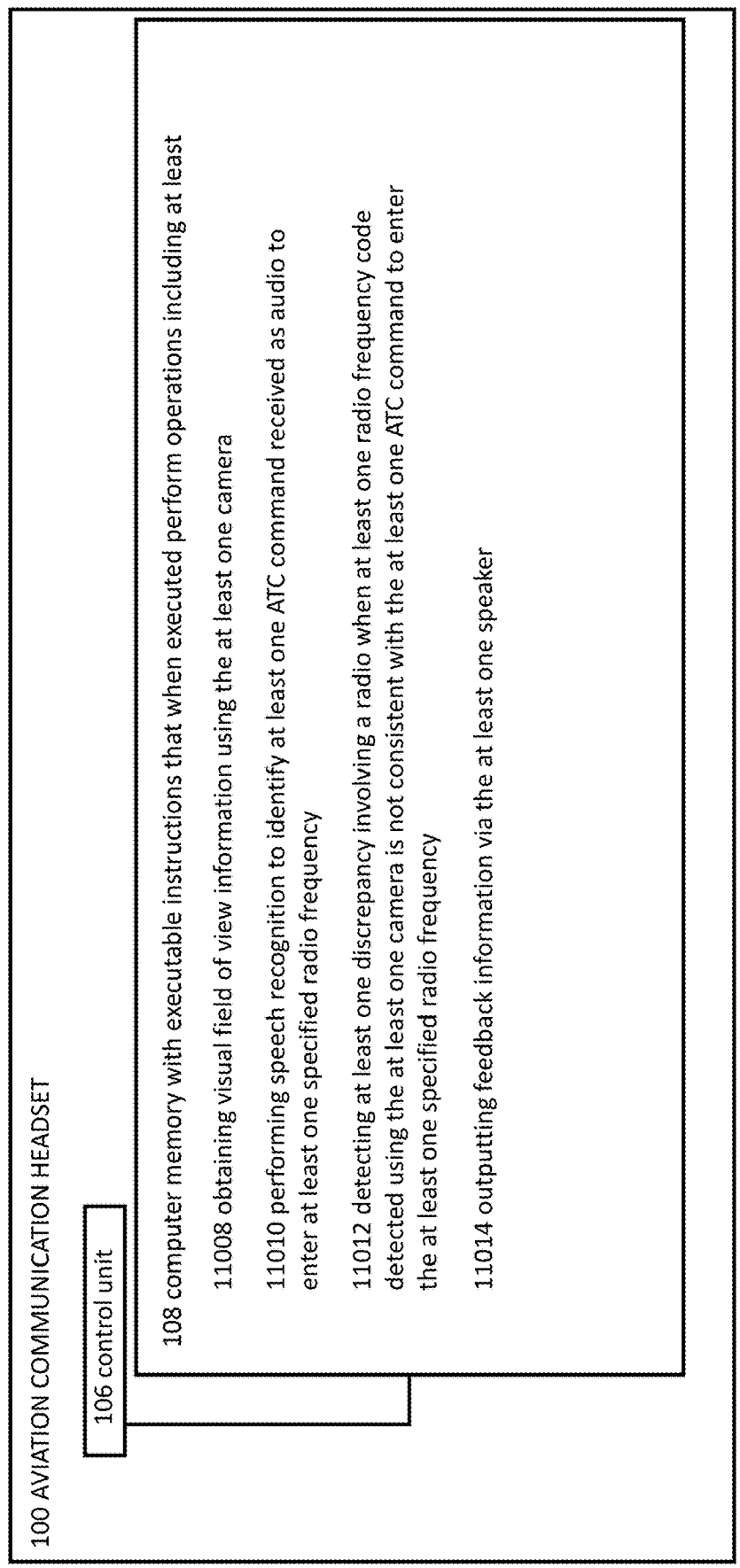

FIG. 110 is a system diagram of a smart aviation communication headset 100, in accordance with an embodiment of the invention. In one embodiment, an aviation communication headset 100 includes, but is not limited to, at least one microphone 114; one or more speakers 112; at least one camera 170 for capturing one or more images in a field of view; and at least one control unit 106 configured by one or more executable instructions stored on computer memory 108 to perform operations including at least: obtaining visual field of view information using the at least one camera at 11008; performing speech recognition to identify at least one ATC command received as audio to enter at least one specified radio frequency at 11010; detecting at least one discrepancy involving a radio when at least one radio frequency code detected using the at least one camera is not consistent with the at least one ATC command to enter the at least one specified radio frequency at 11012; and outputting feedback information via the at least one speaker at 11014. For example, the processor component of the aviation communication headset can intercept audio signals from a radio output and perform speech recognition to identify a radio frequency command. For instance, the processor component can perform speech recognition on audio to recognize, "104ZU Change to My Frequency 125.1". The processor component can then monitor and analyze imagery data captured by the camera of the aviation communication headset to determine whether the radio interface indicates a radio frequency of 125.1. In an event that the imagery data processed by the processor component indicates a change to a frequency other than 125.1, such as 126.1, the processor component can control output to the speakers to warn of the mismatch. For instance, the processor component can output audio data such as "Warning Radio Frequency Mismatch Tune 125.1."

FIG. 111 is a system diagram of a smart aviation communication headset 100, in accordance with an embodiment of the invention. In one embodiment, an aviation communication headset 100 includes, but is not limited to, at least one microphone 114; one or more speakers 112; at least one camera 170 for capturing one or more images in a field of view; and at least one control unit 106 configured by one or more executable instructions stored on computer memory 108 to perform operations including at least: obtaining visual field of view information using the at least one camera at 11108; performing speech recognition to identify at least one ATC command received as audio to enter at least one specified altimeter setting at 11110; detecting at least one discrepancy involving an altimeter when at least one altimeter setting detected using the at least one camera is not consistent with the at least one ATC command to enter the at least one specified altimeter setting at 11112; and outputting feedback information via the at least one speaker at 11114. For example, the processor component can analyze audio obtained from microphone positioned within the earcup of the aviation communication and perform speech recognition to identify a command to set the altimeter. For instance, the speech recognition can identify the ATC instruction of "N104ZU Altimeter 30.10". Upon identifying the altimeter setting, the processor component can analyze imagery data obtained from the camera to determine whether the correct altimeter setting has been entered. For instance, the imagery data can include images of an analog or digital altimeter. In an event that the altimeter setting determined from the imagery data is inconsistent, such as 31.10, the processor component can control an output to the speakers to warn of the mismatch. For instance, the audio output via the speakers can be "Warning Altimeter Mismatch Set Altimeter 30.10".

FIG. 112 is a system diagram of a smart aviation communication headset 100, in accordance with an embodiment of the invention. In one embodiment, an aviation communication headset 100 includes, but is not limited to, at least one microphone 114; one or more speakers 112; at least one camera 170 for capturing one or more images in a field of view; and at least one control unit 106 configured by one or more executable instructions stored on computer memory 108 to perform operations including at least: obtaining visual field of view information using the at least one camera 11208; performing speech recognition to identify at least one ATC command received as audio to climb or descend to a specified altitude, turn or maintain a specified heading, or maintain a specified airspeed at 11210; detecting at least one discrepancy involving altitude, heading, or airspeed when at least one avionics indication detected using the at least one camera is not consistent with the at least one ATC command at 11212; and outputting feedback information via the at least one speaker at 11214. For instance, the processor component can intercept audio signals output from a communication radio to identify a turn heading and altitude, such as during an IFR clearance. For instance, through speech recognition, the processor component can identify an ATC instruction of "N104ZU turn left 10 degrees and descend maintain niner thousand". Upon recognizing the heading and altitude instruction, the processor component can analyze the imagery data obtained from the camera to determine whether the digital avionics system or analog instruments are indicating both a left 10 degree turn and a descent to 9000 MSL. In an event that the correct heading and altitude is not reached within a specified time, such as within 10 seconds, the processor component can output an audio warning signal via the speakers of the aviation communication headset, such as "Warning Descend to 9000 MSL and maintain heading of 170".

Figure 113:
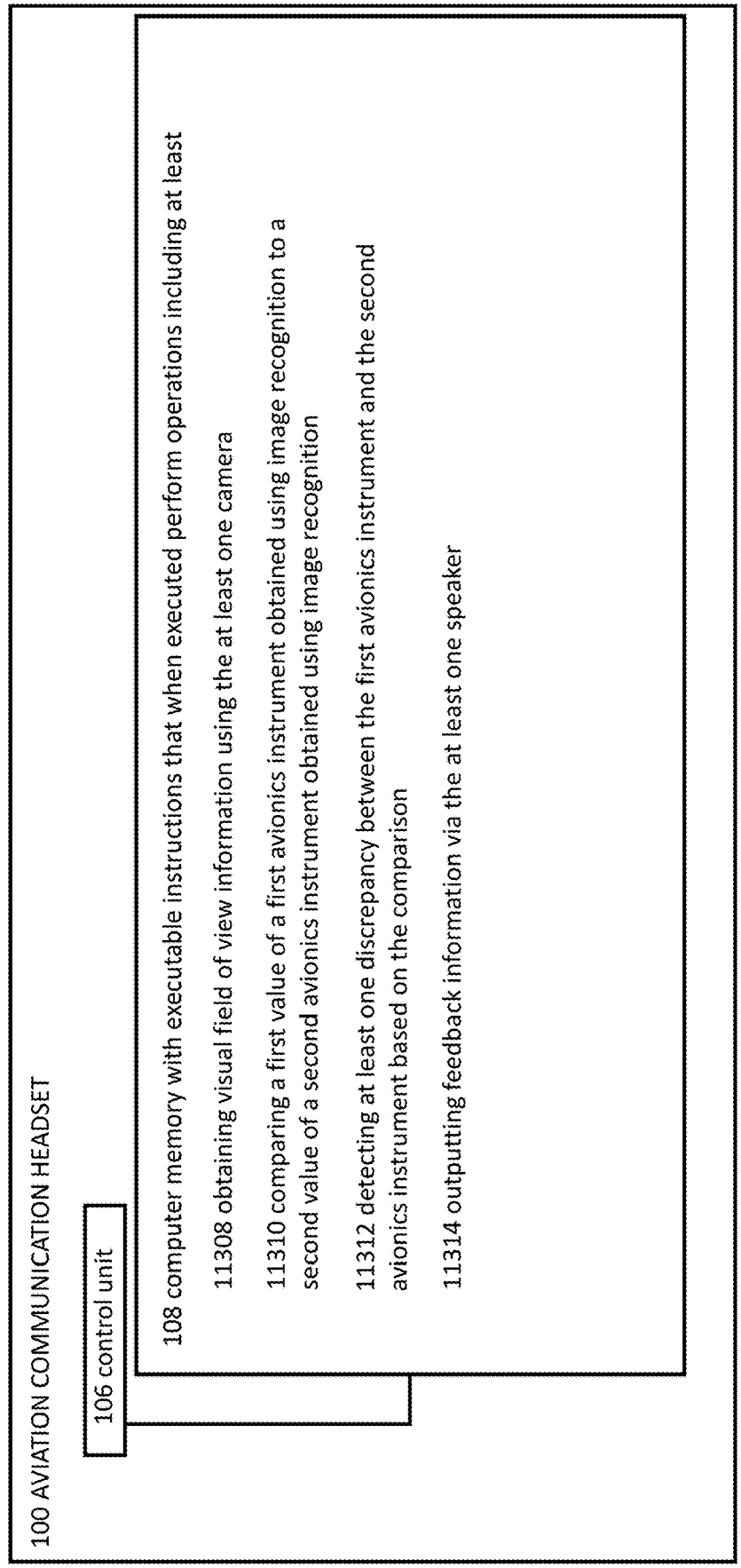

FIG. 113 is a system diagram of a smart aviation communication headset 100, in accordance with an embodiment of the invention. In one embodiment, an aviation communication headset 100 includes, but is not limited to, at least one microphone 114; one or more speakers 112; at least one camera 170 for capturing one or more images in a field of view; and at least one control unit 106 configured by one or more executable instructions stored on computer memory 108 to perform operations including at least: obtaining visual field of view information using the at least one camera at 11308; comparing a first value of a first avionics instrument obtained using image recognition to a second value of a second avionics instrument obtained using image recognition at 11310; detecting at least one discrepancy between the first avionics instrument and the second avionics instrument based on the comparison at 11312; and outputting feedback information via the at least one speaker at 11314. For example, the processor component can analyze incoming image data from the camera and determine whether two instruments are displaying conflicting information. For instance, the processor component can identify the analog altimeter and the analog airspeed indicators and determine whether they are behaving according to specified rules, such as level altitude should have constant airspeed. Similarly, the processor component can compare the turn coordinator imagery data to the attitude indicator imagery data to determine whether one is indicating a turn while the other is indicating level flight. Also, the imagery data corresponding to the attitude indicator can be compared to the imagery data of the airspeed indicator to determine whether one is indicating a climb or descent while the other is indicating the opposite. The imagery data can be analyzed by the processor component to determine failure of a vacuum system, instrument, or electric system by comparing and cross-checking instruments according to one or more specified rules. In addition to monitoring the imagery data of the traditional six-pack instruments, the imagery data of electronic avionics systems can be similarly monitored and analyzed for discrepancies. Likewise, imagery data corresponding to compass, heading indicators, CDI instruments, pitot-static instruments, and navigation systems can be monitored to determine a failure of one or more instruments. In an event of a cross-reference mismatch between instruments as indicated by imagery data analyzed, the processor component can provide a warning output via the speakers. For instance, the processor component can provide the audible warning of "Warning Vacuum System Failure, Cover up Attitude Indicator and Heading Indicator."

Figure 114:
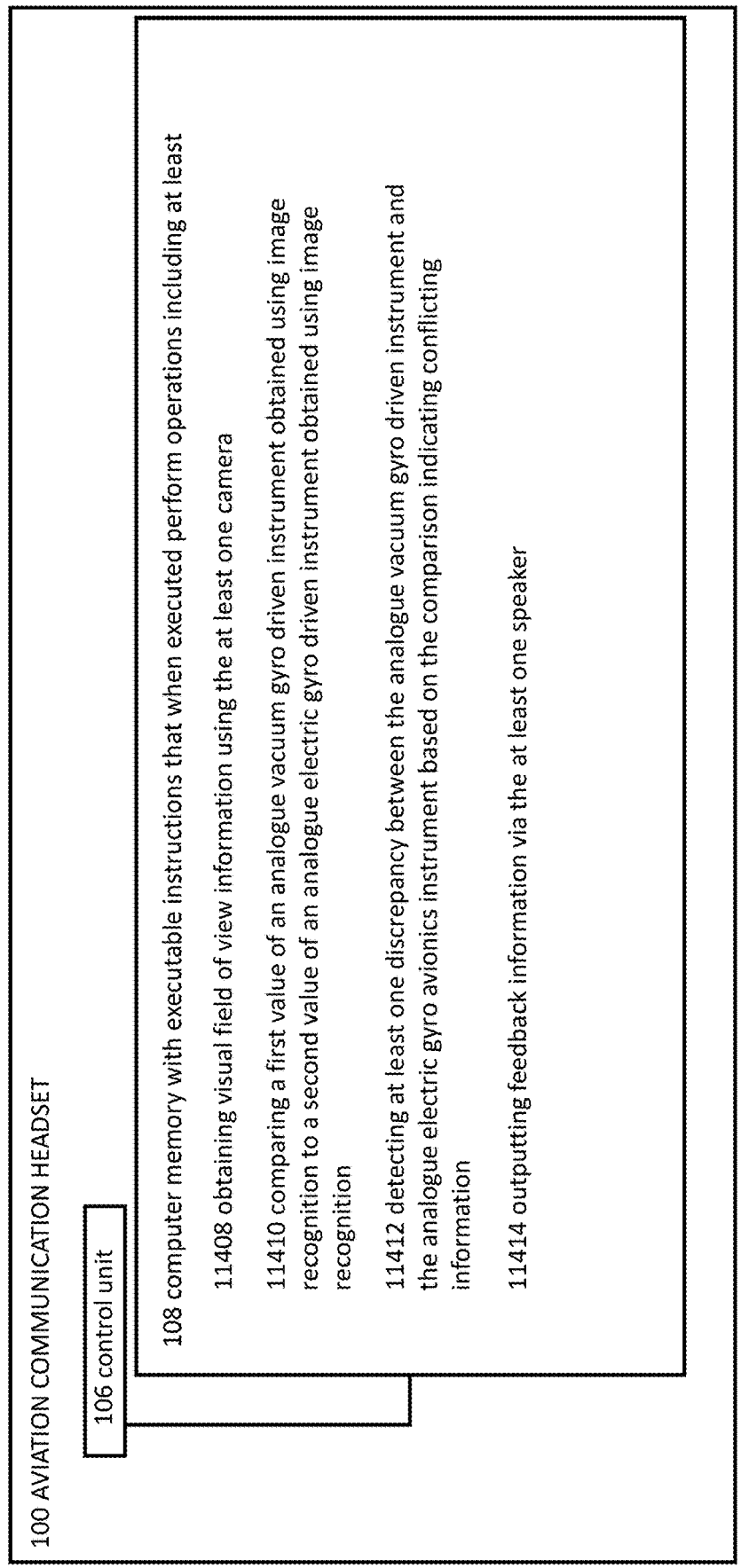

FIG. 114 is a system diagram of a smart aviation communication headset 100, in accordance with an embodiment of the invention. In one embodiment, an aviation communication headset 100 includes, but is not limited to, at least one microphone 114; one or more speakers 112; at least one camera 170 for capturing one or more images in a field of view; and at least one control unit 106 configured by one or more executable instructions stored on computer memory 108 to perform operations including at least: obtaining visual field of view information using the at least one camera at 11408; comparing a first value of an analogue vacuum gyro driven instrument obtained using image recognition to a second value of an analogue electric gyro driven instrument obtained using image recognition at 11410; detecting at least one discrepancy between the analogue vacuum gyro driven instrument and the analogue electric gyro avionics instrument based on the comparison indicating conflicting information at 11412; and outputting feedback information via the at least one speaker at 11414. For instance, the processor component can monitor incoming imagery data and identify the heading indicator, attitude indicator, and the turn coordinator. The heading and attitude indicator typically are powered by a vacuum driving system and the turn coordinator is typically powered by electrical. The processor component can determine whether there is an inconsistency between the instrument outputs using the imagery data, such as the turn coordinator showing a turn to the right and the heading indicator showing a turn to the left. Upon determining a mismatch, the processor component can identify other instruments to cross-check to determine the source of the issue using the imagery data of the camera. For instance, the processor component in this example can look to the imagery data of the attitude indicator or the electronic navigation system to identify a turn to the right. Upon verifying that the turn coordinator is apparently functioning properly from the imagery data, the processor component can signal an audio warning via the speakers, such as "Warning Heading Indicator Malfunction, Cover Heading Indicator".

Figure 115:
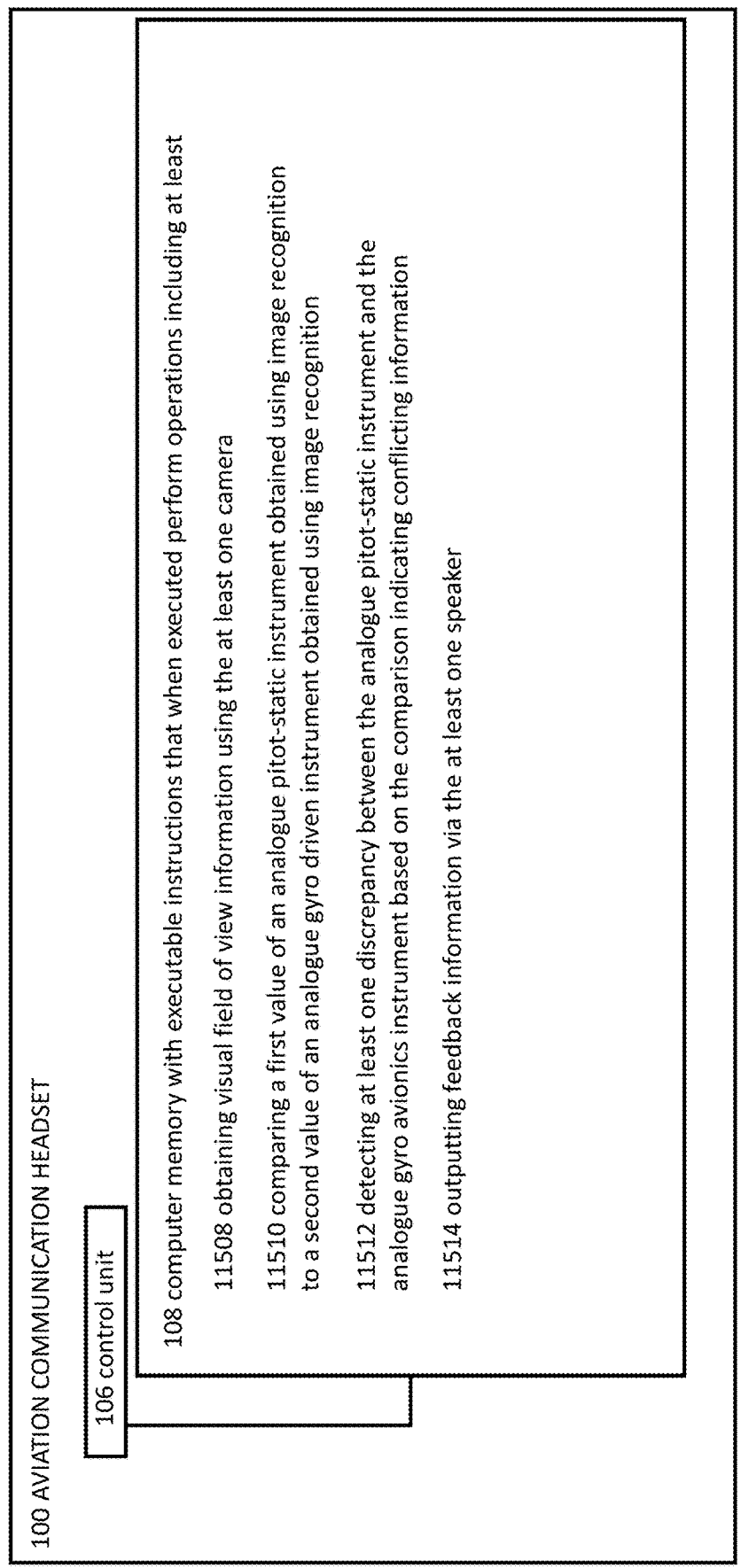

FIG. 115 is a system diagram of a smart aviation communication headset 100, in accordance with an embodiment of the invention. In one embodiment, an aviation communication headset 100 includes, but is not limited to, at least one microphone 114; one or more speakers 112; at least one camera 170 for capturing one or more images in a field of view; and at least one control unit 106 configured by one or more executable instructions stored on computer memory 108 to perform operations including at least: obtaining visual field of view information using the at least one camera at 11508; comparing a first value of an analogue pitot-static instrument obtained using image recognition to a second value of an analogue gyro driven instrument obtained using image recognition at 11510; detecting at least one discrepancy between the analogue pitot-static instrument and the analogue gyro avionics instrument based on the comparison indicating conflicting information at 11512; and outputting feedback information via the at least one speaker at 11514. For example, the processor component can identify the pitot-static instruments such as the vertical speed indicator, airspeed indicator, and altimeter from the imagery data obtained from the camera. The processor component can also identify gyroscopic instruments form the imagery data, such as the turn coordinator, attitude indicator, and heading indicator. These systems can be represented electronically or via analog displays and recognized in either case via the imagery data of the camera. The processor component can perform cross-check and comparing functions of the data indications determined for the instruments using the imagery data. For instance, the processor component may identify that the airspeed indicator is showing a gradual decrease in airspeed using the imagery data while the attitude indicator indicates level flight using the imagery data. The processor component upon identifying the discrepancy can analyze the throttle and mixture and prop settings using the imagery data as well as the other pitot-static instruments using the imagery data. The processor can determine in this instance that the airspeed should not be decreasing due to the throttle, prop, mixture, and gyroscopic outputs indicating an expected constant airspeed. Further, the processor component can verify from the imagery data that the altimeter and vertical speed indicators have consistent issues with a clogged pitot tube or static port. The processor component upon identifying the issue can output a warning indication via the speakers, such as "Warning pitot tube appears to be clogged, apply pitot heat."

Figure 116:
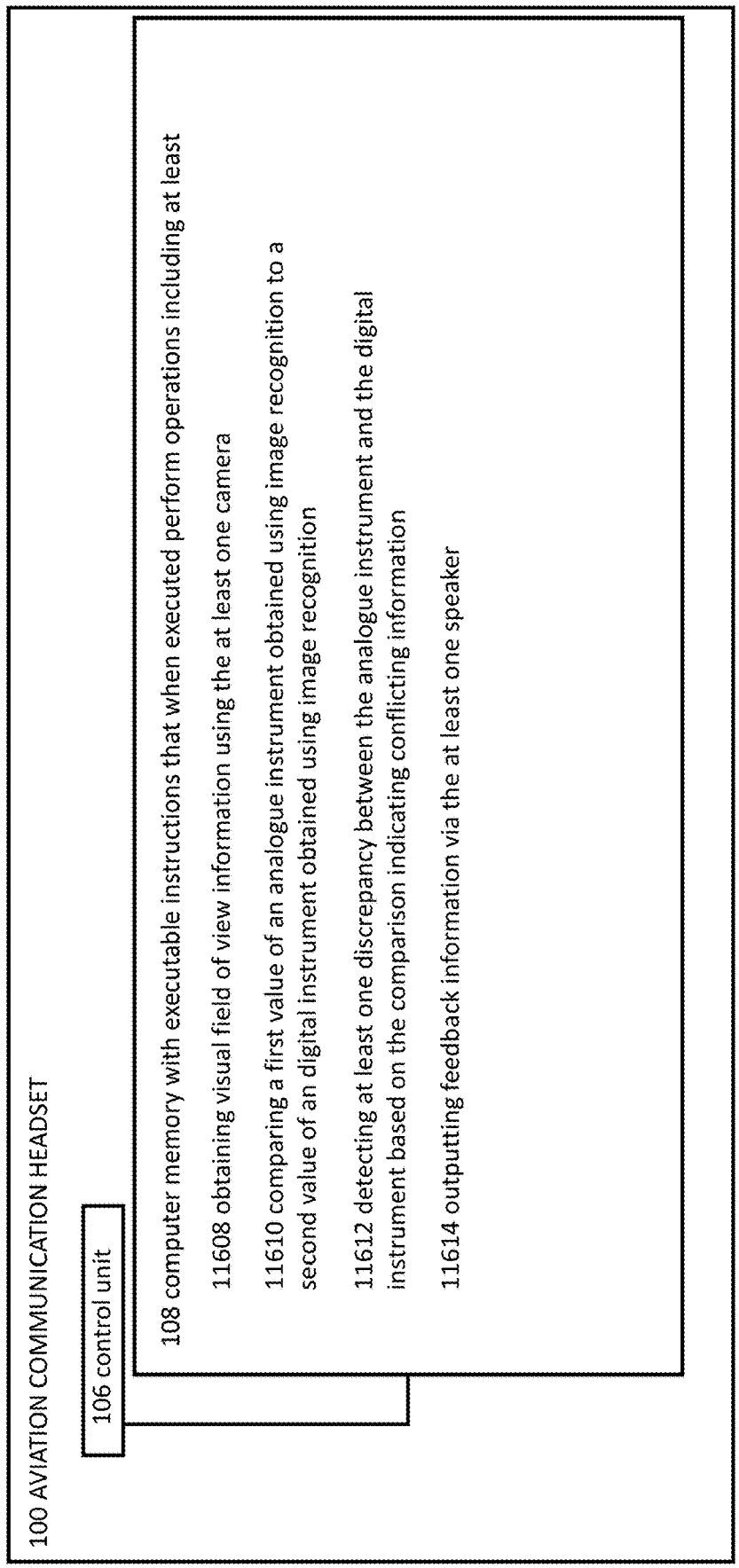

FIG. 116 is a system diagram of a smart aviation communication headset 100, in accordance with an embodiment of the invention. In one embodiment, an aviation communication headset 100 includes, but is not limited to, at least one microphone 114; one or more speakers 112; at least one camera 170 for capturing one or more images in a field of view; and at least one control unit 106 configured by one or more executable instructions stored on computer memory 108 to perform operations including at least: obtaining visual field of view information using the at least one camera at 11608; comparing a first value of an analogue instrument obtained using image recognition to a second value of an digital instrument obtained using image recognition at 11610; detecting at least one discrepancy between the analogue instrument and the digital instrument based on the comparison indicating conflicting information at 11612; and outputting feedback information via the at least one speaker at 11614. For example, the processor component can analyze image data obtained from the camera of the aviation communication headset to identify analog and digital instruments in a field of view. Analog instruments can include vacuum, gyro, compass, and pitot-static instruments. Digital instruments can include GPS, ADAHRS, solid-state sensor, and magnetometer based instruments. Digital instruments can also obtain input from analog sources. Analog instruments can similarly obtain input from digital instruments. The processor component can cross check analog against digital instrument readouts using the image data captured from the camera. Inconsistencies and conflicts can be identified and the processor component can output indications via the speakers. For instance, the processor component can identify an inconsistency between a GPS-based groundspeed and a pitot-static based airspeed using the image capture data from the camera. Alternatively, the processor component can identify an inconsistency between a gyroscopic attitude indicator and a solid-state based digital magnetometer. The processor component can then output an audible alert via the speakers, such as "Check attitude indicator".

FIG. 117 is a system diagram of a smart aviation communication headset 100, in accordance with an embodiment of the invention. In one embodiment, an aviation communication headset 100 includes, but is not limited to, at least one microphone 114; one or more speakers 112; at least one camera 170 for capturing one or more images in a field of view; and at least one control unit 106 configured by one or more executable instructions stored on computer memory 108 to perform operations including at least: obtaining visual field of view information using the at least one camera at 11708; comparing a first value of a first digital instrument obtained using image recognition to a second value of a second digital instrument obtained using image recognition at 11710; detecting at least one discrepancy between the first digital instrument and the second digital instrument based on the comparison indicating conflicting information at 11712; and outputting feedback information via the at least one speaker at 11714. For example, the processor component can analyze the imagery data obtained from the camera of the smart aviation communication headset to identify a digital primary flight display, a digital secondary flight display, and/or a standalone digital magnetometer. The processor component can monitor using the imagery data the digital displays of each of the digital avionics systems, which may each have independent power, ADAHRS, pitot static type inputs. Upon detecting a discrepancy, the processor component can providing an audio output. For instance, the processor component may detect a discrepancy in indicated heading between two different digital avionics systems (e.g., one may indicate a heading of 160 and the other may indicate a heading of 170). Using imagery associated with a compass in a field of view of the camera, the processor component can determine that the magnetic compass supports one of the heading readouts on the digital display. The processor component can then output audio via the speakers, such as "Secondary Flight Deck: Change to Heading of 170".

Figure 118:
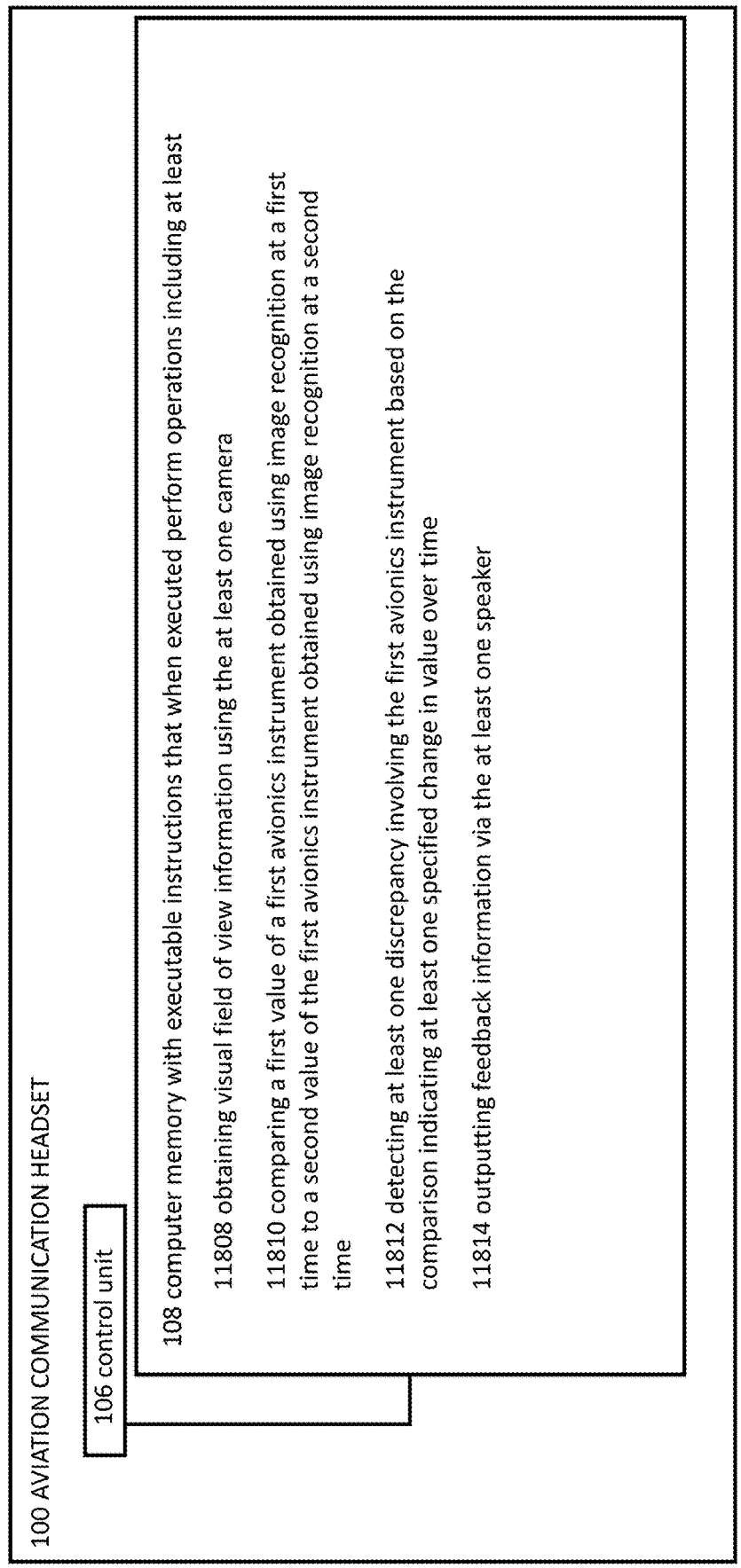

FIG. 118 is a system diagram of a smart aviation communication headset 100, in accordance with an embodiment of the invention. In one embodiment, an aviation communication headset 100 includes, but is not limited to, at least one microphone 114; one or more speakers 112; at least one camera 170 for capturing one or more images in a field of view; and at least one control unit 106 configured by one or more executable instructions stored on computer memory 108 to perform operations including at least: obtaining visual field of view information using the at least one camera at 11908; comparing a value of an avionics instrument obtained using image recognition to at least one specified range of acceptable values for the avionics instrument at 11910; detecting at least one discrepancy involving the avionics instrument based on the value being outside the at least one specified range of acceptable values for the avionics instrument at 11912; and outputting feedback information via the at least one speaker at 11914. For example, the processor component can perform image recognition with respect to image data obtained from the camera of the headset to identify the engine instruments on a digital display. The oil pressure, fuel pressure, fuel flow, oil temperature, RPM, manifold pressure, fuel level, cylinder head temperature, and exhaust temperature can therefore be monitored by the processor using image data obtained from the camera. In an event that the processor detects an unusual discrepancy or change in one instrument, the processor can output a warning regarding such via the speakers of the headset. For instance, the processor can detect an unusual cylinder head temperature in cylinder 2 using a comparison of the image data obtained via the camera with recent or historical cylinder head temperature for cylinder 2. Upon being outside a specific range (e.g., 25 degrees), the processor component can provide an audible output via the speakers of "Warning Cylinder 2 Unusually Hot".

FIG. 119 is a system diagram of a smart aviation communication headset 100, in accordance with an embodiment of the invention. In one embodiment, an aviation communication headset 100 includes, but is not limited to, at least one microphone 114; one or more speakers 112; at least one camera 170 for capturing one or more images in a field of view; and at least one control unit 106 configured by one or more executable instructions stored on computer memory 108 to perform operations including at least: obtaining visual field of view information using the at least one camera at 11908; comparing a value of an avionics instrument obtained using image recognition to at least one specified range of acceptable values for the avionics instrument at 11910; detecting at least one discrepancy involving the avionics instrument based on the value being outside the at least one specified range of acceptable values for the avionics instrument at 11912; and outputting feedback information via the at least one speaker at 11914. For example, the processor component can identify from the image data obtained from the camera of the headset that the fuel flow from an analog fuel flow gauge is below a specified range, such as 5 gallons per hour vs an acceptable range of 8-12 gallons per hour. Upon detecting an out of range instrument value using the image data, the processor component can evaluate other cross-check instruments, such as RPM, mixture control settings, and fuel pressure gauges using the image data. Upon confirming the existence of an unexplained out-of-range instrument reading using the image data, the processor component can signal an output. For instance, the processor component can output audio of "Warning Fuel Flow is Low".

Figure 120:
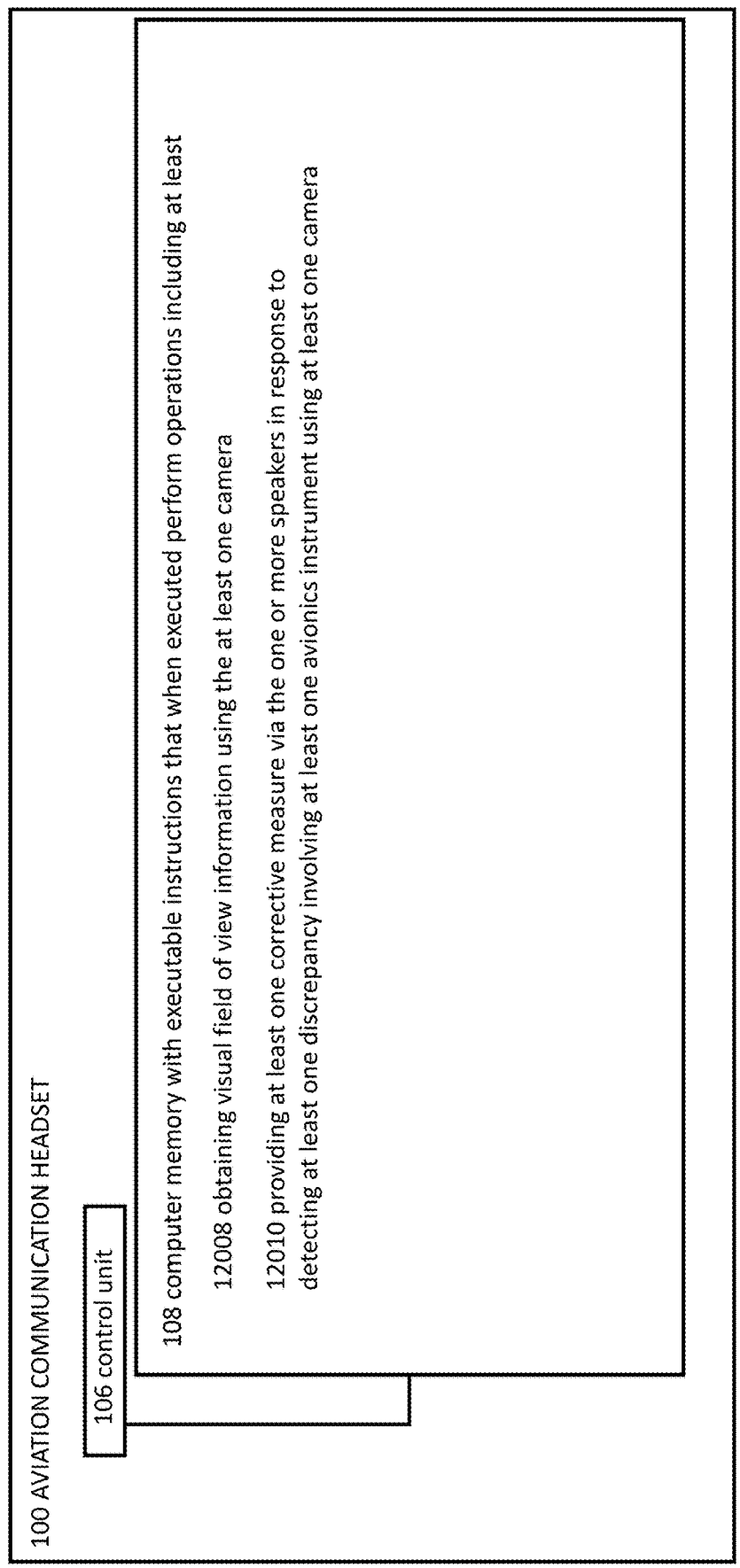

FIG. 120 is a system diagram of a smart aviation communication headset 100, in accordance with an embodiment of the invention. In one embodiment, an aviation communication headset 100 includes, but is not limited to, at least one microphone 114; one or more speakers 112; at least one camera 170 for capturing one or more images in a field of view; and at least one control unit 106 configured by one or more executable instructions stored on computer memory 108 to perform operations including at least: obtaining visual field of view information using the at least one camera at 12008 and providing at least one corrective measure via the one or more speakers in response to detecting at least one discrepancy involving at least one avionics instrument using at least one camera at 12010. For example, the processor component can perform image recognition with respect to the imagery data obtained from the camera to identify high cylinder head temperatures (e.g., over 400 degrees). The processor component can upon detecting a potential trouble situation, can provide an audible alert along with a recommendation. For instance, the processor component can provide an audible output of "High Cylinder Head Temperatures. Increase Mixture. Decrease Angle of Attack. Reduce Power." The processor component can provide checklists audibly via the speaker of the communication headset in an even of a trouble situation detected using the image data of the camera. For instance, on engine shutdown as evidenced by image data showing low RPM, fuel flow, manifold pressure, temperature, etc., the processor component can output an audible checklist such as "Emergency Engine Off: Switch Fuel Tanks, Open Alternative Air, Increase Mixture, Check Ignition, Fuel Boost Pump On. Transponder 7700. Radio 121.5. Mayday." The checklist can be repeated by the processor component in whole or in part.

FIG. 121 is a system diagram of a smart aviation communication headset 100, in accordance with an embodiment of the invention. In one embodiment, an aviation communication headset 100 includes, but is not limited to, at least one microphone 114; one or more speakers 112; at least one camera 170 for capturing one or more images in a field of view; and at least one control unit 106 configured by one or more executable instructions stored on computer memory 108 to perform operations including at least: obtaining visual field of view information using the at least one camera at 12108; outputting feedback information via the at least one speaker at 12110; detecting at least one urgent or emergency situation based at least partly on at least one detected discrepancy at 12112; capturing at least one image or video stream of at least one field of view using at least one camera at 12114; transmitting the at least one image or video stream to at least one specified recipient at 12116; and establishing at least one communication link with the at least one specified recipient to assist with the at least one urgent or emergency situation at 12118. For example, the processor component can detect via image recognition performed with respect to the image data of the camera of the headset, an urgent situation such as inconsistent instruments during an IFR flight in IMC. Upon detecting the issue, the processor component can provide feedback via the speakers of the headset as discussed herein. However, the processor can further identify an emergency contact, such as ATC, flight instructor, trusted pilot friend, or a plurality of individuals, using contact information stored in a registry. The processor component can thereafter establish wireless communication with that individual (e.g., based on first person to acknowledge basis), including audio and image data communication. The processor component can stream imagery obtained using the image capture device of the headset to the person, such as for review using a smartphone device or computer, and enable the person to troubleshoot from remote. The processor can receive and transmit audio to enable real-time conversation with the person reviewing the image data. Thus, a pilot can establish quick communication with a remote trusted individual during and emergency and use the aviation headset to communicate with that person. Image data can be further streamed to enable the person to remotely troubleshoot and provide advice as to what appears to be the problem. The aviation communication headset can have built-in cellular or use BLUETOOTH or wired connection to communicate via a proximate smartphone device.

Figure 122:
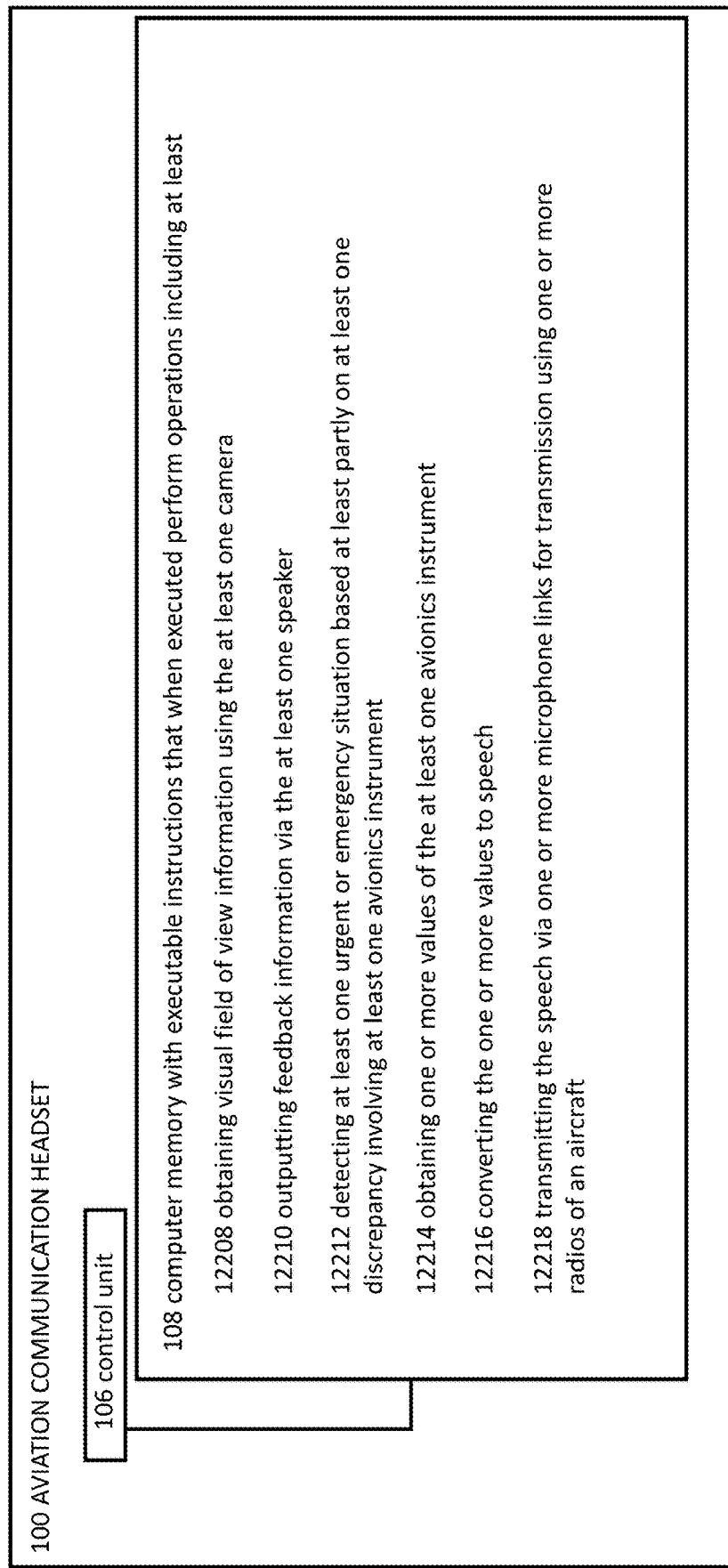

FIG. 122 is a system diagram of a smart aviation communication headset 100, in accordance with an embodiment of the invention. In one embodiment, an aviation communication headset 100 includes, but is not limited to, at least one microphone 114; one or more speakers 112; at least one camera 170 for capturing one or more images in a field of view; and at least one control unit 106 configured by one or more executable instructions stored on computer memory 108 to perform operations including at least: obtaining visual field of view information using the at least one camera at 12208; outputting feedback information via the at least one speaker at 12210; detecting at least one urgent or emergency situation based at least partly on at least one discrepancy involving at least one avionics instrument at 12212; obtaining one or more values of the at least one avionics instrument at 12214; converting the one or more values to speech at 12216; and transmitting the speech via one or more microphone links for transmission using one or more radios of an aircraft at 12218. For example, the processor component can identify an urgent situation using the image data from the camera of the headset as discussed herein. Upon detecting such indication, the processor component can signal an audio output via the speakers. However, the processor component can also translate the readout identified using image recognition to a speech version. For instance, the processor component can determine that the airspeed indictor has dropped to 0 using the image data from the camera of the headset. The processor component can convert this to the following audio: "Pan Pan. N104ZU. Airspeed Zero. Altimeter Four Thousand. GPS Altitude Four Thousand Ten." The processor can then signal for the audio to be transmitted via the communication radio on 121.5. The frequency can be user defined or automatically selected based on emergency frequencies.

Figure 123:
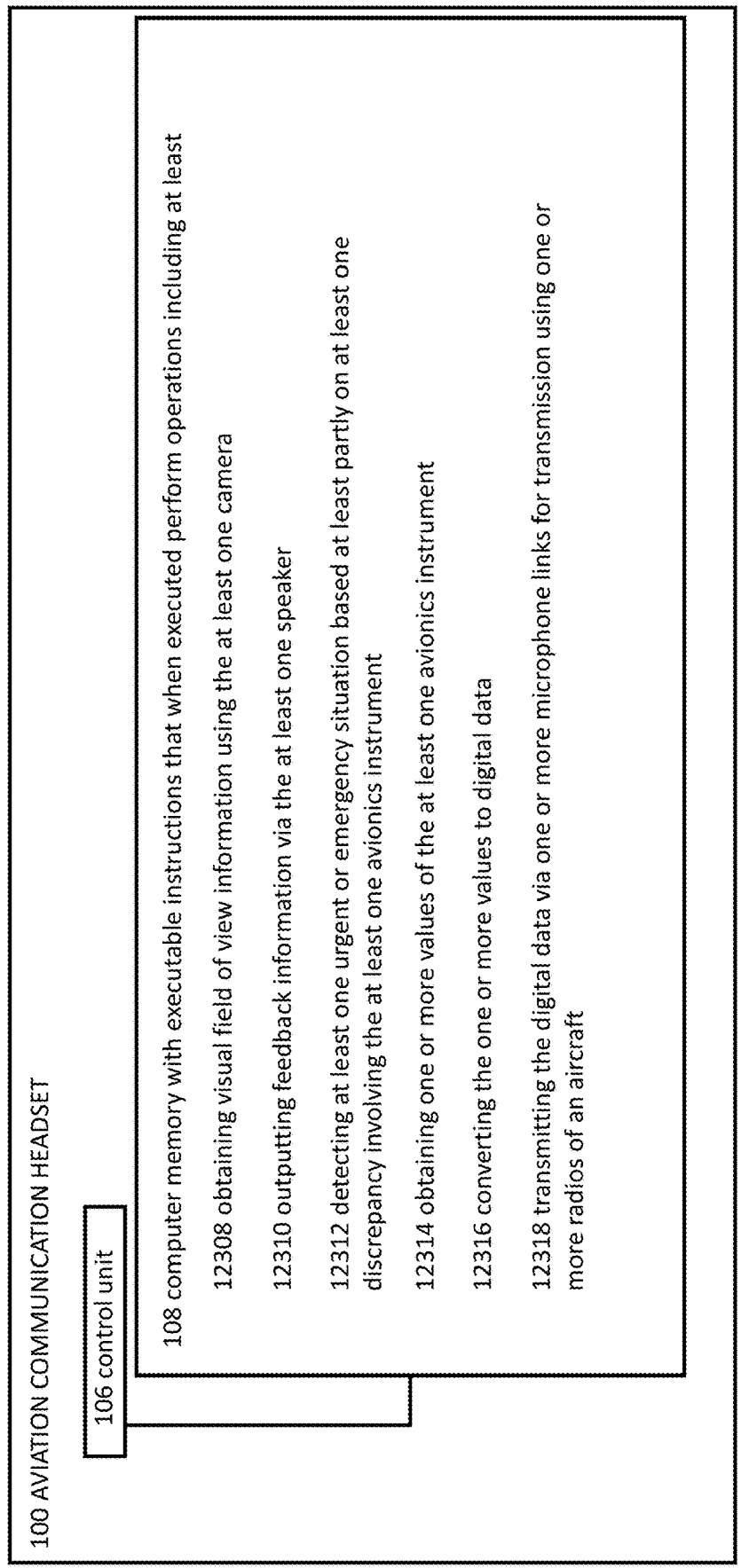

FIG. 123 is a system diagram of a smart aviation communication headset 100, in accordance with an embodiment of the invention. In one embodiment, an aviation communication headset 100 includes, but is not limited to, at least one microphone 114; one or more speakers 112; at least one camera 170 for capturing one or more images in a field of view; and at least one control unit 106 configured by one or more executable instructions stored on computer memory 108 to perform operations including at least: obtaining visual field of view information using the at least one camera at 12308; outputting feedback information via the at least one speaker at 12310; detecting at least one urgent or emergency situation based at least partly on at least one discrepancy involving the at least one avionics instrument at 12312; obtaining one or more values of the at least one avionics instrument at 12314; converting the one or more values to digital data at 12316; and transmitting the digital data via one or more microphone links for transmission using one or more radios of an aircraft at 12318. For example, the processor component can identify using image data of the camera an instance of engine problems and convert the image data into engine monitored values. For instance, the processor can determine the oil pressure as 35, the cylinder head temperatures to be 300/325/325/300/290,/315, the fuel flow to be 12 gallons per hour, the fuel pressure to be 25, etc. The processor can convert these values to digital information and transmit the digital data via the aircraft radio to be received by another aircraft, wherein the other aircraft can be a proximate aircraft that can reproduce the image of the engine parameter values via a digital display for troubleshooting.

Figure 124:
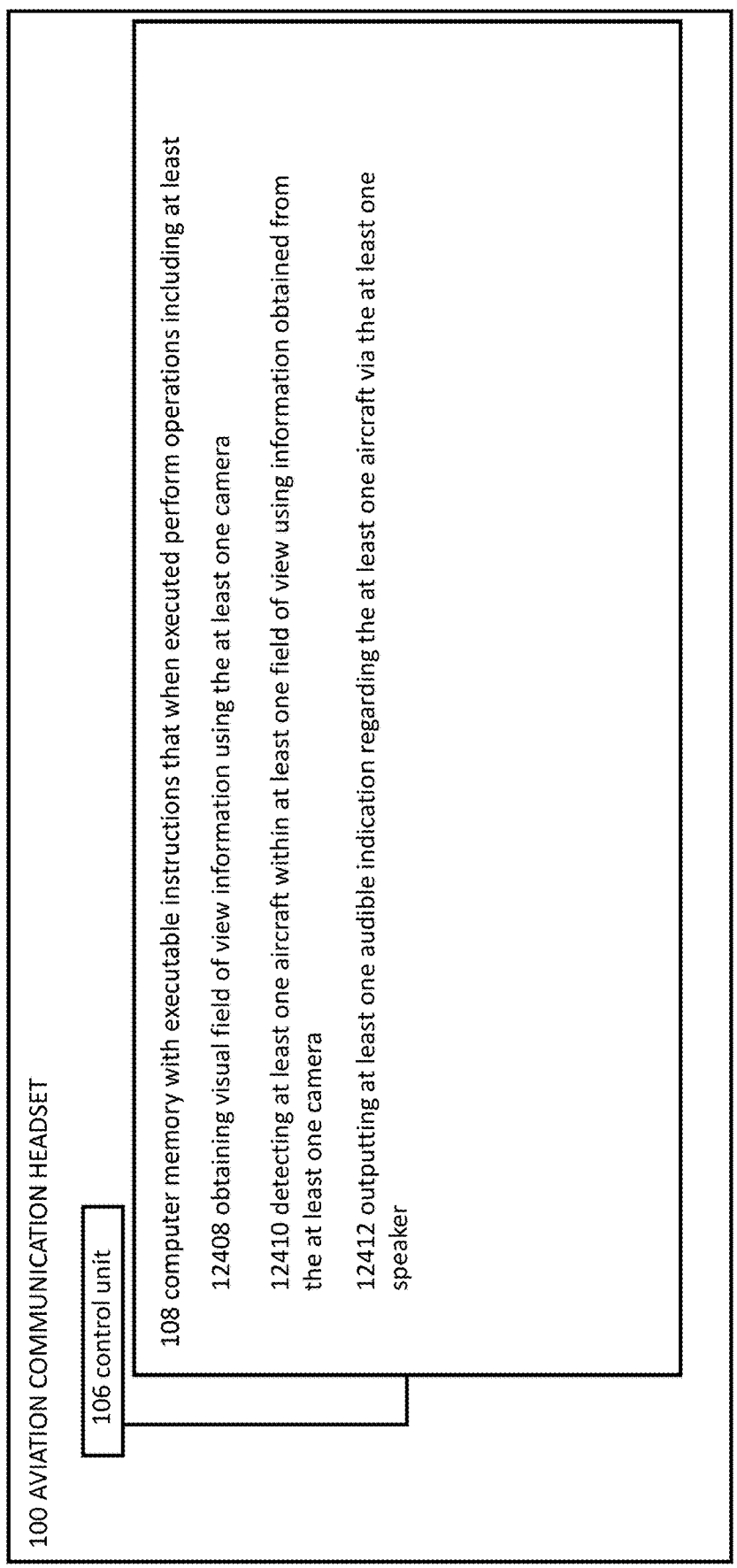

FIG. 124 is a system diagram of a smart aviation communication headset 100, in accordance with an embodiment of the invention. In one embodiment, an aviation communication headset 100 includes, but is not limited to, at least one microphone 114; one or more speakers 112; at least one camera 170 for capturing one or more images in a field of view; and at least one control unit 106 configured by one or more executable instructions stored on computer memory 108 to perform operations including at least: obtaining visual field of view information using the at least one camera at 12408; detecting at least one aircraft within at least one field of view using information obtained from the at least one camera at 12410; outputting at least one audible indication regarding the at least one aircraft via the at least one speaker at 12412. For example, the processor component can perform image recognition on the image data of the camera of the smart aviation communication headset to identify a moving target aircraft within a field of view. The processor component can determine the relative position of the target aircraft within the field of view, relative altitude, and direction of flight based on size and movement information in the image data. The processor component can then provide an audible output via the speakers of the aviation communication headset, such as "Traffic 2 o'clock. 500 Lower. Opposite Direction." The processor component can base the relative location on cues in the image data such as the windscreen center, which can be established as 12 o'clock. Thus, the processor component can calibrate the relative location based on the position of the center of the windscreen rather than the head orientation of a wearer of the headset.

Figure 125:
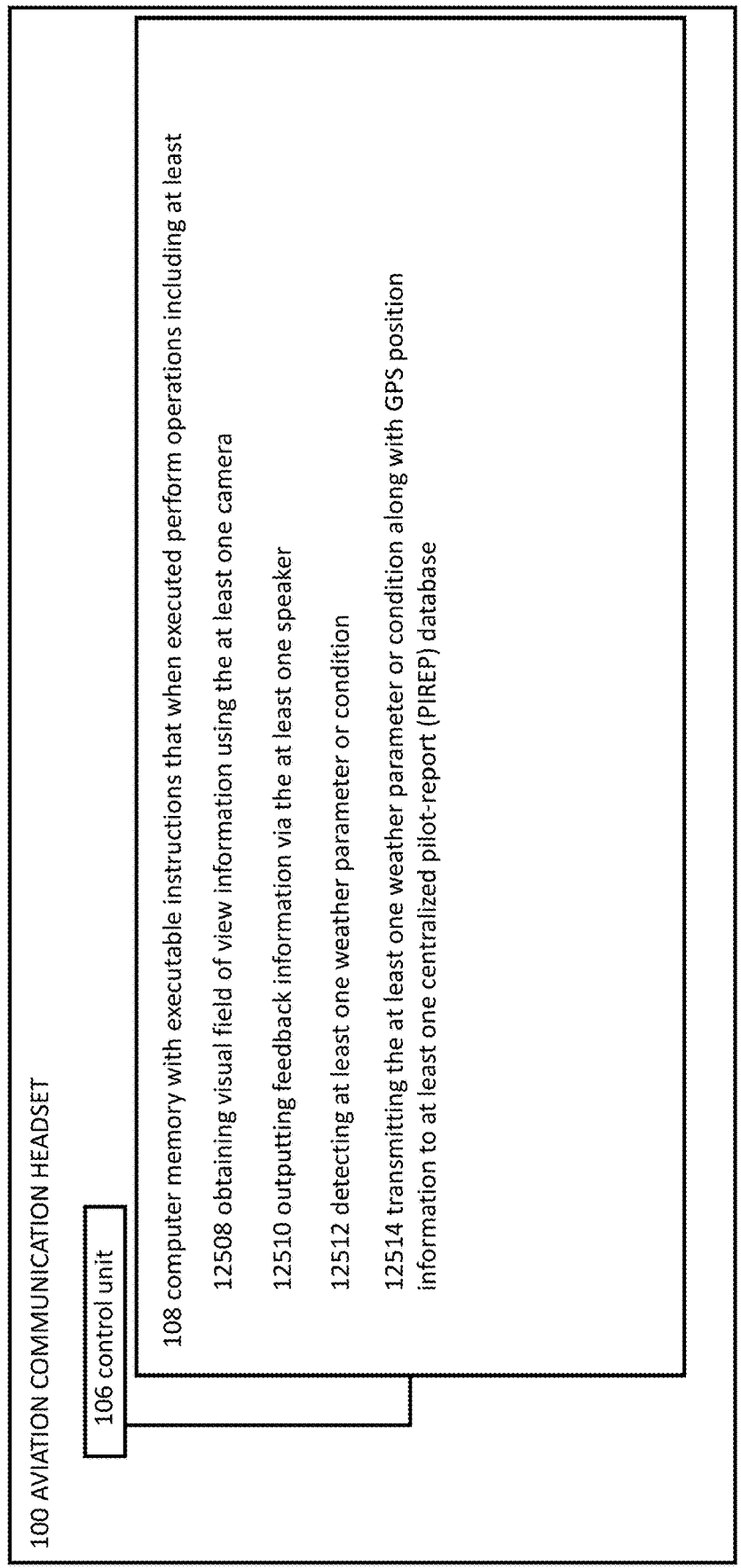

FIG. 125 is a system diagram of a smart aviation communication headset 100, in accordance with an embodiment of the invention. In one embodiment, an aviation communication headset 100 includes, but is not limited to, at least one microphone 114; one or more speakers 112; at least one camera 170 for capturing one or more images in a field of view; and at least one control unit 106 configured by one or more executable instructions stored on computer memory 108 to perform operations including at least: obtaining visual field of view information using the at least one camera at 12508; outputting feedback information via the at least one speaker at 12510; detecting at least one weather parameter or condition at 12512; and transmitting the at least one weather parameter or condition along with GPS position information to at least one centralized pilot-report (PIREP) database at 12514. For example, the processor component can determine cloud coverage, visibility, and turbulence information using the image data of the camera (e.g., shaking or unstable field of view can indicate turbulence). The processor component can translate this information into audio data, such as "IMC. Visibility Nil" or "Clear. Visibility 10" or "Scattered. Visibility 10. Light Chop". The processor component can obtain GPS information, such as using the image data of the camera and transmit this information on a radio frequency for pilot reported weather PIREP. The PIREP transmission can facilitate a more comprehensive weather snapshot based on actual conditions, including cloud bases, cloud tops, visibility, cloud coverage, and turbulence.

Figure 126:
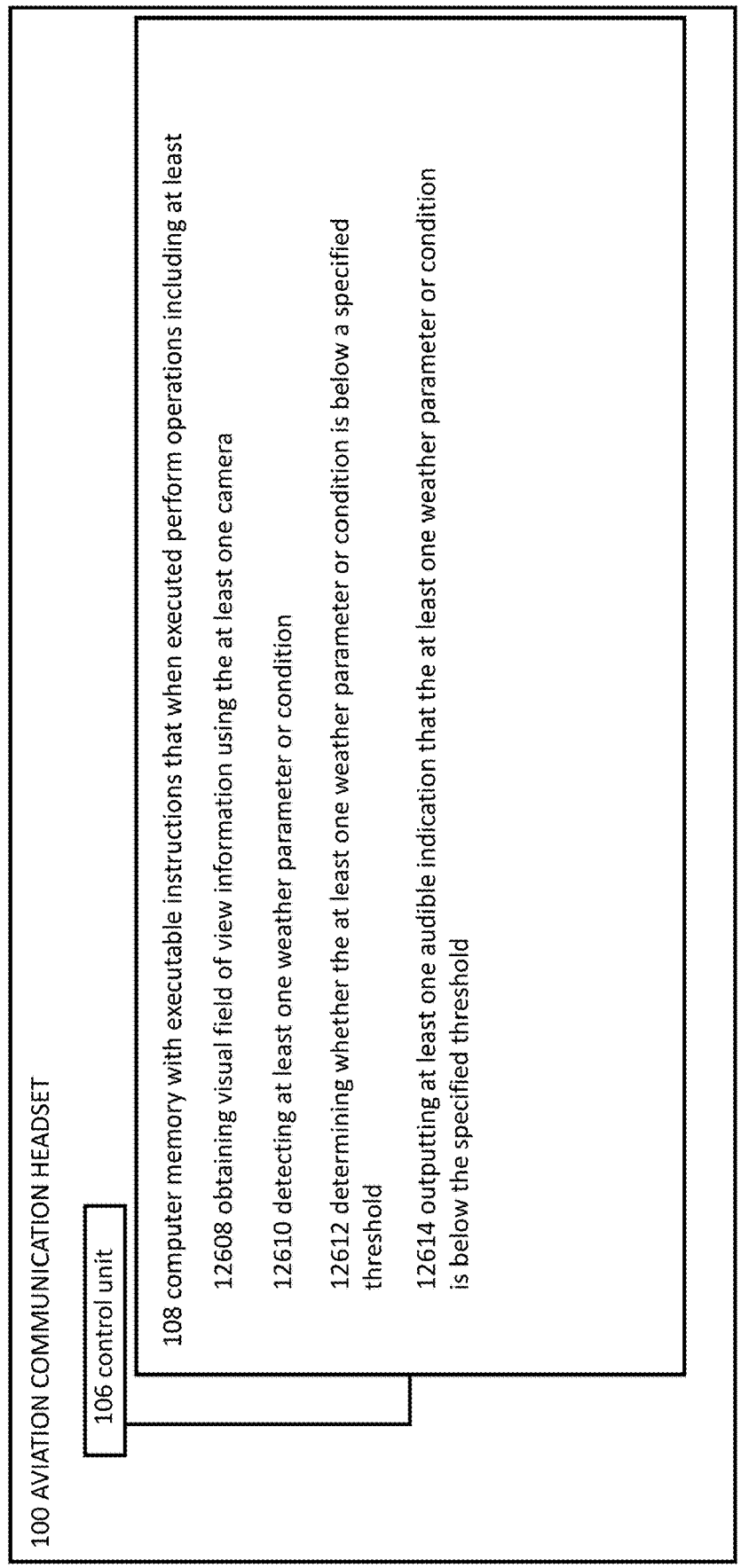

FIG. 126 is a system diagram of a smart aviation communication headset 100, in accordance with an embodiment of the invention. In one embodiment, an aviation communication headset 100 includes, but is not limited to, at least one microphone 114; one or more speakers 112; at least one camera 170 for capturing one or more images in a field of view; and at least one control unit 106 configured by one or more executable instructions stored on computer memory 108 to perform operations including at least: obtaining visual field of view information using the at least one camera at 12608; detecting at least one weather parameter or condition at 12610; determining whether the at least one weather parameter or condition is below a specified threshold at 12612; and outputting at least one audible indication that the at least one weather parameter or condition is below the specified threshold at 12614. For example, a processor component can analyze image data of a camera of the headset to identify visibility conditions, such as on an instrument approach at minimums. The processor component can determine from the image data and known reference values, such as the detection of lights and the length of the MALSR lighting system on an approach, the flight visibility. The processor component can then output the flight visibility in audible form, such as "1 Mile Flight Visibility" via the speakers of the headset. The required flight visibility for a loaded approach, as determined by the processor using the image data of the camera, can be cross-referenced and the processor can output audio such as "Flight Visibility for Approach Satisfied."

While preferred and alternate embodiments of the invention have been illustrated and described, as noted above, many changes can be made without departing from the spirit and scope of the invention. Accordingly, the scope of the invention is not limited by the disclosure of these preferred and alternate embodiments. Instead, the invention should be determined entirely by reference to the claims that follow.

What is claimed is:

1. An accessory device, the accessory device comprising:
   a cushion that is removably attachable to an earcup of a headset, the cushion shaped to circumscribe an ear when worn;
   at least one oximeter positioned at a lower portion of the cushion such that the at least one oximeter is pressed toward a skin surface proximate an earlobe when worn, the at least one oximeter configured to emit light and obtain an intensity of reflected light;
   at least one wireless communication unit incorporated in the cushion; and
   at least one processor incorporated in the cushion and configured to transmit one or more oximeter measurements obtained using the at least one oximeter via the at least one wireless communication unit.

2. The device of claim 1, further comprising an aviation headset.

3. The device of claim 1, wherein the at least one oximeter is exposed via an aperture in the cushion.

4. The device of claim 1, wherein the at least one oximeter comprises a plurality of two or more oximeters spaced apart relative to the cushion to obtain one or more oximeter measurements at different positions.

5. The device of claim 1, wherein the at least one oximeter is positioned at a lower area of the cushion such that the at least one oximeter is pressed toward a skin surface below or in front of an earlobe when the headset is worn.

6. The device of claim 1, wherein the at least one processor is configured to use speech commands for controlling the at least one oximeter or processing one or more oximeter measurements.

7. The device of claim 1, further comprising:
   a carbon monoxide detector configured to detect carbon monoxide.

8. The device of claim 1, further comprising:
   an orientation movement sensor configured to detect movement.

9. The device of claim 1, wherein the cushion further includes one or more of the following types of physiological sensors: body temperature, electrical impulse, or heart rate.

10. The device of claim 1, further comprising:
    a barometric pressure sensory.

11. The device of claim 1, wherein the at least one processor is further configured to initiate an automated action in response to one or more oximeter measurements.

12. The device of claim 1, wherein the at least one processor is further configured to request a response of an individual in response to one or more oximeter measurements.

13. The device of claim 1, wherein the at least one processor is configured to transmit one or more oximeter measurements via the wireless communication unit for output via an aircraft avionics system.

14. The device of claim 1, wherein the at least one wireless communication unit is a BLUETOOTH module that is configured to communicate with at least one of an electronic flight accessory, augmented reality eyewear, a heads-up display, or a mobile device.

15. The device of claim 1, further comprising a field of view camera.

16. The device of claim 1, further comprising a microphone.

17. The device of claim 1, wherein the cushion includes a lip or flap to secure to an earcup of a headset.

18. A headset device comprising:
   a cushion that is removably attachable to an earcup of a headset, the cushion shaped to circumscribe an ear when worn;
   at least one oximeter positioned at a lower portion of the cushion such that the at least one oximeter is pressed toward a skin surface proximate an earlobe when worn, the at least one oximeter configured to emit light and obtain an intensity of reflected light;
   at least one wireless communication unit incorporated in the cushion; and
   at least one processor incorporated in the cushion and configured to transmit one or more oximeter measurements obtained using the at least one oximeter via the at least one wireless communication unit.

19. A system comprising:
   a mobile device; and
   a cushion that is removably attachable to an earcup of a headset, the cushion shaped to circumscribe an ear when worn, the cushion including at least:
     at least one oximeter positioned at a lower portion of the cushion such that the at least one oximeter is pressed toward a skin surface proximate an earlobe when worn, the at least one oximeter configured to emit light and obtain an intensity of reflected light;
     at least one wireless communication unit incorporated in the cushion and configured to wirelessly connect to the mobile device; and
     at least one processor incorporated in the cushion and configured to transmit one or more oximeter measurements obtained using the at least one oximeter via the at least one wireless communication unit to the mobile device.

* * * * *